United States Patent [19]

Barth

[11] 4,179,511

[45] Dec. 18, 1979

[54] ANTIBACTERIAL 3-(5-TETRAZOLYL) PENAM COMPOUNDS

[75] Inventor: Wayne E. Barth, East Lyme, Conn.

[73] Assignee: Pfizer Inc., New York, N.Y.

[21] Appl. No.: 957,197

[22] Filed: Nov. 1, 1978

Related U.S. Application Data

[60] Division of Ser. No. 786,817, Apr. 12, 1977, Pat. No. 4,143,039, which is a continuation-in-part of Ser. No. 561,147, Mar. 24, 1975, which is a continuation-in-part of Ser. No. 491,510, Jul. 24, 1974, abandoned, which is a continuation-in-part of Ser. No. 450,435, Mar. 12, 1974, abandoned, which is a continuation-in-part of Ser. No. 407,097, Oct. 17, 1973, abandoned.

[51] Int. Cl.[2] ............................................ A61K 31/43

[52] U.S. Cl. .................................. 424/271; 424/251; 424/263; 424/270

[58] Field of Search ............... 424/271, 251, 263, 270; 260/306.7 C, 239.1

[56] References Cited

U.S. PATENT DOCUMENTS

| | | | |
|---|---|---|---|
| 3,316,273 | 4/1967 | Gottstein et al. | 260/306.7 C |
| 3,427,302 | 2/1969 | Essery | 260/239.1 |
| 3,468,874 | 9/1969 | Raap et al. | 260/239.1 |

OTHER PUBLICATIONS

Gottstein et al., J. Org. Chem., 31, 1922 (1966).

*Primary Examiner*—Gerald A. Schwartz
*Attorney, Agent, or Firm*—Connolly and Hutz

[57] ABSTRACT

Certain novel 6-acylamino-2,2-dimethyl-3-(5-tetrazolyl)penam derivatives, and salts thereof; their use as broad-spectrum antibacterial agents; and methods for their preparation. Their preparation comprises acylation of the novel intermediate, 6-amino-2,2-dimethyl-3-(5-tetrazolyl)penam or simple derivatives thereof, followed, in some cases, by further transformations of the 6-acylamino group or by removal of a protecting group from the 5-tetrazolyl moiety. Process for the preparation of 6-amino-2,2-dimethyl-3-(5-tetrazolyl)penam, simple derivatives thereof and intermediates therefor.

9 Claims, No Drawings

ANTIBACTERIAL 3-(5-TETRAZOLYL) PENAM COMPOUNDS

CROSS-REFERENCE TO RELATED APPLICATIONS

This application is a division of application Ser. No. 786,817 filed Apr. 12, 1977, now U.S. Pat. No. 4,143,039 of Mar. 6, 1979 which is a continuation-in-part of application Ser. No. 561,147, filed Mar. 24, 1975; which is a continuation-in-part of application Ser. No. 491,510, filed July 24, 1974, and now abandoned; which is a continuation-in-part of application Ser. No. 450,435, filed Mar. 12, 1974, and now abandoned; which in turn is a continuation-in-part of application Ser. No. 407,097, filed Oct. 17, 1973, and now abandoned.

BACKGROUND OF THE INVENTION

2. Field of the Invention

This invention relates to novel antibacterial agents which are of value as animal feed supplements, as therapeutic agents for the control of infectious diseases caused by gram-positive and gram-negative bacteria, and for the sterilization of hospital surfaces and the like; and to novel intermediates for their production. More specifically, the antibacterial compounds of the instant invention are 6-acyl derivatives of 6-amino-2,2-dimethylpenam, which also bear a 5-tetrazolyl group or certain 1- or 2-substituted 5-tetrazolyl groups at the 3-position of the penam nucleus.

2. Description of the Prior Art

In spite of the large number of penam derivatives which have been proposed for use as antibacterial agents, there still exists a need for new agents.

U.S. Pat. Nos. 3,427,302 and 3,468,874 disclose penam derivatives which incorporate a tetrazolyl group as part of the 6-acylamino substituent; however, the compounds of the instant invention are unique in having a tetrazolyl group bonded directly to the penam nucleus.

The vast majority of penam compounds disclosed in the prior art have a carboxylic acid group (or a salt thereof) attached to the 3-position. However, penam compounds with other carboxylic acid derivatives at the C-3 locus are also known. Penam-3-carboxylic acid esters have been disclosed, for example, by Kirchner et al., *Journal of Organic Chemistry,* 14, 388 (1949); Carpenter, *Journal of the American Chemical Society,* 70, 2964 (1948); Johnson, *Journal of the American Chemical Society,* 75, 3636 (1953); Barnden et al., *Journal of the Chemical Society* (London), 3733 (1953) and Jansen and Russell, *Journal of the Chemical Society* (London), 2127 (1965); and penam-3-carboxamides have been reported, for example, by Holysz and Stavely, *Journal of the American Chemical Society,* 72, 4760 (1950), Huang et al., Antimicrobial Agents and Chemotherapy, 493 (1963) and U.S. Pat. No. 3,641,000. Peron et al. (*Journal of Medicinal Chemistry,* 7, 483 [1964]) prepared several 6-(substituted amino)-2,2-dimethyl-penam-3-caroboxylic acid azides, which were subsequently converted into the corresponding 3-isocyanates and 3-benzylcarbamates. Peron et al. (loc. cit.) also reported certain 3-(hydroxymethyl)penam derivatives. Dehydration of the simple amide of benzylpenicillin yields the corresponding nitrile (Khokhlov et al., *Doklady Akad. Sci. Nauk S.S.S.R.,* 135, 875 [1960]).

SUMMARY OF THE INVENTION

It is an object of the instant invention to provide novel 6-acylaminopenam compounds, which are valuable either as new antibacterial agents or as intermediates for the preparation of new antibacterial agents. The said novel penam compounds are those of formulae

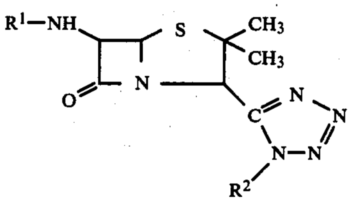
I

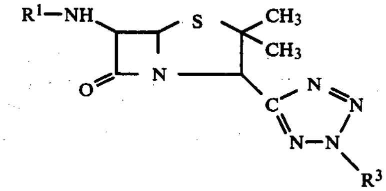
II and the salts thereof;

wherein $R^1$ is an acyl moiety of an organic carboxylic acid;

$R^2$ is selected from the group consisting of hydrogen, trialkylsilyl having from one to four carbon atoms in each of said alkyl groups, alkanoyloxymethyl having from three to eight carbon atoms, 1-(alkanoyloxy)ethyl having from four to nine carbon atoms, 3-phthalidyl and a tetrazolylpenam nitrogen protecting group, the nature of which is to be defined hereinafter;

and $R^3$ is selected from the group consisting of hydrogen, trialkylsilyl having from one to four carbon atoms in each of the said alkyl groups, alkanoyloxymethyl having from three to eight carbon atoms, 1-(alkanoyloxy)ethyl having from four to nine carbon atoms and 3-phthalidyl.

The novel penam compounds which are useful an antibacterial agents are those compounds of formulae I and II wherein $R^1$ is an acyl group and $R^2$ and $R^3$ are each selected from the group consisting of hydrogen, the said alkanoyloxymethyl, the said 1-(alkanoyloxy)ethyl and 3-phthalidyl. Particularly desirable penam compounds of the present invention, by virtue of their high activity against a wide range of pathogenic bacteria, are those compounds of formulae I and II, wherein $R^2$ and $R^3$ are each hydrogen and $R^1$ is mono- or disubstituted acetyl group, such as, for example, 2-arylacetyl, 2-amino-2-arylacetyl and 2-(substituted amino)-2-arylacetyl. The compounds of formulae I and II, wherein $R^1$ is an acyl group, $R^2$ is selected from the group consisting of trialkylsilyl having from one or four carbon atoms in each of said alkyl groups and a tetrazolylpenam nitrogen protecting group, and $R^3$ is trialkylsilyl having from one to four carbon atoms, are useful as intermediates for the preparation of the antibacterial agents of this invention.

It is a further object of this invention to provide novel penam compounds which are useful as intermediates for the preparation of the compounds of formulae I and II. These novel intermediates are those of formulae:

III

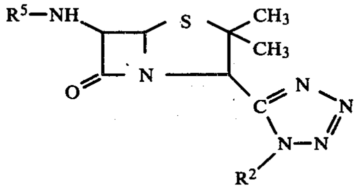

IV

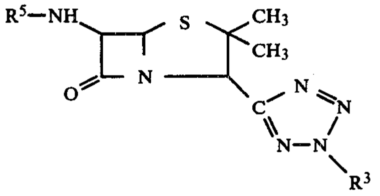

and the salts thereof;

wherein $R^5$ is selected from the group consisting of hydrogen, trialkylsilyl having from one to four carbon atoms in each of the said alkyl groups and an amino protecting group, the nature of which is to be defined hereinafter and $R^2$ and $R^3$ are as previously defined.

The compounds of formulae III and IV, wherein $R^2$, $R^3$ and $R^5$ are each selected from the group consisting of hydrogen and trialkylsilyl having from one to four carbon atoms in each of said alkyl groups are especially valuable for the preparation of the novel penam compounds of formulae I and II.

In this context, the term "amino protecting group" is intended to contemplate all protecting groups known, or obvious, to one with ordinary skill in the art, which will (a) permit synthesis of a compound of formula III wherein $R^5$ is the said amino protecting group and $R^2$ is a tetrazolylpenam nitrogen protecting group; and (b) can be removed either from a compound of formula III, wherein $R^5$ is the said amino protecting group and $R^2$ is a tetrazolylpenum nitrogen protecting group, or from a compound of formula III, wherein $R^5$ is the said amino protecting group and $R^2$ is hydrogen, using conditions wherein the penam ring system remains substantially intact. Thus, when $R^5$ is an amino protecting group, it can represent any group which will effectively protect the 6-amino moiety of 6-aminopenicillanic acid, during the process to be described in detail later in this specification, for the conversion of 6-(protected amino)-penicillanic acid into the said compounds of formula III, and is removable under conditions which do not destroy the $\beta$-lactam ring system. All such groups are to be considered within the scope of this invention, since the importance of the amino protecting group resides in its ability to perform in the above-described manner. Identification and selection of individual groups which can be used will be readily accomplished by one skilled in the art, and the nature of the group chosen does not affect the novelty of the antibacterial agents of this invention in any way. Examples of several groups which can be used as amino protecting groups for the purposes of this invention are enumerated hereinafter.

In like manner, the term "tetrazolylpenam nitrogen protecting group" is intended to connote all groups known, or obvious, to one skilled in the art, which can be used (a) to permit the synthesis of a compound of formula III, wherein $R^5$ is an amino protecting group and $R^2$ is the said tetrazolylpenam nitrogen protecting group, by the process starting with 6-(protected amino)-penicillanic acid described hereinafter; and (b) can be removed from a compound of formula I, wherein $R^1$ is an acyl group and $R^2$ is the said tetrazolylpenam nitrogen protecting group, or from a compound of formula III, wherein $R^5$ is hydrogen and $R^2$ is the said tetrazolylpenam protecting group, or from a compound of formula III, wherein $R^5$ is an amino protecting group and $R^2$ is the said tetrazolylpenam nitrogen protecting group, using conditions wherein the penam ring system remains substantially intact. The tetrazolylpenam nitrogen protecting group is required in order to protect the nitrogen atom which ultimately becomes N-1 of the tetrazole ring in the said compounds of formulae I and III, during the conversion of a 6-(protected amino)-penicillanic acid into a compound of formula III. It is likewise the ability of the tetrazolylpenam nitrogen protecting group to perform a specific function, to be discussed in more detail hereinafter, rather than its precise chemical structure, which is important; and the novelty of the antibacterial agents of the invention does not depend upon the structure of the protecting group. Selection and identification of appropriate protecting groups can be made readily and easily by one skilled in the art, and examples of several applicable groups are given hereinafter.

A still further object of this invention is to provide a process for the production of a compound of formula I and II, which comprises acylating a compound of formula III or IV, wherein $R^5$ is selected from the group consisting of hydrogen and trialkylsilyl having from one to four carbon atoms in each of said alkyl groups, and $R^2$ and $R^3$ are as previously defined.

Yet another object of this invention is to provide a process for the intermediates of formula III, wherein $R^5$ is an amino protecting group and $R^2$ is a tetrazolylpenam nitrogen protecting group, which comprises the novel sequence of: (a) converting a 6-(protected amino)-penicillanic acid into an amide of formula

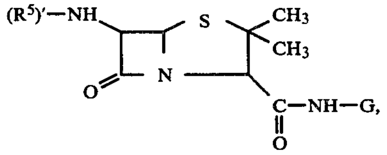

(b) contacting the said amide with an imidoyl halide forming agent, in the presence of a tertiary amine; and (c) contacting the so-produced imidoyl halide with a source of azide ion; wherein $(R^5)'$ is an amino protecting group and G is a tetrazolylpenam nitrogen protecting group or a group which is readily convertible to a tetrazolylpenam nitrogen protecting group during or after the instant process.

The novel intermediates so produced are used to prepare the penam compounds of formulae I and II by methods to be discussed in detail hereinafter.

A further additional object of this invention is to provide a method for the treatment and prevention of infectious diseases caused by gram-positive and gram-negative bacteria; for the topical control of bacteria on human tissue, hospital surfaces and the like; and for the supplementation of animal feeds; which comprises utilizing an effective amount of compound of formula I or II, or a salt thereof, wherein $R^1$ is an acyl group and $R^2$ and $R^3$ are each selected from the group consisting of hydrogen, alkanoyloxymethyl having from three to eight carbon atoms, 1-(alkanoyloxy)ethyl having from four to nine carbon atoms and 3-phthalidyl.

Several other aspects of the invention will become apparent from the discussion which follows.

DETAILED DESCRIPTION OF THE INVENTION

This invention relates to certain novel compositions of matter, which are valuable as antibacterial agents, and as intermediates for the preparation of antibacterial agents. For the sake of convenience these compounds are identified as derivatives of "penam", which has been defined by Sheehan et al., in the *Journal of the American Chemical Society*, 75, 3293 (1953), as referring to the structure:

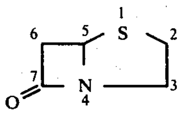

Although the term penam does not normally carry any stereochemical implications, the stereochemistry of the penam compounds of the instant invention corresponds to that found in the naturally-occurring penicillins. Using this terminology, the well-known antibiotic penicillin G (benzylpenicillin) is designated as 6-(2-phenylacetamido)-2,2-dimethylpenam-3-carboxylic acid.

Many of the compounds of this invention are also 5-substituted tetrazoles, and 5-substituted tetrazoles can exist in two isomeric forms, viz:

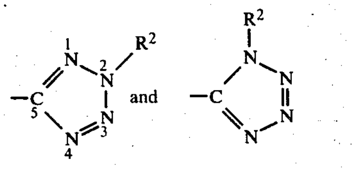

As will be appreciated by one skilled in the art, when the substituent $R^2$ is hydrogen, the two forms co-exist in a dynamic, tautomeric, equilibrium mixture. However, in the case where $R^2$ is a substituent other than hydrogen, the two forms represent different chemical entities, which do not spontaneously interconvert.

The new antibacterial agents of this invention are the compounds of formulae I and II, and the salts thereof, wherein $R^1$ is an acyl moiety of an organic carboxylic acid, and $R^2$ and $R^3$ are each selected from the group consisting of hydrogen, alkanoyloxymethyl having from three to eight carbon atoms, 1-(alkanoyloxy)ethyl having from four to nine carbon atoms and 3-phthalidyl. The possession of antibacterial properties by the said compounds of formulae I and II is not predicated upon the selection of the acyl substituent $R^1$. Indeed, any acyl moiety of any carboxylic acid can serve as $R^1$, and all the compounds of formulae I and II, wherein $R^2$ and $R^3$ are each selected from the group consisting of hydrogen, alkanoyloxymethyl having from three to eight carbon atoms, 1-(alkanoyloxy)ethyl having from four to nine carbon atoms and 3-phthalidyl, which bear an acyl group at $R^1$, have useful antibacterial properties. The carboxylic acid from which the acyl group is derived can be a mono- or polycarboxylic acid. Included within the scope of "acyl" are the acyl moieties of carboxylic acids which themselves cannot be isolated, but which nonetheless exist in the form of their esters, amides, acid chlorides, etc.

However, a particularly favorable configuration of the acyl moiety is:

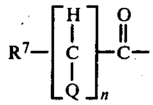

V wherein n is 0 or 1;

$R^7$ is selected from the group consisting of hydrogen, alkyl having from one to twelve carbon atoms, alkenyl having from two to twelve carbon atoms, cycloalkyl having from three to seven carbon atoms, cycloalkenyl having from five to eight carbon atoms, cycloheptatrienyl, 1,4-cyclohexadienyl, 1-aminocycloalkyl having from four to seven carbon atoms, cyanomethyl, 5-methyl-3-phenyl-4-isoxazolyl, 5-methyl-3-(o-chlorophenyl)-4-isoxazolyl, 5-methyl-3-(2,6-dichlorophenyl)-4-isoxazolyl, 5-methyl-3-(2-chloro-6-fluorophenyl)-4-isoxazolyl, 2-alkoxy-1-naphthyl having from one to four carbon atoms in said alkoxy, phenyl, phenoxy, phenylthio, pyridylthio, benzyl, sydnonyl, thienyl, furyl, pyridyl, thiazolyl, isothiazolyl, pyrimidinyl, tetrazolyl, triazolyl, imidazolyl, pyrazolyl, substituted phenyl, substituted phenoxy, substituted phenylthio, substituted pyridylthio, substituted benzyl, substituted thienyl, substituted furyl, substituted pyridyl, substituted tetrazolyl, substituted thiazolyl, substituted isothiazolyl, substituted pyrimidinyl, substituted triazolyl, substituted imidazolyl and substituted pyrazolyl, each substituted moiety being substituted by up to two members selected from the group consisting of fluoro, chloro, bromo, hydroxy, hydroxymethyl, amino, N,N-dialkylamino having from one to four carbon atoms in each of said alkyl groups, alkyl having from one to four carbon atoms, aminomethyl, aminoethyl, alkoxy having from one to four carbon atoms, alkylthio having from one to four carbon atoms, 2-aminoethoxy and N-alkylamino having from one to four carbon atoms;

and Q is selected from the group consisting of hydrogen, alkyl having from one to six carbon atoms, hydroxy, azido, carboxy, sulfo, carbamoyl, phenoxycarbonyl, indanyloxycarbonyl, sulfoamino, aminomethyl, amino and $NH-(CO-CH_2-NH)_m-CO-Z$;

wherein Z is selected from the group consisting of alkyl having from one to six carbon atoms, phenyl, substituted phenyl, furyl, thienyl, pyridyl pyrrolyl, amino, N-alkylamino having from one to six carbon atoms, anilino, substituted anilino, guanidino, alkanoylamino having from two to seven carbon atoms, benzamido, substituted benzamido, thiophenecarboxamido, furancarboxamido, pyridinecarboxamide, aminomethyl, guanidinomethyl, alkanecarboxamidinomethyl having from three to eight carbon atoms, benzamidinomethyl, (substituted benzamidino)-methyl, thiophenecarboxyamidinomethyl, furancarboxamidinomethyl, pyridinecarboxamidinomethyl, pyrrolecarboxamidinomethyl and 2-benzimidazolecarboxamidinomethyl, each substituted moiety being substituted by up to two members selected from the group consisting of fluoro, chloro, bromo, iodo, alkyl having from one to four carbon atoms, alkoxy having from one to four carbon atoms, sulfamyl, carbamoyl and cyano;

and m is 0 or 1;

provided that when $R^7$ is 1-aminocycloalkyl, n is 0;

and provided that when $R^7$ is selected from the group consisting of phenoxy, phenylthio, pyridylthio, substituted phenoxy, substituted phenylthio and substituted pyridylthio and n is 1, Q is selected from the group consisting of hydrogen, alkyl having from one to six carbon atoms, carboxy, sulfo, carbamoyl, phenoxycarbonyl, substituted phenoxycarbonyl, indanyloxycarbonyl and aminomethyl.

Typical examples of the acyl group $R^1$ are:

2,6-dichlorobenzoyl,
2,6-dimethoxybenzoyl,
2-methoxy-1-naphthoyl,
2-ethoxy-1-naphthoyl,
2-cyanoacetyl,
2-(5-tetrazolyl)acetyl,
5-methyl-3-phenyl-4-isoxazolylcarbonyl,
5-methyl-3-(o-chlorophenyl)-4-isoxazolylcarbonyl,
5-methyl-3-(2,6-dichlorophenyl)-4-isoxazolylcarbonyl,
5-methyl-3-(2-chloro-6-fluorophenyl)-4-isoxazolylcarbonyl,
1-aminocyclobutylcarbonyl,
1-aminocyclopentylcarbonyl,
1-aminocyclohexylcarbonyl,
2-phenylacetyl,
2-(2-thienyl)acetyl,
2-(3-thienyl)acetyl,
2-(2-furyl)acetyl,
2-(3-furyl)acetyl,
2-(4-pyridyl)acetyl,
2-(1-tetrazolyl)acetyl,
2-phenoxyacetyl,
2-(phenylthio)acetyl,
2-(2-pyridylthio)acetyl,
2-amino-2-phenylacetyl,
2-amino-2-(p-hydroxyphenyl)acetyl,
2-amino-2-(p-chlorophenyl)acetyl,
2-amino-2-(m-methoxyphenyl)acetyl,
2-amino-2-(2-thienyl)acetyl,
2-amino-2-(3-thienyl)acetyl,
2-amino-2-(2-furyl)acetyl,
2-amino-2-(3-furyl)acetyl,
2-amino-2-(1,4-cyclohexadienyl)acetyl,
2-hydroxy-2-phenylacetyl,
2-hydroxy-2-(3-thienyl)acetyl,
2-hydroxy-2-(3-furyl)acetyl,
2-hydroxy-2-(1,4-cyclohexadienyl)acetyl,
2-carboxy-2-phenylacetyl,
2-carboxy-2-(3-thienyl)acetyl,
2-carboxy-2-(2-furyl)acetyl,
2-carboxy-2-(1,4-cyclohexadienyl)acetyl,
2-sulfo-2-phenylacetyl,
2-sulfo-2-(2-thienyl)acetyl,
2-sulfo-2-(3-furyl)acetyl,
2-sulfo-2-(1,4-cyclohexadienyl)acetyl,
2-(2-aminoacetamido)-2-phenylacetyl,
2-(4-pyridylthio)acetyl,
2-azido-2-phenylacetyl,
3-amino-2-phenylpropionyl,
2-(m-chlorophenyl)acetyl,
4-methyl-1-(2,6-dichlorophenyl)-5-pyrazolylcarbonyl,
2-(sulfoamino)-2-phenylacetyl,
2-(3-[2-furoyl]ureido)-2-phenylacetyl,
2(3-benzoylureido)-2-phenylacetyl,
2-guanylureido-2-phenylacetyl,
2-guanylureido-2-(3-thienyl)acetyl,
2-(2-guanidinoacetamido)-2-phenylacetyl,
2-(2-guanidinoacetamido)-2-(p-hydroxyphenyl)acetyl,
2-(2-benzamidinoacetamido)-2-phenylacetyl,
2-(2-[3,5-dichlorobenzamidino]acetamido)-2-phenylacetyl,
2-(2-benzamidinoacetamido)-2-(p-hydroxyphenyl)acetyl,
2-(2-[4-pyridinecarboxamidino]acetamido)-2-phenylacetyl,
2-(2-[2-furancarboxamidino]acetamido)-2-(3-thienyl)acetyl and
2-(2-[3-(guanyl)ureido]acetamido)-2-(4-hydroxyphenyl) acetyl.

2-(2-[4-Pyridinecarboxamidino]acetamido)-2-phenylacetyl can also be named 2-(2-[2-(4-pyridyl)-1-formamidino]acetamido)-2-phenylacetyl, and refers to the structure:

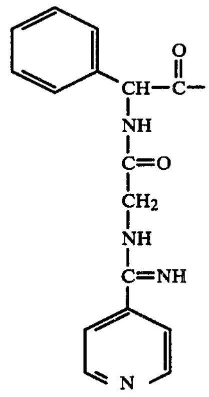

A preferred group of antibacterial agents of the present invention consists of the compounds of formulae I and II, wherein $R^2$ and $R^3$ are each hydrogen and $R^1$ is of formula V, wherein n is 1 and $R^7$ is selected from the group consisting of phenyl, phenoxy, the said substituted phenyl and the said substituted phenoxy. Within this preferred group, especially valuable subgroups are:

(1) compounds of formulae I and II, wherein $R^2$ and $R^3$ are each hydrogen and $R^1$ is of formula V, wherein n is 1, $R^7$ is selected from the group consisting of phenyl, phenoxy, said substituted phenyl and said substituted phenoxy and Q is hydrogen;

(2) compounds of formula I and II, wherein $R^2$ and $R^3$ are each hydrogen and $R^1$ is of formula V, wherein n is 1, $R^7$ is selected from the group consisting of phenyl and said substituted phenyl and Q is amino;

(3) compounds of formulae I and II, wherein $R^2$ and $R^3$ are each hydrogen and $R^1$ is of formulae V, wherein n is 1, $R^7$ is selected from the group consisting of phenyl and the said substituted phenyl and Q is NH—(-CO—$CH_2$—NH)$_m$—CO—Z, wherein m is O and Z is selected from the group consisting of benzamido, said substituted benzamido, thiophenecarboxamido, furancarboxamido and pyridinecarboxamido;

(4) compounds of formulae I and II, wherein $R^2$ and $R^3$ are each hydrogen and $R^1$ is of formula V, wherein n is 1, $R^7$ is selected from the group consisting of phenyl and the said substituted phenyl and Q is NH—(-CO—$CH_2$—NH)$_m$—CO—Z, wherein m is O and Z is aminomethyl;

(5) compounds of formulae I and II, wherein $R^2$ and $R^3$ are each hydrogen and $R^1$ is of formula V, wherein n is 1, $R^7$ is selected from the group consisting of phenyl and the said substituted phenyl and Q is NH—(-CO—$CH_2$—NH)$_m$—CO—Z, wherein m is O and Z is selected from the group consisting of benzamidinomethyl, said substituted benzamidinomethyl, thiophene-carboxamidinomethyl, pyridine-carboxamidinomethyl, 2-benzimidazolecarboxamidinomethyl and pyrrolecarboxamidinomethy; and (6) compounds of formulae I and II, wherein $R^2$ and $R^3$ are each hydrogen and $R^1$ is of formula V, wherein n is 1, $R^7$ is selected from the group consisting of phenyl and the said substituted phenyl and Q is NH—(-CO—$CH_2$—NH)$_m$—CO—Z, wherein Z is guanidino.

A second preferred group of antibacterial agents of this invention consists of the compounds of formulae I and II, wherein $R^2$ and $R^3$ are each hydrogen and $R^1$ is of formula V, wherein n is 1 and $R^7$ is selected from the group consisting of sydnonyl, thienyl, furyl, pyridyl, thiazolyl, isothiazolyl, pyrimidinyl, tetrazolyl, triazolyl, imidazolyl and pyrazolyl, each of which can be substituted as indicated hereinbefore. Within this second preferred group, especially valuable sub-groups are:

(1) the said compounds of formulae I and II, wherein Q is hydrogen;

(2) the said compounds of formulae I and II, wherein Q is amino;

(3) the said compounds of formulae I and II, wherein Q is NH—(CO—$CH_2$—NH)$_m$—CO—Z, wherein m is O and Z is selected from the group consisting of benzamido, the said substituted benzamido, thiophenecarboxamido, furancarboxamido and pyridinecarboxamido;

(4) the said compounds of formulae I and II, wherein Q is NH—(CO—$CH_2$—NH)$_m$—CO—Z, wherein m is O and Z is aminomethyl;

(5) the said compounds of formulae I and II, wherein Q is NH—(CO—$CH_2$—NH)$_m$—CO—Z, wherein Z is guanidino; and (6) the said compounds of formulae I and II, wherein Q is NH—(CO—$CH_2$—NH)$_m$—CO—Z, wherein m is O and Z is selected from the group consisting of benzamidinomethyl, said substituted benzamidinomethyl, thiophenecarboxamidinomethyl, pyridinecarboxamidinomethyl, 2-benzimidazolecarboxamidinomethyl and pyrrolecarboxamidinomethyl.

When $R^7$ is an aromatic carbocyclic group, especially preferred groups are phenyl and 4-hydroxyphenyl; when $R^7$ is a heteroaryl group, particularly preferred groups are thienyl and furyl.

Individual compounds of the instant invention which are extremely valuable are:

6-(2-phenylacetamido)-2,2-dimethyl-3-(5-tetrazolyl)penam, 6-(2-phenoxyacetamido)-2,2-dimethyl-3-(5-tetrazolyl)penam, 6-(D-2-amino-2-phenylacetamido)-2,2-dimethyl-3-(5-tetrazolyl)penam, 6-(D-2-amino-2-[p-hydroxyphenyl]acetamido)-2,2-dimethyl-3-(5-tetrazolyl)penam, 6-(D-2-amino-2-[3-chloro-4-hydroxyphenyl]acetamido)-2,2-dimethyl-3-(5-tetrazolyl)penam, 6-(D-2-amino-2-[2-thienyl]acetamido)-2,2-dimethyl-3-(5-tetrazolyl)penam, 6-(D-2-amino-2-[3-thienyl]acetamido)-2,2-dimethyl-3-(5-tetrazolyl)penam, 6-(D-2-[2-(4-pyridinecarboxamidino)acetamido]-2-[4-hydroxyphenyl]acetamido)-2,2-dimethyl-3-(5-tetrazolyl)penam, 6-(D-2-[3-(guanyl)ureido]-2-[4-hydroxyphenyl]acetamido)-2,2-dimethyl-3-(5-tetrazolyl)penam, 6-(D-2-[2-(2-pyrrolecarboxamidino)acetamido]-2-[4-hydroxyphenyl]acetamido)-2,2-dimethyl-3-(5-tetrazolyl)penam, 6-(D-2-[2-aminoacetamido]-2-phenylacetamido)-2,2-dimethyl-3-(5-tetrazolyl)penam, 6-(D-2-[2-aminoacetamido]-2-[4-hydroxyphenyl]acetamido)-2,2-dimethyl-3-(5-tetrazolyl)penam, 6-(D-2-[2-aminoacetamido]-2-[2-thienyl]acetamido)-2,2-dimethyl-3-(5-tetrazolyl)penam, 6-(D-2-[2-aminoacetamido]-2-[3-thienyl]acetamido)-2,2-dimethyl-3-(5-tetrazolyl)penam, 6-(2-[2-(aminomethyl)phenyl]acetamido)-2,2-dimethyl-3-(5-tetrazolyl)penam, 6-(D-2-[2-(4-pyridinecarboxamidino)acetamido]-2-phenylacetamido)-2,2-dimethyl-3-(5-tetrazolyl)penam 6-(D-2-[2-(3-[guanyl]ureido)acetamido]-2-[4-hydroxyphenyl]acetamido)-2,2-dimethyl-3-(5-tetrazolyl)penam, and 6-(2-[2-(aminomethyl)phenyl]acetamido)-2,2-dimethyl-3-(1-pivaloyloxymethyltetrazol-5-yl)penam.

As will be recognized by one skilled in the art, the acyl group $R^1$ can contain one or more asymmetric centers, and asymmetric centers can exist in one or two forms, the so-called R- and S-forms. Both forms of each asymmetric center, and all combinations of each of the forms, are to be considered within the scope and purview of this invention.

SCHEME I
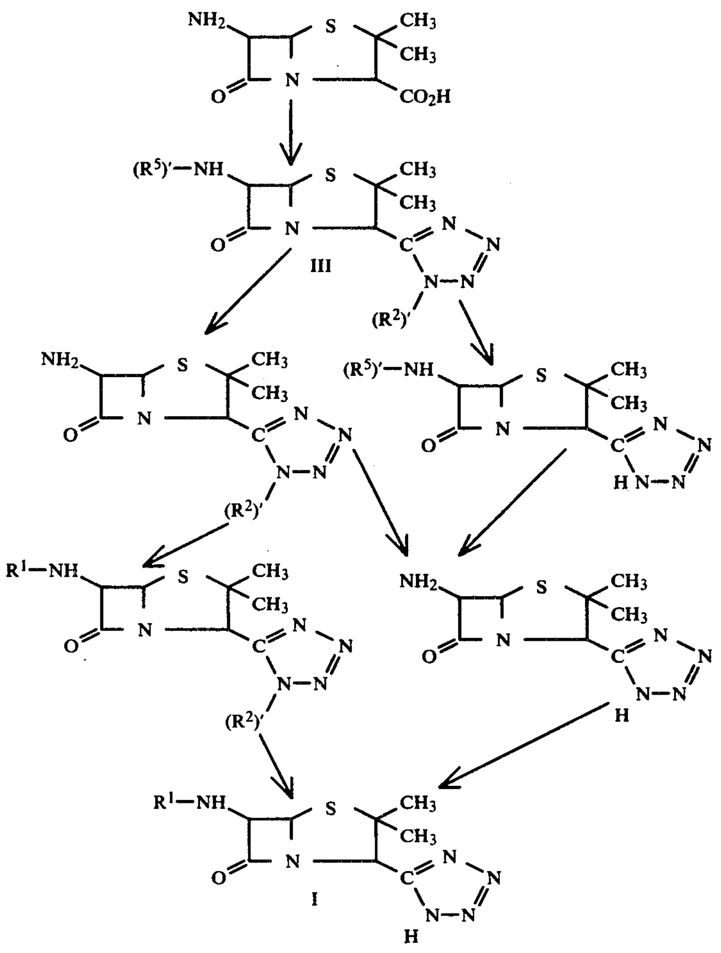
III
I
$R^1$ is an acyl group.
$(R^2)'$ is a tetrazolylpenam nitrogen protecting group.
$(R^5)'$ is an amino protecting group.

SCHEME II

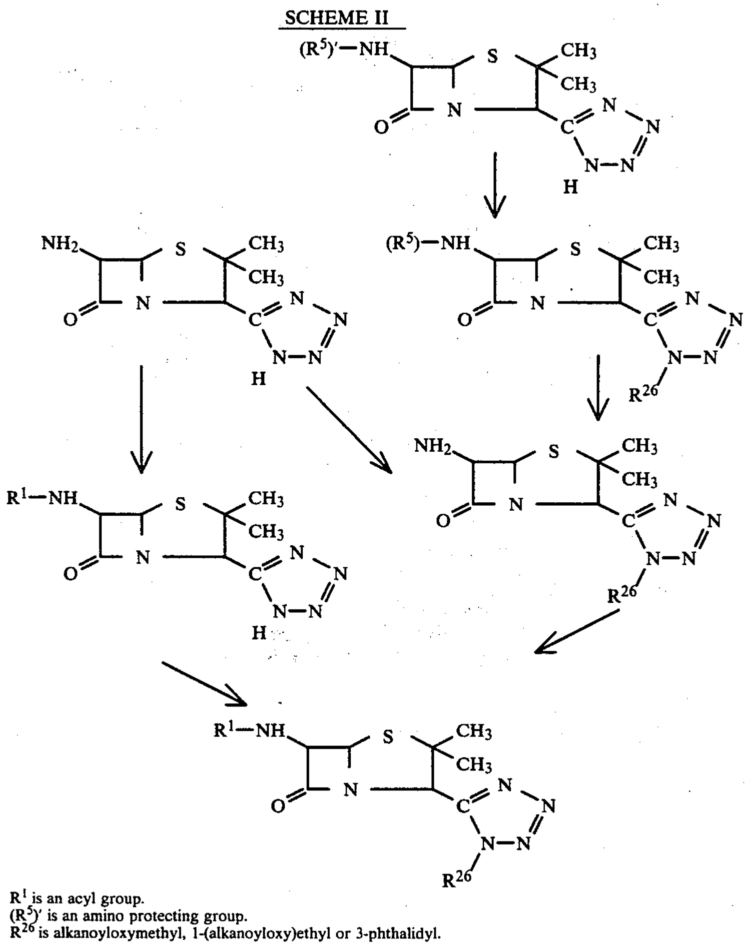

$R^1$ is an acyl group.
$(R^5)'$ is an amino protecting group.
$R^{26}$ is alkanoyloxymethyl, 1-(alkanoyloxy)ethyl or 3-phthalidyl.

When contemplating methods to be used for the synthesis of the antibacterial agents of this invention of formulae I and II, wherein $R^1$ is an acyl group $R^2$ and $R^3$ are each hydrogen, they can be prepared starting from the well-known intermediate 6-aminopenicillanic acid (6-APA), and several of the ways in which this can be accomplished are outlined diagrammatically in Scheme I. Ways in which the antibacterial agents of formulae I and II, wherein $R^1$ is an acyl group and $R^2$ and $R^3$ are each selected from the group consisting of alkanoyloxymethyl, 1-(alkanoyloxy)ethyl and phthalidyl, are prepared, are outlined in Scheme II. However, in Scheme II, for the sake of simplicity, the substituent $R^{26}$ has been shown only at N-1 of the tetrazole ring. However, as explained hereinafter, alkylation of a 5-monosubstituted tetrazole results in a mixture of mono-alkylated products, in which the newly-introduced group is located at either N-1 or N-2 of the tetrazole ring.

From a consideration of Scheme I, the manner in which the compounds of formulae I and III, wherein $R^2$ is a tetrazolylpenam nitrogen protecting group, are useful as intermediates for antibacterial agents of the invention will be apparent. When considering the nature of the said tetrazolylpenam nitrogen protecting group, the group must fulfill two functions. First, it must permit the synthesis of compounds of formula III, wherein $R^5$ is an amino protecting group and $R^2$ is the said tetrazolylpenam nitrogen protecting group. Second it must be removable from a compound of formula I, wherein $R^1$ is an acyl group and $R^2$ is the tetrazolylpenam nitrogen protecting group; or from a compound of formula III, wherein $R^5$ is hydrogen and $R^2$ is the tetrazolylpenam nitrogen protecting group; or from a compound of formula III, wherein $R^5$ is an amino protecting group and $R^2$ is the tetrazolylpenam protecting group, in each case under conditions wherein the penam ring system remains intact. As will be apparent from the discussion which follows, not all the tetrazolylpenam nitrogen protecting groups useful in this invention need be removable from each of the said compounds of formulae I and III. In order to be useful in this invention, the tetrazolylpenam nitrogen protecting group needs to be removable from at least one of the following three types of compounds: (a) compounds of formula I, wherein $R^1$ is acyl and $R^2$ is the said tetrazolylpenam nitrogen protecting group; (b) compounds of formula III, wherein $R^5$ is hydrogen and $R^2$ is the tetrazolylpenam nitrogen protecting group; or (c) compounds of formula III, wherein $R^5$ is an amino protecting group and $R^2$ is the tetrazolylpenam nitrogen protecting group. The conditions which it will be necessary to use for removal of a given tetrazolylpenam nitrogen protecting group will be known, or obvious, to one skilled in the art. Moreover, the reaction conditions which can be used without causing decomposition of the penam ring system are also well-known, and obvious, by reference to the prior art on penam compounds.

An example of a typical tetrazolylpenam nitrogen protecting group is

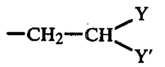

wherein Y is an electron-withdrawing group, and Y' is either hydrogen or a further electron-withdrawing group, which can be the same as or different from Y. The function of the electron-withdrawing group is to render a hydrogen atom, on the carbon atom to which Y and Y' are attached, sufficiently acidic that the group is removable in a retrograde Michael reaction. Such a reaction is well-known in the art. For example consult House, "Modern Synthetic Reactions," W. A. Benjamin, Inc., New York/Amsterdam, 1965, page 207. Typical electron-withdrawing groups are cyano, alkoxycarbonyl having from two to seven carbon atoms, phenoxycarbonyl, alkylsulfonyl having from one to six carbon atoms, phenylsulfonyl and $SO_2$—$NR^{15}R^{16}$, wherein $R^{15}$ and $R^{16}$ are each selected from the group consisting of hydrogen, alkyl having from one to four carbon atoms, phenyl and benzyl. A particularly convenient configuration for this protecting group is that wherein Y' is hydrogen; and preferred values for Y are alkoxycarbonyl having from two to seven carbon atoms and phenylsulfonyl.

A further tetrazolylpenam nitrogen protecting group which can be used is a grouping of formula —C(=O)—O—$R^{14}$. Such a grouping can be removed by mild hydrolysis, such as mild alkaline hydrolysis, or by treatment with a nucleophile, such as a primary or secondary amine, or a thiolate anion. A wide variety of groups can serve as $R^{14}$, but particularly convenient groups are alkyl having from one to six carbon atoms, benzyl, phenyl and substituted phenyl, for example, phenyl substituted by up to two moieties each selected from the group consisting of nitro, fluoro, chloro, bromo, alkyl having from one to four carbon atoms and alkoxy having from one to four carbon atoms.

A still further tetrazolylpenam nitrogen protecting group which can be used is a grouping of formula —$SO_2$—$R^{14}$. Such a group is also removed by hydrolysis, or by treatment with a nucleophilic agent, as indicated for the group C(=O)—O—$R^{14}$ and convenient values for $R^{14}$ are also alkyl having from one to six carbon atoms, benzyl, phenyl and substituted phenyl, for example, phenyl substituted by up to two moieties each selected from the group consisting of nitro, fluoro, chloro, bromo, alkyl having from one to four carbon atoms and alkoxy having from one to four carbon atoms.

A yet further tetrazolylpenam nitrogen protecting group which can be used is:

$$—CH_2—W$$

wherein W is phenyl, substituted phenyl, furyl, substituted furyl, thienyl or substituted thienyl. When W is phenyl or substituted phenyl, this group can be removed by hydrogenolysis. This group can also be removed by solvolysis in trifluoroacetic acid, when the effect of W is sufficient to offer the requisite degree of stability to the incipient carbonium ion:

$$CH_2^+—W$$

Particularly convenient configurations for this protecting group are:

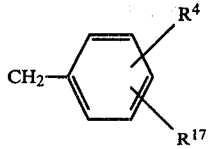
and
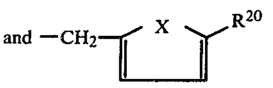

wherein $R^4$ is at the 3-, 4- or 5-position and it is selected from the group consisting of hydrogen, hydroxy, fluoro, chloro, bromo, iodo, alkyl having from one to six carbon atoms, alkoxy having from one to six carbon atoms, phenyl and benzyloxy;

$R^{17}$ is selected from the group consisting of hydrogen, hydroxy, fluoro, chloro, unbranched-alkyl having from one to six carbon atoms and unbranched-alkoxy having from one to six carbon atoms;

$R^{20}$ is selected from the group consisting of hydrogen and methyl;

and X is selected from the group consisting of oxygen and sulfur.

As will be recognized by one skilled in the art, other groups which will also stabilize the carbonium ion $(W—CH_2)+$ can replace those cited above for W.

Still another tetrazolylpenam nitrogen protecting group which can be used is phenacyl or substituted phenacyl. Such a group is removed by reaction with a nucleophilic reagent, such as thiophenoxide. Typical phenacyl groups which can be used are those of formula

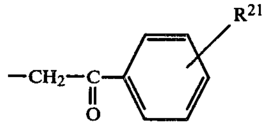

wherein $R^{21}$ is selected from the group consisting of hydrogen, nitro, fluoro, chloro, bromo and phenyl.

Several individual methods for the preparation of the antibacterial agents of this invention are now to be discussed and described in detail. For convenience, they will be designated as Methods A, B, C, D, E and F.

Method A is useful for the synthesis of compounds of formulae I and II, wherein $R^1$ is an acyl group and $R^2$ and $R^3$ are each hydrogen. The method comprises catalytic hydrogenolysis of a compound of formula I, wherein $R^1$ is an acyl group and $R^2$ is

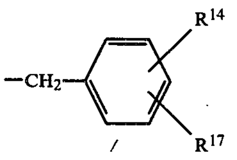

wherein $R^4$ and $R^{17}$ are as previously defined. As will be appreciated by one skilled in the art, conditions must be chosen which do not destroy the β-lactam moiety of the penam nucleus. A particularly convenient procedure comprises shaking or stirring a solution of the reactant in a reaction-inert solvent, such as methanol, ethanol, ethyl acetate or water, or mixtures of these solvents, in the presence of a catalyst, such as 10% palladium-on-carbon, under an atmosphere of hydrogen. When hydrogenation is complete, the catalyst is filtered off, and the product is recovered by solvent evaporation. The catalyst is normally present in an amount from about 10% to about 100% by weight based on the penam starting material, and the hydrogen pressure can vary from about one to about one hundred atmospheres. At or around ambient temperature, the reaction takes a few hours to reach completion.

Method B is useful for preparing compounds of formulae I and II, wherein $R^1$ is an acyl group, and $R^2$ and $R^3$ are each hydrogen. The method comprises treating a compound of formula I, wherein $R^1$ is an acyl group, and $R^2$ is

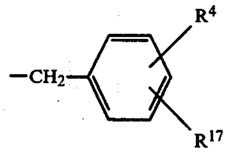

wherein $R^4$ and $R^{17}$ are as previously defined, and wherein at least one of $R^4$ and $R^{17}$ is a hydroxy group at the 2- or the 4-position, with an alkali or alkaline earth metal hydroxide, such as sodium, potassium or barium hydroxide. The reaction is carried out by dissolving the starting material in an appropriate solvent, and then adding at least about one molar equivalent of the hydroxide, at about ambient temperature or slightly below. The reaction is usually complete within about one hour, and in some cases the salt of the product corresponding to the base used precipitates, and it can then be filtered off. In other cases where the product does not precipitate, it can be recovered by solvent evaporation. If desired, it can then be purified by well-known methods such as crystallization, solvent extractions or chromatography. Appropriate solvents for this process are those which will serve to dissolve the starting material, but will not adversely interact with either the starting penam, the product or the particular base chosen. Examples of solvents which find utility are lower-alkanols, such as methanol or ethanol, and water. It appears that the primary function of the basic agent is to remove the hydrogen from the phenolic hydroxy group of the hydroxybenzyl protecting group.

Method C is useful for the preparation of compounds of formulae I and II, wherein $R^1$ is an acyl group and $R^2$ and $R^3$ are each selected from the group consisting of hydrogen, alkanoyloxymethyl having from three to eight carbon atoms, 1-(alkanoyloxy)ethyl having from four to nine carbon atoms and 3-phthalidyl. Broadly, this method comprises acylation of a compound of formula III or IV, or a salt thereof, wherein $R^5$ is selected from the group consisting of hydrogen and trialkylsilyl having from one to four carbon atoms in each of said alkyl groups, and $R^2$ or $R^3$ is selected from the group consisting of hydrogen, alkanoyloxymethyl, 1-(alkanoyloxy)ethyl, phthalidyl and trialkylsilyl having from one to four carbon atoms in each of said alkyl groups, followed, if necessary, by treatment with a protic solvent. The latter treatment is necessary when either $R^2$, $R^3$ or $R^5$ is trialkylsilyl. The acylation is carried out by contacting the said compound of formula III or IV, or a salt thereof, with an activated derivative of the appropriate carboxylic acid, in an appropriate solvent system. An activated derivative commonly used is an acid halide, such as an acid chloride. In a typical acylation procedure, approximately one molar equivalent of an acid chloride is added to a solution of the said compound of formula III or IV, or a salt thereof, dissolved in a solvent such as a chlorinated hydrocarbon, for example, chloroform or methylene chloride; an ether, for example, tetrahydrofuran or 1,2-dimethoxyethane; an ester, for example, ethyl acetate or butyl acetate; a lower aliphatic ketone, for example, acetone or methyl ethyl ketone; or a tertiary amide, for example, N,N-dimethylformamide or N-methylpyrrolidone; at a temperature in the range from about −40° C. to about 30° C., and preferably from about −10° C. to about 10° C., optionally in the presence of about one molar equivalent of an acid-binder, e.g., triethylamine, pyridine or sodium bicarbonate. The reaction is complete within a short period, i.e., approximately one hour, and the product is isolated by techniques well known in the art, having full regard for the sensitive nature of the penam moiety of the product. For example, the reaction mixture is evaporated to dryness and a water-immiscible organic solvent and water are added. In those cases where the product precipitates, it is filtered off. If the product does not precipitate, then the pH of the aqueous phase is adjusted to an appropriate value and the phase containing the product is evaporated. The crude product thus obtained can be purified further if desired. When $R^2$ and $R^3$ are hydrogen, it is convenient to employ a tertiary amine salt, for example, the triethylamine salt, of the compound of formula III or IV. An alternate procedure useful for the acylation of a compound of formula III or IV, wherein $R^2$, $R^3$ and $R^5$ are each hydrogen, with acid halides involves the use of an aqueous solvent system. In this procedure, which approximates the Schotten-Baumann procedure, the acid halide is added to a solution of the starting material in water, or a mixture of water and another inert solvent, at, or slightly below, ambient temperature, with the pH of the solvent being maintained within the range from about 6.0 to about 9.0 before, during, and after the addition. At the end of the reaction, the product can often be induced to precipitate by adjustment of the pH. Alternatively, it can be extracted into a water-immiscible solvent, which is then evaporated to dryness.

Another activated derivative of the carboxylic acid with finds use in Method C is a mixed anhydride. In this case, a carboxylate salt of the appropriate carboxylic acid is treated with about one molar equivalent of a lower-alkyl chloroformate in a reaction-inert, aprotic organic solvent, at a temperature in the range from about −20° C. to about 20° C. and preferably at about 0° C. Appropriate salts for this process are alkali metal salts, such as sodium and potassium salts, and tertiary amine salts, such as triethylamine, tributylamine, N-ethylpiperidine, N,N-dimethylaniline, N-methylmorpholine and pyridine salts; and appropriate solvents are, for example chloroform, methylene chloride, acetonitrile, tetrahydrofuran dioxane and N,N-dimethylformamide. The mixed carboxylic-carbonic anhydride thus formed is usually used in situ to acrylate the said compound of formula III or IV. This is normally carried out by mixing solutions of the preformed mixed anhydride and the compound of formula III or IV. When $R^2$ and $R^3$ are hydrogen, it is particularly convenient to employ a tertiary amine salt, for example the triethylamine salt, of the compound of formula III or IV. The acylation is normally conducted at a temperature in the range from about −30° C. to about 20° C., and preferably at about −10° C., and it usually takes a few hours to reach completion. In most instances the mixed anhydride and the compound of formula III or IV are contacted substantially in a 1:1 molar ratio. The product is usually isolated by evaporating the reaction mixture to dryness, and then adding a water-immiscible organic solvent and water. By careful adjustment of the pH, the product sometimes precipitates. In other cases the phases are separated, and the product-containing phase is evaporated to dryness. The crude product so obtained can be purified further if desired.

Another variation of Method C, comprises conversion of the carboxylic acid to an active ester, followed by treatment with a compound of formula III or IV or a salt thereof. Active esters which can be used in this regard are, for example, phenyl esters, such as p-nitrophenyl and 2,4,5-trichlorophenyl esters, thiol esters, such as thiol phenyl and thiol methyl esters; and N-hydroxy esters, such as N-hydroxysuccinimide and N-hydroxyphthalimide esters. The esters are prepared by methods well established in the art, and the acylation is conveniently conducted by dissolving the active ester and the said compound of formula III or IV, or a salt thereof, in a dipolar aprotic solvent such as N,N-dimethylformamide, N,N-dimethylacetamide or N-methylpyrrolidone. The solution is stored at about ambient temperature for several hours, for example overnight, and then the product is isolated by standard methods. In some instances the product can be isolated very simply by causing it to precipitate by the addition of a non-solvent, such as diethyl ether or acetone. It is then filtered off, and it can be purified further if desired. In many cases the active ester used in this process can be replaced by the corresponding acid azide.

A still further variation of Method C which is useful for the acylation of compounds of formulae III and IV comprises contacting the said compound of formula III or IV with a carboxylic acid in the presence of certain agents known in the art for forming peptide bonds. Such agents include carbodiimides, for example, dicyclohexylcarbodiimide and 1-ethyl-3-(3-dimethylaminopropyl)carbodiimide, alkoxyacetylenes, for example methoxyacetylene and ethoxyacetylene, and N-ethoxycarbonyl-2-ethoxy-1,2-dihydroquinoline. The reaction is carried out in an appropriate solvent, i.e., one which will serve to dissolve the reactants, and does not adversely interact with the starting materials or the product, for example acetonitrile, N,N-dimethylformamide and N-methylpyrrolidone.

Implicit in the above description of Method C, is the observation that in a process for the acylation of a compound of formula III or IV, hydrogen substituents located at $R^2$, $R^3$ or $R^5$ can successfully be replaced by trialkylsilyl substituents. Said trialkylsilyl substituents are then removed, and replaced by hydrogen, at the end of the acylation, simply by brief exposure of the product to a protic solvent system, such as water or a lower-alkanol, for example methanol or ethanol. By virtue of the ready availability of the starting materials, the trimethylsilyl group is a preferred member. It can be introduced into the starting penam of formula III or IV by methods well known in the art, such as, for example, using trimethylchlorosilane or N-trimethylsilylacetamide, as discussed by Birkofer and Ritter in *Angewandte Chemie* (International Edition in English), 4, 417–418 and 426 (1965). Conditions must be chosen, however, which are compatible with the β-lactam group of the penam nucleus. Also operative in Method C are the silylated derivatives formed by interaction of the said compounds of formulae III and IV with dichlorodi(-lower-alkyl)silanes. The silylation step is carried out by methods known in the art (for example, German Pat. No. 1,933,187). After the acylation reaction, the silyl group is removed by treatment with a protic solvent, such as water or a lower-alkanol, for example methanol or ethanol.

Additionally, if desired, the tetrazole ring of a compound of formula III or IV, wherein $R^2$, $R^3$ and $R^5$ are each hydrogen, can be protected by various other groups, prior to acylation by Method C. The protecting group is then removed, after acylation, to liberate the desired antibacterial agent of formula I or II, wherein $R^1$ is acyl and $R^2$ and $R^3$ are each hydrogen. A wide variety of protecting groups can be used for this purpose, such as, for example, triphenylmethyl, substituted triphenylmethyl, alkoxymethyl, benzyloxymethyl, substituted benzyloxymethyl, and cyanomethyl. A particularly convenient group, however, is the triphenylmethyl group.

It will be appreciated by one skilled in the art that not all the variations discussed under Method C are equally effective or convenient in all cases, for the acylation of a compound of formula III or IV. The relative effectiveness of a particular variation will differ according to a number of factors, such as, for example, the precise structure of the said compound of formula III or IV, the availability of starting materials, the scale of the reaction and, in particular, the structure and reactivity of the acyl group being introduced. In practice, one skilled in the art will select the most appropriate variation in each case, having full regard for the relevant factors. Moreover, in some instances certain further precautions and modifications become necessary or desirable, especially in the cases wherein $R^1$ has the formula V and n is 1. For example, in the case wherein $R^1$ is of formula V, wherein n is 1 and Q is phenoxycarbonyl, substituted phenoxycarbonyl or indanyloxycarbonyl, use can be made of the acylation technique taught in U.S. Pat. No. 3,679,801. Further, in the preparation of the compounds of formulae I and II, wherein $R^1$ is of formula V, wherein n is 1, Q is carboxy and $R^7$ is selected from the group consisting of phenyl, substituted phenyl, heterocyclyl and substituted heterocyclyl, the mono-acid chloride of the 2-substituted malonic acid precursor is an effective and useful acylating agent in Method C. Preparation and use of the said mono-acid chlorides is taught in Belgian Pat. No. 788,928. In the case wherein $R^1$ is of the formula V, wherein n is 1 and Q is or contains a basic, primary or secondary, amino group, it is necessary to protect the amino group in the starting carboxylic acid, prior to activation of the carboxy group of the said acid. After the amino group has been protected, the carboxy group is activated, the acylation is carried out by one of the methods described under Method C, and then the antibacterial penam compound of formula I or II is obtained by removal of the protecting group. A wide variety of protecting groups known in the art for protecting amino groups during peptide synthesis can be used for this purpose. Groups which have been found to be particularly suitable are the benzyloxycarbonyl group use of which is taught by Doyle, et al. in the *Journal of the Chemical Society* (London), 1440 (1962), and the enamines formed by interaction of the starting amino-acid with a β-dicarbonyl compound, as taught by Dane and Dockner in the *Angewandte Chemie* (International Edition in English) 3, 439 (1964), and in *Chemische Berichte der Deutschen Chemischen Gesellschaft*, 98, 789 (1965). For the use of other protecting groups, consult Greenstein and Winitz, "Chemistry of the Amino Acids," John Wiley & Sons, Inc., New York/London, 1961, pp. 882-922. In certain instances where n is 1 and Q is or contains a basic amino group, a particularly valuable acylation procedure comprises use of the acid chloride hydrochloride of the precursor acid. The acid chloride hydrochlorides are prepared, and the acylation is conducted, by the methods described for the preparation of 2-amino-2-phenylacetyl chloride hydrochloride and the subsequent acylation of 6-aminopenicillanic acid, respectively (U.S. Pat. No. 3,140,282).

Method D is useful for the preparation of compounds of formulae I and II, wherein $R^1$ is an acyl group and $R^2$ and $R^3$ are each alkanoyloxymethyl, 1-(alkanoyloxy)ethyl or 3-phthalidyl. This Method comprises alkylation of the corresponding compound of formula I or II, wherein $R^1$ is an acyl group and $R^2$ and $R^3$ are each hydrogen, with an alkanoyloxymethyl, 1-(alkanoyloxy)ethyl or 3-phthalidyl halide. In this context, the term "halide" is intended to contemplate iodide, bromide and chloride. The reaction is conveniently carried out by dissolving a tetrazolate salt of the said compound of formula I or II, wherein $R^2$ and $R^3$ are each hydrogen, in a suitable, polar, organic solvent, such as N,N-dimethylformamide, and then adding about one molar equivalent of the alkanoyloxymethyl halide. When the reaction has proceeded essentially to completion, the product is isolated by standard techniques. It is often sufficient simply to dilute the reaction medium with an excess of water, and then adjust the pH to an appropriate value. If the product precipitates, it is extracted into a water-immiscible organic solvent and then recovered by solvent evaporation. The value to which the pH must be adjusted will vary according to the structure of the substituent $R^1$, but its approximate value will be readily known to one skilled in the art. Salts of the starting material which are commonly used are alkali metal salts, such as sodium and potassium salts, and tertiary amine salts, such as triethylamine, N-ethylpiperidine, N,N-dimethylaniline and N-methylmorpholine salts. The reaction is usually run at about ambient temperature, and the length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is customary, when utilizing a chloro compound, to add up to one molar equivalent of an alkali metal iodide. This has the effect of speeding up the reaction, and it is postulated that this technique brings about a halogen exchange, thereby generating in situ some of the more reactive iodo compound. With full regard for the foregoing factors, reaction times of several hours, e.g., overnight, are quite commonly used. As discussed earlier, for any given substituent $R^1$, the compounds of formulae I and II, wherein $R^2$ and $R^3$ are each hydrogen, co-exist in an equilibrium mixture, and it is found that the crude product obtained from alkylation of this mixture also comprises a mixture. The mixture consists of mono-alkylated products, in which the newly-introduced alkanoyloxymethyl group is located at either the N-1 or N-2 position of the tetrazole moiety. The ratio of products varies according to a variety of factors, such as the structure of the penam, the structure of the alkylating agent, and the conditions under which the reaction is run. In some instances one isomer may be produced almost exclusively. Although this mixture of products can be separated by conventional means, for example by chromatography, both isomers have antibacterial properties, and the mixture of isomers can be used for the further synthetic transformations to be described hereinafter, if desired.

The alkanoyloxyalkyl halides are either known compounds, or they are prepared by known procedures (Ulich and Adams, *Journal of the Americal Chemical Society,* 43, 662 [1921]; Daehne et al., *Journal of Medicinal Chemistry,* 13, 607 [1970]).

Method E is valuable for the preparation of compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is selected from the group consisting of carboxy, sulfoamino, carbamoyl, amino and NH—(CO—$CH_2$—NH)$_m$—CO—Z. This Method comprises carrying out further transformations on certain of the compounds of formulae I and II which are prepared by Method C.

Thus, the compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is carboxy, can be obtained from the corresponding compound of formula I or II, wherein Q is phenoxycarbonyl, substituted phenoxycarbonyl or indanyloxycarbonyl, by mild hydrolysis of the phenoxycarbonyl, substituted phenoxycarbonyl or indanyloxycarbonyl group to liberate a carboxy group. The reaction is carried out by exposing the starting material to a mildly-alkaline aqueous solvent system until hydrolysis is substantially complete, for example according to the procedure of U.S. Pat. No. 3,679,801.

The compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula I, wherein $R^7$ is as previously defined, n is 1 and Q is sulfoamino, can be obtained from the corresponding compound of formula I or II, wherein Q is amino, via direct sulfonation. The sulfonation can conveniently be carried out using the methods described in U.S. Pat. No. 3,381,001.

The compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is carbamoyl, can be obtained from the corresponding compound of formula I or II, wherein Q is phenoxycarbonyl or, preferably, phenoxycarbonyl substituted by one or more electron-withdrawing groups, by treatment with ammonia. Particularly convenient substituted phenoxycarbonyl groups are nitro- and dinitro-substituted phenoxycarbonyl groups, and the reaction is carried out using well-known methods (Consult Johnson, *Journal of the American Chemical Society,* 75, 3636, [1953]).

The compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is NH—(CO—$CH_2$—NH)$_m$—CO—Z, wherein m is O and Z is selected from the group consisting of alkyl having from one to six carbon atoms, phenyl, substituted phenyl, furyl, thienyl, pyridyl and pyrrolyl, are prepared from the corresponding compound of formula I or II, wherein Q is amino by reaction with an activated derivative of the appropriate carboxylic acid. The techniques for activation of a carboxylic acid, and for acylation, discussed above under Method C can be used in the instant process. In many instances, use of the acid chloride of the carboxylic acid is a particularly convenient technique.

The compounds of formulae I and II, wherein $R^2$ and $R^3$ are each selected from the group consisting of hydrogen, alkanoyloxymethyl, 1-(alkanoyloxy)ethyl or phthalidyl, and $R^1$ is of formula V, wherein $R^7$ is as previously defined, n is 1 and Q is NH—(CO—$CH_2$—NH)$_m$—CO—Z, wherein m is O and Z is aminomethyl, are prepared from the corresponding compound of formula I or II, wherein Q is amino, via coupling with glycine. The coupling procedure comprises the steps of: (1) protecting the amino function of the glycine; (2) activating the carboxyl group of the N-protected glycine; (3) reacting the so-produced intermediate with the said compound of formula I or II, or a salt thereof; and (4) removing the N-protecting group. Convenient techniques for achieving these steps are taught in Belgian Patent No. 681,660. The product from step (4) can then be coupled with a further glycine unit, to preduce the corresponding compounds of formulae I and II, wherein Q is NH—(CO—$CH_2$—NH-)$_m$—CO—Z, wherein m is 1 and Z is aminomethyl.

The compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is NH—(CO—$CH_2$—NH)$_m$—CO—Z, wherein m is O and Z is anilino or substituted anilino, are prepared from the corresponding compound of formula I or II, wherein Q is amino, by reaction with phenyl isocyanate or a substituted phenyl isocyanate. The reaction is carried out by contacting substantially equimolar proportions of the isocyanate and the penam compound, or a salt thereof (e.g., the triethylamine salt), in a reaction-inert organic solvent (e.g., N,N-dimethylformamide) at about ambient temperature. The reaction requires a few hours (e.g., about three hours,) and the product can be isolated simply by evaporation of the solvent.

The compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is NH—(CO—$CH_2$—NH)$_m$—CO—Z, wherein m is O and Z is guanidino, are prepared from the corresponding compound of formula I or II, wherein Q is amino, via reaction with a guanylcarbamoylating agent. The guanylcarbamoylating agents obtained by treatment of 4-guanylsemicarbazide either with a source of nitrous acid, or with certain oxidizing agents, are particularly valuable in this process. Preparation and use of these carbamoylating agents are described in U.S. Pat. Nos. 3,579,501 and 3,579,514. The term "amidino" is an accepted synonym for guanyl.

The compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is NH—(CO—$CH_2$—NH)$_m$—CO—Z, wherein m is O and Z is guanidinomethyl, are prepared from the corresponding compound of formula I or II, wherein Q is amino via reaction with the acid chloride hydrochloride of guanidinoacetic acid. The reaction is normally carried out by treating a solution of the starting penam compound, or a salt thereof, in a polar, organic solvent such as N,N-dimethylformamide or N,N-dimethylacetamide, at about 0° C., with guanidinoacetyl chloride hydrochloride. The reaction commonly takes about two hours to reach completion. The reaction mixture is then filtered, and the crude product is caused to precipitate by addition of an excess of a non-solvent, such as acetone, and then filtered off. A salt of the starting material is used in those cases wherein $R^2$ or $R^3$ is hydrogen, and appropriate salts are, for example, alkali metal salts and tertiary amine salts. In order to achieve a good yield of product, it is usually necessary to utilize at least one molar equivalent, and preferably up to about four molar equivalents, of the acylating agent.

The compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is NH—(CO—$CH_2$—NH)$_m$—CO—Z, wherein m is O and Z is selected from the group consisting of acylamino, benzamido, substituted benzamido, thiophenecarboxamido, furancarboxamido and pyridinecarboxamido, are prepared from the corresponding compound of formula I or II, wherein Q is amino, by reaction with the appropriate acylisocyanate. The acylisocyanates are prepared, and the reaction is carried out, according to the procedures described in U.S. Pat. No. 3,479,339.

The compounds of formulae I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is NH—(CO—$CH_2$—NH)$_m$—CO—Z, wherein m is 1 and Z is selected from the group consisting of alkyl having from one to six carbon atoms, phenyl, substituted phenyl, furyl, thienyl, pyridyl, pyrrolyl, aminomethyl, anilino, substituted anilino, guanidino, guanidinomethyl, acylamino, benzamido, substituted benzamido, thiophenecarboxamido, furancarboxamido and pyridinecarboxamido, are prepared in a manner analogous to that described for the corresponding compound wherein m is O, except that the corresponding compound of formula I or II, wherein Q is NH—CO—$CH_2$—$NH_2$ replaces the compound wherein Q is amino.

The compounds of formula I and II, wherein $R^2$ and $R^3$ are each selected from the group consisting of hydrogen, alkanoyloxymethyl, 1-(alkanoyloxy)ethyl and 3-phthalidyl, and $R^1$ is of formula V, wherein $R^7$ is as previously defined, n is 1 and Q is NH—(CO—$CH_2$—NH)$_m$—CO—Z, wherein m is O and Z is selected from the group consisting of alkanecarboxamidinomethyl having from three to eight carbon atoms, benzamidinomethyl, substituted benzamidinomethyl, thiophenecarboxamidinomethyl, furancarboxamidinomethyl, pyridinecarboxamidinomethyl, pyrrolecarboxamidinomethyl and 2-benzimidazolecarboxamidinomethyl are prepared from the corresponding compound of formula I or II, wherein Q is NH—CO—$CH_2$—$NH_2$ by reaction with the appropriate imidate ester (e.g. ethyl benzimidate). The reaction is normally carried out by contacting substantially equimolar quantities of the imidate ester and the penam compound, or a salt thereof (e.g. the triethylamine salt), in a reaction-inert organic solvent (e.g. chloroform, N,N-dimethylformamide or N,N-dimethylacetamide) at about ambient temperature. The reaction usually takes several hours (e.g. about six hours), and the product is isolated by evaporating the solvent. Alternatively, in some instances, the product can be induced to precipitate by the addition of a non-solvent, such as hexane, ether or acetone. The imidate esters used in the instant process are either known compounds or they are prepared by known methods. For example, they can be prepared by the acid-catalyzed addition of an alkanol to the appropriate nitrile (the Pinner reaction), by reaction of the corresponding carboxamide with a trialkyloxonium fluoborate (e.g. triethyloxonium fluoborate), or, in some cases, by the base-catalyzed addition of an alkanol to a nitrile. The base-catalyzed reaction is particularly convenient when the cyano moiety is bonded to an electron-withdrawing group (e.g. 4-cyanopyridine). Consult Shriner and Neumann, *Chemical Reviews*, 35, 354–358 (1944); Meerwein, *Organic Syntheses*, Collective Volume V, 1080–1082 (1973); Schaefer and Peters, *Journal of Organic Chemistry*, 26, 412 (1961); Belgian Pat. No. 803,094 and references cited.

Method F is valuable for the preparation of compounds of formulae I and II, wherein $R^1$ is an acyl group and $R^2$ and $R^3$ are each hydrogen. The Method comprises hydrolysis of the corresponding compound of formula I, wherein $R^1$ is an acyl group and $R^2$ is a group of formula $—C(=O)—O—R^{14}$ or $SO_2—R^{14}$ wherein $R^{14}$ is selected from the group consisting of alkyl having from one to six carbon atoms, benzyl, phenyl, and phenyl substituted by up to two moieties selected from the group consisting of nitro, fluoro, chloro, bromo, alkyl having from one to four carbon atoms and alkoxy having from one to four carbon atoms. The hydrolysis is normally carried out by contacting the starting material with an aqueous or partially aqueous solvent system, at a temperature normally in the range from about −5° C. to about 30° C., and preferably from about 10° C. to 25° C., at a pH in the range from about 7.5 to 9.5, and usually at about 8.5, until hydrolysis is substantially complete. The reaction usually takes about 1 hour to reach completion. It is usual, although not essential, to use a co-solvent in this process. Co-solvents which can be used are those which are miscible with water, and will serve to dissolve the starting penam compound. Typical examples of co-solvents which can be used are acetone; lower alkanols, such as methanol and ethanol; ethylene glycol; mono- and di(lower-alkyl) ethers of ethylene glycol, such as 2-methoxyethanol and 1,2-dimethoxyethane; tetrahydrofuran; dioxane and acetonitrile. The product is isolated by methods well-known in the art.

The starting penam compounds used in Method A are prepared by acylation of the appropriate corresponding compound of formula III, or a salt thereof, wherein $R^5$ is selected from the group consisting of hydrogen and trialkylsilyl having from one to four carbon atoms in each of said alkyl groups and $R^2$ is

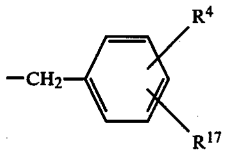

wherein $R^4$ is at the 3-, 4- or 5-position and it is selected from the group consisting of hydrogen, hydroxy, fluoro, chloro, bromo, iodo, alkyl having from one to six carbon atoms, alkoxy having from one to six carbon atoms, phenyl and benzyloxy; and $R^{17}$ is selected from the group consisting of hydrogen, hydroxy, fluoro, chloro, unbranched-alkyl having from one to six carbon atoms and unbranched-alkoxy having from one to six carbon atoms.

The acylation comprises treating the said compound of formula III with an activated derivative of the appropriate carboxylic acid. The activation of the carboxylic acids, and the acylation, are carried out using the procedures described hereinbefore under Method C.

The starting penam compounds of formula I, wherein $R^2$ is

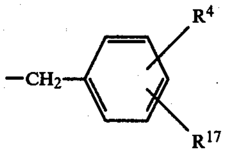

wherein at least one of $R^4$ and $R^{17}$ is a hydroxy group at the 2- or the 4-position, used in Method B, can be prepared by hydrogenolysis of the corresponding compound wherein any hydroxy group at $R^4$ or $R^{17}$ is protected as its benzyl ether. The reaction is carried out by treating the starting material with hydrogen gas in the presence of a catalyst, and the procedure discussed above under Method A is conveniently used. As will be appreciated by one skilled in the art, it is often unnecessary to isolate the product from the instant hydrogenolysis, and the product can be used in situ for Method B. Indeed, in some instances, when the hydrogenolysis is performed in the presence of a basic agent, Method B occurs concomitantly with hydrogenolysis. Moreover, under certain hydrogenolysis conditions, formation of the penam compound of formula I, wherein $R^2$ is a hydroxybenzyl group, is immediately followed by in situ hydrogenolytic removal of the hydroxybenzyl group. This produces the corresponding compounds of formula I or II, wherein $R^2$ and $R^3$ are each hydrogen.

The starting penam compounds of formulae III and IV, wherein $R^2$, $R^3$, and $R^5$ are each hydrogen, used in Method C, can be obtained from the appropriate compound of formula III, or an acid addition salt thereof, wherein $R^5$ is hydrogen and $R^2$ is selected from the group consisting of

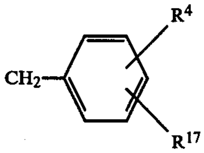

and

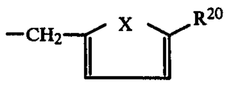

wherein $R^4$ is at the 3-, 4- or 5-position and it is selected from the group consisting of hydrogen, hydroxy, fluoro, chloro, bromo, iodo, alkyl having from one to six carbon atoms, alkoxy haivng from one to six carbon atoms, phenyl and benzyloxy; $R^{17}$ is selected from the group consisting of hydrogen, hydroxy, fluoro, chloro, unbranched-alkyl having from one to six carbon atoms and unbranched-alkoxy having from one to six carbon atoms; $R^{20}$ is selected from the group consisting of hydrogen and methyl; and X is selected from the group consisting of oxygen and sulfur, provided that at least one substituent selected from the group consisting of 2-hydroxy, 4-hydroxy, 4-alkoxy having from one to six carbon atoms, 2-unbranched-alkoxy having from one to six carbon atoms and 4-benzyloxy is present by treatment with trifluoroacetic acid. Although this is not essential, it is usually preferable to add to the reaction an alkoxybenzene, such as anisole, phenetole or veratrole. The reaction is conveniently carried out by dissolving the starting material in a small volume of trifluoroacetic acid, containing anisole, maintaining the solution at a temperature in the range from about 20° C. to about 70° C., and preferably at about 30°-40° C., for an appropriate time period, and then precipitating the product by the addition of a non-solvent. The product can then be recovered by filtration.

Alternatively, particularly when operating on a small scale, it is sometimes convenient to arrest the reaction by rapid evaporation of the trifluoroacetic acid, at or about ambient temperature, in vacuo. The amount of trifluoroacetic acid used in this process is not critical, provided that enough is present to efficiently dissolve the starting material, and from about ten molar equivalents to about one hundred molar equivalents based on the penam compound are commonly used. About one molar equivalent of anisole is normally used, but larger amounts, even as large as ten molar equivalents, may be added if desired. A starting material which operates particularly efficiently in this process is a sulfonate salt, for example, the methanesulfonate or p-toluenesulfonate salt, of the said compound of formula III. The time course of the instant reaction varies according to a variety of factors, such as the reaction temperature, the strucutre of the starting material, the concentration of the solution. However, a convenient mode of operation involves monitoring pilot reactions using nuclear magnetic resonance spectroscopy, so that the time period which leads to the optimum conversion to product for a given set of reaction conditions can be determined. When working at about 35° C., reaction times in the range from about 0.1 to about 1.5 hours are commonly employed.

The starting penam compounds of formula III and IV, wherein $R^2$, $R^3$ and $R^5$ are each hydrogen, used in Method C, can also be obtained by hydrogenolysis of the appropriate compound of formula III, or an acid-addition salt thereof, wherein $R^5$ is hydrogen and $R^2$ is

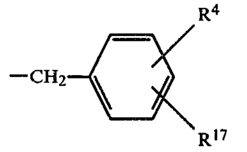

wherein $R^4$ is at the 3-, 4- or 5-position and it is selected from the group consisting of hydrogen, hydroxy, fluoro, chloro, bromo, iodo, alkyl having from one to six carbon atoms, alkoxy having from one to six carbon atoms, phenyl and benzyloxy, and $R^{17}$ is selected from the group consisting of hydrogen, hydroxy, fluoro, chloro, unbranched-alkyl having from one to six carbon atoms and unbranched-alkyl having from one to six carbon atoms. The conditions discussed hereinbefore under Method A can be used for this transformation.

A still further method for obtaining the starting materials of formula III and IV, wherein $R^2$, $R^3$ and $R^5$ are each hydrogen, comprises removal of a triphenylmethyl or substituted triphenylmethyl protecting group from a compound of formula III or IV, wherein $R^5$ is triphenylmethyl or substituted triphenylmethyl and $R^2$ or $R^3$ is hydrogen. The triphenylmethyl or substituted triphenylmethyl group is removed by treatment of the said compound of formula III or IV with acid, and a wide variety of acidic reagents and conditions known in the art for removal of the triphenylmethyl group are operable in this process. For example, it is possible to use a sulfonic acid, such as methanesulfonic acid, benzenesulfonic acid or p-toluenesulfonic acid; an anhydrous hydrohalic acid, such as hydrogen chloride or hydrogen bromide; or an alkanoic acid, such as acetic acid, propionic acid, chloroacetic acid, trifluoroacetic acid and the like. The reaction is normally carried out by dissolving the starting material in an appropriate solvent and adding about two molar equivalents of the acid reagent, at or about ambient temperature. Reaction is complete within about one hour, and the product is present in the reaction medium in the form of the acid-addition salt corresponding to the acidic reagent used. A solvent should be chosen which will dissolve the starting penam, and examples of solvents which find use are: ethers, such as diethyl ether, tetrahydrofuran, dioxane and 1,2-dimethoxyethane; chlorinated hydrocarbons, such as chloroform, methylene chloride and 1,2-dichloroethane; lower aliphatic ketones, such as acetone, methyl ethyl ketone and methyl isobutyl ketone; esters, such as ethyl acetate and butyl acetate; hydrocarbons, such as hexane, cyclohexane and benzene; and lower alkanols, such as methanol, ethanol and butanol. Although it is common to use about two molar equivalents of acid in this process, only one molar equivalent is necessary when either the reaction is carried out in the presence of one molar equivalent of water, or the acid is introduced as a monohydrate. However, as will be realized by one skilled in the art, the product from this reaction should not be exposed to an excess of acid for prolonged periods, since in this case there is a danger of destroying the β-lactam system. A particularly convenient mode of operation for this process, is to choose an acid-solvent system such that the starting material is soluble, but the acid-addition salt generated during the reaction precipitates as it is formed. It can then be recovered by filtration at the end of the reaction. When using the combination of p-toluenesulfonic acid in acetone, the p-toluenesulfonate salt of the product often precipitates.

In like manner, the starting materials of formula III, wherein $R^5$ is hydrogen and $R^2$ is selected from the group consisting of $-C(=O)-O-R^{14}$, $-SO_2-R^{14}$ and $(R^6)'$, wherein $R^{14}$ is selected from the group consisting of alkyl having from one to six carbon atoms, benzyl, phenyl and phenyl substituted by up to two moieties selected from the group consisting of nitro, fluoro, chloro, bromo, alkyl having from one to four carbon atoms and alkoxy having from one to four carbon atoms; and $(R^6)'$ is selected from the group consisting of

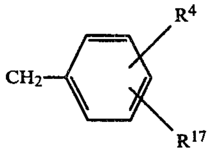

and

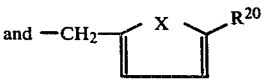

wherein $R^4$ is at the 3-, 4- or 5-position and it is selected from the group consisting of hydrogen, hydroxy, fluoro, chloro, bromo, iodo, alkyl having from one to six carbon atoms, alkoxy having from one to six carbon atoms, phenyl and benzyloxy; $R^{17}$ is selected from the group consisting of hydrogen, hydroxy, fluoro, chloro, unbranched-alkyl having from one to six carbon atoms and unbranched-alkoxy having from one to six carbon atoms; $R^{20}$ is selected from the group consisting of hydrogen and methyl; and X is selected from the group consisting of oxygen and sulfur, are prepared from the corresponding compound wherein $R^5$ is triphenylmethyl, or substituted triphenylmethyl. The triphenylmethyl or substituted triphenylmethyl group is removed by treatment with acid, exactly as described hereinbefore.

The starting materials of formulae III and IV, wherein $R^5$ is triphenylmethyl or substituted triphenylmethyl, and $R^2$ or $R^3$ is hydrogen, are prepared by a retrograde Michael reaction, on a corresponding compound of formula III, wherein $R^2$ is $CH_2CH_2$—Y, wherein Y is selected from the group consisting of cyano, alkoxycarbonyl having from two to seven carbon atoms, phenoxycarbonyl, alkylsulfonyl having from one to four carbon atoms, phenylsulfonyl and —$SO_2$—$NR^{15}R^{16}$, wherein $R^{15}$ and $R^{16}$ are each selected from the group consisting of hydrogen, alkyl having from one to four carbon atoms, phenyl and benzyl. The retrograde Michael reaction comprises treating the said compound with about one equivalent of base, using conditions known in the art for retrograde Michael reactions, but which are compatible with the penam ring system. Typically, the said compound of formula IV is treated with about one equivalent of a relatively non-nucleophilic base, in a non-hydroxylic solvent, at a temperature in the range from about 0° C. to about 25° C., for a period of from about ten minutes to about two hours, (Consult further *Journal of the Chemical Society* [London], Part B, 5867 [1970]).

Preparation of those starting materials for Method C which are compounds of formulae III and IV, wherein $R^5$ is hydrogen, $R^2$ and $R^3$ are each selected from the group consisting of alkanoyloxymethyl having from three to eight carbon atoms, 1-(alkanoyloxy)ethyl having from four to nine carbon atoms and 3-phthalidyl, is achieved by alkylation of a tetrazolate salt, such as the triethylamine salt of the corresponding compound of formula III or IV, wherein $R^2$ and $R^3$ are hydrogen, using the appropriate alkanoyloxyalkyl or phthalidyl halide. The procedure of Method D is used in this process, except that it is common to utilize at least two molar equivalents, and preferably about three molar equivalents, of the alkylating agent.

Thus, valuable starting materials for production of the antibacterial compounds of this invention are the novel penam compounds of formula III, wherein $R^2$ is a tetrazolylpenam nitrogen protecting group and $R^5$ is an amino protecting group. These compounds can be prepared by a novel three-step sequence of reactions, which forms an important embodiment of this invention, and which is now to be described in detail for the specific case wherein $R^5$ is triphenylmethyl and $R^2$ is selected from the group consisting of $CH_2CH_2V$, C(=O)—O—$R^{14}$ and $(R^6)'$, wherein Y, $R^{14}$ and $(R^6)'$ are as previously defined.

The said novel penam derivatives of formula III are prepared starting from the well-known intermediate, 6-triphenylmethylaminopenicillanic acid, via certain transformations of the C-3 carboxy function. Preparation of 6-triphenylmethylaminopenicillanic acid is taught by Sheehan and Henery-Logan in the *Journal of the American Chemical Society,* 81, 5838 (1959).

In Step 1, 6-(triphenylmethylamino)penicillanic acid is converted into an amide of formula VI,

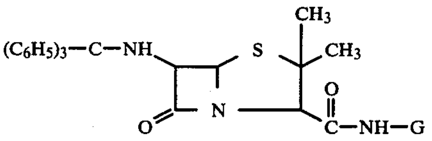

VI wherein G is selected from the group consisting of —C(=O)—O—$R^{14}$, —$SO_2$—$R^{14}$, $CH_2CH_2Y$ and $(R^6)'$; wherein Y and $R^{14}$ are as previously defined and $(R^6)'$ is selected from the group consisting of

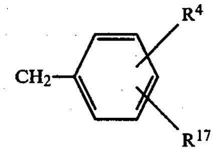

and

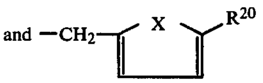

wherein $R^4$, $R^{17}$, $R^{20}$ and X are as previously defined.

In the case wherein G is —$CH_2CH_2Y$ or $(R^6)'$, the amide of formula VI is prepared by activation of the 3-carboxy group of 6-(triphenylmethylamino)penicillanic acid, e.g. by the mixed anhydride formation, followed by reaction with an amine of formula $NH_2CH_2CH_2Y$ or $(R^6)'$—$NH_2$. Thus, formation of the mixed anhydride involves suspending or dissolving an appropriate carboxylate salt of the 6-triphenylmethylamino-penicillanic acid in a reaction-inert organic solvent, and then adding to this suspension or solution a reagent selected from pivaloyl chloride and lower-alkyl chloroformates. Appropriate salts are, for example, alkali metal salts, such as sodium or potassium salts, and amine salts, such as triethylammonium, pyridinium, N-ethylpiperidinium or N,N-dimethylanilinium salts. Appropriate solvents are those which serve to dissolve at least one of the reactants, and the mixed anhydride product, and do not adversely interact with the reactants or product. Examples of such solvents are chlorinated hydrocarbons, such as chloroform, methylene chloride; aromatic hydrocarbons, such as benzene, toluene and xylene; and ethers, such as diethyl ether, tetrahydrofuran and 1,2-dimethoxyethane. The reaction is usually carried out at a temperature in the range from about −50° C. to about 30° C., and preferably at about 0° C. At about 0° C., the reaction commonly requires about one hour. The 6-triphenylmethylaminopenicillanic acid salt and the pivaloyl chloride or lower-alkyl chloroformate are normally present in roughly equimolar proportions, although in some instances a small excess of the acid chloride component is used. The product can be isolated simply by filtering off the insoluble materials, and then evaporating the solvent in vacuo to give the crude product. The latter can be used directly, or purified further by methods known in the art. If desired, however, the mixed anhydride product need not be isolated. It can be used in situ for reaction with the amine of formula $NH_2CH_2CH_2Y$ or $(R^6)'$—$NH_2$. Reaction of the mixed anhydride with the amine of the formula $(R^6)'$—$NH_2$ or $NH_2CH_2CH_2Y$ is usually carried out simply by contacting the reactants in an inert solvent, for about 0.5 to about 2.0 hours, at a temperature in the range from about −30° C. to about 30° C. and preferably at around 0° C. The same solvents identified above for mixed anhydride formation are useful for the instant reaction, and the reagents are usually used in approximately equimolar proportions. As will be realized by one skilled in the art, the product should not be exposed to an excess of the starting amine, since this runs the risk of causing extensive decomposition of the penam β-lactam. In the cases wherein this reaction is conducted in a water-immiscible solvent, the product is usually isolated by washing the reaction mixture with water and then concentrating the organic solvent to dryness in vacuo, to give the crude product. The latter product can be used immediately for Step 2, or, if desired, it can be purified further by well-known methods. However, it is sometimes convenient simply to wash the reaction mixture with water, and then use the so-produced solution of amide directly in Step 2. In the cases wherein the reaction is conducted in a water-miscible solvent, the product is usually isolated by first removing the water-miscible solvent by evaporation in vacuo, replacing it by a water-immiscible solvent, and then proceeding as described above.

When the amine $(R^6)'-NH_2$ is of formula

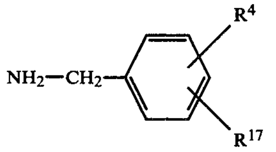

wherein either $R^4$ or $R^{17}$ is a hydroxy group, it is convenient to protect the phenolic hydroxy group of the hydroxybenzylamide produced, before proceeding to Step 2. A wide variety of protecting groups known in the art for protecting hydroxy groups are operative for this purpose. For example, the hydroxy group can be protected as an alkoxymethyl or tetrahydropyranyl ether, or it can be silylated. The types of silyl derivatives, and the methods of preparation, referred to hereinbefore under "Method C" are useful in the instant process.

In the case wherein g is $-C(=O)-O-R^{14}$ or $-SO_2-R^{14}$, the amide of formula VI is prepared by reaction of 6-(triphenylmethylamino)penicillanic acid with the appropriate isocyanate of formula $R^{14}-O-C(=O)-N=C=O$ or $R^{14}-SO_2-N=C=O$. The reaction is usually carried out by contacting substantially equimolar quantities of the reactants, in a reaction inert organic solvent, at a temperature in the range from about 0° C. to about 30° C., for a period of from about one hour to about twenty hours. The product can be isolated simply by removal of the solvent in vacuo or the solution of the amide of formula VI can be used in situ for Step 2. The isocyanates of formula $R^{14}-O-(C=O)-N=C=O$ are prepared by reaction of a carbamate of formula $R^{14}-O-C(=O)-NH_2$ with oxalyl chloride, and the isocyanates of formula $R^{14}-SO_2-N=C=O$ are prepared by reaction of a sulfonamide of formula $R^{14}-SO_2-NH_2$ with oxalyl chloride. [See *J. Hetero. Chem.*, 6, 261 (1969).]

In Step 2 of the said novel three-step series of reactions, the product from Step 1 is converted into an imidoyl chloride of formula

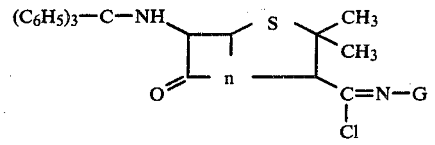

where G is selected from the group consisting of $-CH_2CH_2-Y$, $-C(=O)-O-R^{14}$, $-SO_2R^{14}$ and $(R^6)'$, wherein Y, $R^{14}$ and $(R^6)'$ are as previously defined. For imidoyl chloride formation, a convenient method comprises dissolving the said amide in a reaction-inert organic solvent and then treating the solution with phosgene and a tertiary amine. About one molar equivalent of phosgene is usually used, but amounts up to about two or three molar equivalents are sometimes employed. The tertiary amine is preferalby present in a molar amount equal to or greater than the amount of phosgene. The reaction is carried out at a temperature in the range from about −20° C. to about 30° C., and preferably at about 25° C., and it usually requires a few hours to reach completion. It is sometimes advantageous from a standpoint of hastening complete conversion to imino chloride, to add further quantities of tertiary maine and phosgene as the reaction proceeds. A variety of tertiary amines can be used in this process, for example trimethylamine, triethylamine, N,N-dimethylaniline, N-methylmorpholine and pyridine, and the like, and typical solvents which can be used are chlorinated hydrocarbons, such as chloroform, methylene chloride and 1,2-dichloroethane, and ethers such as tetrahydrofuran and 1,2-dimethoxyethane. If desired, the imidoyl chloride can be isolated by evaporation of the filtered reaction mixture, but in many instances it is convenient to use the imino chloride in situ.

Several other reagents, for example, thionyl chloride or a phosphorous halide such as phosphorus pentachloride are operative in the imidoyl chloride forming reaction. Moreover, if desired, use can be made of the corresponding imidoyl bromide.

In Step 3 of the said novel three-step series of reactions, the above imidoyl chloride is converted into a tetrazolylpenam compound of formula

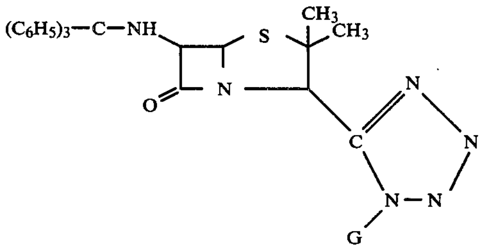

wherein G is as previously defined. This transformation comprises treating the said imidoyl chloride with a source of azide ion and a convenient way of carrying out this transformation involves dissolving the imidoyl halide in an appropriate solvent, and then adding about one molar equivalent, or sometimes a small excess, of the azide ion source. The reaction mixture is then stored at or about ambient temperatures for several hours, for example, overnight, until conversion into tetrazole is substantially complete. A wide variety of azide ion sources are operative in this process, and examples of those which are particularly valuable are trialkylsilyl azides having from one to four carbon atoms in each of said alkyl groups, such as trimethylsilyl azide and triethylsilyl azide; salts of hydrazoic acid, such as potassium azide and sodium azide, tributylammonium azide, N,N-dimethylanilinium azide, N-methylmorpholinium azide and pyridinium azide; tetramethylguanidinium azide. Appropriate solvents are those which will serve to dissolve both the imidoyl halide and the azide ion source, but do not adversely react with either the reactants or the products of the process. In the cases where the azide ion source is a trialkylsilyl azide or a trisubstituted ammonium azide, chlorinated hydrocarbon solvents, such as chloroform, methylene chloride and 1,2-dichloroethane, are commonly used. However, dipolar aprotic solvents such as N-methylpyrrolidone, can also be used; and in the cases where a metal salt of hydrazoic acid constitutes the azide ion source, these dipolar aprotic solvents become the solvent-type of choice. As regards ease of operation, and availability of reagents, the use of trimethylsilyl azide in chloroform is particularly convenient. As indicated earlier, the reaction takes several hours to reach completion. However, the conversion to tetrazole can often be hastened by adding further quantities of azide ion during the course of the reaction. Product isolation is achieved using standard methods. When a low boiling chlorinated hydrocarbon is the solvent, the reaction solution is washed with dilute alkali and then the organic solvent is evaporated off. When a dipolar aprotic solvent is the solvent, the reaction mixture is usually first diluted with a large excess of dilute alkali, and then, after appropriate adjustment of the pH, the product is isolated by solvent extraction.

As indicated hereinbefore, synthesis of the antibacterial agents of this invention involves the use of two kinds of protecting groups, and these groups have been identified in terms of their ability to function in a particular fashion.

The tetrazolylpenam nitrogen protecting group has been identified in terms of its ability to fulfill two functions. The first of these, its capacity to be removed under certain specified conditions, has already been discussed. The second of these is its ability to permit the synthesis of a compound of formula III, wherein $R^5$ is an amino protecting group and $R^2$ is the said tetrazolylpenam nitrogen protecting group.

From the foregoing discussion it will be apparent that the tetrazolylpenam nitrogen protecting group must be a group which will permit operation of the above-described three-step series of reactions. That is, it must be of such a nature that the amide of formula VI can be prepared, that the amide can be converted to an imidoyl halide, and that the imidoyl halide can be converted to the said 1-protected 5-tetrazolylpenam compound of formula III, substantially as described.

In like manner, the amino protecting group must fulfill two functions. The first of these is that, after attachment to the 6-amino function of 6-aminopenicillanic acid, it must permit operation of the above-described three-step series of reactions. That is, it must protect the penam ring system during formation of the amide of formula VI, during conversion into an imidoyl halide, and during conversion into the 1-protected 5-tetrazolylpenam compounds of formula III. The second function of an amino protecting group for use in this invention is that it must be removable, under conditions which do not decompose the penam ring system, from either: (a) a compound of formula III, wherein $R^5$ is the said amino protecting group and $R^2$ is a tetrazolylpenam nitrogen protecting group; (b) a compound of formula III or IV, wherein $R^5$ is the said amino protecting group and $R^2$ or $R^3$ is hydrogen; or (c) a compound of formula III wherein $R^5$ is the said amino protecting group, and $R^2$ is selected from the group consisting of alkanoyloxymethyl, 1-(alkanoyloxy)ethyl and 3-phthalidyl. Selection of appropriate amino protecting groups will be achieved readily and easily by one skilled in the art. In particular all such groups known in the art for peptide synthesis and which fit the above criteria are operative. However, particularly convenient protecting groups are triphenylmethyl, substituted triphenylmethyl and $\beta,\beta,\beta$-trihaloethoxycarbonyl groups, such as $\beta,\beta,\beta$-tribromoethoxycarbonyl and $\beta,\beta,\beta$-trichloroethoxycarbonyl. Examples of substituted triphenylmethyl groups which are especially valuable are those of formula

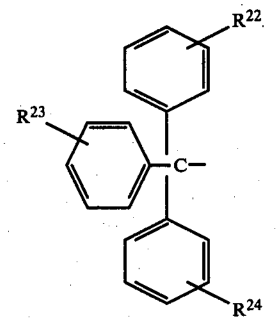

wherein $R^{22}$, $R^{23}$ and $R^{24}$ are each selected from the group consisting of hydrogen, fluoro, chloro, bromo, alkyl having from one to four carbon atoms, alkoxy having from one to four carbon atoms and phenyl. Because of its readily availability, the triphenylmethyl group is especially valuable.

The amines of formulae $NH_2CH_2CH_2Y$ and $NH_2—(R^6)'$, used in Step 1 above, are either known compounds or they are prepared by known methods from commercially-available starting materials. For example, amines of formula

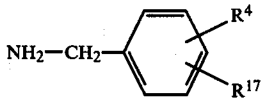

VII can conveniently be prepared from the corresponding aldehyde of formula

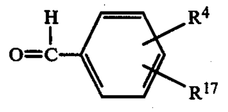

via conversion to the oxime followed by reduction, or in cases where the $R^4$ and/or $R^{17}$ groups would be unaffected, by the reductive alkylation of ammonia. (Consult Harrison and Harrison, "Compendium of Organic Synthetic Methods," Wiley-Interscience, 1971, pages 233–235 and 258–261).

A further sub-class of novel 3-(5-tetrazolyl)penam compounds which are valuable antibacterial agents, and which fall within the scope and purview of the instant invention is those compounds of formulae:

VIII

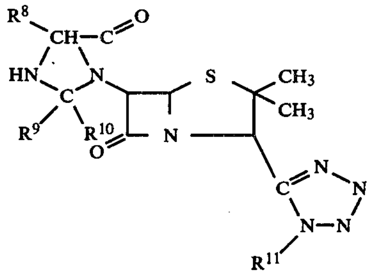

IX

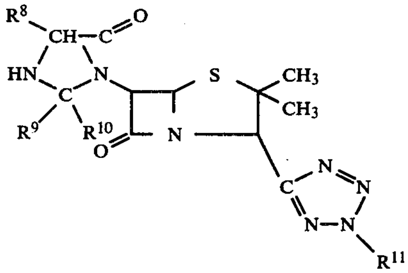

wherein $R^8$ is selected from the group consisting of phenyl, 1,4-cyclohexadienyl, 3-sydnonyl, thienyl, furyl, pyridyl, thiazolyl, isothiazolyl, tetrazolyl, triazolyl, imidazolyl, pyrazolyl, substituted phenyl, substituted thienyl, substituted furyl, substituted pyridyl, substituted thiazolyl, substituted isothiazolyl, substituted triazolyl, substituted imidazolyl and substituted pyrazolyl, each substituted moiety being substituted by up to two members selected from the group consisting of fluoro, chloro, bromo, hydroxy, alkyl having from one to six carbon atoms, alkoxy having from one to six carbon atoms, amino and alkylthio having from one to six carbon atoms; $R^9$ and $R^{10}$ are each selected from the group consisting of hydrogen, methyl and ethyl; and $R^{11}$ is selected from the group consisting of hydrogen, alkanoyloxymethyl having from three to eight carbon atoms, 1-(alkanoyloxy)ethyl having from four to nine carbon atoms and phthalidyl. The compounds of formula VIII and IX are prepared from the corresponding compound of formula I or II, wherein $R^1$ is of formula V wherein n is 1, Q is amino and $R^7$ is as defined above for $R^8$, and $R^2$ and $R^3$ are as defined above for $R^{11}$, by condensation of the said compound of formula I and II with the appropriate aldehyde or ketone of formula $R^9$—CO—$R^{10}$. The condensation reaction is usually carried out by contacting the starting penam compound with a large excess of the aldehyde or ketone in the presence of at least one molar equivalent of a tertiary amine, at or slightly below room temperature. A sufficient amount of the aldehyde or ketone is normally used so that a further solvent is not necessary. However, a further diluent which does not adversely react with either the starting materials or the product can be used if desired. Examples of tertiary amines which are operative in the process are triethylamine, tributylamine, pyridine, N,N-dimethylaniline, N-methylmorpholine and quinoline. Although at least one equivalent of tertiary amine is required, it is common to use a fairly large excess, up to about ten molar equivalents. The instant process normally requires a reaction time of several hours, for example overnight. In those cases wherein the product is out of solution at the end of the reaction it is filtered off. Alternatively, when the product is in solution at the end of the reaction, it is recovered by evaporation of the solvent in vacuo.

A still further sub-class of novel 3-(5-tetrazolyl)penam compounds which are valuable antibacterial agents, and which fall within the scope and purview of this invention, is those compounds of formulae:

X

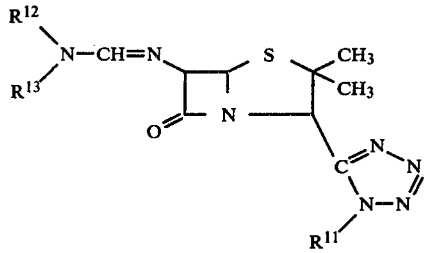

XI

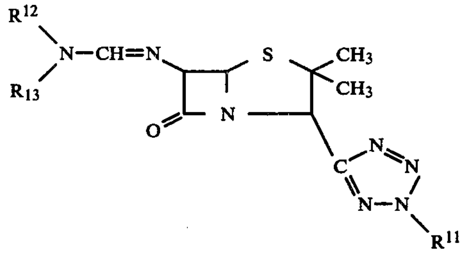

wherein $R^{12}$ and $R^{13}$ are each alkyl having from one to six carbon atoms, or, when taken together with the nitrogen to which they are attached, they represent a member selected from the group consisting of pyrrolidino, morpholino, piperidino and azacycloheptan-1-yl; and $R^{11}$ is as defined above. The compounds of formula X and XI, are prepared from the appropriate corresponding compound of formula III or IV, wherein $R^2$ and $R^3$ are as defined above for $R^{11}$ and $R^5$ is hydrogen, by introducing the formamidine moiety, using the methods taught by Lund and Tybring (*Nature,* New Biology, 236, 135 [1972]).

A characteristic feature of the compounds of formulae I, II, III, IV, VIII, IX, X and XI, wherein $R^2$, $R^3$ or $R^{11}$ are hydrogen, is their ability to form salts. By virtue of the acidic nature of a 5-monosubstituted tetrazole, the said compounds have the ability to form salts with basic agents, and these salts, referred to generically as "tetrazolate" salts in this specification, are to be considered within the scope of this invention. The salts can be prepared by standard techniques, such as contacting the acidic and basic components, usually in a 1:1 molar ratio, in an aqueous, non-aqueous or partially aqueous medium, as appropriate. They are then recovered by filtration, by precipitation with a non-solvent followed by filtration, by evaporation of the solvent, or, in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine, p-toluidine and octylamine; secondary amines, such as diethylamine, N-methylaniline, morpholine, pyrrolidine and piperidine; tertiary amines, such as triethylamine, N,N-dimethylaniline, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; and bicarbonates, such as sodium bicarbonate and potassium bicarbonate.

Further, the compounds of formulae I and II, wherein $R^1$ contains one or more acidic functions (e.g. carboxy, sulfo etc.), have the ability to form other salts (e.g., salts of the carboxylate and sulfonate type). These salts, which can be prepared in exactly the same manner and using the same basic agents, as described above for the tetrazolate salts, are also within the purview of this invention. Clearly, certain of the compounds of formulae I and II can form both mono- and poly-salts. When considering poly-salts, the various cationic moieties can be the same or different.

The compounds of formulae I, II, III and IV which contain a basic group, have the ability to form acid-addition salts. Said acid-addition salts are also to be considered as being within the scope of this invention. Examples of acid-addition salts which are particularly valuable are: hydrochloride, hydrobromide, phosphate, perchlorate, citrate, tartrate, pamoate, glutarate, benzoate, sulfate, lactate, and arylsulfonate salts.

When therapeutic use in mammals is being contemplated for a salt of a compound of the instant invention, it is of course essential to use a pharmaceutically-acceptable salt. However, other salts are useful for a variety of other purposes; such as, for example, isolating and purifying individual compounds, changing the solubility characteristics of an individual compound, and for interconverting pharmaceutically-acceptable salts with their non-salt counterparts.

The antibacterial penam compounds of the instant invention show activity against a wide variety of gram-positive and gram-negative bacteria. The in vitro activity can be demonstrated by the conventional two-fold serial dilution technique in Brain-Heart Infusion broth (Difco). The broth is inoculated with the bacterial culture, and with the test antibiotic, and then it is incubated overnight. On the next day, the test is read visually. The minimum inhibitory concentration (MIC) is the lowest concentration of antibiotic which prevents turbidity, i.e. which prevents growth of the microorganism. In vitro activities of several of the penam compounds of the invention are presented later in this specification.

The in vitro activity of the antibacterial compounds of the instant invention makes them particularly suitable for topical application, for example, in the form of creams and ointments, and for the sterilization of sick-room and hospital surfaces, equipment, and the like.

The antibacterial penam compounds of the instant invention are also active in vivo. In determining such activity, the test antibiotic is administered to infected mice, using a multiple dosing regimen. The severity of the infection varies from about one to about ten times that needed to kill 100% of the mice under the conditions of the test. At the end of the test, the activity of a compound is assessed by counting the number of survivors among the treated animals. Both the subcutaneous (SC) and the oral (PO) dosage routes are used. Results are given in Table I for two of the compounds of the invention. The ability of the compounds to protect mice against systemic infections caused by a lethal intraperitoneal inoculum of *Staphylococcus aureus* or of *Escherichia coli* is presented.

TABLE I

| Compound | Dosage (mg./kg.) | Dosage | Percentage Protection *S. aureus* | Percentage Protection *E. coli* |
|---|---|---|---|---|
| 6-(D-2-amino-2-[3-thienyl]-acetamido)-2,2-dimethyl-3-(5-tetrazolyl)-penam | 50 | SC | 40 | 20 |
| 6-(D-2-amino-2-[3-thienyl]-acetamido)-2,2-dimethyl-3-(5-tetrazolyl)-penam | 25 | SC | 60 | 20 |
| 6-(D-2-amino-2-[3-thienyl]-acetamido)-2,2-dimethyl-3-(5-tetrazolyl)-penam | 12 | SC | 50 | |
| 6-(D-2-amino-2-[3-thienyl]-acetamido)-2,2-dimethyl-3-(5-tetrazolyl)-penam | 6 | SC | 50 | |
| 6-(D-2-amino-2-[3-thienyl]-acetamido)-2,2-dimethyl-3-(5-tetrazolyl)-penam | 200 | PO | | 0 |
| 6-(D-2-amino-2-[p-hydroxy-phenyl]acet-amido)-2,2-di-methyl-3-(5-tetrazolyl)-penam | 50 | SC | 80 | 100 |
| 6-(D-2-amino-2-[p-hydroxy-phenyl]acet-amido)-2,2-di-methyl-3-(5-tetrazolyl)-penam | 25 | SC | 70 | 80 |
| 6-(D-2-amino-2-[p-hydroxy-phenyl]acet-amido)-2,2-di-methyl-3-(5-tetrazolyl)-penam | 12 | SC | 50 | |
| 6-(D-2-amino-2-[p-hydroxy-phenyl]acet-amido)-2,2-di-methyl-3-(5-tetrazolyl)-penam | 6 | SC | 50 | |
| 6-(D-2-amino-2-[p-hydroxy-phenyl]acet-amido)-2,2-di-methyl-3-(5-tetrazolyl)-penam | 200 | PO | | 100 |

The in vivo activity of the antibacterial compounds of this invention makes them suitable for the control of bacterial infections in mammals, including man, by both the oral and parenteral modes of administration. The compounds will find wide use in the control of infections caused by susceptible gram-positive and gram-negative bacteria in human subjects.

When considering therapeutic use of a compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial penam compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets of oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial penam compounds of this invention are of use in human subjects and the daily dosages to be used will not differ significantly from other, clinically-used, penam antibiotics. The prescribing physician will ultimately determine the appropriate dose for a given human subject, and this can be expected to vary according to the age, weight, and response of the individual patient, as well as the nature and the severity of the patient's symptoms, The compounds of this invention will normally be used orally at dosages in the range from about 10 to about 200 mg. per kilogram of body weight per day, and parenterally at dosages from about 5 to about 100 mg. per kilogram of body weight per day. These figures are illustrative only, however, and in some cases it may be necessary to use dosages outside these limits.

Certain of the compounds of this invention have the ability to form solvates (e.g. hydrates), and all such hydrates are to be considered within the scope and purview of the invention.

The following examples are provided solely for the purpose of further illustration. Infrared (IR) spectra are measured as potassium bromide discs (KBr discs) or as Nujol mulls, and diagnostic absorption bands are reported in wave numbers ($cm^{-1}$). Nuclear magnetic resonance spectra (NMR) are measured at 60 MHz for solutions in deuterochloroform ($CDCl_3$), perdeutero dimethyl sulfoxide (DMSO-$d_6$) or deuterium oxide ($D_2O$), and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

PREPARATION

2-(3-[p-Methoxybenzimidoyl]ureido)acetyl Chloride Hydrochloride

A mixture of 8.96 g. of ethyl p-methoxybenzimidate, 6.45 g. of ethyl 2-(isocyanato)acetate and 70 ml. of benzene is stirred at room tempe rature overnight, and then it is diluted with an excess of hexane. The solid which forms is filtered off and dried: 14.15 g., m.p. 84°–85.5° C.

To 14.10 g. of the above product in 175 ml. of ethanol, at −75° C., is added 11 ml. of liquid ammonia. The cooling bath is then removed, and the reaction mixture is stirred overnight. The solvent is removed by evaporation in vacuo, leaving an oil, which solidifies on trituration with hexane. After drying, the solid weighs 12.2 g. and has m.p. 85°–88° C.

The latter solid is stirred with 300 ml. of 4 N hydrochloric acid overnight, to effect hydrolysis. The product is filtered off and dried giving 11.05 g., m.p. 213°–215° C.

This latter product is stirred with 5.20 g. of phosphorus pentachloride in 125 ml. of methylene chloride overnight, and then the solid which is out of solution is filtered off. It is re-suspended in 125 ml. of methylene chloride, 5.20 g. of phosphorus pentachloride is added, and it is again stirred overnight. The solid is again filtered off, giving 5.22 g. of 2-(3-[p-methoxybenzimidoyl-]ureido)acetyl chloride hydrochloride, m.p. 146°–152° C. IR spectrum (Nujol mull): 1790 $cm^{-1}$.

In like manner, ethyl benzimidate is converted into 2-(3-[benzimidoyl]ureido)acetyl chloride hydrochloride.

Ethyl 2-(p-chlorophenyl)acetimidate is converted into 2-(3-[2-(p-chlorophenyl)acetimidoyl]ureido)acetyl chloride hydrochloride using the above procedure, except that the hydrolysis step is carried out using 1 N sodium hydroxide and dimethoxyethane (3:1), followed by acidification with 4 N hydrochloric acid.

EXAMPLE I

The following ingredients are blended together in the indicated proportions by weight.

| | |
|---|---|
| Sucrose, U.S.P. | 80.0 |
| Tapioca starch | 13.5 |
| Magnesium stearate | 6.5 |
| 6-(D-2-Amino-2-phenyl acetamido)-2,2-dimethyl-3-(5-tetrazolyl)penam | 100.0 |

After the composition is thoroughly blended, tablets are punched from the mixture, each tablet being of such size as to contain 100 mg of the penam compound.

Tablets are also prepared containing respectively 50 and 250 mg of active ingredient, by selecting the appropriate proportions of penam compound and excipient blend in each case.

EXAMPLE II

The following ingredients are blended together in the indicated proportions by weight.

| | |
|---|---|
| Calcium carbonate | 17.6 |
| Dicalcium phosphate | 18.8 |
| Magnesium trisilicate | 5.2 |
| Lactose, U.S.P. | 5.2 |
| Potato starch | 0.8 |

-continued

| | |
|---|---|
| 6-(D-2-Amino-2-[3-thienyl] acetamido)-2,2-dimethyl-3-(5-tetrazolyl)penam | 50.0 |

The thoroughly-mixed pharmaceutical composition is filled into soft gelatin capsules, such that each capsule contains 100 mg of active ingredient.

Capsules are also prepared containing respectively 50 and 250 mg of active ingredient by varying the proportions of penam compound and excipient blend.

EXAMPLE III

The sodium salt of 6-(D-2-amino-2-[p-hyroxyphenyl-]acetamido)-2,2-dimethyl-3-(5-tetrazolyl)penam is thoroughly mixed and ground with sodium citrate (4% by weight). The ground, dry mixture is sterilized and packed into sterile vials, which are then stoppered with serum caps under sterile conditions. When it is intended to use this preparation, sufficient sterile water is injected into the vials to dissolve the contents, and give a solution containing 25 mg/ml of active ingredient. For parenteral use, the solution is withdrawn from the vials using a hypodermic syringe.

In a similar manner, by varying the amount of water added, solutions containing respectively 10, 50, 100, and 200 mg/ml of active ingredient are prepared.

EXAMPLE IV 6-(Triphenylmethylamino)-2,2-dimethyl-3-(1-[4-methoxybenzyl]tetrazol-5-yl)penam 6-(Triphenylmethylamino)-2,2-dimethyl-3-(N-[4-methoxybenzyl]carbamoyl)penam—To a stirred slurry of 216 g. of 6-aminopenicillanic acid in 1,500 ml. of anhydrous chloroform is added 278 ml. of triethylamine, and the mixture is then stirred at ambient temperature until a clear solution is obtained. This requires about 15 minutes. The solution is cooled to about 0° C., and then 306 g. of triphenylmethyl chloride is added. The stirring is continued at about 0° C. for 30 minutes, and then at ambient temperature for a further 24 hours. The mixture is cooled to about 0° C. again, and 14 ml. of triethylamine, followed by 95 ml. of ethyl chloroformate, is added. During this process the temperature rises to about 15° C., and a precipitate forms. To facilitate stirring a further 200 ml. of chloroform is added. The stirring is continued for 30 minutes. Then, at about 0° C., 50 ml. of 4-methoxybenzylamine (available from the Aldrich Chemical Company, Inc.) is injected into the reaction medium, below the surface of the solvent. At 10 minute intervals, three further aliquots of 4-methoxybenzylamine (35 ml., 25 ml. and 21 ml.) are injected in the reaction in similar fashion. The total volume of 4-methoxybenzylamine added is 131 ml. The cooling bath is then removed, and the reaction is stirred for a further 1 hour. The chloroform solution is washed successively with five 2,000-ml. portions of water and one 2,000-ml. portion of saturated brine. The chloroform is finally dried using anhydrous sodium sulfate.

Examination of the reaction mixture at this point by NMR spectroscopy, reveals that the conversion into amide is approximately 85% complete. Accordingly, the chloroform solution is cooled in an ice-bath and 21 ml. of triethylamine, followed in about 5 minutes by 14.2 ml. of ethyl chloroformate, is added. After a further 15 minutes, 9.8 ml. of 4-methoxybenzylamine is added, and then in another 5 minutes a further 9.8 ml. of 4-methoxybenzylamine is added. The reaction is concentrated in vacuo giving 6-(triphenylmethylamino)-2,2-dimethyl-3-(N-[4-methoxybenzyl]carbamoyl)penam, as an amorphous solid.

6-(Triphenylmethylamino)-2,2-dimethyl-3-(chloro-[N-(4-methoxybenzyl)imino]methyl)penam—The amide described above is dissolved in 480 ml. of pyridine, and then the solution is cooled to about −5° C. To this solution is added dropwise, with stirring during 10 minutes, 108 ml. of thionyl chloride. The reaction mixture is then allowed to warm slowly to ambient temperature for a further 21 hours. All the volatile components are removed in vacuo leaving the crude imino chloride as an amorphous solid. The NMR spectrum (in $CHCl_3$) of this product shows absorption bands at 4.70 ppm (singlet, C-3 hydrogen), 4.65 ppm (singlet, benzyl hydrogens), 4.30–4.60 ppm (multiplet, C-5 and C-6 hydrogens), 3.75 ppm (singlet, methoxy hydrogens), 1.57 ppm (singlet, C-2 methyl hydrogens) and 1.38 ppm (singlet, C-2 methyl hydrogens).

6-(Triphenylmethylamino)-2,2-dimethyl-3-(1-[4-methoxybenzyl]tetrazol-5-yl)penam—The imino chloride described above is re-dissolved in 500 ml. of chloroform and then the solution is cooled to about −5° C. in an ice-salt bath. To the solution is then added, with stirring, 160 ml. of trimethylsilyl azide (available from the Aldrich Chemical Company, Inc.). After being allowed to warm to ambient temperature, the reaction mixture is stirred for a further 22 hours. It is then cooled to about 0° C. and 2,000 ml. of 1.5 N sodium hydroxide solution is added, followed by sufficient additional 1.5 N sodium hydroxide to bring the pH of the aqueous to 6.0. The aqueous phase is separated off, and the chloroform phase is washed successively with five 2,000-ml. portions of water and one 500-ml. portion of saturated brine. The chloroform is then dried by filtration through anhydrous sodium sulfate, and finally concentrated to dryness. The residue is triturated with 1,000 ml. of ether, and then filtered off. This affords 150 g. of crude product, m.p. 174°–178° C. The crude product is purified by re-dissolving it in chloroform and filtering the solution through chromatographic grade silica gel. The chloroform is removed by evaporation in vacuo, and the residue is again triturated with ether. This affords 128 g. of 6-(triphenylmethylamino)-2,2-dimethyl-3-(1-[4-methoxybenzyl]tetrazol-5-yl)penam as a light tan solid, m.p. 193°–195° C. The infrared spectrum (KBr disc) of the product shows an absorption band at 1790 $cm^{-1}$ ($\beta$-lactam carbonyl). The NMR spectrum (in $CDCl_3$) shows absorption bands at 7.25 ppm (multiplet, aromatic hydrogens), 5.50 ppm (broad singlet, benzyl hydrogens, 5.05 ppm (singlet, C-3 hydrogen), 4.40 ppm (broad singlet, C-5 and C-6 hydrogens), 3.80 ppm (singlet, methoxy hydrogens), 1.45 ppm (singlet, C-2 methyl hydrogens) and 0.70 ppm (singlet, C-2 methyl hydrogens).

EXAMPLE V

The following compounds are prepared by repeating the procedure of Example IV, except that where necessary the triphenylmethyl chloride is replaced by an equimolar amount of the appropriately-substituted triphenylmethyl chloride, and where necessary the 4-methoxybenzylamine is replaced by an equimolar amount of the requisite amine.

6-(triphenylmethylamino)-2,2-dimethyl-3-(1-benzyltetrazol-5yl)penam, 6-(triphenylmethylamino)-2,2-dimethyl-3-(1-[2-methoxybenzyl]tetrazol-5-yl)penam,
6-(triphenylmethylamino)-2,2-dimethyl-3-(1-[4-isopropoxybenzyl]tetrazol-5-yl)penam,
6-(triphenylmethylamino)-2,2-dimethyl-3-(1-[3-chlorobenzyl]tetrazol-5-yl)penam,
6-(triphenylmethylamino)-2,2-dimethyl-2-(1-[3-methylbenzyl]tetrazol-5-yl)penam,
6-(triphenylmethylamino)-2,2-dimethyl-3-(1-[3-chloro-4-methoxybenzyl]tetrazol-5-yl)penam,
6-(triphenylmethylamino)-2,2-dimethyl-3-(1-furfuryltetrazol-5-yl)penam,
6-(diphenyl-3-tolylmethylamino)-2,2-dimethyl-3-(1-[4-ethoxybenzyl]tetrazol-5-yl)penam, and
6-(diphenyl-2-methoxyphenylmethylamino)-2,2-dimethyl-3-(1-[4-phenylbenzyl]tetrazol-5-yl)penam,
respectively.

Substituted triphenylmethyl chlorides are prepared according to procedures well known in the art. See "Organic Syntheses", John Wiley & Sons,Inc., 1955, Collective Volume 3, pages 839–846.

EXAMPLE VI

The following compounds are prepared by repeating the procedure of Example IV, except that where necessary the triphenylmethyl chloride is replaced by an equimolar amount of the appropriately-substituted triphenylmethyl chloride, and where necessary the 4-methoxybenzylamine is replaced by an equimolar amount of the requisite amine.

6-(diphenyl-4-bromophenylmethylamino)-2,2-dimethyl-3-(1-[2-thienylmethyl]tetrazol-5-yl)penam,
6-(di[4-methoxyphenyl]phenylmethylamino)-2,2-dimethyl-3-(1-benzyltetrazol-5-yl)penam,
6-(di[3-chlorophenyl]phenylmethylamino)-2,2-dimethyl-3-(1-[4-methoxybenzyl]tetrazol-5-yl)penam,
6-(di[2-tolyl]phenylmethylamino)-2,2-dimethyl-3-(1-[2,4-dimethoxybenzyl]tetrazol-5-yl)penam,
6-(tri[3-ethoxyphenyl]methylamino)-2,2-dimethyl-3-(1-[4-ethylbenzyl]tetrazol-5-yl)penam, and
6-(triphenylmethylamino)-2,2-dimethyl-3-(1-[5-methylfurfuryl]tetrazol-5-yl)penam,
respectively.

Substituted triphenylmethyl chlorides are prepared according to procedures well known in the art. See "Organic Syntheses", John Wiley & Sons, Inc., 1955, Collective Volume 3, pages 839–846.

EXAMPLE VII

6-(triphenylmethylamino)-2,2-dimethyl-3-(1-[4-benzyloxybenzyl]tetrazol-5-yl)penam 6-(Triphenylmethylamino)-2,2-dimethyl-3-(N-4-benzyloxybenzyl]carbamoyl)penam—To a stirred solution of 20.0 g. of 6-triphenylmethylamino-penicillanic acid (Sheehan and Henery-Logan, *Journal of the American Chemical Society,* 81, 5836 [1959]) in 140 ml. of acetone, at 0°–5° C., is added 6.08 ml. of triethylamine followed by 5.78 ml. of isobutyl chloroformate. After a further 10 minutes, the mixture is filtered directly into a stirred solution of 9.28 g. of 4-benzyloxybenzylamine in 1,000 ml. of water and 300 ml. of acetone at ambient temperature. The mixture so obtained is stirred for 4 minutes, and then an additional 500 ml. of water is added. Stirring is continued for a further 7 minutes, and then the reaction mixture is extracted with ether. The ether is dried using anhydrous magnesium sulfate, and then evaporated to dryness in vacuo. The crude product so obtained is re-dissolved in 200 ml. of ether, which is then added dropwise over 10 minutes to 2,500 ml. of hexane. The solid which precipitates is filtered off, giving 21.5 g. of 6-(triphenylmethylamino)-2,2-dimethyl-3-(N-[4-benzyloxybenzyl]carbamoyl)penam.

6-(Triphenylmethylamino)-2,2-dimethyl-3-(chloro-[N-(4-benzyloxybenzyl)imino]methyl)penam—To a stirred solution of 2.0 g. of the above-described amide in 10 ml. of dry chloroform, at 0°–5° C., is added 0.99 ml. of pyridine, followed by 5.42 ml. of a 2.26 M solution of phosgene in chloroform. The reaction mixture is then stirred at ambient temperature overnight. At this point, it is evaporated to dryness in vacuo, yielding a viscous gum, which is extracted with 100 ml. of ether. The ether is filtered, and evaporation of the filtrate affords the imino chloride as a yellow foam. 6-(Triphenylmethylamino)-2,2-dimethyl-3-(1-[4-benzyloxybenzyl]tetrazol-5-yl)penam—The above-described imino chloride is re-dissolved in 8 ml. of dry N,N-dimethylformamide. To this solution is added 249 mg. of potassium azide, and the turbid solution is stirred at ambient temperature for 2.25 hours. The solvent is evaporated at ambient temperature, under high vacuum, leaving a brown gum. This residue is partitioned between 60 ml. of water and 150 ml. of ether. The ether phase is separated off, washed with saturated brine, dried using anhydrous sodium sulfate, and finally evaporated to dryness in vacuo. The residue is 980 mg. of 6-(triphenylmethylamino)-2,2-dimethyl-3-(1-[4-benzyloxybenzyl]tetrazol-5-yl)penam. Its NMR spectrum (in $CDCl_3$) shows absorption bands at 7.30 ppm (multiplet, aromatic hydrogens), 5.45 ppm (quartet, benzyl hydrogens), 5.05 ppm (singlet, C-3 hydrogen), 5.00 ppm (singlet, benzyl hydrogens), 4.40 ppm (multiplet, C-5 and C-6 hydrogens), 1.40 ppm (singlet, C-2 hydrogen) and 0.70 ppm (singlet, C-2 hydrogen).

EXAMPLE VIII

The procedure of Example VII is repeated, except that the 4-benzyloxybenzylamine used therein is replaced by an equimolar amount of the appropriate amine, to produce the following congeners:

6-(triphenylmethylamino)-2,2-dimethyl-3-(1-[4-methoxybenzyl]tetrazol-5-yl)penam,
6-(triphenylmethylamino)-2,2-dimethyl-3-(1-[4-n-hexyloxybenzyl]tetrazol-5-yl)penam,
6-(triphenylmethylamino)-2,2-dimethyl-3-(1-[4-fluorobenzyl]tetrazol-5-yl)penam,
6-(triphenylmethylamino)-2,2-dimethyl-3-(1-[4-isopropylbenzyl]tetrazol-5-yl)penam,
6-(triphenylmethylamino)-2,2-dimethyl-3-(1-[3,4-dimethoxybenzyl]tetrazol-5-yl)penam,
6-(triphenylmethylamino)-2,2-dimethyl-3-(1-[3,5-dichlorobenzyl]tetrazol-5-yl)penam,
6-(triphenylmethylamino)-2,2-dimethyl-3-(1-[3-chloro-4-ethoxybenzyl]tetrazol-5-yl)penam,
6-(triphenylmethylamino)-2,2-dimethyl-3-(1-furfuryltetrazol-5-yl)penam,
6-(triphenylmethylamino)-2,2-dimethyl-3-(1-[5-methyl-2-thienyl)methyl]tetrazol-5-yl)penam, and
6-(triphenylmethylamino)-2,2-dimethyl-3-(1-[3tolyl]tetrazol-5-yl)penam,
respectively.

EXAMPLE IX

6-Triphenylmethylamino)-2,2-dimethyl-3-(1-[4-methoxybenzyl]-tetrazol-5-yl)penam (A)

6-(Triphenylmethylamino)-2,2-dimethyl-3-(N-[4-methoxybenzyl]carbamoyl)penam.

To a stirred slurry of 86.4 g. (0.4 mole) of 6-aminopenici llanic acid in 600 ml. of anhydrous chloroform is added 111.2 ml. (0.8 mole) of triethylamine, and the mixture is stirred at ambient temperature until a clear solution is obtained (ca. 15 minutes). To this solution is then added, portionwise over about 25 minutes, 134.9 g. (0.44 mole) of 90% pure triphenylmethyl chloride, at ambient temperature. Stirring is contained for a further 64 hours, and then 5.6 ml. of triethylamine is added. The solution is cooled to 0°-5° C., and then an ice-cold solution of 38 ml (0.4 mole) of ethyl chloroformate in 80 ml. of chloroform is added dropwise during 30 minutes with the reaction temperature being maintained between 4° and 9° C. After a further 15 minutes of stirring, 52.4 ml. (0.4 mole) of 4-methoxybenzylamine is injected into the reaction medium, below the surface of the solvent, at 4° and 9° C., and over a period of 30 minutes. Stirring is continued for a further 30 minutes at 3° to 6° C., for 20 minutes while the reaction medium warms to 20° C. The reaction mixture is then washed with water, followed by brine. Finally, it is dried using magnesium sulfate to give a chloroform solution of 6-(triphenylmethylamino)-2,2-dimethyl-3-(N-[4-methylbenzyl]carbamoyl)penam.

(B)

6-(Triphenylmethylamino)-2,2-dimethyl-3-(1-[p-methoxybenzyl]tetrazol-5-yl)penam.

To a chloroform solution containing 69.4 g. (0.120 mole) of 6-(triphenylmethylamino)-2,2-dimethyl-3-(N-[4-methoxybenzyl]carbamoyl) penam, and having a volume of 133.3 ml., prepared by the method described in (A) above, is added a further 132.7 ml. of chloroform, followed by 29.1 ml. (0.360 mole) of pyridine. This solution is cooled to 10° C., and then 26.22 g. (0.216 mole) of phosphorus pentachloride is added during 15 minutes, with stirring. Stirring is continued at ca. 10° C. for 10 minutes, and then at ambient temperature for a further 1.5 hours, giving a solution of the imino chloride. To a one-sixth aliquot of this imino chloride solution is added 4.85 ml. (0.060 mole) of pyridine, followed by 2.42 ml. (0.060 mole) of methanol at ca. 25° C., with stirring. After a further 15 minutes of stirring 2.03 g. (0.038 mole) of ammonium chloride, followed by 2.59 g (0.039 mole) of 95% pure sodium azide, is added. The reaction mixture is then stirred at ambient temperature for a further 4 hours. At this point, 400 ml, of water and 200 ml. of chloroform are added, and then the layers are separated. The organic phase is washed with water, dried using magnesium sulfate, and then concentrated to a small volume in vacuo. This final chloroform solution is added dropwise with stirring to a large volume of diisopropylether, and, after 30 minutes, the precipitate which has formed is filtered off. This affords 6.1 g. of 6-(triphenylmethylamino)-2,2-dimethyl-3-(1-[4-methoxybenzyl]tetrazol-5-yl)penam. The infrared spectrum of the product (KBr disc) shows an absorption band at 1790 $cm^{-1}$ ($\beta$-lactam); and the NMR spectrum (in $CDCl_3$) shows absorptions at 7.25 ppm (multiplet, aromatic hydrogens, 5.40 ppm (broad singlet, benzyl hydrogens), 5.05 ppm (singlet, C-3 hydrogen), 4.50-4.30 ppm (multiplet, C-5 and C-6 hydrogens), 3.70 ppm (singlet, methoxy hydrogens), 3.50-3.10 ppm (broad peak, NH), 1.50 ppm (singlet, C-2 methyl hydrogens) and 0.75 ppm (singlet, C-2 methyl hydrogens).

EXAMPLE X

When the procedure of Example IX is repeated, and the 4-methoxybenzylamine used therein is replaced by an equimolar amount of the appropriate amine, the following compounds are obtained;

6-(triphenylmethylamino)-2,2-dimethyl-3-(1-[4-ethoxybenzyl]-tetrazol-5-yl)penam, 6-(triphenylmethylamino)-2,2-dimethyl-3-(1-[3-chloro-4-methoxybenzyl]tetrazol-5-yl)penam, 6-(triphenylmethylamino)-2,2-dimethyl-3-(1-furfuryl-tetrazol-5-yl)penam, respectively.

EXAMPLE XI 6-(Triphenylmethylamino)-2,2-dimethyl-3-(1-furfuryl-tetrazol-5-yl)penam (A)

6-(triphenylmethylamino)-2,2-dimethyl-3-(N-furfuryl-carbamoyl)penam.

To a stirred slurry of 216 g. (1 mole) of 6-aminopenicillanic acid in 1500 ml. of chloroform, is added, at 25°-30° C., 278 ml. (2 mole) of triethylamine. To the solution thus obtained is added, portionwise during 25 minutes, 306 g. (1.1 mole) of triphenylmethyl chloride, at 25°-30° C. Stirring is then continued for 44 hours at ambient temperature.

A 522-ml. portion (0.25 mole) of the above 6-(triphenylmethylamino)-penicillanic acid solution is cooled to 4° C., and then 3.5 ml. of triethylamine is added. With vigorous stirring is then added 23.75 ml. of ethyl chloroformate at 5°-10° C. Stirring is continued for a further 30 minutes at ca. 6° C. at the end of the addition, and then 8.43 ml. of furfurylamine is injected into the reaction medium below the surface of the solvent. At 10 minute intervals, three further portions of furfurylamine (5.90 ml., 4.22 ml. and 3.54 ml.) are then injected into the reaction medium in similar fashion. The total volume of furfurylamine added is 22.09 ml. (0.25 mole), and the temperature is maintained at ca. 6° C. throughout the addition of the amine. When the addition of the amine is complete, the cooling bath is removed and the reaction medium is stirred at ca. 25° C. for 45 minutes. In is then washed successively with three portions of water, and one portion of brine. Finally, it is dried using anhydrous magnesium sulfate. This affords 610 ml. of a chloroform solution of 6-(triphenylmethylamino)-2,2-dimethyl-3-(N-furfurylcarbamoyl)penam. The NMR spectrum of this solution showed absorptions at 7.3 ppm (17H, m), 6.2 ppm (1H, m), 4.35 ppm (3H, m), 4.05 ppm (2H, s), 1.6 ppm (3H, s) and 1.35 (3H, s).

(B)

6-(triphenylmethylamino)-2,2-dimethyl-3-(1-furfuryl-tetrazol-5-yl)penam.

To a stirred solution of 3.05 g. (5.7 mmole) of 6-(triphenylmethylamino)-2,2-dimethyl-3-(N-furfurylcarbamoyl)penam, in 8 ml. of chloroform, at 0° C., is added 1.35 ml. (17 mmole) of pyridine, followed by 2.64 ml. of a 4.33 M solution of phosgene in chloroform. Stirring is then continued for 1 hour at 25° C. The chloroform, and excess phosgene and pyridine, are then removed by evaporation in vacuo, and the residue is redissolved in 5 ml. of chloroform. The solution is cooled to 0° C., and then 2.25 g. (14.4 mmole) of tetramethylguanidinium azide is added in several small portions. Stirring is continued for 15 minutes at ambient temperature, and then 20 ml. of chloroform, followed by 30 ml. of water, are added and the pH is adjusted to 6.5. The chloroform layer is separated off, washed with water, followed by brine, and then dried ($MgSO_4$). Removal of the solvent by evaporation in vacuo leaves 3.37 g. of a dark-red foam. The foam is re-dissolved in a small volume of chloroform and absorbed onto a column of chromatrographic silica gel. Elution of the column with chloroform, followed by evaporation of the appropriate fractions in vacuo, affords 6-(triphenylmethylamino)-2,2-dimethyl-3-(1-furfuryltetrazol-5-yl) penam. The NMR spectrum of the product ($CDCl_3$) shows absorptions at 7.40 ppm (m, 16H), 6.40 ppm (m, 2H) 5.50 ppm (s, 2H), 5.20 ppm (s, 1H), 4.90 ppm (m, 2H), 1.60 ppm (s, 3H), and 0.80 ppm (s, 3H).

EXAMPLE XXII

The procedure of Example XXI is repeated, except that where necessary the triphenylmethyl chloride used therein is replaced by an equimolar amount of the appropriately-substituted triphenylmethyl chloride, and where necessary the furfuryl amine is replaced by the requisite amine, to produce the following congeners:

6-(triphenylmethylamino)-2,2-dimethyl-3-(1-benzyltetrazol-5-yl)penam,
6-(triphenylmethylamino)-2,2-dimethyl-3-(1-[4-methoxybenzyl]tetrazol-5-yl)penam,
6-(triphenylmethylamino)-2,2-dimethyl-3-(1-[5-methylfurfuryl]tetrazol-5-yl)penam,
6-(diphenyl-3-chlorophenylmethylamino)-2,2-dimethyl-3-(1-[4-iodobenzyl]tetrazol-5-yl)penam,
6-(diphenyl-2-fluorophenylmethylamino)-2,2-dimethyl-3-(1-[4-tolylmethyl]tetrazol-5-yl)penam,
6-(diphenyl-2-methoxyphenylmethylamino)-2,2-dimethyl-3-(1-[4-biphenylylmethyl]tetrazol-5-yl)penam,
6-(diphenyl-4-tolylmethylamino)-2,2-dimethyl-3-(1-[4-benzyloxybenzyl]tetrazol-5-yl)penam,
6-(diphenyl-4-chlorophenylmethylamino)-2,2-dimethyl-3-(1-[3,4-diethoxybenzyl]tetrazol-5-yl)penam,
6-(diphenyl-4-isopropylphenylmethylamino)-2,2-dimethyl-3-(1-[2-methoxybenzyl]tetrazol-5-yl)penam,
6-(diphenyl-4-n-butylphenylmethylamino)-2,2-dimethyl-3-(1-[4-isopentylbenzyl]tetrazol-5-yl)penam,
6-(diphenyl-3-isopropoxyphenylmethylamino)-2,2-dimethyl-3-(1-[3-chloro-4-ethoxybenzyl]tetrazol-5-yl)penam,
6-(diphenyl-3-n-butoxyphenylmethylamino)-2,2-dimethyl-3-(1-[3-n-pentyloxy-4-benzyloxybenzyl]tetrazol-5-yl)penam,
6-(tri[3-methoxyphenyl]methylamino)-2,2-dimethyl-3-(1-[4-n-hexylbenzyl]tetrazol-5-yl)penam and
6-(tri[4-biphenylyl]methylamino)-2,2-dimethyl-3-(1-[4-methoxybenzyl]tetrazol-5-yl)penam, respectively.

EXAMPLE XIII

6-(Triphenylmethylamino)-2,2-dimethyl-3-(1-[4-hydroxybenzyl]tetrazol-5-yl)penam

(A)

6-(Triphenylmethylamino)-2,2-dimethyl-3-(N-[4-hydroxybenzyl]carbamoyl)penam

To a stirred slurry of 43.2 g. (0.20 mole) of 6-aminopenicillanic acid in 300 ml. of chloroform is added 55.6 ml. (0.40 mole) of triethylamine, followed by 61.2 g. (0.22 mole) of triphenylmethyl chloride, at ambient temperature. Stirring is then continued for a further 48 hours at ambient temperature.

A 120-ml. portion (containing 0.060 mole of triethylammonium 6-[triphenylmethylamino]penicillanate) of the above chloroform solution is withdrawn. It is diluted with a further 40 ml. of chloroform, and then 1.67 ml. (0.012 mole) of triethylamine is added. The mixture is cooled to ca. 4° C., in an ice-bath, and then 6.84 ml. of ethyl chloroformate is added all at once, with stirring. Stirring is continued for 30 minutes with ice-bath cooling, and then 7.5 g. (0.060 mole) of 4-hydroxybenzylamine is added. Stirring is continued for 10 minutes with ice-bath cooling, and then for a further 1 hour without cooling. At this point, the chloroform solution is washed with water, followed by brine, and then dried using anhydrous sodium sulfate. Removal of the solvent by evaporation in vacuo affords the crude amide. The crude amide is re-dissolved in 50 ml. of chloroform and absorbed on a column of chromatographic grade silica gel. The column is eluted with chloroform, taking 400 ml. fractions. Fractions 9 to 15 are combined and concentrated to an oil, which solidifies on trituration with methylene chloride. After further trituration with ether, there is obtained 12.63 g. of 6-(triphenylmethylamino)-2,2-dimethyl-3-(N-[4-hydroxybenzyl]carbamoyl)penam, m.p. 166°-168° C. (dec.). The infrared spectrum of the product ($CHCl_3$ solution) shows absorptions at 1785 $cm^{-1}$ ($\beta$-lactam) and 1675 $cm^{-1}$ (amide I). The NMR spectrum of the product ($CDCl_3$) shows absorptions at 7.60-6.40 ppm (multiplet, 20H, aromatic hydrogens and amide hydrogen), 4.70-4.10 ppm (multiplet, 5H, C-5 and C-6 hydrogens, benzyl methylene hydrogens and C-3 hydrogen), 2.98 ppm (doublet, 1H, amine nitrogen), 1.64 ppm (singlet, 3H, C-2 methyl hydrogens) and 1.31 ppm (singlet, 3H, C-2 methyl hydrogens).

(B)

6-(Triphenylmethylamino)-2,2-dimethyl-3-(1-[4-hydroxybenzyl]tetrazol-5-yl)penam.

To a stirred solution of 1.69 g. (3 m mole) of 6-(triphenylmethylamino)-2,2-dimethyl-3-(N-[4-hydroxybenzyl]carbamoyl)penam (prepared as described in A) in 9 ml. of chloroform is added 1 ml. (12 mmole) of pyridine. The solution is cooled to ca. 4° C. in an ice-bath and 0.80 ml. of chlorotrimethylsilane is added. The solution is stirred for 40 minutes at ambient temperature, and then it is again cooled to ca. 4° C. Phosgene (1.5 ml. of a 4.3 M solution in chloroform (6.45 mmole) is added and the cooling bath is removed. Stirring is continued for a further 1.5 hours, and then all the volatile components are removed by evaporation in vacuo.

The oily residue is redissolved in 6 ml. of chloroform and the solution is cooled to ca. 4° C. in an ice-bath. To the stirred solution is added 0.95 g. (6 mmole) of tetramethylguanidinium azide, and then stirring is contin- 6-amino-2,2-dimethyl-3-(1-[4-isopropylbenzyl]tetrazol-5-yl)penam,
6-amino-2,2-dimethyl-3-(1-[(5-methyl-2-thienyl)methyl]tetrazol-5-yl)penam,
6-amino-2,2-dimethyl-3-(1-[5-methylfurfuryl]tetrazol-5-yl)penam,
6-amino-2,2-dimethyl-3-(1-[4-iodobenzyl]tetrazol-5-yl)penam,
6-amino-2,2-dimethyl-3-(1-[4-biphenylylmethyl]tetrazol-5-yl)penam,
6-amino-2,2-dimethyl-3-(1-[4-n-hexylbenzyl]tetrazol-5-yl)penam,
6-amino-2,2-dimethyl-3-(1-[4-hydroxybenzyl]tetrazol-5-yl)penam, and
6-amino-2,2-dimethyl-3-(1-[2-hydroxybenzyl]tetrazol-5-yl)penam,
respectively.

EXAMPLE XIX

6-Amino-2,2-dimethyl-3-(1-[4-benzyloxybenzyl]tetrazol-5-yl)penam

A solution consisting of 558 mg. of 6-(triphenylmethylamino)-2,2-dimethyl-3-(1-[4-benzyloxybenzyl]tetrazol-5-yl)penam, 156 mg. of p-toluenesulfonic acid monohydrate and 1 ml. of acetone is stored at ambient temperature for 2.5 hours. It is then added with stirring to 50 ml. of ether. After stirring for a further 10 minutes, the solid which has precipitated is filtered off. This affords 394 mg. of the p-toluenesulfonate of the product. A 304-mg. aliquot of this p-toluenesulfonate salt is dissolved in 10 ml. of methylene chloride, and to the solution is added 69.7 μl. of triethylamine. After 3 minutes, 5 ml. of water are added and the mixture is stirred vigorously. The organic phase is then separated off, diluted with ether, dried using anhydrous magnesium sulfate, and evaporated to dryness in vacuo. The residue is 189 mg. (69% yield) of 2-amino-2,2-dimethyl-3-(1-[4-benzyloxybenzyl]tetrazol-5-yl)penam. The NMR spectrum (in $CDCl_3$) of the product shows absorption bands at 7.40 ppm (singlet, phenyl hydrogens), 7.15 ppm (quartet, phenylene hydrogens), 5.55 ppm (broad singlet, C-5 and benzyl hydrogens), 5.20 ppm (singlet, C-3 hydrogens), 5.10 ppm (singlet, benzyl hydrogens), 4.60 ppm (doublet, C-6 hydrogen), 1.50 ppm (singlet, C-2 methyl hydrogens) and 0.90 ppm (singlet, C-2 hydrogens).

EXAMPLE XX

6-Amino-2,2-dimethyl-3-(1-furfuryltetrazol-5-yl)penam

To a stirred solution of 0.422 g. (0.75 mmole) of 6-(triphenylmethylamino)-2,2-dimethyl-3-(1-furfuryltetrazol-5-yl)penam in 1 ml. of acetone at ambient temperature, is added 0.142 g. (0.75 mmole) of p-toluenesulfonic acid monohydrate. Stirring is continued for 30 minutes, and then the solvent is removed by evaporation in vacuo. This affords the title compound as its p-toluenesulfonate salt. IR (Nujol mull): 1780 $cm^{-1}$ (β-lactam). NMR (DMSO-$d_6$): 7.20 ppm (q, 4H), 6.40 ppm (m, 2H), 5.90 ppm (s, 2H), 5.60 ppm (m, 2H), 5.00 ppm (d, 1H), 2.20 ppm (s, 3H), 1.60 ppm (s, 3H), 0.80 ppm (s, 3H).

EXAMPLE XXI

6-Amino-2,2-dimethyl-3-(1-[5-methylfurfuryl]tetrazol-5-yl)penam

To a stirred solution of 1.827 g. of 6-(triphenylmethylamino)-2,2-dimethyl-3-(1-[5-methylfurfuryl]tetrazol-5-yl)penam in 3 ml. of acetone is added a solution of 0.59 g. of p-toluenesulfonic acid monohydrate in 2 ml. of acetone. The mixture is stirred at ambient temperature for 30 minutes, and then the precipitate which has formed is filtered off. This affords 0.87 g. (54% yield) of the title compound as its p-toluenesulfonate salt. The NMR spectrum of the product ($CDCl_3$) shows absorptions at 7.28 ppm (q, 4H), 6.50 ppm (d, 1H), 6.01 ppm (s, 1H), 5.86 ppm (s, 2H), 5.71 ppm (s, 1H), 5.68 ppm (d, 1H), 5.09 ppm (d, 1H), 2.00 ppm (2s, 6H), 1.66 ppm (s, 3H) and 0.88 ppm (s, 3H).

EXAMPLE XXII

6-Amino-2,2-dimethyl-3-(1-[2,4-dimethoxybenzyl]tetrazol-5-yl)penam

To a stirred solution of 2.0 g. of 6-(triphenylmethylamino)-2,2-dimethyl-3-(1-[2,4-dimethoxybenzyl]tetrazol-5-yl)penam in 40 ml. of methylene chloride, is added a solution of 0.600 g. of p-toluenesulfonic acid monohydrate in 4 ml. of acetone. The resulting clear solution is stirred at ambient temperature for 18 hours, and then the solvent is removed by evaporation in vacuo. The residue is triturated with ether, to give 1.76 g. (99% yield) of a white solid, which is the title compound as its p-toluenesulfonate salt. The NMR spectrum (DMSO-$d_6$) shows absorptions at 7.65 ppm (m, 5H), 6.90 ppm (m, 2H), 5.95 ppm (m, 3H), 5.40 ppm (d, 1H), 3.95 ppm (s, 3H), 2.45 ppm (s, 3H), 1.95 ppm (s, 3H) and 1.15 ppm (s, 3H).

EXAMPLE XXIII

6-Amino-2,2-dimethyl-3-(5-tetrazolyl)penam

A stirred solution of 32.0 g. of 6-amino-2,2-dimethyl-3-(1-[4-methoxybenzyl]tetrazol-5-yl)penam p-toluenesulfonate, and 24 ml. of anisole, in 96 ml. of trifluoroacetic acid is maintained at 40±1° C. for 35 minutes. The trifluoroacetic acid is then removed rapidly by vacuum distillation. A 120-ml. portion of ether is added to the residue, which produces a white flocculent suspension. The suspension and solvent is cooled to about 0° C., and to it is then added, portionwise, 80 ml. of 2 N sodium hydroxide, giving two clear phases. The pH of the aqueous phase at this point is about 2.7. The layers are separated, and the ether phase is discarded. The pH of the aqueous phase is raised to 4.1 with 2 N sodium hydroxide. This aqueous phase is then washed with 100 ml. of ether and filtered. It is combined with the corresponding aqueous phases from four other identical experiments, and the total aqueous solution is lyophilized to give crude 6-amino-2,2-dimethyl-3-(5-tetrazolyl)penam. This crude product is slurried in a small amount of water and filtered off. It is then re-suspended in water and brought into solution by raising the pH to 7.4 by the addition of sodium hydroxide solution. The clear solution is extracted with ether and the extracts are discarded. The pH of the aqueous phase is adjusted to 4.1 using dilute hydrochloric acid, and the product which precipitates is filtered off. The infrared spectrum of the product shows an absorption at 1795 $cm^{-1}$. Its NMR spectrum (in DMSO-$d_6$) shows absorptions at 5.65 ppm (doublet C-5 hydrogen), 5.20 ppm (singlet, C-3 hydrogen), 4.70 ppm (doublet, C-6 hydrogen), 1.65 ppm (singlet, C-2 methyl hydrogens) and 1.10 ppm (singlet, C-2 methyl hydrogens).

ued for a further 1 hour at ambient temperature. At this point, 25 ml. of water is added, followed by sufficient 1 N sodium hydroxide to bring the pH of the aqueous phase to 10. The chloroform layer is separated off, washed with water, dried using sodium sulfate, and evaporated to dryness in vacuo. The oily residue (2.3 g.) is dissolved in a small volume of chloroform and absorbed on a column of 30 g. of chromatographic silica gel. The column is eluted with chloroform, taking 50-ml. fractions. Fractions 13 to 19 are combined and concentrated in vacuo to give 0.71 g. of 6-(triphenylmethylamino)-2,2-dimethyl-3-(1-[4-hydroxybenzyl]tetrazol-5-yl)penam. The infrared spectrum of the product (in $CHCl_3$) shows an absorption at 1780 $cm^{-1}$ (β-lactam). The NMR spectrum ($CDCl_3$) shows absorptions at 7.80–6.67 ppm (multiplet, 20H, aromatic hydrogens and phenolic hydrogen), 5.66–5.10 ppm (quarter, 2H, benzyl methylene hydrogens), 5.02 ppm (singlet, 1H, C-3 hydrogen), 4.60–4.20 ppm (multiplet, 2H, C-5 and C-6 hydrogen), 3.10 ppm (doublet, 1H, amine hydrogen), 1.44 ppm (singlet, 3H, C-2 methyl hydrogens) and 0.71 ppm (singlet, 3H, C-2 methyl hydrogens).

EXAMPLE XIV

The procedure of Example XIII is repeated, except that where necessary the triphenylmethyl chloride is replaced by the appropriately-substituted triphenylmethyl chloride, and where necessary the 4-hydroxybenzylamine is replaced by the requisite amine, to produce the following congeners:

6-(triphenylmethylamino)-2,2-dimethyl-3-(1-[2-hydroxybenzyl]tetrazol-5-yl)penam,
6-(triphenylmethylamino)-2,2-dimethyl-3-(1-[3-hydroxybenzyl]tetrazol-5-yl)penam,
6-(diphenyl-[3-methoxyphenyl]methylamino)-2,2-dimethyl-3-(1-[4-hydroxybenzyl]tetrazol-5-yl)penam,
6-(di[4-chlorophenyl]phenylmethylamino)-2,2-dimethyl-3-(1-[4-hydroxybenzyl]tetrazol-5-yl)penam,
6-(tri[4-tolyl]methylamino)-2,2-dimethyl-3-(1-[4-hydroxybenzyl]tetrazol-5-yl)penam, and
6-(triphenylmethylamino)-2,2-dimethyl-3-(1-[4-hydroxy-3-methylbenzyl]tetrazol-5-yl)penam,
respectively.

EXAMPLE XV

6-(Triphenylmethylamino)-2,2-dimethyl-3-(1-[5-methylfurfuryl]tetrazol-5-yl)penam The title compound is prepared according to the procedure of Example XI, but using 5-methylfurfurylamine in place of furfurylamine. The NMR spectrum ($CDCl_3$) of the product shows absorptions at 7.36 ppm (m, 15H), 6.33 ppm (m, 1H), 5.93 ppm (m, 1H), 5.50 ppm (s, 2H), 5.20 ppm (s, 1H), 4.50 ppm (m, 2H), 3.23 ppm (d, 1H), 2.26 ppm (s, 3H), 1.63 (ppm (s, 3H) and 0.90 ppm (m, 3H).

EXAMPLE XVI

6-(Triphenylmethylamino)-2,2-dimethyl-3-(1-[2,4-dimethoxybenzyl]tetrazol-5-yl)penam.

The title compound is prepared in 46% overall yield from 6-(triphenymethylamino)penicillanic, by replacing the furfurylamine of Example XI by 2,4-dimethoxybenzylamine. The crude product is purified by recrystallization from a mixture of methylene chloride and methanol. The NMR spectrum of the product ($CDCl_3$) shows absorptions at 7.40 ppm (m, 16H), 6.45 ppm (m, 2H), 5.40 ppm (s, 2H), 4.50 ppm (m, 2H), 3.75 ppm (s, 3H), 3.70 ppm (s, 3H), 1.55 ppm (s, 3H) and 0.90 (s, 3H).

EXAMPLE XVII

6-Amino-2,2-dimethyl-3-(1-[4-methoxybenzyl]tetrazol-5-yl)penam p-toluenesulfonate To a stirred slurry of 143 g. of 6-(triphenylmethylamino)-2,2-dimethyl-3-(1-[4-methoxybenzyl]tetrazol-5-yl)penam in 1,000 ml. of dry acetone is added 45.0 g. of p-toluenesulfonic acid monohydrate, at ambient temperature. The solids slowly dissolve, giving a clear solution. After about 15 minutes, the product starts to precipitate. Stirring is continued for a further 45 minutes after the product starts to appear, and then a first crop of product is filtered off and washed with chloroform. The acetone is evaporated to dryness, and the solid residue is slurried for 45 minutes in 300 ml. of chloroform. This affords a second crop of product. The two crops are combined, slurried for 1 hour in 1,000 ml. of chloroform, filtered off, and dried in vacuo giving 123 g. of 6-amino-2,2-dimethyl-3-(1-[4-methoxybenzyl]-tetrazol-5-yl)penam p-toluenesulfonate, m.p. 174°–175.5° C. The infrared spectrum (KBr disc) of the product shows an absorption band at 1795 $cm^{-1}$. The NMR spectrum (in DMSO-$d_6$) shows absorption bands at 7.20 ppm (multiplet, aromatic hydrogens), 5.80 ppm (multiplet, benzyl hydrogens, C-5 hydrogen and C-3 hydrogens), 5.20 ppm (doublet, C-6 hydrogen), 3.75 ppm (singlet, methoxy hydrogens, 2.35 ppm (singlet, sulfonate methyl hydrogens), 1.70 ppm (singlet, C-2 methyl hydrogens) and 0.85 ppm (singlet, C-2 methyl hydrogens).

EXAMPLE XVIII

By reacting the appropriate 6-(triphenylmethylamino)-2,2-dimethyl-3-(1-substituted tetrazol-5-yl)penam or 6-(substituted triphenylmethylamino)-2,2-dimethyl-3-(1-substituted tetrazol-5-yl)penam, chosen from those in Examples V to VIII and X to XVI, with p-toluenesulfonic acid, according to the procedure of Example XVII, the following compounds are obtained as their p-toluenesulfonate salts:

6-amino-2,2-dimethyl-3-(1-benzyltetrazol-5-yl)penam,
6-amino-2,2-dimethyl-3-(1-[2-methoxybenzyl]tetrazol-5-yl)penam,
6-amino-2,2-dimethyl-3-(1-[4-isopropoxybenzyl]tetrazol-5-yl)penam,
6-amino-2,2-dimethyl-3-(1-[3-chlorobenzyl]tetrazol-5-yl)penam,
6-amino-2,2-dimethyl-3-(1-[3-chloro-4-methoxybenzyl]-tetrazol-5-yl)penam,
6-amino-2,2-dimethyl-3-(1-furfuryltetrazol-5-yl)penam,
6-amino-2,2-dimethyl-3-(1-[4-ethoxybenzyl]tetrazol-5-yl)penam,
6-amino-2,2-dimethyl-3-(1-[4-phenylbenzyl]tetrazol-5-yl)penam,
6-amino-2,2-dimethyl-3-(1-[2-thienylmethyl]tetrazol-5-yl)penam,
6-amino-2,2-dimethyl-3-(1-[3-tolyl]tetrazol-5-yl)penam,
6-amino-2,2-dimethyl-3-(1-[2,4-dimethoxybenzyl]tetrazol-5-yl)penam,
6-amino-2,2-dimethyl-3-(1-[4-n-hexyloxybenzyl]tetrazol-5-yl)penam,
6-amino-2,2-dimethyl-3-(1-[4-fluorobenzyl]tetrazol-5-yl)penam,
6-amino-2,2-dimethyl-3-(1-[3,4-dimethoxybenzyl]tetrazol-5-yl)penam,

EXAMPLE XXIV

Reaction of the p-toluenesulfonate salt of a 6-amino-2,2-dimethyl-3-(1-substituted-tetrazol-5-yl)penam, selected from:

6-amino-2,2-dimethyl-3-(1-[2-methoxybenzyl]tetrazol-5-yl)penam,
6-amino-2,2-dimethyl-3-(1-[4-isopropoxybenzyl]tetrazol-5-yl)penam,
6-amino-2,2-dimethyl-3-(1-[3-chloro-4-methoxybenzyl]-tetrazol-5-yl)penam,
6-amino-2,2-dimethyl-3-(1-furfuryltetrazol-5-yl)penam,
6-amino-2,2-dimethyl-3-(1-[4-ethoxybenzyl]tetrazol-5-yl)penam,
6-amino-2,2-dimethyl-3-(1-[4-phenylbenzyl]tetrazol-5-yl)penam,
6-amino-2,2-dimethyl-3-(1-[2-thienylmethyl]tetrazol-5-yl)penam,
6-amino-2,2-dimethyl-3-(1-[4-n-hexyloxybenzyl]tetrazol-5-yl)penam,
6-amino-2,2-dimethyl-3-(1-[3,4-dimethoxybenzyl]tetrazol-5-yl)penam,
6-amino-2,2-dimethyl-3-(1-[5-methyl-2-thienyl]tetrazol-5-yl)penam,
6-amino-2,2-dimethyl-3-(1-[5-methylfurfuryl]tetrazol-5-yl)penam,
6-amino-2,2-dimethyl-3-(1-[4-biphenylmethyl]tetrazol-5-yl)penam,
6-amino-2,2-dimethyl-3-(1-[2,4-dimethoxybenzyl]tetrazol-5-yl)penam,
6-amino-2,2-dimethyl-3-(1-[4-hydroxybenzyl]tetrazol-5-yl) penam,
6-amino-2,2-dimethyl-3-(1-[2-hydroxybenzyl]tetrazol-5-yl)penam, with trifluoroacetic acid and anisole, according to the procedure of Example XXIII, produces 6-amino-2,2-dimethyl-3-(5-tetrazolyl)penam in each case.

EXAMPLE XXV 6-(Triphenylmethylamino)-2,2-dimethyl-3-(5-tetrazolyl)penam

To a stirred solution of 1.69 g. (3 m mole) of 6-(triphenylmethylamino)-2,2-dimethyl-3-(N-[4-hydroxybenzyl]carbamoyl)penam prepared as described in Example XIII in 9 ml. of chloroform is added 1 ml. (12 mmole) of pyridine. The solution is cooled to ca. 4° C. in an ice-bath and 0.80 ml. of chlorotrimethylsilane is added. The solution is stirred for 40 minutes at ambient temperature, and then it is again cooled to ca. 4° C. Phosgene (1.5 ml. of a 4.3 M solution in chloroform 6.45 mmole) is added and the cooling bath is removed. Stirring is continued for a further 1.5 hours, and then all the volatile components are removed by evaporation in vacuo. The oily residue is redissolved in 6 ml. of chloroform and the solution is cooled to ca. 4° C. in an ice-bath. To the stirred solution is added 0.95 g. (6 mmole) of tetramethylguanidinium azide, and then stirring is continued for a further 1 hour at ambient temperature. At this point, 25 ml. of water is added, followed by sufficient 1 N sodium hydroxide to bring the pH of the aqueous phase to 10. The chloroform layer is removed, washed with water, dried using sodium sulfate, and evaporated to dryness in vacuo. This affords crude 6-(triphenylmethylamino)-2,2-dimethyl-3-(1-[4-trimethylsilyloxybenzyl]tetrazol-5-yl)penam, which is purified by chromatography on silica gel using chloroform as eluant.

To a stirred solution of 200 mg. of the purified trimethylsilyloxybenzyl derivative, in 4 ml. of tetrahydrofuran, is added 0.3 ml. of 1.0 N sodium hydroxide. The solution is stirred at ambient temperature for 50 minutes, and then the pH is adjusted to 5.7 using 5% hydrochloric acid. The solvent is removed by evaporation in vacuo to yield crude 6-(triphenylmethylamino)-2,2-dimethyl-3-(5-tetrazolyl)penam.

EXAMPLE XXVI

When the procedure of Example XXV is repeated, but using as starting material 6-(triphenylmethylamino)-2,2-dimethyl-3-(N-[2-hydroxybenzyl]carbamoyl)penam, there is produced 6-(triphenylmethylamino)-2,2-dimethyl-3-(5-tetrazolyl)penam.

The 6-(triphenylmethylamino)-2,2-dimethyl-3-(N-[2-hydroxybenzyl]carbamoyl)penam is prepared according to the procedure of Example XIII, Part A, but using 2-hydroxybenzylamine in place of 4-hydroxybenzylamine.

EXAMPLE XXVII

Starting with the appropriate 6-(substituted triphenylmethylamino)-2,2-dimethyl-3-(N-[4-hydroxybenzyl]carbamoyl)penam, and following the procedure of Example XXV, there is obtained the following congeners:

6-(diphenyl-[3-methoxyphenyl]methylamino)-2,2-dimethyl-3-(5-tetrazol-5-yl)penam,
6-(diphenyl-[2-fluorophenyl]methylamino)-2,2-dimethyl-3-(5-tetrazol-5-yl)penam,
6-(di[4-chlorophenyl]phenylmethylamino)-2,2-dimethyl-3-(5-tetrazol-5-yl)penam and
6-(tri[4-tolyl]methylamino)-2,2-dimethyl-3-(5-tetrazolyl)penam, respectively.

The starting materials used in this Example are prepared by the method of Example XIII, Part A, but using the appropriately-substituted triphenylmethyl chloride.

EXAMPLE XXVIII 6-(Triphenylmethylamino)-2,2-dimethyl-3-(1-[ethoxycarbonyl]tetrazol-5-yl)penam (A)

6-(Triphenylmethylamino)-2,2-dimethyl-3-(N-ethoxycarbonylcarbamoyl)penam.

To a stirred solution of 4.58 g. (10 mmole) 6-(triphenylmethylamino)penicillanic acid and 1.45 ml. (10 mmole) of triethylamine, in 75 ml. of acetonitrile, is added 1.15 g. (10 mmole) of ethoxycarbonyl isocyanate dissolved in 5 ml. of acetonitrile. The resulting solution is stirred at ca. 25° C. for 16 hours, and then the solvent is removed by evaporation in vacuo. The residue is re-dissolved in chloroform, and the chloroform solution is washed successively with water, sodium bicarbonate solution and sodium chloride solution. The chloroform solution is then dried using anhydrous magnesium sulfate, and evaporated in vacuo. The residue is again re-dissolved in chloroform, and the chloroform solution is washed with dilute hydrochloric acid, dried using magnesium sulfate, and again evaporated in vacuo. This affords the crude product, which is purified by chromatography using silica gel as the adsorbant and eluting the column with chloroform containing 4% by volume of ethanol. The final yield of 6-(triphenylmethylamino)-2,2-dimethyl-3-(N-[ethoxycarbonyl]carbamoyl)-penam is 2.54 g. (48% yield).

(B)
6-(Triphenylmethylamino)-2,2-dimethyl-3-(1-[ethoxycarbonyl]tetrazol-5-yl)penam To a stirred solution of 529 mg. (1 mmole) of 6-triphenylmethylamino)-2,2-dimethyl-3-(N-[ethoxycarbonyl]carbamoyl)penam and 240 mg. (3 mmole) of pyridine, in 25 ml. of methylene chloride, is added 208 mg. (1 mmole) of phosphorus pentachloride, at 0° C. The reaction mixture is stirred at 0° C. for 0.5 hour and then at ca. 25° C. for 2 hours. The solvents and the excess pyridine are then removed by evaporation in vacuo, and the residue is re-dissolved in 15 ml. of chloroform. The latter chloroform solution is cooled to 0° C., and 0.47 g. (3 mmole) of tetramethylguanidinium azide is added in several small portions with stirring. Stirring is continued for 2 hours at ambient temperature, and then to the reaction mixture is added a further 15 ml. of chloroform followed by 30 ml. of water. The pH is adjusted to 6.5, and then the chloroform layer is removed. The chloroform solution is washed with water followed by brine, and then it is dried using anhydrous sodium sulfate. Removal of the solvent by evaporation in vacuo affords crude 6-(triphenylmethylamino)-2,2-dimethyl-3-(1-[ethoxycarbonyl]tetrazol-5-yl)penam. The crude product is purified further by chromatography using silica gel.

EXAMPLE XXIX

Starting with 6-(triphenylmethylamino)penicillanic acid, or the appropriately-substituted 6-(triphenylmethylamino)penicillanic acid, and the requisite isocyanate of formula $R^{14}O—C(=O)—N=C=O$, and following the procedure of Example XXVIII, the following compounds are prepared:

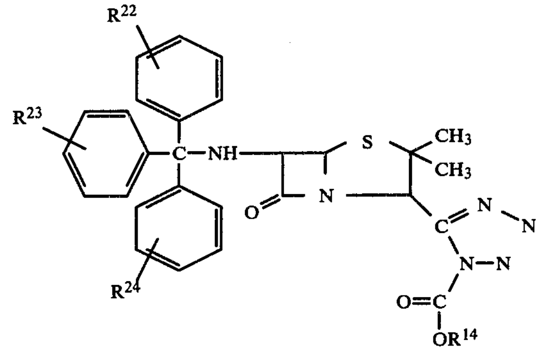

| $R^{22}$ | $R^{23}$ | $R^{24}$ | $R^{14}$ |
|---|---|---|---|
| H | H | H | $CH_3$ |
| H | H | H | $CH_3CH_2CH_2$ |
| H | H | H | $(CH_3)_2CHCH_2$ |
| H | H | H | $CH_3(CH_2)_4CH_2$ |
| H | H | H | $C_6H_5CH_2$ |
| H | H | H | $4\text{-}O_2NC_6H_4$ |
| H | H | H | $2\text{-}FC_6H_4$ |
| H | H | H | $3\text{-}BrC_6H_4$ |
| H | H | H | $C_6H_5$ |
| H | H | H | $4\text{-}(CH_3[CH_2]_2CH_2)C_6H_4$ |
| H | H | H | $3\text{-}CH_3OC_6H_4$ |
| H | H | H | $4\text{-}([CH_3]_2CHO)C_6H_4$ |
| H | H | H | $2,4\text{-}Cl_2C_6H_3$ |
| H | H | H | $3,4\text{-}(CH_3CH_2O)_2C_6H_3$ |
| H | H | H | $3,5\text{-}(CH_3)_2C_6H_3$ |
| H | H | H | $4\text{-}Cl\text{-}3\text{-}CH_3C_6H_3$ |
| $3\text{-}CH_3$ | H | H | $4\text{-}(CH_3CH_2CH_2O)\text{-}2\text{-}O_2NC_6H_3$ |
| $4\text{-}CH_3CH_2CH_2$ | H | H | $4\text{-}(CH_3[CH_2]_2CH_2O)C_6H_4$ |
| 4-Br | H | H | $CH_3CH_2$ |
| 2-F | H | H | $C_6H_5CH_2$ |
| $3\text{-}C_6H_5$ | H | H | $C_6H_5$ |
| $3\text{-}CH_3CH_2O$ | H | H | $4\text{-}O_2NC_6H_4$ |
| 4-Cl | 4-Cl | H | $2,4\text{-}(O_2N)_2C_6H_3$ |
| $4\text{-}CH_3$ | $3\text{-}CH_3O$ | $3\text{-}CH_3O$ | $CH_3CH_2$ |
| $4\text{-}CH_3$ | $4\text{-}CH_3$ | $4\text{-}CH_3$ | $C_6H_5$ |

EXAMPLE XXX

Starting with 6-(triphenylmethylamino)penicillanic acid, or the appropriately-substituted 6-(triphenylmethylamino)penicillanic acid, and the requisite isocyanate of formula $R^{14}—SO_2—N=C=O$, and following the procedure of Example XXVIII, the following compounds are prepared:

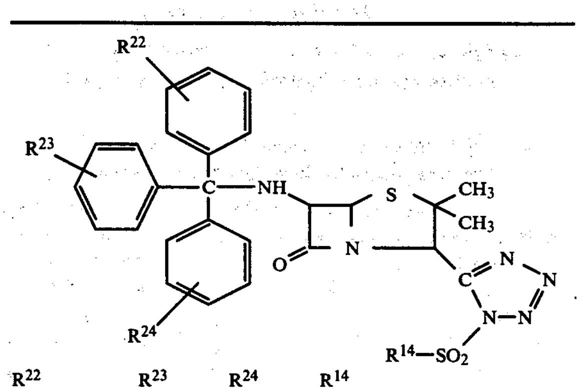

| $R^{22}$ | $R^{23}$ | $R^{24}$ | $R^{14}$ |
|---|---|---|---|
| H | H | H | $CH_3$ |
| H | H | H | $CH_3CH_2$ |
| H | H | H | $(CH_3)_2CHCH_2$ |
| H | H | H | $C_6H_5CH_2$ |
| H | H | H | $C_6H_5$ |
| H | H | H | $4\text{-}O_2NC_6H_4$ |
| H | H | H | $3\text{-}FC_6H_4$ |
| H | H | H | $2\text{-}ClC_6H_4$ |
| H | H | H | $4\text{-}BrC_6H_4$ |
| H | H | H | $2\text{-}(CH_3CH_2)C_6H_4$ |
| H | H | H | $3\text{-}(CH_3CH_2CH_2CH_2)C_6H_4$ |
| H | H | H | $4\text{-}CH_3OC_6H_4$ |
| H | H | H | $3\text{-}([CH_3]_2CHCH_2O)C_6H_4$ |
| H | H | H | $2,4\text{-}Cl_2C_6H_3$ |
| H | H | H | $3\text{-}CH_3\text{-}4\text{-}CH_3OC_6H_3$ |
| H | H | H | $2,4\text{-}(O_2N)_2C_6H_3$ |
| H | H | H | $2\text{-}CH_3O\text{-}5\text{-}O_2NC_6H_3$ |
| $2\text{-}CH_3$ | H | H | $CH_3$ |
| $3\text{-}CH_3CH_2$ | H | H | $C_6H_5CH_2$ |
| 3-Cl | H | H | $4\text{-}O_2NC_6H_4$ |
| $4\text{-}CH_3O$ | H | H | $C_6H_5$ |
| $4\text{-}C_6H_5$ | H | H | $CH_3CH_2$ |
| 3-Cl | 3-Cl | H | $4\text{-}ClC_6H_4$ |
| $3\text{-}CH_3O$ | $3\text{-}CH_3O$ | $3\text{-}CH_3O$ | $2,4\text{-}(O_2N)_2C_6H_3$ |

Example XXXI 6-(Triphenylmethylamino)-2,2-dimethyl-3-(5-tetrazolyl)penam

To a stirred mixture of 2 ml. of tetrahydrofuran and 4 ml. of water is added 150 mg. of 6-(triphenylmethylamino)-2,2-dimethyl-3-(1-[ethoxycarbonyl]tetrazol-5-yl)penam. The pH of the mixture is adjusted to 9.5, and stirring is continued at that pH for a further 30 minutes, at ambient temperature. The bulk of the tetrahydrofuran is removed by evaporation in vacuo, and the residue is portioned between water and ethyl acetate at pH 9. The ethyl acetate is removed and discarded. Fresh ethyl acetate is added and the pH is adjusted to 2.0. The ethyl acetate layer is removed, washed with water, dried using anhydrous sodium sulfate, and evaporated in vacuo to give the crude title compound.

EXAMPLE XXXII

Reaction of any of the 6-(triphenylmethylamino)-2,2-dimethyl-3-(1-substituted tetrazol-5-yl)penam or 6-(substituted triphenylmethylamino)-2,2-dimethyl-3-(1-substituted tetrazol-5-yl)penam compounds, listed in Examples XXIX and XXX, with water at pH 9.5, according to the procedure of Example XXXI, results in removal of the C(=O)—O—$R^{14}$ or $SO_2$—$R^{14}$ group and its replacement by hydrogen. In this way, the following compounds are obtained:

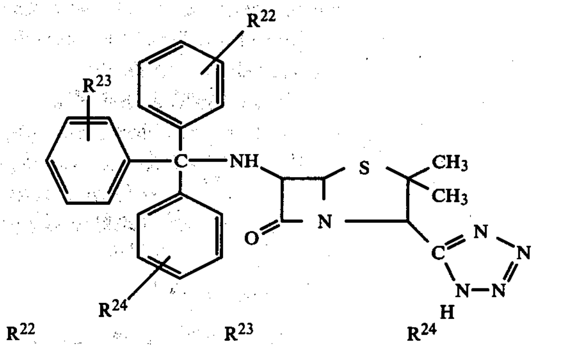

| $R^{22}$ | $R^{23}$ | $R^{24}$ |
|---|---|---|
| H | H | H |
| $3\text{-}CH_3$ | H | H |
| $4\text{-}CH_3CH_2CH_2$ | H | H |
| 4-Br | H | H |
| 2-F | H | H |
| $3\text{-}C_6H_5$ | H | H |
| $3\text{-}CH_3CH_2O$ | H | H |
| 4-Cl | 4-Cl | H |
| $4\text{-}CH_3$ | $3\text{-}CH_3O$ | $3\text{-}CH_3O$ |
| $4\text{-}CH_3$ | $4\text{-}CH_3$ | $4\text{-}CH_3$ |
| $2\text{-}CH_3$ | H | H |
| $3\text{-}CH_3CH_2$ | H | H |
| 3-Cl | H | H |
| $4\text{-}CH_3O$ | H | H |
| $4\text{-}C_6H_5$ | H | H |
| 3-Cl | 3-Cl | H |
| $3\text{-}CH_3O$ | $3\text{-}CH_3O$ | $3\text{-}CH_3O$ |

EXAMPLE XXXIII

6-Amino-2,2-dimethyl-3-(5-tetrazolyl)penam

To a slurry of dry acetone (5 ml.) and 6-triphenylmethylamino-2,2-dimethyl-3-(5-tetrazolyl)penam (483 mg., 1.0 mmole) at room temperature is added p-toluenesulfonic acid monohydrate (209 mg., 1.1 mmole). The resulting solution is stirred for 10 minutes, and then ether (30 ml.) is added over a five minute period. The mixture is stirred for ten minutes after which the solvent is decanted from the residue. The residue is dissolved in tetrahydrofuran (30 ml.) and placed on a column (300×6 mm.) packed with 10 g. of Florisil (synthetic magnesium silicate). The column is eluted with tetrahydrofuran until a total of 125 ml. is collected. The eluate is concentrated to dryness under reduced pressure at 40° C. to give 210 mg. of solid. The solid is slurried in ether (30 ml.), filtered, washed with ether and air-dried. Yield=121 mg. (50%). NMR (DMSO-$d_6$): 5.88 (s, 3H), 5.10 (s, 3H) 5.52 (d, 1H), 4.60 (d, 2H), 1.59 (s, 3H) and 1.08 ppm (s, 3H).

EXAMPLE XXXIV

When each of the 6-(substituted triphenylmethylamino)-2,2-dimethyl-3-(5-tetrazolyl)penam compounds described in Example XXXII is reacted with p-toluenesulfonic acid, according to the procedure of Example XXXIII, the product in each case is 6-amino-2,2-dimethyl-3-(5-tetrazolyl)penam.

EXAMPLE XXXV

6-Amino-2,2-dimethyl-3-(1-[ethoxycarbonyl]tetrazol-5-yl)penam

To a stirred solution of 554 mg. of 6-triphenylmethylamino-2,2-dimethyl-3-(1-[ethoxycarbonyl]tetrazol-5-yl)penam in 2 ml. of acetone is added a solution of 190 mg. of p-toluenesulfonic acid of 1 ml. of acetone. Stirring is continued for a further 3 hours, and then the acetone is removed by evaporation in vacuo. The residue is slurried in ether, filtered and dried, to give the title compound as its p-toluenesulfonate salt.

The above p-toluenesulfonate salt is added to a mixture of 15 ml. of water and 15 ml. of chloroform. The pH of the aqueous phase is adjusted to 7.0, and the chloroform layer is removed. The chloroform is dried using sodium sulfate, and then it is evaporated in vacuo to give the title compound as its free base.

EXAMPLE XXXVI

Reaction of the appropriate 6-(triphenylmethylamino)-2,2-dimethyl-3-(1-substituted tetrazol-5-yl)penam or 6-(substituted triphenylmethylamino)-2,2-dimethyl-3-(1-substituted tetrazol-5-yl)penam, chosen from those in Examples XXIX and XXX, with p-toluenesulfonic acid, according to the procedure of Example XXXV, provides the following compounds as their p-toluenesulfonate salts.

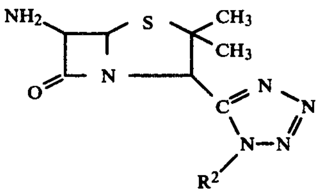

| $R^2$ |
| --- |
| $CO_2CH_3$ |
| $CO_2(CH_2CH_2CH_3)$ |
| $CO_2(CH_2CH[CH_3]_2)$ |
| $CO_2CH_2C_6H_5$ |
| $CO_2(4-C_6H_4NO_2)$ |
| $CO_2(2-C_6H_4F)$ |
| $CO_2(3-C_6H_4Br)$ |
| $CO_2C_6H_5$ |
| $CO_2(4-C_6H_4CH_2CH_2CH_2CH_3)$ |
| $CO_2(3-C_6H_4CH_3)$ |
| $CO_2(4-C_6H_4OCH[CH_3]_2)$ |
| $CO_2(2,4-C_6H_3Cl_2)$ |
| $CO_2(3,4-C_6H_3[OCH_2CH_3]_2)$ |
| $CO_2(3,5-C_6H_3[CH_3]_2)$ |
| $CO_2(C_6H_3-4-Cl-3-CH_3)$ |
| $CO_2(C_6H_3-4-[OCH_2CH_2CH_3]-2-NO_2)$ |
| $CO_2(4-C_6H_4OCH_2CH_2CH_2CH_3)$ |
| $CO_2(2,4-C_6H_3[NO_2]_2)$ |
| $SO_2CH_3$ |
| $SO_2CH_2CH_3$ |
| $SO_2(CH_2CH[CH_3]_2)$ |
| $SO_2CH_2C_6H_5$ |
| $SO_2C_6H_5$ |
| $SO_2(4-C_6H_4NO_2)$ |
| $SO_2(3-C_6H_4F)$ |
| $SO_2(2-C_6H_4Cl)$ |
| $SO_2(4-C_6H_4Br)$ |
| $SO_2(2-C_6H_4CH_2CH_3)$ |
| $SO_2(3-C_6H_4CH_2CH_2CH_2CH_3)$ |
| $SO_2(4-C_6H_4OCH_3)$ |
| $SO_2(3-C_6H_4OCH_2CH[CH_3]_2)$ |
| $SO_2(2,4-C_6H_3Cl_2)$ |
| $SO_2(C_6H_3-3-CH_3-4-OCH_3)$ |
| $SO_2(2,4-C_6H_3[NO_2]_2)$ |
| $SO_2(C_6H_3-2-OCH_3-2-NO_2)$ |

EXAMPLE XXXVII

6-(Triphenylmethylamino)-2,2-dimethyl-3-(1-[2-methoxycarbonylethyl]tetrazol-5-yl)penam

A. 6-(Triphenylmethylamino)-2,2-dimethyl-3-(N-[2-methoxycarbonylethyl]carbamoyl)penam To a stirred solution of 35 g. of 6-(triphenylmethylamino)penicillanic acid in 250 ml. of dry, ethanol-free chloroform, is added 11.7 ml. of triethylamine at 0°-3° C. The solution thus obtained is then added dropwise, with stirring, at 0°-6° C., to a second solution, prepared from 7.3 ml. of ethyl chloroformate in 155 ml. of dry, ethanol-free chloroform. Stirring is continued for a further 10 minutes. This affords a chloroform solution of the mixed anhydride of 6-(triphenylmethylamino)penicillanic acid.

In a separate flask, a solution of β-alanine methyl ester is prepared by adding 11.7 ml. of triethylamine to a slurry of 10.73 g. of β-alanine methyl ester hydrochloride and 2 g. of anhydrous sodium sulfate in 115 ml. of dry, ethanol-free chloroform, at ca. 10° C. Stirring is continued for a further 10 minutes.

The latter amino-ester solution is then added dropwise, with stirring at 3°-6° C., to the above-described mixed anhydride solution. After the end of the addition, stirring is continued for a further 2 hours.

At this point, the reaction solution is washed successively with three portions of water ane one portion of brine. The solution is then dried using anhydrous sodium sulfate, and evaporated in vacuo to give 40.1 g. of crude 6-(triphenylmethylamino)-2,2-dimethyl-3-(N-[2-methoxycarbonylethyl]carbamoyl)penam as a glassy solid, m.p. 60°-70° C. The crude product is purified by extracting it into refluxing ether, treating the filtered solution with activated carbon, and then re-precipitating the product by the addition of petroleum ether.

B. 6-(Triphenylmethylamino)-2,2-dimethyl-3-(1-[2-methoxycarbonylethyl]tetrazol-5-yl)penam To a stirred solution of 2 g. of the amide described under A above, in 5 ml. of dry, ethanol-free chloroform, is added, at ca. 0° C., 1.36 ml. of pyridine, followed by a solution of 620 mg. of phosgene in 4 ml. of dry, ethanol-free chloroform. The solution is stirred for 2.5 hours, at ambient temperature, and then the solvent is removed by evaporation in vacuo. The residue is re-dissolved in 9 ml. of dry, ethanol-free chloroform, and 580 mg. of tetramethylguanidinium azide is added. The reaction mixture is stirred for 45 minutes, at which point a further 200 mg. of tetramethylguanidinium azide is added. The reaction mixture is then stirred 18 hours to complete the conversion to tetrazole. To the reaction solution is then added saturated sodium bicarbonate solution, in sufficient quantity that the pH of the aqueous phase is 7.6. The chloroform layer is removed, washed with water at pH 5, washed with water at pH 7, dried using anhydrous sodium sulfate, and finally evaporated in vacuo. This affords 2.19 g. of crude product, which is recrystallized from methanol giving 1.11 g (48% yield) of product with m.p. 100°-105° C. The NMR spectrum ($CDCl_3$) shows absorptions at 7.40 ppm (m, 15H), 5.15 ppm (s, 1H), 3.80 (m, 4H), 3.70 ppm (s, 3H), 3.10 ppm (t, 2H), 1.70 ppm (s, 3H) and 1.17 ppm (s, 3H), and further indicates that the product contains methanol of solvation.

EXAMPLE XXXVIII

The procedure of Example XXXVII is repeated, except that where necessary the 6-(triphenylmethylamino)penicillanic acid is replaced by the appropriately-substituted 6(triphenylmethylamino)penicillanic acid, and where necessary the β-alanine methyl ester is replaced by the appropriate amine to produce the following compounds

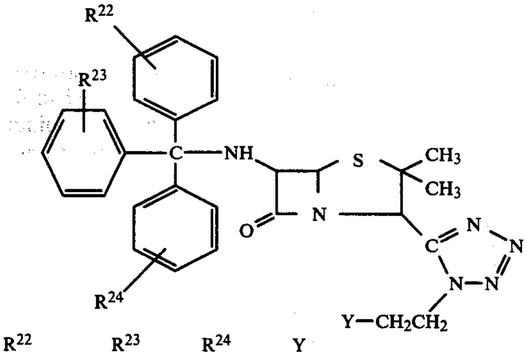

| $R^{22}$ | $R^{23}$ | $R^{24}$ | Y |
|---|---|---|---|
| H | H | H | $C(=O)OCH_2CH_3$ |
| H | H | H | $C(=O)OCH(CH_3)_2$ |
| H | H | H | $C(=O)OCH_2(CH_2)_4CH_3$ |
| H | H | H | $C(=O)OC_6H_5$ |
| H | H | H | $SO_2CH_3$ |
| H | H | H | $SO_2CH_2(CH_2)_2CH_3$ |
| H | H | H | $SO_2NHC_6H_5$ |
| H | H | H | $SO_2N(C_6H_5)_2$ |
| H | H | H | $SO_2N(CH_3)C_6H_5$ |
| H | H | H | $SO_2OCH_3$ |
| H | H | H | $SO_2OCH_2CH_3$ |
| H | H | H | $SO_2OCH_2CH(CH_3)_2$ |
| H | H | H | $SO_2C_6H_5$ |
| H | H | H | $SO_2NH_2$ |
| H | H | H | $SO_2NHCH_3$ |
| H | H | H | $SO_2N(CH_2CH_2CH_3)_2$ |
| H | H | H | $SO_2NHCH_2C_6H_5$ |
| H | H | H | CN |
| 2-F | H | H | $C(=O)OCH_3$ |
| 3-$CH_3O$ | H | H | $SO_2CH_2CH_3$ |
| 3-$C_6H_5$ | H | H | $SO_2NH(CH_2[CH_2]_2CH_3)$ |
| 3-Cl | 3-Cl | H | $C(=O)OCH_3$ |
| 4-$CH_3$ | 4-$CH_3$ | 4-$CH_3$ | $C(=O)OCH_2CH_3$ |

EXAMPLE XXXIX 6-(Triphenylmethylamino)-2,2-dimethyl-3-(1-[2-methoxycarbonylethyl]tetrazol-5-yl)penam To a stirred solution of 8 g. of 6-(triphenylmethylamino)-2,2-dimethyl-3-(N-[2-methoxycarbonylethyl]carbamoyl)penam (prepared as described in Example XXXVII, Part A) in 20 ml. of dry, ethanol-free chloroform, is added 5.4 ml. of pyridine. To this solution is then added a solution of 2.7 g. of phosgene in 16 ml. of dry, ethanol-free chloroform, at ca. 0° C. The reaction mixture is stirred at ambient temperature for 1.5 hours, and then the solvent is removed by evaporation in vacuo. The viscous residue is re-dissolved in 36 ml. of dry chloroform, the solution is cooled to ca 0° C., and 2.6 ml. of trimethylsilyl azide is added. The reaction mixture is stirred at ambient temperature for 17 hours. At this point 1.26 g. of solid sodium bicarbonate is added to the chloroform solution, followed by sufficient aqueous saturated sodium bicarbonate to give a pH of 7.6. The chloroform is separated, washed with water, washed with brine, dried using anhydrous sodium sulfate, treated with 200 mg. of activated carbon, and finally evaporated in vacuo. The residue is triturated with cyclohexane, and then recrystallized from methanol, giving 3.85 g. (46% yield) of the title compound, m.p. 94°-98° C. After further recrystallization of the product from methanol, the melting point is raised to 104°-106° C. The NMR spectrum ($CDCl_3$) shows absorptions at 7.40 ppm (m, 15H), 5.15 ppm (s, 1H), 3.80 ppm (m, 4H), 3.70 ppm (s, 3H), 3.10 ppm (t, 2H), 1.70 ppm (s, 3H) and 1.17 ppm (s, 3H), and further indicates that the product contains ca. 3% of methanol of solvation.

EXAMPLE XL 6-(Triphenylmethylamino)-2,2-dimethyl-3-(5-tetrazolyl)penam

To a stirred solution of 600 mg. of 6-(triphenylmethylamino)-2,2-dimethyl-3-(1-[2-methoxycarbonylethyl]tetrazol-5-yl)penam (containing ca 4.5% of methanol) in 1 ml. of chloroform, is added a solution of 375.2 mg. of diazabicyclo[4.3.0]non-5-ene in 0.5 ml. of chloroform. Stirring is continued for a further 3 hours, and then the solution is diluted with a further 2 ml. of chloroform. The latter solution is washed quickly with 5 ml. of 2 N hydrochloric acid, and then a further 5 ml. of 2 N hydrochloric are added. The resulting mixture is cooled to ca 0° C., and the solid which precipitates is filtered off, giving 323 mg. (71% yield) of the title compound. The NMR spectrum (DMSO-$d_6$) of the product shows absorptions at 7.40 ppm (m, 15H), 5.30 ppm (s, 1H), 4.60 ppm (m, 2H), 1.58 ppm (s, 3H) and 0.78 ppm (s, 3H).

EXAMPLE XLI

Reaction of any of the 6-(triphenylmethylamino)-2,2-dimethyl-3-(1-substituted tetrazol-5-yl)penam or 6-(substituted triphenylmethylamino)-2,2-dimethyl-3-(1-substituted tetrazol-5-yl)penam compounds, listed in Example XXXVIII, with diazabicyclo[4.3.0]non-5-ene, according to the procedure of Example XL, results in removal of the 2-substituted ethyl substituent from the tetrazole ring, and its replacement by hydrogen. In this way, the following compounds are obtained:

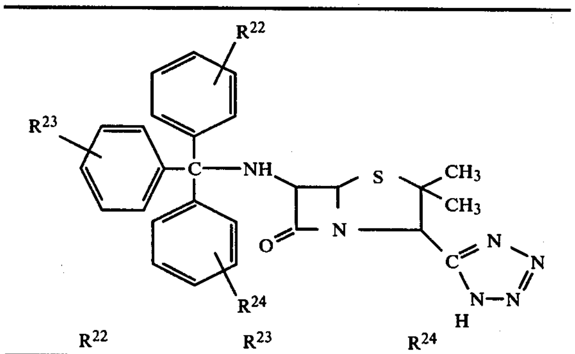

| $R^{22}$ | $R^{23}$ | $R^{24}$ |
|---|---|---|
| H | H | H |
| 2-F | H | H |
| 3-$CH_3O$ | H | H |
| 3-$C_6H_5$ | H | H |
| 3-Cl | 3-Cl | H |
| 4-$CH_3$ | 4-$CH_3$ | 4-$CH_3$ |

The above 6-(substituted triphenylmethylamino)-2,2-dimethyl-3-(5-tetrazolyl)penam compounds are converted into 6-amino-2,2-dimethyl-3-(5-tetrazolyl)penam by reaction with p-toluenesulfonic acid, according to the procedure of Example XXXIII.

EXAMPLE XLII

6-(2-Phenylacetamido)-2,2-dimethyl-3-(5-tetrazolyl)penam

A flask containing 965 mg. of 6-amino-2,2-dimethyl-3-(1-[4-methoxybenzyl]tetrazol-5-yl)penam p-toluenesulfonate, 40 drops of anisole, and 5 ml. of trifluoroacetic acid is immersed in a water-bath maintained at 35°-40° C. The progress of the reaction is followed by removing samples at intervals, and recording their nuclear magnetic resonance spectra. After about 25 minutes, the removal of the 4-methoxybenzyl group is found to be approximately 90% complete. At this point the reaction solution is added to a rapidly-stirred, ice-cold solution of 10 ml. of pyridine in 50 ml. of chloroform. Stirring is continued for 5 minutes, and then 0.24 ml. of phenylacetyl chloride is added. The cooling bath is removed and the reaction mixture is stirred for a further 20 minutes. A 100-ml. portion of water is added, and the pH of the aqueous phase is then adjusted to 2.5 by the dropwise addition of 0.5 N hydrochloric acid. The chloroform layer is separated off, washed with saturated brine, dried using anhydrous sodium sulfate and then it is evaporated to dryness in vacuo. The crude product thus obtained is re-dissolved in chloroform, and the solution is divided into two equal portions. To one of these portions is added an equal volume of water. The layers are stirred vigorously and the pH of the aqueous phase is raised to 6.9 by the dropwise addition of 0.1 N sodium hydroxide solution. The chloroform is separated off and discarded, and then an equal quantity of fresh chloroform is added to the aqueous phase. The layers are stirred vigorously and the pH is adjusted to 2.5 using dilute hydrochloric acid. The chloroform is separated off, washed with saturated brine, dried using anhydrous magnesium sulfate and then evaporated to dryness in vacuo.

This affords 197 mg. of an oily residue. The residue is re-dissolved in 3 ml. of chloroform which is then added dropwise to 30 ml. of hexane. The fluffy white solid which precipitates is filtered off, giving 80 mg. of 6-(2-phenylacetamido)-2,2-dimethyl-3-(5-tetrazolyl)penam. IR(KBr disc): 1795, 1660 and 1510 $cm^{-1}$. NMR (in $CDCl_3$): 7.20 (broad s,5H), 5.55 (m,2H), 5.15 (s,1H), 3.60 (broad s,2H), 1.40 (s,3H) and 1.05 ppm (s,3H).

EXAMPLE XLIII

6-(2-Phenylacetamido)-2,2-Dimethyl-3-(5-Tetrazolyl)Penam

A mixture of p-toluenesulfonic acid monohydrate (788 mg., 4.14 mmoles), acetone (35 ml.) and 6-triphenylmethylamino-2,2-dimethyl-3-(5-tetrazolyl)penam (2.0 g., 4.14 mmole) is stirred for twenty minutes at room temperature and is then diluted with water (100 ml.) and isopropylether (100 ml.). The biphasic mixture is stirred vigorously and adjusted to pH 7 with 2 N sodium hydroxide. Phenylacetyl chloride (700 mg., 4.55 mmole freshly distilled) is added and the reaction mixture maintained at pH 5.5-6.5 by addition of 2 N sodium hydroxide as necessary. Reaction is continued until the pH levels off at 6.5. The two phases are separated and the aqueous phase is washed with ether (2×50 ml.). Chloroform (100 ml.) is added and the pH is adjusted to 2 by addition of 6 N HCl. The mixture is stirred, the phases separated and the aqueous phase extracted with chloroform (2×50 ml.). The chloroform phases are combined, dried ($Na_2SO_4$), and then concentrated under reduced pressure to about 50 ml. volume. A 1:1 solution of ether-hexane is added dropwise with vigorous stirring until precipitation of the product is complete. The white precipitate is filtered and air-dried. The yield is 850 mg. (57.4%), m.p. 168°-170°. NMR (DMSO-$d_6$): 7.30 (s, 5H), 5.80-5.42 (m, 2H), 5.28 (s, 1H), 3.60 (s, 2H), 1.68 (s, 3H) and 1.10 ppm (s, 3H).

EXAMPLE XLIV

6-(3-[2-Chlorophenyl]-5-methyl-4-isoxazolecarboxamido)-2,2-dimethyl-3-(5-tetrazolyl)penam A stirred slurry of 240 mg. of 6-amino-2,2-dimethyl-3-(5-tetrazolyl)-penam in 10 ml. of water is cooled to 0° C., and then the pH is adjusted to 7.1 using 1 N sodium hydroxide. The resultant solution is diluted with 10 ml. of acetone, and then a solution of 281 mg. of 3-(2-chlorophenyl)-5-methylisoxazole-4-carbonyl chloride (Doyle, et al., *Journal of the Chemical Society* [London], 5838 [1963]) in 10 ml. of dry acetone is added portionwise during 3-4 minutes. During the addition the pH of the solution is maintained in the range from 5.5 to 6.5 by adding 0.1 N sodium hydroxide. At the end of the addition the reaction is stirred an additional 15 minutes at about 0° C. At this point, the acetone is removed by evaporation under reduced pressure at about 15° C., the resultand aqueous phase is filtered and the pH is lowered to 2 with dilute hydrochloric acid. The product is extracted into chloroform. The extract is dried using anhydrous sodium sulfate, and then it is evaporated in vacuo to give the crude product as a gum. The gum is re-dissolved in 3 ml. of tetrahydrofuran, and then the solution is added to 15 ml. of water at 10° C. The pH of the solution is raised to 7.0 by the addition of 0.1 N sodium hydroxide, the solution is filtered, and then it is lyophilized. This affords 430 mg. of the sodium salt of 6-(3-[2-chlorophenyl]-5-methyl-4-isoxazolecarboxamido)-2,2-dimethyl-3-(5-tetrazolyl)penam as an amorphous solid. The infrared spectrum (KBr disc) of the product shows absorption bands at 1770 $cm^{-1}$ (β-lactam carbonyl), 1650 $cm^{-1}$ (amide I band) and 1520 $cm^{-1}$ (amide II band). The NMR spectrum (in $CDCl_3$) shows absorption bands at 7.40 ppm (multiplet, aromatic hydrogens), 5.90 and 5.60 (2 doublets, C-5 and C-6 hydrogens), 5.15 ppm (singlet, C-3 hydrogen), 2.80 ppm (singlet, isoxazole methyl hydrogens), 1.50 ppm (singlet, C-2 methyl hydrogens) and 1.05 ppm (singlet, C-2 methyl hydrogens).

EXAMPLE XLV

When the procedure of Example XLIV is repeated, and the 3-(2-chlorophenyl)-5-methylisoxazole-4-carbonyl chloride used therein is replaced by 3-phenyl-5-methylisoxazole-4-carbonyl chloride, 3-(2,6-dichlorophenyl)-5-methylisoxazole-4-carbonyl chloride and 3-(2-chloro-6-fluorophenyl)-5-methylisoxazole-4-carbonyl chloride, respectively, there is produced:

6-(3-phenyl-5-methyl-4-isoxazolecarboxamido)-2,2-dimethyl-3-(5-tetrazolyl)penam, 6-(3-[2,6-dichlorophenyl]-5-methyl-4-isoxazolecarboxamido)-2,2-dimethyl-3-(5-tetrazolyl)penam, and 6-(3-[2-chloro-6-fluorophenyl]-5-methyl-4-isoxazolecarboxamido)-2,2-dimethyl-3-(5-tetrazolyl)penam, respectively.

The starting acid chlorides used in this experiment are prepared by the action of thionyl chloride on the corresponding acids, which in turn are prepared by the published methods (Long, et al., *Journal of the Chemical Society* [London], 5838 [1963]; U.S. Pat. No. 2,996,501).

EXAMPLE XLVI

6-(2-Azido-2-phenylacetamido)-2,2-dimethyl-3-(5-tetrazolyl)penam

A solution of 1.61 grams (9.1 mmole) of 2-azido-2-phenylacetic acid [Forster and Mueller, *J. Chem. Soc.*, 97, 138 (1910)] and 5 ml. of thionyl chloride is heated under reflux for hour. The reaction solution is evaporated under reduced pressure to furnish a residue of 2-azido-2-phenylacetyl chloride which is dissolved in 10 ml. of dichloromethane and is added over 5 minutes to a stirred ice-bath cooled solution of 2.4 grams (10 mmole) of 6-amino-2,2-dimethyl-3-(5-tetrazolyl)penam, 2.02 grams (20 mmole) of triethylamine and 50 ml. of dichloromethane. After 30 minutes the reaction solution is allowed to warm to room temperature. After a further 3 hours, the more volatile components of the solution are evaporated under reduced pressure and the residue is taken up in 50 ml. of water. The aqueous solution is washed twice with 25 ml. portions of ethyl acetate, and it is then adjusted to pH 2.5 by the careful addition of 6 N hydrochloric acid. The resulting cloudy mixture is extracted twice with 30 ml. portions of ethyl acetate. After being dried using anhydrous sodium sulfate, the combined extracts are filtered and the solvent is evaporated in vacuo. The residue is dissolved in 10 ml. of dichloromethane; 1.0 ml. of triethylamine is added, and the resulting solution is poured into 350 ml. of rapidly stirred diethyl ether. The solid which precipitates is filtered off giving 1.62 g. (38% yield) of the title compound as its triethylamine salt. IR (KBr disc): 1792 $cm^{-1}$ ($\beta$-lactam) and 1693 $cm^{-1}$ (amide I). NMR (in $D_2O/NaHCO_3$): 7.40 ppm (s,5H, aromatic hydrogens), 5.60 and 5.80 ppm (m and m, 2H, C-5 and C-6 hydrogens), 5.30 ppm (m,2H, C-3 hydrogen and side-chain methine hydrogen), 3.20 (q,6H, $NC\underline{H}_2CH_3$), 1.60 ppm (s,3H, C-2 methyl hydrogens), 1.30 ppm (t,9H, $NCH_2C\underline{H}_3$), 1.10 ppm (s,3H, C-2 methyl hydrogens).

EXAMPLE XLVII

6-(2-Cyanoacetamido)-2,2-dimethyl-3-(5-tetrazolyl)penam

To a solution of 2.0 g. of 2-cyanoacetic acid and 2.7 g. of N-hydroxysuccinimide, in 50 ml. of tetrahydrofuran, is added 4.85 g. of dicyclohexylcarbodiimide. The mixture is stirred at ambient temperature overnight, and then the precipitate is filtered off and discarded. Evaporation of the solvent then affords the N-hydroxysuccinimide ester of cyanoacetic acid, which after recrystallization from chloroform has m.p. 123°-30° C. and is suitable for use as described below. (A more highly purified sample has m.p. 128°-130° C.)

To a stirred suspension of 177 mg. of 6-amino-2,2-dimethyl-3-(5-tetrazolyl)penam in 10 ml. of methylene chloride, under nitrogen, is added 157 mg. of triethylamine. Stirring is continued until a clear solution is obtained (ca. 35 minutes). To this solution is then added 135 mg. of the N-hydroxysuccinimide ester of cyanoacetic acid, all in one portion. After stirring for a further 2.5 hours, the reaction mixture is poured into 15 ml. of water, and the pH of the aqueous phase is adjusted to 8.0. The methylene chloride layer is separated off and discarded. The aqueous phase is acidified to pH 2, and then extracted with ethyl acetate. The ethyl acetate is dried using anhydrous sodium sulfate, and then to it is added a solution of 110 mg. of sodium 2-ethylhexanoate in a small volume of ethyl acetate. The precipitate which forms is filtered off, to give 138 mg. (57% yield) of the sodium salt of 6-(2-cyanoacetamido)-2,2-dimethyl-3-(5-tetrazolyl)penam. The infrared spectrum (KBr disc) of the product shows absorption bands at 2260 $cm^{-1}$ (cyano), 1775 $cm^{-1}$ ($\beta$-lactam carbonyl), 1680 $cm^{-1}$ (amide I band) and 1550 $cm^{-1}$ (amide II band). The NMR spectrum (in $D_2O$) shows absorptions at 5.90 and 5.40 ppm (2 doublets, C-5 and C-6 hydrogens), 5.30 ppm (singlet, C-3 hydrogen) 1.65 ppm (singlet, C-2 methyl hydrogens) and 1.00 ppm (singlet, C-2 methyl hydrogens).

EXAMPLE XLVIII

6-(2-[1-Tetrazolyl]acetamido)-2,2-dimethyl-3-(5-tetrazolyl)penam

To a stirred solution of 90 mg. of tetrazole-1-acetic acid and 71 mg. of triethylamine, in 5 ml. of chloroform, cooled to 0° C., is added 85 mg. of pivaloyl chloride. Stirring is continued at 0° C. for a further 30 minutes, and then the resultant solution is added to an ice-cold solution prepared from 169 mg. of 6-amino-2,2-dimethyl-3-(5-tetrazolyl)penam, 142 mg. of triethylamine and 5 ml. of chloroform. This combined solution is stirred at about 0° C. for 2.5 hours. It is then warmed to ambient temperature and poured into 20 ml. of water. The pH of the aqueous phase is raised to 7.0, the layers are separated, and the chloroform is discarded. The aqueous phase is acidified to pH 2, and then it is extracted with ethyl acetate. The ethyl acetate is dried, and then to it is added a solution of 100 mg. of sodium 2-ethylhexanoate in a small volume of ethyl acetate. The solid which precipitates is filtered off, giving 80 mg. (31% yield) of the sodium salt of 6-(2-[1-tetrazolyl]acetamido)-2,2-dimethyl-3-(5-tetrazolyl)penam. The infrared spectrum of the product (KBr disc) shows absorption bands at 1785 $cm^{-1}$ ($\beta$-lactam carbonyl), 1695 $cm^{-1}$ (amide I band) and 1575 $cm^{-1}$ (amide II band). The NMR spectrum (in $D_2O$) shows absorption bands at 5.90-5.40 ppm (multiplet, C-5 and C-6 hydrogens), 5.25 ppm (broad singlet, tetrazole hydrogen), 5.20 ppm (singlet, C-3 hydrogen), 1.70 ppm (singlet, C-2 methyl hydrogens) and 1.00 ppm (singlet, C-2 methyl hydrogens).

The tetrazole-1-acetic acid used in this Example is obtained by the method described in U.S. Pat. No. 3,468,874.

EXAMPLE XLIX

Using the procedure of Example XLVIII, and replacing the tetrazole-1-acetic acid by the appropriate acid, the following compounds are prepared as their sodium salts.

6-(2-[2-tetrazolyl]acetamido)-2,2-dimethyl-3(5-tetrazolyl)penam, 6-(D-2-hydroxy-2-phenylacetamido)-2,2-dimethyl-3-(5-tetrazolyl)penam, 6-(D-2-hydroxy-2-[p-hydroxyphenyl]acetamido)-2,2-dimethyl-3-(5-tetrazolyl)penam, 6-(D-2-hydroxy-2-[p-hydroxyphenyl]acetamido)-2,2-dimethyl-3-(5-tetrazolyl)penam, 6-(D-2-hydroxy-2-[2-furyl]acetamido)-2,2-dimethyl-3-(5-tetrazolyl)penam, 6-(D-2-hydroxy-2-[2-thienyl]acetamido)-2,2-dimethyl-3-(5-tetrazolyl)penam, 6-(2-[2-(hydroxymethyl)phenyl]acetamido)-2,2-dimethyl-3-(5-tetrazolyl)penam and
6-(2-[4-(hydroxymethyl)phenyl]acetamido)-2,2-dimethyl-3-(5-tetrazol-5-yl)penam,
respectively.

EXAMPLE LI

The procedure of Example L is repeated, using the appropriate acid chloride, to provide the following compounds

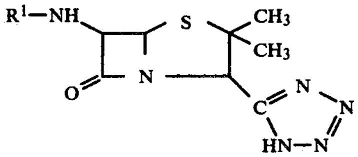

| $R^1$ | Yield (%) | Melting Point (°C.) | Infrared Spectrum ($cm^{-1}$) | NMR Spectrum (ppm) |
|---|---|---|---|---|
| 2-(2-thienyl)acetyl | 26 | 192–194 | 1808, 1718, 1678 | 7.10(m,1H), 7.00(m,2H), 5.70(m,2H), 5.30(s,1H), 3.90 (s,2H), 1.70(s,3H), 1.10(s,3H) . DMSO-$d_6$. |
| phenoxycarbonyl | 43 | 102–118 | 1795, 1740 | 9.00(s,1H), 7.40–7.70(m,5H), 6.20(d,1H), 5.70(m,2H), 5.35(s,1H), 1.90(s,3H), 1.13(s,3H) . CDCl-$d_3$. |
| benzyloxycarbonyl | 30 | 145–170 | 1800, 1725 | 11.30(s,1H), 7.40(s,5H), 5.70(m,2H), 5.30(s,1H), 5.15 (s,2H), 1.70(s,3H), 1.10(s,3H) . $CDCl_3$. |
| ethoxycarbonyl | 32 | 80–115 | 1800, 1725 | 10.70(s,1H), 5.75(m,2H), 5.16(s,1H), 4.20(q,2H), 1.75 (s,3H), 1.50–1.10(m,6H) . $CDCl_3$. |

The tetrazole-2-acetic acid is prepared by the method described in U.S. Pat. No. 3,468,874. D-2-Hydroxy-2-phenylacetic acid is commercially available. D-2-Hydroxy-2-(p-hydroxyphenyl)acetic acid, D-2-hydroxy-2-(m-chlorophenyl)acetic acid, D-2-hydroxy-2-(2-furyl)acetic acid and D-2-hydroxy-2(2-thienyl)acetic acid are each prepared from the corresponding aldehyde, using the method of Corson et al., Organic Synthesis, Collective Volume I, p. 336.

EXAMPLE L

6-(2-Phenoxyacetamido)-2,2-dimethyl-3-(5-tetrazolyl)penam

A stirred slurry of 480 mg. of 6-amino-2,2-dimethyl-3-(5-tetrazolyl)penam in 10 ml. of water is cooled to 0° C., and then the pH is adjus using 1 N sodium hydroxide. To this solution is then added 0.25 ml. of phenoxyacetyl chloride, in portions, with the pH of the solution being maintained between 7 and 8 during the addition, using 0.1 N sodium hydroxide. The solution is stirred a further 30 minutes at 0° C. at pH 8. It is then extracted with chloroform, and the extracts are discarded. The aqueous phase is acidified to pH 2 with dilute hydrochloric acid, and then it is further extracted with chloroform. The latter extracts are dried using calcium sulfate and then evaporated in vacuo to give the crude product as a gummy solid. This is purified by dissolving it in 20 ml. of chloroform, and adding the resultant solution dropwise to 250 ml. of hexane. The precipitate which forms is filtered off, giving 385 mg. of 6-(2-phenoxyacetamido)-2,2-dimethyl-3-(5-tetrazolyl)penam as a white amorphous solid. The infrared spectrum (KBr disc) of the product shows absorption bands at 1785 $cm^{-1}$ (β-lactam carbonyl), 1670 $cm^{-1}$ (amide I band) and 1540 $cm^{-1}$ (amide II band). The NMR spectrum (in DMSO-$d_6$) shows absorption bands at 7.50–6.70 ppm (multiplet, aromatic hydrogens), 5.70 ppm (multiplet, C-5 and C-6 hydrogens), 5.35 ppm (singlet, C-3 hydrogen), 4.60 ppm (singlet, methylene hydrogens), 1.60 ppm (singlet, C-2 methyl hydrogens), and 1.05 ppm (singlet, C-2 methyl hydrogens).

EXAMPLE LII

6-(Acetamido-2,2-dimethyl-3-(5-tetrazolyl)penam

The procedure of Example L is repeated, except that the phenoxyacetyl chloride used therein is replaced by acetic anhydride. This affords a 48% yield of the title compound. IR (KBr disc): 1780 $cm^{-1}$ (β-lactam), 1645 $cm^{-1}$ (amide I). NMR (in DMSO-$d_6$): 5.65 ppm (m, 2H), 5.25 ppm (s, 1H), 1.95 ppm (s, 3H), 1.70 ppm (s, 3H), and 1.10 ppm (s, 3H).

EXAMPLE LIII

Reaction of 6-amino-2,2-dimethyl-3-(5-tetrazolyl)penam with the appropriate acid chloride, according to the procedure of Example L provides the following compounds:

6-(2[cyclopent-2-enyl]acetamido)-2,2-dimethyl-3-(5-tetrazolyl)penam,
6-(2-[cyclohex-2-enyl]acetamido)-2,2-dimethyl-3-(5-tetrazolyl)penam,
6-(2-[cyclohept-1-enyl]acetamido)-2,2-dimethyl-3-(5-tetrazolyl)penam,
6-(2-[cyclooct-1-enyl]acetamido)-2,2-dimethyl-3-(5-tetrazolyl)penam and,
6-(2-[cyclohept-2,4,6-trienyl]acetamido)-2,2-dimethyl-3-(5-tetrazolyl)penam,
respectively.

EXAMPLE LIV

The procedure of Example L is repeated, except that the phenoxyacetyl chloride used therein is replaced by an equimolar amount of the appropriate acid chloride, to produce the following congeners:

6-propionamido-2,2-dimethyl-3-(5-tetrazolyl)penam,
6-octanamido-2,2-dimethyl-3-(5-tetrazolyl)penam,
6-acrylamido-2,2-dimethyl-3-(5-tetrazolyl)penam,
6-(3-methylacrylamido)-2,2-dimethyl-3-(5-tetrazolyl)penam,
6-(3,3-dimethylacrylamido)-2,2-dimethyl-3-(5-tetrazolyl)penam,
6-(2-cyclopentylacetamido)-2,2-dimethyl-3-(5-tetrazolyl)penam,
6-(2-cyclohexylacetamido)-2,2-dimethyl-3-(5-tetrazolyl)penam, 6-(2-cycloheptylacetamido)-2,2-dimethyl-3-(5-tetrazolyl)penam,
6-(2-[cyclohex-3-enyl]acetamido)-2,2-dimethyl-3-(5-tetrazolyl)penam,
6-(2-[cyclohex-1-enyl]acetamido)-2,2-dimethyl-3-(5-tetrazolyl)penam,
6-(o-methoxybenzamido)-2,2-dimethyl-3-(5-tetrazolyl)penam,
6-(2,6-dimethoxybenzamido)-2,2-dimethyl-3-(5-tetrazolyl)penam,
6-(2,6-diethoxybenzamido)-2,2-dimethyl-3-(5-tetrazolyl)penam,
6-(2,6-dipropoxybenzamido)-2,2-dimethyl-3-(5-tetrazolyl)penam,
6-(2,6-dibutoxybenzamido)-2,2-dimethyl-3-(5-tetrazolyl)penam,
6-(2-methoxy-1-naphthamido)-2,2-dimethyl-3-(5-tetrazolyl)penam,
6-(2-ethoxy-1-naphthamido)-2,2-dimethyl-3-(5-tetrazolyl)penam,
6-(2-n-butoxy-1-naphthamido)-2,2-dimethyl-3-(5-tetrazolyl)penam,
6-(4-isothiazolecarboxamido)-2,2-dimethyl-3-(5-tetrazolyl)penam,
6-(2-imidazolecarboxamido)-2,2-dimethyl-3-(5-tetrazolyl)penam,
6-(2-azido-2-phenylacetamido)-2,2-dimethyl-3-(5-tetrazolyl)penam,
6-(3-phenylpropionamido)-2,2-dimethyl-3-(5-tetrazolyl)penam,
6-(2-[phenylthio]acetamido)-2,2-dimethyl-3-(5-tetrazolyl)penam,
6-(2-[3-sydnonyl]acetamido)-2,2-dimethyl-3-(5-tetrazolyl)penam,
6-(2-[3-thienyl]acetamido)-2,2-dimethyl-3-(5-tetrazolyl)penam,
6-(2-[2-furyl]acetamido)-2,2-dimethyl-3-(5-tetrazolyl)penam,
6-(2-[3-methyl-2-thienyl]acetamido)-2,2-dimethyl-3-(5-tetrazolyl)penam,
6-(2-[1-pyrazolyl]acetamido)-2,2-dimethyl-3-(5-tetrazolyl)penam,
6-(2-[1,2,4-triazol-1-yl]acetamido)-2,2-dimethyl-3-(5-tetrazolyl)penam,
6-(2-[2,4-dimethylthiazol-5-yl]acetamido)-2,2-dimethyl-3-(5-tetrazolyl)penam,
6-(2-[N-methylpyrrol-2-yl]acetamido)-2,2-dimethyl-3-(5-tetrazolyl)penam,
6-(2-[1-pyrrolyl]acetamido)-2,2-dimethyl-3-(5-tetrazolyl)penam,
6-(2-[p-chlorophenyl]acetamido)-2,2-dimethyl-3-(5-tetrazolyl)penam,
6-(2-[m-methoxyphenyl)acetamido]-2,2-dimethyl-3-(5-tetrazolyl)penam, and
6-(2-[p-tolyl]acetamido)-2,2-dimethyl-3-(5-tetrazolyl)penam, respectively.

The acid chlorides used in this Example are prepared from the corresponding acids, using methods well known in the art (Buehler and Pearson, "Survey of Organic Syntheses," Wiley-Interscience, 1970, pp. 859–867). 2-(Cycloheptyl)acetic acid and 2-cyclohex-1-enyl)acetic acid are prepared from their corresponding nitriles (which are items of commerce) by hydrolysis, using methods discussed by Buehler and Pearson (loc. cit., pp. 752–753). 2-(Cyclohex-b 3-enyl)acetic acid is prepared by the method of Boehme, *Journal of Organic Chemistry*, 26, 2107 (1961). The 2,6-dialkoxybenzoic acids are prepared according to Doyle, et al., *Journal of the Chemical Society* (London), 1453 (1962), and the 2-alkoxy-1-naphthoic acids according to British Pat. No. 880,400. 2-(3-Sydnonyl)acetic acid is prepared by the method of Stewart, *Chemistry and Industry* (London), 1411 (1961). The 2-(3-thienyl)acetic acid, 2-(2-furyl)acetic acid, 2-(3-methyl-2-thienyl)acetic acid, 2-(1-pyrazolyl)acetic acid, 2-(1,2,4-triazol-1-yl)acetic acid, 2-(2,4-dimethylthiazol-5-yl)acetic acid, 2-(N-methylpyrrolyl)acetic acid and 2-(1-pyrrolyl)acetic acid are prepared by methods disclosed in Belgian Pat. No. 618,663. All the other acids are items of commerce.

EXAMPLE LV

6-(3-[Carbamoyl]acrylamido)-2,2-dimethyl-3-(5-tetrazolyl)penam

To a stirred mixture of 1.15 g. (10 m mole) of maleamic acid and 1.40 ml. of triethylamine in 40 ml. of dry tetrahydrofuran, at 0° C., is added 1.57 ml (12 m mole) of isobutyl chloroformate followed by three drops of N-methylmorpholine. Stirring is continued for a further 30 minutes at 0° C. To this mixed anhydride is then added a solution prepared by adding 2.40 g. (10 m mole) of 6-amino-2,2-dimethyl-3-(5-tetrazolyl)penam to a mixture of 15 ml. of water and 15 ml. of tetrahydrofuran and adjusting the pH to 7.5. The resulting mixture is then stirred for a further 1 hour at 0° C. At this point, the tetrahydrofuran is removed by evaporation in vacuo, and the residue is diluted with more water. The pH is adjusted to 8.0 with 6 N sodium hydroxide, and then the mixture is extracted with ethyl acetate. The extracts are discarded. The pH of the residual aqueous phase is adjusted to 2.0 with 4 N hydrochloric acid and then the product is extracted into ethyl acetate. The organic layer is dried and concentrated in vacuo to give 6-(3-[carbamoyl]acrylamido)-2,2-dimethyl-3-(5-tetrazolyl)penam (1.03 g., 33% yield). The infrared spectrum (KBr disc) of the product shows absorption band at 1818 $cm^{-1}$ ($\beta$-lactam) and 1692 $cm^{-1}$. The NMR spectrum (DMSO-$d_6$) shows bands at 7.00 and 6.25 (quartet, 2H, J=12 Hz, olefinic hydrogens), 5.80–5.48 ppm (multiplet, 2H, C-5 and C-6 hydrogens), 5.26 ppm (singlet, 1H, C-3 hydrogen), 1.65 ppm (singlet, 3H, C-2 methyl hydrogens) and 1.06 ppm (singlet, 3H, C-2 methyl hydrogens).

EXAMPLE LVI

6-Formamido-2,2-dimethyl-3-(5-tetrazolyl)penam

To a stirred solution of 480 mg. of 6-amino-2,2-dimethyl-3-(5-tetrazolyl)penam and 0.56 ml. of triethylamine in 5 ml. of methylene chloride, at 0° C., is added 0.3 ml. of formic acetic anhydride. Stirring is continued for a further 45 minutes, at 0° C., and then the solvent is removed by evaporation in vacuo. The residue is partitioned between water and ethyl acetate, and then the ethyl acetate is separated off and dried. Evaporation of the ethyl acetate in vacuo affords 0.216 g. of 6-formamido-2,2-dimethyl-3-(5-tetrazolyl)penam as a foam. The NMR spectrum ($CDCl_3$) shows absorptions at 8.20 ppm (singlet, 1H, formamido hydrogen), 5.80 ppm (multiplet, 2H C-5 and C-6 hydrogen), 5.30 ppm (singlet, 1H, C-3 hydrogen), 1.70 ppm (singlet, 3H, C-2 methyl hydrogens) and 1.10 ppm (singlet, 3H, C-2 methyl hydrogens). The infrared spectrum of the sodium salt (KBr disc) shows absorptions at 1760 $cm^{-1}$ and 1660 $cm^{-1}$.

EXAMPLE LVII 6-(2-Bromoacetamido)-2,2-dimethyl-3-(5-tetrazolyl)penam

To a stirred suspension of 3.0 g (0.0125 mole) of 6-amino-2,2-dimethyl-3-(5-tetrazolyl)penam in 15 ml of water is added 1.74 g (0.0125 mole) of bromoacetic acid dissolved in 5 ml of water. The pH of the mixture is adjusted to 6.0 using 20% sodium hydroxide solution. The resulting clear solution is cooled to 0° C., and then 2.4 g (0.0125 mole) of 1-ethyl-3-(3-dimethylaminopropyl)carbodiimide hydrochloride is added. The solution is stirred at 0° C. for a further 2.5 hr, during which time the pH is maintained between 6 and 7 by the addition of 6 N hydrochloric acid. At this point, the pH is adjusted to 7.0 and the reaction mixture is extraced with ethyl acetate. The extract is discarded. The pH of the reaction mixture is then lowered to 2.0 (6 N hydrochloric acid), and the product is extracted into ethyl acetate. The ethyl acetate is washed with water, dried, and evaporated to give 3.2 g (72% yield) of 6-(2-bromoacetamido)-2,2-dimethyl-3-(5-tetrazolyl)penam as a white foam. The infrared spectrum (KBr disc) of the product shows absorption bands at 1795 $cm^{-1}$ (β-lactam), 1670 $cm^{-1}$ (amide I) and 1530 $cm^{-1}$ (amide II). The NMR spectrum ($CDCl_3$) shows absorption bands at 10.6–9.6 ppm (broad singlet, tetrazole hydrogen), 8.8 ppm (doublet, amide hydrogen), 5.8–5.4 ppm (multiplet, C-5 and C-6 hydrogens), 5.35 ppm (singlet, C-3 hydrogen), 4.0 ppm (singlet, methylene hydrogen), 1.90 ppm (singlet, C-2 methyl hydrogens) and 1.15 ppm (singlet, C-2 methyl hydrogens).

The above product is dissolved in 15 ml of water containing 1 equivalent of sodium bicarbonate. The resulting solution is then lyophilized leaving the sodium salt of the title compound (3.4 g, 72% yield).

EXAMPLE LVIII 6-(2-[4-Pyridylthio]acetamido)-2,2-dimethyl-3-(5-tetrazolyl)penam

To a stirred suspension of 1.0 g (0.0028 mole) of 6-(2-bromoacetamido)-2,2-dimethyl-3-(5-tetrazolyl)penam in 25 ml of methylene chloride is added 0.28 g (0.0028 mole) of triethylamine. The mixture is stirred at ambient temperature until a clear solution is obtained, and then 0.39 g of 4-mercaptopyridine is added. Stirring is continued for a further 4 hours at ambient temperature, and then the solid which has precipitated is filtered off. It is washed with methylene chloride, followed by ether, to give 0.68 g (78% yield) of 6(2-[4-pyridylthio]acetamido)-2,2-dimethyl-3-(5-tetrazolyl)penam, m.p. 120° C. (dec.). The infrared spectrum of the product (KBr disc) shows absorption bands at 1790 $cm^{-1}$ (β-lactam), 1670 $cm^{-1}$ (amide II). The NMR spectrum (DMSO-$d_6$) show absorption bands at 9.0–7.0 ppm (multiplet, pyridine hydrogens), 5.9–5.5 ppm (multiplet, C-5 and C-6 hydrogen), 4.0 ppm (singlet, methylene hydrogens), 1.7 ppm (singlet, C-2 methyl hydrogens) and 1.1 (singlet, C-2 methyl hydrogens).

EXAMPLE LIX 6-(2-[N,N-Diethylamidinothio]acetamido)-2,2-dimethyl-3-(5-tetrazolyl)penam To a stirred solution of 1.40 g (0.039 mole) of 6-(2-bromoacetamido)-2,2-dimethyl-3-(5-tetrazolyl)penam in 25 ml of methylene chloride is added 0.54 ml (0.039 mole) of triethylamine, followed by 0.52 g (0.039 mole) of N,N-diethylthiourea. Stirring is continued for a further 45 minutes, and then the solvent is decanted from the oil which has separated. The oil is triturated with ether, giving a white solid, which is filtered off. The yield is 1.28 g (76% of theory) of 6-(2-[N,N-diethylamidinothio]acetamido)-2,2-dimethyl-3-(5-tetrazolyl)penam. The infrared spectrum (KBr disc) of the product shows absorption bands at 1780 $cm^{-1}$ (β-lactam) and 1670 $cm^{-1}$ (amide I). The NMR spectrum (DMSO-$d_6$) shows absorption bands at 5.65 ppm (multiplet, C-5 and C-6 hydrogens), 5.15 ppm (singlet, C-3 hydrogen), 4.10 ppm (singlet, methylene hydrogens), 3.45 ppm (quartet, ethyl hydrogens), 1.60 ppm (singlet, C-2 methyl hydrogens), 1.10 ppm (triplet, ethyl hydrogens) and 1.00 ppm (singlet, C-2 methyl hydrogens).

EXAMPLE LX 5-(2,6-Dimethoxybenzamido)-2,2-dimethyl-3-(5-tetrasolyl)penam

To a stirred solution of 1.2 g. (5 mmole) of 6-amino-2,2-dimethyl-3-(5-tetrazolyl)penam, 1.01 g. (10 mmole) of triethylamine and 50 ml. of methylene chloride, is added 1.0 g. (5 mmole) of 2,6-dimethoxybenzoyl chloride (Norris and Ware, *J. Amer. Chem. Soc.*, 61, 1418 [1936], at ca. 0° C. Stirring is then continued for three hours at ambient temperature. To the reaction mixture is added 50 ml. of water, and the pH of the aqueous phase is adjusted to 8.0. The organic phase is separated off and discarded. The pH of the residual aqueous phase is lowered to 2.5, and the precipitate which forms is filtered off. This affords 1.2 g. (59% yield) of the title compound, m.p. 215° C. (dec.). IR (KBr disc): 1808, 1643 and 1605 $cm^{-1}$. NMR (in $D_2O$/Na $HCO_3$): 7.50 ppm (t, 1H), 6.90 ppm (d, 2H), 5.90 and 6.0 ppm (q, 2H), 5.40 ppm (s, 1H), 4.00 ppm (s, 6H), 1.80 ppm (s, 3H) and 1.20 ppm (s, 3H).

EXAMPLE LXI 6-(2-Ethoxy-1-naphthamido)-2,2-dimethyl-3-(5-tetrazolyl)penam

Following the procedure of Example LX, the title compound is prepared from 2.84 g. (0.012 mol) of 6-amino-2,2-dimethyl-3-(5-tetrazolyl) penam and 1.39 (0.006 mol) of 2-ethoxy-1-naphthoyl chloride and is isolated as the sodium salt by standard procedures: yield 1.5 (54%); IR (KBr); 1780, 1715, 1667 $cm^{-1}$; NMR ($D_2O$) 8.0–6.8 ppm (m, 6H), 5.85 (s, 1H), 5.40 (s, 1H), 5.25 (s, 1H), 3.90 (q, 2H), 1.45 (s, 3H), 1.25 (t, 3H) 1.00 (s, 3H).

EXAMPLE LXII

6-Phenylpyruvamido-2,2-dimethyl-3-(5-tetrazolyl)penam

To a stirred solution of 960 mg. (4 mmole) of 6-amino-2,2-dimethyl-3-(5-tetrazolyl)penam and 1.2 g. (12 mmole) of triethylamine in 20 ml. of methylene chloride, is added a solution of 728 mg. (4 mmole) of phenylpyruvoyl chloride in 5 ml. of methylene chloride, at 0° C. The cooling bath is removed, and when the reaction mixture has attained room temperature, the solvent is removed by evaporation in vacuo. The residue is partitioned between ethyl acetate and water, the pH is adjusted to 7.8, and then the ethyl acetate layer is separated and discarded. The pH of the residual aqueous phase is adjusted to 2.5, and the product is extracted into ethyl acetate. The ethyl acetate is washed with water, followed by brine, and then dried using sodium sulfate. To the ethyl acetate is added 404 mg. of triethylamine, and then the solvent is evaporated to dryness in vacuo. This affords 1.26 g. (65% yield) of the title compound as its triethylamine salt. IR (KBr disc); 1760 and 1670 $cm^{-1}$ . NMR (in $CDCl_3$): 7.4–7.0 ppm (m, 5H); 6.0–5.2 ppm (m, 3H), 3.6 ppm (s, 2H), 1.6 ppm (s, 3H), 1.1 ppm (s, 3H).

EXAMPLE LXIII

Following the procedure of Example LXII, and reacting either 6-amino-2,2-dimethyl-3-(5-tetrazolyl)penam or 6-(D-2-amino-2-phenylacetamido)-2,2-dimethyl-3-(5-tetrazolyl)penam with the appropriate acid chloride, the following compounds are prepared:

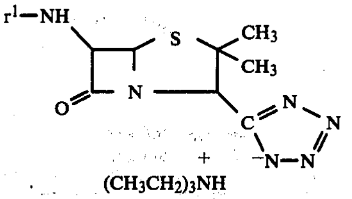

$(CH_3CH_2)_3NH$

| $R^1$ | Yield (%) | Infrared Spectrum ($cm^{-1}$) | NMR Spectrum* ($CDCl_3$; ppm) |
|---|---|---|---|
| ethoxycarbonyl | 60 | 1780, 1710, 1515, 1270 | 5.9–5.4(m), 5.38(s), 1.7(s), 1.1(s). |
| benzoyl | 85 | 1785, 1670 | 8.4–7.5(m), 5.9–5.4(m), 5.38(s), 1.8(s), 1.2(s). |
| acetyl | 58 | 1785, 1700, 1640 | 6.0–5.4(m), 3,2(s), 3.1(s). |
| 2-benzoylformamido)-2-phenylacetyl | 66 | 1785, 1670, 1600 | 8.2–7.2(m,10H), 5.8(m,3H), 5.4(s,1H), 1.4(s,3H), 0.9(s,3H). |
| 2-(acetylformamido)-2-phenylacetyl | 37 | 1785, 1680 | 7.4(s,5H), 5.8–5.2(m,4H), 2.4(s,3H), 1.4(s,3H), 1.0(s,3H). |
| 2-(ethoxycarbonylformamido)-2-phenylacetyl | 78 | 1785, 1680 | 9.8–9.2(s), 8.8–8.1(s), 7.7–7.1(m), 5.9–5.2(m), 4.6–4.0(q), 1.5(s), 1.0(s). |
| 2-(phenoxycarbonylamido)-2-phenylacetyl | 60 | 1785, 1725, 1600 | 5.8–5.2(m,4H), 1.5(s,3H), 1.0(s,3H). |
| 2-(ethoxycarbonylamino)-2-phenylacetyl | 80 | 1785, 1680 | 7.5–7.2(s,1H), 6.9–6.4(m,5H), 5.7–5.4(m,4H), 4.3–3.9(q,2H), 1.9(s,3H), 1.1(s,3H). |
| 2-(benzyloxycarbonylamino)-2-phenylacetyl | 35 | 1785, 1680 | 7.4(s,5H), 7.3(s,5H), 5.8–5.1(m,4H), 3.2–2.8(q,2H), 1.9(s,3H), 1.0(s,3H). |

*the absorption bands due to the triethylamine have been omitted from this tabulation.

EXAMPLE LXIV

Reaction of 6-(D-2-amino-2-phenylacetamido)-2,2-dimethyl-3-(5-tetrazolyl)penam with the appropriate acid chloride, according to the procedure of Example LXII, provides the following compounds, which are isolated as the free acids by elimination of the final triethylamine treatment.

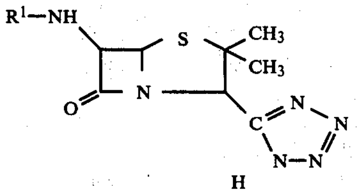

| $R^1$ | Yield (%) | Melting Point (° C.) | Infrared Spectrum ($cm^{-1}$) | NMR Spectrum (DMSO-$d_6$/$CDCl_3$; pm) |
|---|---|---|---|---|
| 2-(2-phenylacetamido)-2-phenylacetyl | 77 | 130–140 | 1800,1655, 1515 | 10.42(m,1H), 8.07(d,1H), 7.33(m,10H), 5.73(d,1H), 5.63(m,2H), 5.10(s,1H), 3.67(s,2H), 1.67(s,3H), 1.08(s,3H), |
| 2-benzamido-2-phenylacetyl | 65 | 145–165 | 1785,1640, 1515 | 8.20(d,1H), 7.90(m,3H), 7.50(m,8H), 6.00(d,1H), 5.60(m,2H), 5.23(s,1H), 1.53(s,3H), 1.03(s,3H), |
| 2-acetamido-2-phenylacetyl | 74 | 140–160 | 1790,1655, 1525 | 8.10(d,1H), 7.40(m,5H), 5.8(d,1H), 5.60(m,2H), 5.20(s,1H), 1.67(s,3H), 1.08(s,3H), |
| 2-butyramido-2-phenylacetyl | 74 | 146–160 | 1795,1695, 1650 | 8.84(t,1H), 8.07(d,1H), 7.50(m,5H), 5.90)d,1H), 5.70(m,2H), 5.27(s,1H), 2.27(t,2H), 1.87(m,5H), 1.07(m,6H), |
| 2-(2-furancarboxamido)-2-phenylacetyl | 73 | 143–165 | 1795,1665 1600,1515 | 8.60(m,1H), 7.90(d,1H), 7.6-7.0(m,7H), 7.5(q,1H), 6.00(d,1H), 5.60(m,2H), 5.23(s,1H), 1.58(s,3H), 1.03(s,3H), |
| 2-(2-thiophenecarboxamido)-2-phenylacetyl | 88 | 130–155 | 1800,1695, 1640,1540, 1505 | 8.50(m,1H), 8.10(d,1H), 7.80-7.00(m,8H), 5.95(d,1H), 5.60(m, 2H), 5.10(s,1H), 1.60(s,3H), 1.10(s,3H), |
| 2-(2-[2-thienyl]acetamido)-2-phenylacetyl | 69 | 134–148 | 1795,1655, 1530 | 8.91(m,1H), 8.33(d,1H), 7.50-7.10(m,5H), 6.90(m,2H), 5.75(d, 1H), 5.60(m,2H), 5.20(s,1H), 3.83(s,2H), 1.60(s,3H), 1.05(s,3H), |
| 2-(3-pyridinecarboxamido)-2-phenylacetyl | 62 | 164–185 | 1785,1660, 1600,1530 | 9.10(s,1H), 8.70(m,3H), 8.30(m,1H), 7.50(m,7H), 6.00(d,1H), 5.67(q,2H), 5.20(s,1H), 1.60(s,3H), 1.05(s,3H), |
| 2-(2-yrrolecarboxamido)-2-phenylacetyl | 58 | 170–195 | 1795,1695 1640,1560 1515 | 10.80(s,1H), 8.60(d,1H), 7.90(d,1H), 7.30(m,5H), 6.90(t,2H), 6.20(m,2H), 5.23(s,1H), 1.53(s,3H), 1.00(s,3H), |

-continued

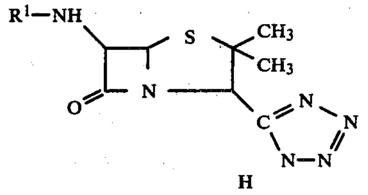

| $R^1$ | Yield (%) | Melting Point (° C.) | Infrared Spectrum ($cm^{-1}$) | NMR Spectrum ($DMSO-d_6/CDCl_3$; pm) |
|---|---|---|---|---|
| 2-(2-[4-bromophenyl]acetamido)-2-phenylacetyl | 75 | 140–162 | 1800,1647 | 8.83(m,1H), 8.35(d,1H), 7.35(m,9H), 5.6(m,3H), 5.2(s,1H), 3.6(s,2H), 1.6(s,3H), 1.05(s,3H), |
| 2-(2-[4-methoxyphenyl]acetamido)-2-phenylacetyl | 70 | 134–150 | 1798,1652 | 8.67(m,1H), 7.83(d,1H), 7.4(m,7H), 6.95(d,2H), 5.9 (d,1H), 5.67(m,2H), 5.32(s,1H), 3.88(s,3H), 3.68 (s,2H), 1.72(s,3H), 1.17(s,3H), |
| 2-(4-pyridinecarboxamido)-2-phenylacetyl | 52 | 160–180 | 1795,1666 | 9.33(m,2H), 8.75(m,4H), 7.8(m,2H), 7.4(m,5H), 6.0(d,1H), 5.65(m,2H), 5.2(s,1H), 1.6(s,3H), 1.05(s,3H), |
| 2-(2-[4-nitrophenyl]acetamido)-2-phenylacetyl | 49 | 145–170 | 1795,1653 | 8.6(m,2H), 8.1(d,2H), 7.4(m,7H), 5.7(m,3H), 5.2(s,1H), 3.7(s,2H), 1.6(s,3H), 1.05(s,3H), |
| 2-(2-[2-furyl]acetamido)-2-phenylacetyl | 73 | 165–184 | 1795,1653 | 9.0(m,1H), 8.1(d,1H), 7.4(m,6H), 6.3(m,2H), 5.8(d,1H), 5.6(m,2H), 5.23(s,1H), 3.73(s,2H), 1.7(s,3H), 1.12(s,3H), |
| 2-(4-nitrobenzamido)-2-phenylacetyl | 81 | 160–178 | 1795,1653 | 8.83(m,3H), 8.2(q,4H), 7.4(m,5H), 6.0(d,2H), 5.6(m,2H), 5.2(s,1H), 1.6(s,3H), 1.05(s,3H), |
| 2-(2-phenoxyacetamido)-2-phenylacetyl | 77 | 120–128 | 1795,1667 | 8.6(m,1H), 8.07(d,1H), 6.8-7.6(m,10H), 5.9(d,1H), 5.6 (m,2H), 5.2(s,1H), 4.6(m,2H), 1.6(s,3H), 1.07(s,3H), |
| 2-(2-cyanoacetamido)-2-phenyacetyl | | 135–145 | 2250,1790 1667 | 9.1(d,1H), 7.45(m,5H), 5.75(d,1H), 5.63(m,2H), 5.15(s,1H), 3.80(s,2H), 1.6(s,3H), 1.03(s,3H), |
| 2-(2-azidoacetamido)-2-phenylacetyl | 41 | 138–147 | 2100,1795 1667 | 7.5(m,5H), 5.93(d,1H), 5.73(m,2H), 5.17(s,1H), 4.12(s,2H), 1.67(s,3H), 1.1(s,3H), |

EXAMPLE LXV

6-(D-2-Amino-2-phenylacetamido)-2,2-dimethyl-3-(5-tetrazolyl)penam

A stirred suspension of 200 mg. of 6-amino-2,2-dimethyl-3-(5-tetrazolyl)penam in 5 ml. of water is cooled to 0°–5° C. in an ice-bath. The pH is then adjusted to 7.0 using dilute sodium hydroxide solution. At this point, 274 mg. of D-2-amino-2-phenylacetyl chloride hydrochloride (Hardcastle et al., *Journal of Organic Chemistry*, 31, 897 [1966]) is added portionwise during 15 minutes at 0°–5° C., and with the pH maintained between 6 and 7 by the addition of dilute sodium hydroxide. At the end of the addition, the reaction mixture is stirred for a further 15 minutes and then filtered. The pH of the mother liquors is adjusted to 4.4 with dilute hydrochloric acid, and then the solution is stored overnight in the refrigerator. The solution is then filtered, and the mother liquors are placed on a column of 25 g. of Sephadex LH-20 (Pharmacia Fine Chemicals, Inc.) made up in water. The column is eluted with water, taking fractions, and the composition of the fractions is assayed by thin-layer chromatography. The fractions containing the pure product are combined, and evaporated under high vacuum to a volume of approximately 1 ml. After this solution has been set aside for a short period, the product crystallizes out. It is filtered off, washed briefly with water and dried. The yield is 55 mg. of pure 6-(D-2-amino-2-phenylacetamido)-2,2-dimethyl-3-(5-tetrazolyl)penam, m.p. 192°–196° C. The infrared spectrum (KBr disc) shows absorptions at 1770 $cm^{-1}$ ($\beta$-lactam carbonyl), 1680 $cm^{-1}$ (amide I band) and 1520 $cm^{-1}$ (amide II band).

EXAMPLE LXVI

When the procedure of Example LXV is repeated, and the D-2-amino-2-phenylacetyl chloride hydrochloride used there is replaced by an equivalent amount of the appropriate acid chloride hydrochloride, the following compounds are produced.

(6-(DL-2-amino-2-phenylacetamido)-2,2-dimethyl-3-(5-tetrazolyl)penam,
6-(DL-3-amino-2-phenylpropionamido)-2,2-dimethyl-3-(5-tetrazolyl)penam,
6-(2-[2-pyridyl]acetamido)-2,2-dimethyl-3-(5-tetrazolyl)penam,
6-(2-[3-pyridyl]acetamido)-2,2-dimethyl-3-(5-tetrazolyl)penam,
6-(2-[4-pyridyl]acetamido)-2,2-dimethyl-3-(5-tetrazolyl)penam,
6-(2-[4-pyridylthio]acetamido)-2,2-dimethyl-3-(5-tetrazolyl)penam,
6-(2-[p-aminophenyl]acetamido)-2,2-dimethyl-3-(5-tetrazolyl)penam,
6-(1-aminocyclobutanecarboxamido)-2,2-dimethyl-3-(5-tetrazolyl)penam,
6-(1-aminocyclopentanecarboxamido)-2,2-dimethyl-3-(5-tetrazolyl)penam,
6-(1-aminocyclohexanecarboxamido)-2,2-dimethyl-3-(5-tetrazolyl) penam,
6-(1-aminocycloheptanecarboxamido)-2,2-dimethyl-3-(5-tetrazolyl)penam,
6-(2-[m-(N-methylamino)phenyl]acetamido)-2,2-dimethyl-3-(5-tetrazolyl)penam and
6-(2-[p-(N-n-butylamino)phenyl]acetamido)-2,2-dimethyl-3-(5-tetrazolyl)penam,
respectively.

DL-2-Amino-2-phenylacetic acid, 2-pyridylacetic acid, 4-pyridylacetic acid and p-aminophenylacetic acid are items of commerce. DL-3-amino-2-phenylpropionic acid is prepared by the method of Testa et al., *Annalen der Chemie*, 614, 167 (1958), and (4-pyridylthio)acetic acid is prepared by the method described in Netherlands Pat. No. 6,912,855. The 1-aminocycloalkanecarboxylic acids are prepared by the method of Alburn et al., *Antimicrobial Agents and Chemotherapy*, 586 (1967). The amino-acids are converted into their acid chloride hydrochlorides by sequential treatment with hydrogen chloride gas and phosphorous pentachloride (Hardcastle et al., *Journal of Organic Chemistry*, 31 897 [1966].

EXAMPLE LXVII

Acylation of 6-amino-2,2-dimethyl-3-(5-tetrazolyl)penam with the acid chloride hydrochloride of 2-(N-methylamino)-2-phenylacetic acid, 2-(N-ethylamino)-2-phenylacetic acid, 2-(N-isobutylamino)-2-phenylacetic acid, 2-(N-n-hexylamino)-2-phenylacetic acid, 2-(N-methylamino)-2-(2-thienyl)acetic acid and 2-N-methylamino)-2-(p-chlorophenyl)acetic acid, respectively, according to the procedure of Example LXV produces the following congeners:

6-(2[N-methylamino]-2-phenylacetamido)-2,2-dimethyl-3-(5-tetrazolyl)penam,
6-(2-[N-ethylamino]-2-phenylacetamido)-2,2-dimethyl-3-(5-tetrazolyl)penam,
6-(2-[N-isobutylamino]-2-phenylacetamido)-2,2-dimethyl-3-(5-tetrazolyl)penam,
6-(2-[N-n-hexylamino]-2-phenylacetamido)-2,2-dimethyl-3-(5-tetrazolyl)penam,
6-(2-[N-methylamino]-2-[2-thienyl]acetamido)-2,2-dimethyl-3-(5-tetrazolyl)penam and
6-(2-[N-methylamino]-2-[p-chlorophenyl]acetamido)-2,2-dimethyl-3-(5-tetrazolyl)penam,
respectively.

2-(N-Methylamino-2-phenylacetic acid is prepared by the method of Araga et al. (*Nippon Kagaku Zasshi*, 86, 111 [1965]; *Chemical Abstracts*, 62 16365 [1965]). The other amino-acids are prepared in analogous fashion, using the appropriate aldehyde and amine. Acid chloride hydrochlorides are prepared by the method of Hardcastle et al. (Journal of Organic Chemistry, 31, 897 [1966]).

EXAMPLE LXVIII

6-(D-2-Amino-2-phenylacetamido)-2,2-dimethyl-3-(5-tetrazolyl) penam

To a stirred solution of 23.8 ml. of ethyl chloroformate in 600 ml. of acetone, is added 25 ml. of a 3% solution of N-methylmorpholine in acetone. The resulting solution is cooled to −40° C., and then 75.2 g. of sodium N-(2-methoxycarbonyl-1-methylvinyl)-D-2-amino-2-phenylacetate is added. The temperature is adjusted to −20° C. and stirring is continued for 28 minutes. The solution is re-cooled to −40° C., and an ice-cold solution, prepared by suspending 60.0 g. of 6-amino-2,2-dimethyl-3-(5-tetrazolyl)penam in 250 ml. of water and then adjusting the pH to 7.0, is added. The resulting solution is stirred for 30 minutes without further cooling, and then the acetone is removed by evaporation in vacuo. To the aqueous residue is added an equal volume of tetrahydrofuran, and then, at 5° C. the pH is adjusted to 1.5 with dilute hydrochloric acid. The mixture is held at this temperature and pH for 30 minutes, and then the tetrahydrofuran is removed by evaporation in vacuo. The aqueous residue is extracted with ethyl acetate, followed by ether, and the extracts are discarded. The pH of the remaining aqueous phase is raised to 5.4, and the product begins to crystallize out. After 1 hour it is filtered off and dried. The crude yield is 68.8 g.

The product is suspended in water at 25° C., and the pH is lowered to 1.5. After stirring for a short period, the insoluble materials are filtered off, and the filtrate is extracted with ether. The aqueous solution is then cooled to 5° C., and the pH is adjusted to 5.2. The solid which precipitates is filtered off, giving 62.7 g. (58.7% yield) of 6-(D-2-amino-2-phenylacetamido)-2,2-dimethyl-3-(5-tetrazolyl)penam trihydrate, m.p. 201°-202° C., $[\alpha]_D^{25}+228.2$ (1% in $CH_3OH$). IR (KBr disc): 1780 $cm^{-1}$ (β-lactam). NMR (in DMSO-$d_6$/$D_2O$): 7.60 ppm (s, 5H), 5.70 ppm (d, 1H), 5.55 ppm (d, 1H), 5.20 ppm (s, 1H), 5115 ppm (d, 1H), 1.50 ppm (s, 3H), 0.90 ppm (s, 3H).

Analysis—Calcd. for $C_{16}H_{19}O_2N_7S.3H_2O$ (percent): C, 44.95; H, 5.89; N, 22.94; S, 7.50. Found (percent): C, 45.01; H, 5.84; N, 22.81; S, 7.34.

The sodium N-(2-methoxycarbonyl-1-methylvinyl)-D-2-amino-2-phenylacetate is prepared from methyl acetoacetate and D-2-amino-2-phenylacetic acid by the procedure used by Long et al. (*J. Chem. Soc., London, Part C,* 1920 [1971]) for the corresponding p-hydroxy compound.

EXAMPLE LXIX

The procedure of Example LXVIII is repeated, except that the sodium N-(2-methoxycarbonyl-1-methylvinyl)-2-amino-2-phenylacetate is replaced by the appropriate α-amino acid, protected as its acetoacetic ester enamine derivative. This affords the following compounds. In some instances, the products are purified by Sephadex chromatography of their sodium salts.

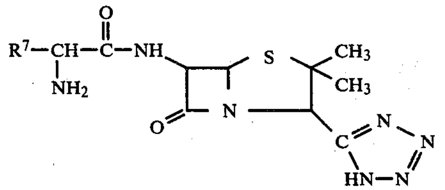

| $R^7$ | Side-chain Configuration | Yield (%) | Infrared Spectrum ($cm^{-1}$) | NMR Spectrum (ppm) |
|---|---|---|---|---|
| m-hydroxyphenyl[1] | D | 5 | 1776, 1686 | 7.55-6.73(m,4H), 5.72(d,1H), 5.44(d,1H), 5.24(s,1H), 5.12(s,1H), 1.37(s,3H), 0.90 (s,3H), ($D_2O$), |
| 3,4-dihydroxyphenyl | DL | 3 | 1770, 1684 | 6.97(s,1H), 6.80(s,2H), 5.75-5.34(m,2H), 5.03(s,1H), 4.93 and 4.86(2s,1H), 1.56 and 1.50(2s,3H), 0.96 and 0.92(2s,3H). (DMSO-$d_6$) |
| p-methoxyphenyl | D | 30 | 1775 | 7.56-6.90(q,4H), 5.60(m,2H), 5.16(s,1H), 5.10(s,1H), 4.77(m,2H), 3.84(s,3H), 1.56 (s,3H), 1.00(s,3H). (DMSO-$d_6$). |
| p-hydroxyphenyl | L | 7 | | 7.35(d,2H), 6.85(d,2H), 5.68(d,1H), 5.50 (d,1H), 5.08(s,1H), 4.98(s,1H), 1.58(s,3H), |

-continued

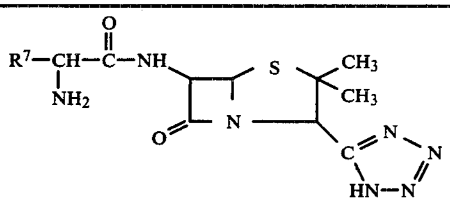

| $R^7$ | Side-chain Configuration | Yield (%) | Infrared Spectrum ($cm^{-1}$) | NMR Spectrum (ppm) |
|---|---|---|---|---|
| | | | | 1.00(s,3H). (DMSO-$d_6$). |
| 2-thienyl | D | 28 | 1770 | 7.74–7.10(m,3H), 5.75–5.54(m,2H), 5.44(s,1H), 5.12(s,1H), 1.52(s,3H), 0.96(s,3H). (DMSO-$d_6$). |
| p-(N,N-dimethyl-amino)phenyl | DL | 27 | 1775, 1690 | 7.44–6.79(q,4H), 5.84–5.46(m,2H), 5.23–4.99 (m,2H), 2.94(s,6H), 1.59 and 1.50(2s,3H), 1.00 and 0.93(2s,3H). (DMSO-$d_6$). |
| 3-chloro-4-hydroxy-phenyl[1] | D | 44 | 1783 | 7.63–6.88(m,3H), 5.60(d,1H), 5.43(d,1H), 5.06(s,1H), 5.03(s,1H), 1.42(s,3H), 0.90 (s,3H). (DMSO-$d_6$). |
| p-chlorophenyl[1 3] | DL | 7 | 1785, 1695 | 7.53(s,4H), 5.63(d,1H), 5.53(d,1H), 5.30 (s,1H), 3.20(q,6H), 1.63(s,3H), 1.26(t,9H), 1.06(s,3H). ($D_2O$). |
| m-chlorophenyl[1 3] | DL | 14 | 1780, 1700 | 7.43(m,4H), 5.76(m,1H), 5.50(m,1H), 5.28 (d,1H), 5.16(s,1H), 3.16(q,6H), 1.36(s,3H), 1.26(t,9H), 0.96(d,3H). ($D_2O$). |
| m-nitrophenyl[1 3] | DL | 22 | 1785, 1666 | 7.8–8.6(m,4H), 5.9(m,1H), 5.5(d,1H), 5.15(s,1H), 5.10 (s,1H), 3.10(q,6H), 1.7(s,3H), 1.3(t,3H), 1.0(s,3H) (DMSO-$d_6$/$D_2O$). |
| p-sulfamoylphenyl | DL | | 1775, 1650 | 8.2–7.2(m,4H), 5.8–5.3(m,2H), 5.2(s,1H), 5.10(s,1H), 1.5 and 1.3(d,3H) 1.0 and 0.7(d,3H) (DMSO-$d_6$/$D_2O$). |
| p-fluorophenyl | D | | 1775, 1650 | 8.0–7.0(m,4H), 6.7(d,1H), 6.5(d,1H), 5.2 (s,1H), 5.1 (s,1H), 1.4(s,3H) 0.9(s,3H) (DMSO-$d_6$/$D_2O$). |
| 2-furyl | D | 18 | 1780, 1695 | 7.5(m,1H), 6.5(m,2H), 5.8(s,1H), 5.5(m,2H), 5.3(s,1H), 1.6(s,3H), 1.0(s,3H) ($D_2O$). |
| 2-tetrahydrofuryl | D | 50 | 1780, 1690 | 5.6(m,2H), 5.2(s,1H), 4.1(m,1H), 3.7(m,3H), 1.8(m,4H), 1.6(s,3H), 1.0(s,3H) (DMSO-$d_6$/$D_2O$). |
| 3-pyridyl | DL | | 1775 | 9.0–8.6(m,2H), 8.1–7.7(m,1H), 7.7–7.4(m,1H), 5.8–5.5 (m,2H), 5.2–5.0(m,2H), 1.5(d,3H), 0.9(d,2H) (DMSO-$d_6$). |
| 2-bromo-5-hydroxy-phenyl[2] | DL | 28 | 1780, 1690 | 7.56(m,2H), 7.03(m,1H), 5.76(m,1H), 5.56(m, 1H), 5.30(s,1H), 5.15(s,1H), 1.46(s,3H), 0.96(s,3H). (DMSO-$d_6$/$D_2O$). |
| m-fluorophenyl[1] | D | 17 | 1780, 1670 | 7.58–7.23(m,4H), 5.33(d,1H), 5.26(d,1H), 5.16(s,1H), 5.10(s,1H), 1.43(s,3H), 0.90 (s,3H). (DMSO-$d_6$/$D_2O$). |
| hydrogen | — | | 1785 | 6.35(m), 5.76–5.46(m,2H), 5.12(s,1H), 3.71 (s,2H), 1.62(s,3H), 1.00(s,3H). (DMSO-$d_6$). |
| isopropyl | D | 30 | 1775, 1680 | 5.85(d,1H), 5.55(d,1H), 5.35(s,1H), 3.9(m, 1H), 2.08(m,1H), 1.67(s,3H), 1.07(s,3H), 1.00(d,6H). ($D_2O$). |
| benzyl | D | 41 | 1775, 1680 | 7.36(s,5H), 5.73(d,1H), 5.53(d,1H), 5.35(s, 1H), 3.10(m,3H), 1.53(s,3H), 1.00(s,3H). |
| 3-indolylmethyl | D | 58 | 1775, 1680 | 7.30(m,5H), 5.42(d,1H), 5.30(d,1H), 5.23(s,1H), 3.80(m,1H), 3.20(m,2H), 1.33(s,3H), 0.94(s, 3H). ($D_2O$). |

The starting enamines are obtained by condensation of the appropriate glycine with methyl acetoacetate, according to the procedure of Long, et al. (*Journal of the Chemical Society* [London], Part C, 1920 [1971]). Those α-amino acids which are described in the literature are prepared by the published procedures. The new α-amino acids are prepared from the corresponding aldehydes via a Strecker synthesis, techniques for which are discussed by Greenstein and Winitz in "Chemistry of the Amino Acids," John Wiley and Sons, Inc., New York/London, 1961, pp. 698–700, and references cited therein. the Strecker synthesis produces DL amino acids, which are resolved into their optical isomers by conventional means (consult Greenstein and Winitz, loc. cit., pp. 715–755; Nishimura, et al., *Nippon Kagaku Zasshi,* 82, 1688 [1961] [*Chemical Abstracts,* 58, 11464 (1963)]); and Belgian patent No. 795,874). See also British patent No. 1,221,227.

5-(3-Pyridyl)hydantoin is prepared by the method of Henze and Knowles, *J. Org. Chem.*, 19, 1127 (1954), and it is hydrolysed to 2-amino-2-(3-pyridyl)acetic acid by the method described by Davis et al. (*Archives Biochem and Biophys.* 87, 88 [1960]) for the corresponding 4-isomer.

EXAMPLE LXX

Starting with the appropriate 2-substituted sodium N-(2-methoxycarbonyl-1-methylvinyl)-2-aminoacetate, and following the procedure of Example LXVIII, the following compounds are prepared:

6-(D-2-amino-2-[p-fluorophenyl]acetamido)-2,2-dimethyl-3-(5-tetrazolyl)penam, 6-(L-2-amino-2-[p-fluorophenyl]acetamido)-2,2-dimethyl-3-(5-tetrazolyl)penam, 6-(D-2-amino-2-[o-chlorophenyl]acetamido)-2,2-dimethyl-3-(5-tetrazolyl)penam, 6-(L-2-amino-2-[o-chlorophenyl]acetamido)-2,2-dimethyl-3-(5-tetrazolyl)penam,
6-(D-2-amino-2-[m-bromophenyl]acetamido)-2,2-dimethyl-3-(5-tetrazolyl)penam,
6-(L-2-amino-2-[m-bromophenyl]acetamido)-2,2-dimethyl-3-(5-tetrazolyl)penam,
6-(D-2-amino-2-[m-chlorophenyl]acetamido)-2,2-dimethyl-3-(5-tetrazolyl)penam,
6-(L-2-amino-2-[m-chlorophenyl]acetamido)-2,2-dimethyl-3-(5-tetrazolyl)penam,
6-(D-2-amino-2-[p-chlorophenyl]acetamido)-2,2-dimethyl-3-(5-tetrazolyl)penam,
6-(L-2-amino-2-[p-chlorophenyl]acetamido)-2,2-dimethyl-3-(5-tetrazolyl)penam,
6-(DL-2-amino-2-[2,4-dichlorophenyl]acetamido)-2,2-dimethyl-3-(5-tetrazolyl)penam,
6-(DL-2-amino-2-[3,4-dichlorophenyl]acetamido)-2,2-dimethyl-3-(5-tetrazolyl)penam,
6-(D-2-amino-2-[o-fluorophenyl]acetamido)-2,2-dimethyl-3-(5-tetrazolyl)penam,
6-(DL-2-amino-2-[o-fluorophenyl]acetamido)-2,2-dimethyl-3-(5-tetrazolyl)penam,
6-(D-2-amino-2-[m-fluorophenyl]acetamido)-2,2-dimethyl-3-(5-tetrazolyl)penam,
6-(L-2-amino-2-[m-fluorophenyl]acetamido)-2,2-dimethyl-3-(5-tetrazolyl)penam,
6-(D-2-amino-2-[p-bromophenyl]acetamido)-2,2-dimethyl-3-(5-tetrazolyl)penam,
6-(L-2-amino-2-[m-hydroxyphenyl]acetamido)-2,2-dimethyl-3-(5-tetrazolyl)penam,
6-(DL-2-amino-2-[p-hydroxyphenyl]acetamido)-2,2-dimethyl-3-(5-tetrazolyl)penam,
6-(D-2-amino-2-[m-tolyl]acetamido)-2,2-dimethyl-3-(5-tetrazolyl)penam,
6-(L-2-amino-2-[m-tolyl]acetamido)-2,2-dimethyl-3-(5-tetrazolyl)penam,
6-(DL-2-amino-2-[p-isopropylphenyl]acetamido)-2,2-dimethyl-3-(5-tetrazolyl)penam,
6-(D-2-amino-2-[p-amylphenyl]acetamido)-2,2-dimethyl-3-(5-tetrazolyl)penam,
6-(DL-2-amino-2-[o-methoxyphenyl]acetamido)-2,2-dimethyl-3-(5-tetrazolyl)penam,
6-(DL-2-amino-2-[p-isopropoxyphenyl]acetamido)-2,2-dimethyl-3-(5-tetrazolyl)penam,
6-(D-2-amino-2-[m-butoxyphenyl]acetamido)-2,2-dimethyl-3-(5-tetrazolyl)penam,
6-(L-2-amino-2-[m-butoxyphenyl]acetamido)-2,2-dimethyl-3-(5-tetrazolyl)penam,
6-(DL-2-amino-2-[p-amyloxyphenyl]acetamido)-2,2-dimethyl-3-(5-tetrazolyl)penam,
6-(D-2-amino-2-[p-amyloxyphenyl]acetamido)-2,2-dimethyl-3-(5-tetrazolyl)penam,
6-(DL-2-amino-2-[3,4-dimethoxyphenyl]acetamido)-2,2-dimethyl-3-(5-tetrazolyl)penam,
6-(DL-2-amino-2-[3,5-dimethoxyphenyl]acetamido)-2,2-dimethyl-3-(5-tetrazolyl)penam,
6-(DL-2-amino-2-[p-methylthiophenyl]acetamido)-2,2-dimethyl-3-(5-tetrazolyl)penam,
6-(DL-2-amino-2-[p-isopropylthiophenyl]acetamido)-2,2-dimethyl-3-(5-tetrazolyl)penam,
6-(D-2-amino-2-[1,4-cyclohexadienyl]acetamido)-2,2-dimethyl-3-(5-tetrazolyl)penam,
6-(L-2-amino-2-[1,4-cyclohexadienyl]acetamido)-2,2-dimethyl-3-(5-tetrazolyl)penam,
6-(DL-2-amino-2-cyclopropylacetamido)-2,2-dimethyl-3-(5-tetrazolyl)penam,
6-(DL-2-amino-2-cyclopentylacetamido)-2,2-dimethyl-3-(5-tetrazolyl)penam,
6-(D-2-amino-2-cyclohexylacetamido)-2,2-dimethyl-3-(5-tetrazolyl)penam,
6-(DL-2-amino-2-cycloheptylacetamido)-2,2-dimethyl-3-(5-tetrazolyl)penam,
6-(D-2-aminopropionamido)-2,2-dimethyl-3-(5-tetrazolyl)penam,
6-(D-2-aminobutyramido)-2,2-dimethyl-3-(5-tetrazolyl)penam,
6-(D-2-aminovaleramido)-2,2-dimethyl-3-(5-tetrazolyl)penam,
6-(DL-2-amino-2-allylacetamido)-2,2-dimethyl-3-(5-tetrazolyl)penam,
6-(DL-2-amino-2-(2-butenyl)acetamido)-2,2-dimethyl(5-tetrazolyl)penam,
6-(L-2-amino-2-[3-thienyl]acetamido-2,2-dimethyl-3-(5-tetrazolyl)penam,
6-(L-2-amino-2-[2-thienyl]acetamido)-2,2-dimethyl-3-(5-tetrazolyl)penam,
6-(D-2-amino-2-[3-furyl]acetamido)-2,2-dimethyl-3-(5-tetrazolyl)penam,
6-(D-2-amino-3-[5-ethyl-2-thienyl]acetamido)-2,2-dimethyl-3-(5-tetrazolyl)penam,
6-(D-2-amino-2-[3-hydroxymethyl)phenyl]acetamido)-2,2-dimethyl-3-(5-tetrazolyl)penam,
6-(D-2-amino-2-[4-(hydroxymethyl)phenyl]acetamido)-2,2-dimethyl-3-(5-tetrazolyl)penam,
6-(DL-2-amino-2-[4-isothiazolyl]acetamido)-2,2-dimethyl-3-(5-tetrazolyl)penam respectively.

The starting 2-substituted sodium N-(2-methoxycarbonyl-1-methylvinyl)-2-amino-acetates are obtained by condensation of the appropriate 2-substituted glycines with methyl acetoacetate, according to the procedure of Long, et al. (*Journal of the Chemical Society* [London], Part C, 1920 [1971]). Those 2-substituted glycines which are described in the literature are prepared by the published procedures. The new 2-substituted glycines are prepared from the corresponding aldehydes via a Strecker synthesis, techniques for which are discussed by Greenstein and Winitz in "Chemistry of the Amino Acids," John Wiley and Sons, Inc., New York/London, 1961, pp. 698–700, and references cited therein. The Strecker synthesis produces DL amino acids, which are resolved into their optical isomers by conventional means (consult Greenstein and Winitz, loc. cit., pp. 715–755; Nishimura, et al., Nippon Kagaku Zasshi, 82, 1688 [1961] [Chemical Abstracts, 58, 11464 (1963)]).

EXAMPLE LXXI

6-(D-2-Amino-2-[4-hydroxyphenyl]acetamido)-2,2-dimethyl-3-(5-tetrazolyl)penam To a stirred solution of 0.19 ml. of ethyl chloroformate in 15 ml. of dry acetone, cooled to 0° C., is added 1 drop of N-methylmorpholine, followed by 576 mg. of sodium N-(2-methoxycarbonyl-1-methylvinyl)-D-2-amino-2-(4-hydroxyphenyl)acetate (Long et al., Journal of the *Chemical Society* [London], Part C, 1920 [1971]). The mixture is stirred for a further 30 minutes, and then it is cooled to about −35° C. To it is then added an ice-cold solution of the sodium salt of 6-amino-2,2-dimethyl-3-(5-tetrazolyl)penam, prepared by adding 10% sodium hydroxide to a suspension of 436 mg. of 6-amino-2,2-dimethyl-3-(5-tetrazolyl)penam in 5 ml. of water (to give a pH of 7.8), followed by dilution with 25 ml. of acetone. The cooling bath is removed, and the reaction mixture is stirred for a further 30 minutes. At this point, the acetone is removed by evaporation under reduced pressure, and then 20 ml. of methyl isobutyl ketone is added to the aqueous residue. The two-phase system is cooled to 10° C., acidified to pH=0.9 with dilute hydrochloric acid, and then it is stirred at 10° C. for 1 hour. The methyl isobutyl ketone is removed and discarded. The pH of the aqueous phase is raised to 6.6, and then it is stored in the refrigerator for 3 hours. The precipitate which forms is filtered off, giving 320 mg. of 6-(D-2-amino-2-[4-hydroxyphenyl]acetamido-2,2-dimethyl-3-(5-tetrazolyl)penam. The infrared spectrum (KBr disc) of the product shows absorptions at 1775 $cm^{-1}$ (β-lactam carbonyl) and 1680 $cm^{-1}$ (amide I band). The NMR spectrum (in DMSO-$d_6$/$D_2O$) shows absorptions at 7.35 and 6.85 ppm (2 doublets, aromatic hydrogens), 5.60 ppm (quartet, C-5 and C-6 hydrogens), 5.10 ppm (multiplet, benzyl hydrogen and C-3 hydrogen), 1.45 ppm (singlet, C-2 methyl hydrogens) and 0.95 ppm (singlet, C-2 methyl hydrogens).

EXAMPLE LXXII

6-(D-2-Amino-2-[3-thienyl]acetamido)-2,2-dimethyl-3-(5-tetrazolyl)penam

The procedure of Example LXXI is repeated, except that the sodium N-(2-methoxy-carbonyl-1-methyl-vinyl)-D-2-amino-2-(4-hydroxyphenyl)acetate used therein is replaced by an equimolar amount of N-(2-methoxy-carbonyl-1-methyl-vinyl)-D-2-amino-2-(3-thienyl)acetate. There is obtained a 38% yield of 6-(D-2-amino-2-[3-thienyl]acetamido)-2,2-dimethyl-3-(5-tetrazolyl) penam. The infrared spectrum of the product (KBr disc) shows absorptions at 1770 $cm^{-1}$ (β-lactam carbonyl), 1680 $cm^{-1}$ (amide I band) and 1505 $cm^{-1}$ (amide II band). The NMR spectrum (in DMSO-$D_6$/$D_2O$) shows absorptions at 7.60–7.05 ppm (multiplet, aromatic), 5.70–5.35 (multiplet, C-5 and C-6 hydrogens), 5.30 and 5.10 ppm (2 singlets, methine hydrogen and C-3 hydrogen), 1.50 ppm (singlet C-2 methyl hydrogens) and 0.95 ppm (singlet, C-2 methyl hydrogens).

The sodium N-(2-methoxycarbonyl-1-methylvinyl)-D-2-amino-2-(3-thienyl)acetate used in this Example is prepared from D-2-(3-thienyl)glycine and methyl acetoacetate using the method described by Long, et al. (*Journal of the Chemical Society* [London], Part C, 1920 [1971]) for the condensation of D-2-(4-hydroxyphenyl)glycine with methyl acetoacetate. The D-2-(3-thienyl)glycine is prepared from thiophene-3-aldehyde by a Strecker reaction, followed by resolution of the DL-2-(3-thienyl)glycine so produced into its optical antipodes (Nishimura et al., *Nippon Kagaku Zasshi,* 82 1688 [1961])(*Chemical Abstracts,* 58, 11464 [1963]).

EXAMPLE LXXIII

6-(D-2-Amino-2-[4-aminophenyl]acetamido)-2,2-dimethyl-3-(5-tetrazolyl)penam

A mixture of 23.9 g. of D-2-amino-2-(4-aminophenyl)acetic acid dihydrochloride (United States patent No. 3,634,405), 45.4 ml. of triethylamine and 90 ml. of methanol is stirred at 25° C. for 10 minutes, and then it is heated under reflux for 30 minutes. It is cooled to 25° C. again, and 31.5 ml. of methyl acetoacetate is added. This new reaction mixture is stirred at ambient temperature for 20 minutes, and then it is heated under reflux for 40 minutes. The cooled reaction mixture is then poured, with stirring into 3,000 ml. of ether. The solid which precipitates is filtered off and discarded. Removal of the solvent by evaporation in vacuo leaves 42.3 g. (93% yield) of the required triethylammonium N,N'-bis(2-methoxycarbonyl-1-methylvinyl)-D-2-amino-2-(4-aminophenyl)acetate.

To 19.0 g. of the above bis-enamine in 200 ml. of tetrahydrofuran is added with vigorous stirring 8 drops of N-methylmorpholine, followed by 5.38 ml. of isobutyl chloroformate, at 0°–5° C. Stirring is continued for 1 hour at 0°–5° C. at the end of the addition. A solution is then prepared by suspending 9.85 g. of 6-amino-2,2-dimethyl-3-(5-tetrazolyl)penam in 80 ml, if water, cooling to 0°–5° C., adding 6 N sodium hydroxide to give a pH of 7.5, and finally diluting with 200 ml. of tetrahydrofuran. This latter solution is then added to the above mixed anhydride solution at ca. −40° C. The resulting mixture is stirred at 0°–5° C. for 1 hour. The pH is then lowered to 2.0, and the stirring is continued for a further 30 minutes at 0°–5° C. At this point, the bulk of the tetrahydrofuran is removed by evaporation in vacuo, and then the residual aqueous phase is washed twice with ethyl acetate. The aqueous phase is then cooled to 5° C., adjusted to pH 6.0, filtered, and lyophilized. This affords the title compound in a crude state. It is purified by chromatography on Sephadex LH-20. The final yield is 591 mg. (3.7%). IR (KBr disc): 1770 $cm^{-1}$. NMR (DMSO-$d_6$): 7.18 and 6.60 ppm (q, J=8 Hz, 4H), 5.61 and 5.50 ppm (q, J=4 Hz, 2H), 5.03 ppm (s, 1H), 4.91 ppm (s, 1H), 1.51 ppm (s, 3H) and 0.95 ppm (s, 3H).

EXAMPLE LXXIV

6-(D-2-Amino-2-[3-aminophenyl]acetamido)-2,2-dimethyl-3-(5-tetrazolyl)penam

To a stirred solution of 5.0 g. of D-2-amino-2-(3-nitrophenyl)acetic acid in 26 ml. of 1.0 N sodium hydroxide, at 5° C., is added 4.4 g. of benzyl chloroformate. Stirring is continued for 1 hour with the pH being maintained between 9 and 11. The reaction mixture is washed with ethyl acetate, and then the pH is lowered to 2.0. The aqueous residue is then extracted with ethyl acetate. The extract is dried using anhydrous sodium sulfate, and then it is evaporated in vacuo to give 5.3 g. of N-(benzyloxycarbonyl)-D-2-amino-2-(3-nitrophenyl)acetic acid, $[\alpha]_D^{24}=-108°$ (C=1, $CH_3OH$).

To a stirred suspension of 5.0 g. (15 mmole) of the above benzyloxycarbonyl derivative, and 3.6 g. of 6-amino-2,2-dimethyl-3-(5-tetrazolyl)penam in 70 ml. of water is added sufficient 20% sodium hydroxide to adjust to pH to 6.0. The resulting solution is cooled to 5° C., and to this is added a solution of 2.8 g. (15 mmole) of 1-ethyl-3,3'dimethylaminopropylcarbodiimide hydrochloride in 10 ml of water. The pH of the solution is maintained between 6.0–6.2 for 2 hours. The reaction is then warmed to room temperature and the pH adjusted to 7.0. The solution is washed with 50 ml. of ethyl acetate and the pH is then readjusted to 2.0 (6 N hydrochloric acid). The solution is extracted with 300 ml. ethyl acetate, and the ethyl acetate layer dried and evaporated, to yield 3.5 grams of 6-(2-[N-benzyloxycarbonylamino]-2-phenylacetamido-2,2-dimethyl-3-(5-tetrazolyl)penam.

A suspension of 3.4 g. of the above penam compound in 60 ml. of water is adjusted to pH 7.0 using 1.0 N sodium hydroxide. To the resultant solution is added 3.4 g. of 10% palladium-on-carbon, and the mixture is shaken for 2 hours under an atmosphere of hydrogen at 50 psi. The reaction mixture is then filtered, acidified to pH 2.0, and extracted with ethyl acetate. The extracts are discarded, and the pH of the aqueous phase is adjusted to 5.5. The solution is then lyophilized. The residue is stirred with 30 ml. of N,N-dimethylformamide for 20 minutes, and then the insoluble material is removed by filtration and discarded. The filtrate is added dropwise to 800 ml. of hexane. The resulting precipitate is collected by filtration to give 0.78 g. of 6-(D-2-amino-2-[3-aminophenyl]acetamido)-2,2-dimethyl-3-(5-tetrazolyl)-penam. IR (KBr disc): 1775 and 1650 $cm^{-1}$. NMR ($DMSO-d_6/D_2O$): 6.7–7.4 ppm (m, 4H), 6.4–6.8 ppm (m, 2H), 5.10 ppm (s, 1H), 5.00 ppm (s, 1H) 1.50 ppm (s, 3H) 0.90 ppm (s, 3H). $[\alpha]_D^{24}=196$ (C=0.1 1 N HCl).

EXAMPLE LXXV 6-(2-[4-Aminomethylphenyl]acetamido)-2,2-dimethyl-3-(5-tetrazolyl)penam Sodium 4-[(1-methoxycarbonyl-2-propenyl-)aminomethyl]phenylacetate is prepared from 4-aminomethylphenylacetic acid [Zaugg and Horrom, *J. Am. Chem. Soc.* 80, 4317 (1958)] and methyl acetoacetate by the method described by Dane and Dockner [*Chem. Ber.*, 98, 789 (1965)]. A suspension of this salt (2.15 g, 7.5 mmole), 7 drops of N-methylmorpholine and 100 ml. of tetrahydrofuran is stirred at −20° C.; ethyl chloroformate (0.81 g. 7.5 mmole) is added and the mixture is stirred for 60 minutes. 6-Amino-2,2-dimethyl-3-(5-tetrazolyl)penam (1.80 g., 7.5 mmoles) is suspended in a 50:50 mixture of tetrahydrofuran and water (40 ml), and the pH is adjusted to 7.5 with 1 N sodium hydroxide solution whereby a homogeneous solution is obtained. This is added to the above suspension, in one portion, the new mixture is stirred at −20° C. for 1 hour and then it is allowed to warm to room temperature over 1 hour. Most of the tetrahydrofuran is removed in vacuo, the resultant aqueous solution is cooled in an ice bath, and the pH is adjusted to 1.5 with 3 N hydrochloric acid. After 30 minutes the pH is adjusted to 2.5, and the solution is extracted with ethyl acetate. The aqueous phase is adjusted to pH 6.0 and freeze-dried. The resultant lyophylate is combined with that from another preparation (5 mmoles) and chromatographed on Sephadex LH-20 (150 g) eluting with water. Like fractions (tlc analysis) are combined and freeze-dried, yielding the title compound as a colorless amorphous solid (570 mg., 11% yield), m.p. 190°–200° C. IR(KBr): 1770, 1650 and 1515 $cm^{-1}$. NMR ($DMSO-d_6-D_2O$): 7.4 ppm (s, 4H), 5.65 ppm (d, J=4 Hz, 1H), 5.45 ppm (d, J=4 Hz, 1H), 5.2 ppm (s, 1H), 4.1 ppm (s, 2H), 3.6 ppm (s, 2H), 1.6 ppm (s, 3H) and 1.0 ppm (s, 3H).

When the above procedure is repeated and the 4-aminomethylphenylacetic acid is replaced by an equimolar amount of 3-(2-aminoethyl)phenylacetic acid, 4-(2-aminoethyl)-phenylacetic acid, 5-(2-aminoethyl)-1-tetrazolylacetic acid and 5-(2-aminoethyl)-2-tetrazolylacetic acid, respectively, there is obtained:

6-(2-[3-(2-aminoethyl)phenyl]acetamido)-2,2-dimethyl-3-(5-tetrazolyl)penam, 6-(2-[4-(2-aminoethyl)phenyl]acetamido)-2,2-dimethyl-3-(5-tetrazolyl)penam, 6-(2-[5-(2-aminoethyl)-1-tetrazolyl]acetamido)-2,2-dimethyl-3-(5-tetrazolyl)penam and 6-(2-[5-(2-aminoethyl)-2-tetrazolyl]acetamido)-2,2-dimethyl-3-(5-tetrazolyl)penam, respectively.

EXAMPLE LXXVI 6-(2-[2-Azidomethylphenyl]acetamido)-2,2-dimethyl-3-(5-tetrazolyl)penam A stirred suspension of 21.73 g. of 6-amino-2,2-dimethyl-3-(5-tetrazolyl)penam in 400 ml. of a 50:50 mixture of tetrahydrofuran-water is cooled to ca. 0° C. and the pH is adjusted to 7.5 using 1.0 N sodium hydroxide. To the solution thus obtained, is added 17.3 g. of 2-(2-azidomethylphenyl)acetic acid (U.S. Pat. No. 3,766,175), followed by 17.4 g. of 1-(3-dimethylaminopropyl)-3-ethylcarbodiimide hydrochloride. The pH drops to 5.5. The reaction mixture is then stirred at ambient temperature, at pH 6, for 3 hours. At this point, the bulk of the tetrahydrofuran is removed by evaporation in vacuo, and the residual aqueous phase is extracted with ethyl acetate. The organic extract is discarded and the aqueous phase is cooled to ca. 0° C. The pH is then adjusted to 2 and the product is extracted into ethyl acetate. The ethyl acetate is dried and evaporated, leaving 34.8 g. of the title compound as a tan solid. IR($CHCl_3$) 2100, 1790, 1680 and 1515 $cm.^{-1}$ NMR ($DMSO-d_6$): 7.37 (s, 4H), 5.60 (m, 2H, 5.23 (s, 1H), 4.55 (s, 2H), 3.70 (s, 2H), 1.66 (s, 3H) and 1.06 ppm (s, 3H).

The above product is dissolved in 400 ml. of 50:50 tetrahydrofuran-water at ca. 0° C. and the pH is adjusted to 7.0 with 1.0 N sodium hydroxide. The tetrahydrofuran is removed by evaporation under reduced pressure, and the residual aqueous phase is lyophilized to give 28.8 g. (73% yield) of the title compound as its sodium salt.

EXAMPLE LXXVII

6-[2-[o-(aminomethyl)phenyl]acetamido)-2,2-dimethyl-3-(5-tetrazolyl)penam

To a stirred mixture of 2.25 g. of sodium N-(1-methyl-2-methoxycarbonylvinyl)-2-(o-[aminomethyl]phenyl-)acetate and 2 drops of N-methylmorpholine in 20 ml. of tetrahydrofuran, at −10° C., is added 0.856 g. of ethyl chloroformate. Stirring is continued for a further 15 minutes at ca. −5° C., and then the mixture is cooled to −30° C. To this mixture is then added a solution prepared by adding 1.68 g. of 6-amino-2,2-dimethyl-3-(5-tetrazolyl)penam to 20 ml. of 1:3 water-tetrahydrofuran and adjusting the pH to 7.0. After the addition, the cooling bath is removed, and the reaction mixture is allowed to warm to ambient temperature. The tetrahydrofuran is removed by evaporation in vacuo, and 15 ml. of tetrahydrofuran are added to the aqueous residue. The pH is adjusted to 1.5, and then the mixture is stirred at this pH for 30 minutes. The pH is then raised to 3.0 and the tetrahydrofuran is removed by evaporation in vacuo. The aqueous residue is washed with ethyl acetate, and then the aqueous solution is concentrated to small volume. The solid which precipitates is filtered off giving 0.52 g. of 6-(2-[o-(aminomethyl)phenyl-]acetamido]-2,2-dimethyl-3-(5-tetrazolyl)penam. The infrared spectrum of the product (KBr disc) shows absorptions at 1780 $cm^{-1}$ ($\beta$-lactam) and 1645 $cm^{-1}$. The NMR spectrum ($DMSO-d_6/D_2O$) shows absorptions at 7.45 ppm (singlet, 4H), 5.60 ppm (quartet, 2H), 5.10 ppm (singlet, 1H), 4.10 ppm (singlet, 2H), 3.80 ppm (singlet, 2H), 1.65 ppm (singlet, 3H), and 0.95 ppm (singlet, 3H).

The starting sodium N-(1-methyl-2-methoxycarbonylvinyl)-2-(o-[aminomethyl]phenyl)acetate is prepared from 2-(o-[aminomethyl]phenyl)acetic acid (U.S. Pat. No. 3,766,175) and methyl acetoacetate using the method to Long et al. (*Journal of the Chemical Society* [London], Part C, 1920 [1971]) for the condensation of D-2-(p-hydroxyphenyl)glycine with methyl acetoacetate.

EXAMPLE LXXVIII 6-(2-[3-Azidomethyl-2-thienyl]acetamido)-2,2-dimethyl-3-(5-tetrazolyl)penam (A) 3-Bromomethyl-2-thienyl Methyl Ketone.

A mixture of 14 g. (0.1 mole) of 3-methyl-2-thienyl methyl ketone (Hartough and Kosak; *J. Amer. Chem. Soc.*, 69, 3093 [1947]), 18 g. (0.1 mole) of N-bromosuccinimide, 0.3 g. of azoisobutyronitrile and 300 ml. of carbon tetrachloride is heated under reflux for 4 hours. The cooled reaction mixture is filtered, and the filtrate is washed with saturated sodium bicarbonate solution and then dried. Evaporation of the solvent in vacuo leaves a solid, which is recrystallized from hexane, giving 16 g. (73% yield) of the bromomethyl compound, m.p. 62°-64° C.

(B) 3-Azidomethyl-2-thienyl Methyl Ketone.

To a solution of 5 g. (0.023 mole) of the above bromomethyl compound in 42 ml. of acetone and 4 ml. of water is added 1.56 g. (0.026 mole) of solid sodium azide. After the exothermic reaction subsided, the mixture is stirred for 2.5 hours at ambient temperature. The acetone is removed by evaporation, the residue is diluted with water, and the product is extracted into ether. The extract is washed with sodium bicarbonate solution, dried, and evaporated to give 4 g. (97% yield) of the azidomethyl compound as a yellow oil.

(C) 2-(3-Azidomethyl-2-thienyl)acetic Acid.

To a solution of 20.5 g. (0.113 mole) of the above azidomethyl compound in 230 ml. of methanol and 46 ml. of 70% aqueous perchloric acid, is added 55.1 g. (0.124 mole) of thallium (III) nitrate. The mixture is stirred at ambient temperature for 24 hours, and then 0.18 mole of sodium chloride is added. After 15 minutes, the reaction mixture is filtered and the filtrate is concentrated to half volume. A 150-ml. quantity of water is added and the solution is again concentrated to half volume. A further 150-ml. quantity of water is added and the mixture is extracted with ether. The extracts are washed with sodium bicarbonate solution, dried, and evaporated giving crude methyl 2-(3-azidomethyl-2-thienyl)acetate. This product is purified by chromatography on florisil. Yield 17.2 g. (72%).

A solution of 15.6 g. of the above ester in 200 ml. of tetrahydrofuran and 30 ml. of 3 N hydrochloric acid is heated under reflux for 5 hours. The cooled solution is then basified to pH 10 and the mixture is extracted with ether. The ether is discarded and the pH of the residual aqueous phase is lowered to 2. The product is then extracted into ether. The ether is dried and evaporated to give 10.5 g. (72% yield) of the acid as an oily solid.

(D)
6-(2-[3-Azidomethyl-2-thienyl]acetamido)-2,2-dimethyl-3-(5-tetrazolyl)penam.

A solution of 5.48 g. (0.0228 mole) of 6-amino-2,2-dimethyl-3-(5-tetrazolyl)penam in 200 m.l of 1:1 tetrahydrofuran-water is adjusted to pH 7.5, and then 4.5 g. (0.0228 mole) of 2-(3-azidomethyl-2-thienyl)acetic acid is added. The mixture is cooled to 0°-5° C., and 4.37 g. (0.0288 mole) of 1-ethyl-3-(3-dimethylaminopropyl)carbodiimide hydrochloride is added. The reaction mixture is stirred at pH 6 and at 0°-5° C. for 2.5 hours. At this point, the tetrahydrofuran is removed by evaporation in vacuo and the pH is adjusted to 7.5. The aqueous residue is washed with ethyl acetate and then the pH is lowered to 2.2. The product is extracted into ethyl acetate. The ethyl acetate is dried and evaporated in vacuo. This affords 8.1 g. (88% yield) of the title compound as a foam. IR (KBr disc): 2100, 1800, 1666, 1529 and 1250 $cm^{-1}$. NMR ($CDCl_3$): 7.3 (d, 1H), 7.0 (d, 1H), 5.7 (m, 2H), 5.3 (s, 1H), 4.4 (s, 2H), 3.9 (s, 2H), 1.6 (s, 3H) and 1.1 ppm (s, 3H).

EXAMPLE LXXIX 6-(2-[3-Aminomethyl-2-thienyl]acetamido)-2,2-dimethyl-3-(5-tetrazolyl)penam To a solution of 1.68 g. (0.004 mole) of 6-(2-[3-aminomethyl-2-thienyl]acetamido)-2,2-dimethyl-3-(5-tetrazolyl)penam in 100 ml. of water at pH 7.2 is added 3 ml. of dioxane and 600 mg. of 10% palladium on carbon. The mixture is shaken under an atmosphere of hydrogen at ca. 50 psi for 1.5 hours. The catalyst is then removed by filtration, and the pH of the aqoueus phase is adjusted to 5.4. The aqueous solution is then lyophilized to give the title compound in crude form. It is purified by chromatography using Sephadex and eluting with water. The purified products weighs 340 mg. 122% yield) and has m.p. 187°-195° C. (dec.). IR(KBr disc) 330, 1770, 1650, 1530 and 1315 $cm.^{-1}$. NMR ($D_2O$): 7.4 (d, 1H), 7.1 (d, 1H), 5.75 (d, 1H), 5.5 (d, 1H), 5.3 (s, 1H), 4.2 (s, 2H), 4.0 (s, 2H), 1.55 (s, 3H) and 1.0 ppm (s, 3H).

EXAMPLE LXXX 6-(2-[5-Azidomethyl-2-thienyl]acetamido)-2,2-dimethyl-3-(5-tetrazolyl)penam The title compound is prepared from 5-methyl-2-thienyl methyl ketone (Hartough and Kosak, *J. Amer. Chem. Soc.*, 69, 3093 [1947]) using the procedure of Example LXXVIII. IR (KBr disc): 3300, 2102, 1790, 1665 and 1540 $cm^{-1}$. NMR ($CDCl_3$): 6.9 (m, 2H), 5.7 (m, 2H), 5.25 (s, 1H), 4.4 (s, 2H), 3.8 (s, 2H), 1.6 (s, 3H) and 1.05 ppm (s, 3H).

EXAMPLE LXXXI 6-(2-[5-Aminomethyl-2-thienyl]acetamido)-2,2-dimethyl-3-(5-tetrazolyl)penam Hydrogenation of 6-(2-[5-azidomethyl-2-thienyl]acetamido)-2,2-dimethyl-3-(5-tetrazolyl)penam, according to the procedure of Example LXXIX, gives a 23% yield of the title compound. IR(KBr disc): 3330, 1785, 1665 and 1530 $cm^{-1}$. NMR ($D_2O$): 7.0 (q, 2H), 5.8 (d, 1H), 5.5 (d, 1H), 5.4 (s, 1H), 4.35 (s, 2H), 3.9 (s, 2H), 1.6 (s, 3H) and 1.0 ppm (s, 3H).

EXAMPLE LXXXII 6-(2-[2-(aminomethyl)phenylthio]acetamido)-2,2-dimethyl-3-(5-tetrazolyl)penam The title compound is prepared in 14% yield, as a colorless amorphous solid, by acylation of 6-amino-2,2-dimethyl-3-(5-tetrazolyl)penam with 2-(2-[aminomethyl]phenylthio)acetic acid (U.S. Pat. No. 3,766,176), using the method of Example LXXVII. IR(KBr disc): 1780 and 1665 $cm^{-1}$. NMR (DMSO-$d_6$/$D_2O$): 7.50 ppm (m, 4H), 5.70 ppm (d, 1H), 5.43 ppm (d, 1H), 5.19 ppm (s, 1H), 4.35 ppm (s, 2H), 3.94 ppm (s, 2H), 1.60 ppm (s, 3H), and 1.00 ppm (s, 3H).

EXAMPLE LXXXIII

6-(1-Aminocyclohexanecarboxamido)-2,2-dimethyl-3-(5-tetrazolyl)penam

The pH of a stirred suspension of 720 mg. (3.0 mmole) of 6-amino-2,2-dimethyl-3-(5-tetrazolyl)penam in 50 ml. of water, at 0° C., is adjusted to 7 using 1.0 N sodium hydroxide. When all the solid has dissolved, the pH is lowered to 6.0 (1.0 N hydrochloric acid), and then 750 mg. (3.4 mmole) of 2,4-oxazaspiro[4.5]decane-1,3-dione (Alburn, et al., Antimicrobial Agents and Chemotherapy, 586 [1967]) is added. The reaction mixture is stirred at ca. 0° C., and at pH 6, for 1 hour. It is then filtered. The pH is adjusted to 4.2, and the reaction is lyophilized. The residue is dissolved in 5 ml. of methylene chloride containing 606 mg of triethylamine. This new solution is added dropwise with stirring to 100 ml of ether, and the solid which precipitates is filtered off. This affords 1.3 g (93% yield) of a 2:1 complex of the title compound and triethylamine. IR (KBr disc): 1786, 1680 and 1640 $cm^{-1}$. NMR (in $D_2O$): 5.90 ppm (d, 1H), 5.40 ppm (d, 1H), 5.30 ppm (s, 1H), 3.10 ppm (q, 3H), 1.90–1.50 ppm (m, 10H), 1.60 ppm (s, 3H), 1.20 ppm (t, 4.5H), 1.00 ppm (s, 3H).

EXAMPLE LXXXIV

6-(D-2-Amino-2-[1,4-cyclohexadienyl]acetamido)-2,2-dimethyl-3-(5-tetrazolyl)penam Following the procedure use to prepare 6-(1-aminocyclohexanecarboxamido)-2,2-dimethyl-3-(5-tetrazolyl)penam (Example LXXXIII) the title compound is prepared from 0.5 g (2.8 mmole) of D-4-(1,4-cyclohexadienyl)-1,3-oxazolidin-2,5-dione and 6-amino-2,2-dimethyl-3-(5-tetrazolyl)penam; the product is isolated as a 1:2 complex with triethylamine: yield 520 mg (36%); IR (KBr) 1779, 1678 $cm^{-1}$. NMR (in $D_2O$): 6.10 ppm (s, 1H), 5.80 (s, 2H), 5.90 ppm (d, 1H), 5.60 ppm (d, 2H), 5.40 ppm (s, 1H), 4.50 ppm (s, 1H), 3.30 ppm (q, 12H), 2.80 ppm (broad s, 4H), 1.70 ppm (s, 3H), 1.40 ppm (5, 18H), 1.20 ppm (s, 3H).

D-4-(1,4-cyclohexadienyl)-1,3-oxazolidin-2,5-dione is prepared from 2.0 g (13.1 mmole) D-2-(1,4-cyclohexadienyl)glycine (Dolfini et al., J. Med. Chem. 14, 117 [1971]) and phosgene by the method described by Alburn, et al. [Antimicrobial Agents and Chemotherapy, 586 [1967]): yield 1.2 g (51%).

EXAMPLE LXXXV

6-(D,L-3-Amino-2-phenylpropionamido)-2,2-dimethyl-3-(5-tetrazolyl)penam

Sodium D,L-3-([1-methoxycarbonyl-2-propenyl]amino)-2-phenylpropionate is prepared from DL-3-amino-2-phenylpropionic acid [Testa, Fava and Fontanella, *Annalen,* 614, 167 (1958)] and methyl acetoacetate by the method described by Dane and Dockner [*Chem. Ber.,* 98, 789 (1965)]. A suspension of 1.43 grams (5 mmole) of this salt, one drop of N-methylmorpholine, 5 ml. of tetrahydrofuran and 30 ml. of dichloromethane is stirred at 0° C.; 0.6 grams (5 mmole) of 2,2-dimethylpropionyl chloride is then added, and the mixture is stirred for 30 minutes. A solution of 1.2 grams (5 mmole) of 6-amino-2,2-dimethyl-3-(5-tetrazolyl)penam, 1.01 grams (10 mmole) of triethylamine, and 30 ml. of dichloromethane is added to the suspension, and the new mixture is cooled and stirred for two hours. The volatile components are evaporated under reduced pressure, and the residue is dissolved in 60 ml. of water. This mixture is stirred and cooled in an ice bath while it is adjusted to pH 2.7 by the addition of 1 N hydrochloric acid. After an hour some gummy material is filtered, and the filtrate is cooled and is adjusted to pH 4.5 by the addition of 2 N sodium hydroxide. After stirring the new mixture for 30 minutes another small amount of solid matter is filtered, and the filtrate is lyophilized. The lyophilate is slurried in 50 ml. of dichloromethane and this mixture is filtered. The insoluble portion is dissolved in 100 ml. of dichloromethane and 4 ml. of triethylamine; a small amount of insoluble matter is filtered, and the filtrate is evaporated. The residue from the filtrate is triturated under ether to furnish the title compound as an amorphous 1:3 complex with triethylamine: yield 600 mg. (17%). IR (KBr disc): 1792, 1681 and 1618 $cm^{-1}$. NMR (in $D_2O$): 7.50 ppm (s,5H), 5.80 ppm (d,1H), 5.60 ppm (d,1H), 5.30 ppm (s,1H), 4.20–3.50 ppm (m,3H), 3.30 ppm (q,18H), 1.50 ppm (s,3H), 1.30 ppm (t,27H), 1.00 ppm (s,3H).

Using the above procedure, 6-(L-2-amino-3-[4-hydroxyphenyl]propionamido)-2,2-dimethyl-3-(5-tetrazolyl)penam is prepared as its sodium salt from 1.5 g. of sodium N-(1-methoxycarbonyl-2propenyl)-L-2-(4-hydroxyphenyl)propionate and 1.2 g. of 6-amino-2,2-dimethyl-3-(5-tetrazolyl)penam. The crude product is purified by chromatography using 25 g. of LH 20 grade dextran gel as the column packing, and eluting with water. The final yield is 90 mg. IR(KBr disc): 1780, 1688 and 1620 $cm^{-1}$. NMR (in $D_2O$): 6.9 ppm (q,4H), 5.7 ppm (d,1H), 5.4 ppm (d,1H), 5.2 ppm (s,1H), 3.1–2.7 ppm (m,3H), 1.4 ppm (s,3H) and 1.0 ppm (s,3H).

EXAMPLE LXXXVI

6-(2-[2-(2-Aminoethoxy)phenyl]acetamido)-2,2-dimethyl-3-(5-tetrazolyl)penam

The title compound is prepared in 64% yield from 2-(2-[2-aminoethoxy]phenyl)acetic acid (U.S. Pat. No. 3,759,905) and 6-amino-2,2-dimethyl-3-(5-tetrazolyl)penam, by a procedure analogous to that of Example LXXXV. IR (KBr disc): 1780 $cm^{-1}$ ($\beta$-lactam) and 1667 $cm^{-1}$ (amide I). NMR (in $D_2O$): 7.1 ppm (m,4H), 5.7 ppm (d,1H), 5.5 ppm (d,1H), 5.2 ppm (s,1H), 3.7–3.3 ppm (m,4H), 3.1 ppm (q,12H), 1.6 ppm (s,3H), 1.2 ppm (t,18H), 1.0 ppm (s,3H). The product is a 1:2 complex of the title compound and triethylamine.

EXAMPLE LXXXVII

6-(2-[3-(2-Aminoethoxy)phenyl]acetamido)-2,2-dimethyl-3-(5-tetrazolyl)penam

The title compound is prepared in a manner analogous to that used to make its isomer 6-(2-[2-(2-aminoethoxyphenyl]acetamido)-2,2-dimethyl-3-(5-tetrazolyl)penam (Example LXXXVI, and consists of a 1:1 molar ratio of the tetrazole product to triethylamine. The starting material, 2-[3-(2-aminoethoxy)phenyl]acetic acid, is obtained by the procedure described in U.S. Pat. No. 3,579,905. On a 3.5 mmol scale the yield is 600 mg. (33%): IR (KBr) 1780 and 1660 $cm^{-1}$; NMR ($D_2O$—$NaHCO_3$) 7.4–6.7 ppm (m,3H), 5.70 (d,1H), 5.40 (d,1H), 5.25 (s,1H), 4.35–4.00 (m,2H), 3.70–3.35 (m,4H), 3.15 (q,6H), 1.50 (s,3H), 1.25 (t,9H), 0.95 (s,3H).

EXAMPLE LXXXVIII 6-(2-[4-(2-Aminoethoxy)phenyl]acetamido)-2,2-dimethyl-3-(5-tetrazolyl)penam The title compound is prepared in a manner analogous to that used to make its isomer 6-(2-[2-(2-aminoethoxy)phenyl]acetamido)-2,2-dimethyl-3-(5-tetrazolyl)penam (Example LXXXVI), and consists of a 3:1 molar ratio of the tetrazole product to triethylamine. The starting material, 2-[4-(2-aminoethoxy)phenyl]acetic acid is obtained by the procedure described in U.S. Pat. No. 3,759,905. On a 5.0 mmol scale the yield is 1.35 g. (60%): IR (KBr) 1785 and 1667 $cm^{-1}$; NMR ($D_2O$) 7.10 ppm (q,4H), 5.75 (d, 1H), 5.40 (d,H), 5.30 (s,1H), 4.40–4.05 (m,2H), 3.7–3.4(m,4H), 3.20(q,2H), 1.60(s,3H), 1.35 (t,3H), 1.05 (s,3H).

EXAMPLE LXXXIX 6-(2-[4-(2-Azidoethoxy)phenyl]acetamido)-2,2-dimethyl-3-(5-tetrazolyl)penam A stirred mixture of 1.2 g. (5 mmol) of 6-amino-2,2-dimethyl-3-(5-tetrazolyl)penam, 1.1 (5 mmol) of 4-(2-azidoethoxy)phenylacetic acid [U.S. Pat. No. 3,759,905], and 20 ml of water is adjusted to pH 7 by the careful addition of 6 N sodium hydroxide. After a clear solution is obtained, the pH is adjusted to 6 by the careful addition of 6 N hydrochloric acid. With ice-bath cooling and continuous stirring, the solution is treated with 0.96 g. (5 mmol) of 1-(3-dimethylaminopropyl)-3-ethylcarbodiimide hydrochloride. The reaction solution is stirred, cooled and maintained at pH 6 for 90 minutes. The solution is then adjusted to pH 6.9 and is washed twice with 20-ml. portions of ethyl acetate. The aqueous solution is then adjusted to pH 2.0, and the product is extracted into ethyl acetate. The extract is then stirred with 20 ml. of water and the mixture is then adjusted to pH 6.8. The aqueous phase is separated, and is then lyophilized to furnish the title compound as its sodium salt: yield 1.31 g(56%); IR (KBr) 2105, 1770 and 1660 $cm^{-1}$; NMR ($D_2O$) 7.4–6.8 ppm (m, 4H), 5.80 (d, 1H), 5.55 (d, 1H), 5.40 (s, 1H), 4.3–4.0 (m, 2H), 3.9–3.4 (m, 4H), 1.55 (s, 3H), 1.00 (s, 3H).

EXAMPLE XC 6-(D-2-[2-Aminoacetamido]-2-phenylacetamido)-2,2-dimethyl-3-(5-tetrazolyl)penam To 0.418 g. of sodium N-(2-ethoxycarbonyl-1-methylvinyl)-2-aminoacetate in 10 ml. of tetrahydrofuran is added 2 drops of N-methylmorpholine and 0.19 ml. of ethyl chloroformate with stirring. Stirring is continued for a further 30 minutes at −10° C. and then the solution is cooled to −30° C. To this solution is then added 0.708 g. of 6-(D-2-amino-2-phenylacetamido)-2,2-dimethyl-3-(5-tetrazolyl)penam dissolved in 10 ml. of 1:1 tetrahydrofuran-water and adjusted to pH 8.7. Stirring is then continued for a further 30 minutes without cooling. At this point, the pH is adjusted to 1.5, and the reaction mixture is stirred at 0° C. for 30 minutes. The tetrahydrofuran is removed by evaporation in vacuo; and then the aqueous residue is washed with ether, washed with ethyl acetate, adjusted to pH 6.4 and lyophilized to give a white solid. The solid is stirred for 20 minutes in 20 ml. of N,N-dimethylformamide, and the solid which does not dissolve is filtered off and discarded. The filtrate is added dropwise to 200 ml. of chloroform, and the solid which precipitates is filtered off and dried giving 0.3 g. (36.6% yield) of the title compound, m.p. 211°–230° C. (dec.). IR (KBr disc): 1770 $cm^{-1}$ (β-lactam). NMR (in DMSO-$d_6$): 9.50–9.15 ppm (d, 2H), 7.40 ppm (s, 5H), 6.80–5.30 ppm (m, 9H), 5.00 ppm (s, 1H), 3.65 ppm (s,2H), 1.50 ppm (s, 3H), 0.90 ppm (s, 3H).

EXAMPLE XCI 6-(2-[2-Aminoacetamido]-2-[p-hydroxyphenyl]acetamido)-2,2-dimethyl-3-(5-tetrazolyl)penam The title compound is prepared in 45% yield from 6-(2-amino-2-[p-hydroxyphenyl]acetamido)-2,2-dimethyl-3-(5-tetrazolyl)penam and sodium N-(2-ethoxycarbonyl-1-methylvinyl)-2aminoacetate, using the procedure of Example XC. The product has m.p. 173°–188° C. (dec.). IR (KBr disc): 1785 $cm^{-1}$ (β-lactam). NMR (DMSO-$d_6$): 7.55–710 ppm (m, 2H), 7.00–6.00 ppm (m, 2H), 5.75–5.40 ppm (m, 3H), 5.10 ppm (s, 1H), 3.65 ppm (m, 2H), 1.55 ppm (s, 3H), 0.95 ppm (s, 3H).

EXAMPLE XCII

Reaction of the appropriate 6-(2-amino-2-substitutedacetamido)-2,2-dimethyl-3-(5-tetrazolyl)penam or 6-(2-[2-aminoacetamido]-2-substituted acetamido)-2,2-dimethyl-3-(5-tetrazolyl)penam, with sodium N-(2-ethoxycarbonyl-1-methylvinyl)-2-aminoacetate, according to the procedure of Example XC, provides the following compounds:

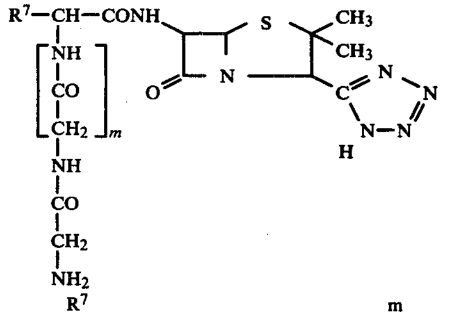

| $R^7$ | m |
|---|---|
| methyl | 0 |
| isopropyl | 0 |
| allyl | 0 |
| cyclohexyl | 0 |
| 3-cyclohexenyl | 0 |
| 1,4-cyclohexadienyl | 0 |
| benzyl | 0 |
| p-chlorophenyl | 0 |
| p-hydroxybenzyl | 0 |
| m-bromophenyl | 0 |
| p-fluorophenyl | 0 |
| o-chlorophenyl | 0 |
| 3,4-dichlorophenyl | 0 |
| 3-chloro-4-hydroxyphenyl | 0 |
| p-methoxyphenyl | 0 |
| m-butoxyphenyl | 0 |
| p-(hydroxymethyl)phenyl | 0 |
| 3,4-dimethoxyphenyl | 0 |
| m-tolyl | 0 |
| 2-thienyl | 0 |
| 3-thienyl | 0 |
| 2-furyl | 0 |
| 3-furyl | 0 |
| 3-pyridyl | 0 |
| 5-ethyl-2-thienyl | 0 |
| methyl | 1 |
| phenyl | 1 |
| p-hydroxyphenyl | 1 |
| p-chlorophenyl | 1 |

EXAMPLE XCIII 6-(D-2-[3-Aminopropionamido]-2-phenylacetamido)-2,2-dimethyl-3-(5-tetrazolyl)penam To a stirred solution of 0.95 ml. of ethyl chloroformate and 2 drops of N-methylmorpholine, in 30 ml. of tetrahydrofuran, is added 2.39 g. of N-(2-ethoxycarbonyl-1-methylvinyl)-3-aminopropionic acid, at −10° C. Stirring is continued for 30 minutes, and then the reaction mixture is cooled to 31 30° C. To it is then added a solution prepared by suspending 3.8 g. of 6-(D-2-amino-2-phenylacetamido)-2,2-dimethyl-3-(5-tetrazolyl)penam trihydrate in 15 ml. of water and 15 ml. of tetrahydrofuran and adjusting the pH to 7.8. After the addition, the cooling bath is removed and stirring is continued for a further 30 minutes. The temperature of the reaction mixture is then adjusted to 0° C., the pH is adjusted 1.5, and stirring is continued for 30 minutes. At this point, the tetrahydrofuran is removed by evaporation in vacuo, the aqueous residue is extracted with ethyl acetate, and then the pH of the aqueous residue is adjusted to 6.0. Lyophilization of the aqueous residue then affords the crude product. It is purified by stirring with 400 ml. of dimethylformamide, filtering, and added the filtrate slowly to 500 ml. of chloroform. The purified product is filtered off. The yield is 3.30 g, mp 190° C. (dec.). IR (KBr disc): 1765 $cm^{-1}$. NMR (DMSO-$d_6$): 9.4–8.8 ppm (m,2H), 8.0–7.1 ppm (m,10H), 5.9–5.3 ppm (m,3H), 5.0 ppm (s,1H), 3.3–2.5 ppm (m,4H), 1.55 ppm (s,3H) and 0.9 ppm (s,3H).

EXAMPLE XCIV 6-(2-[Benzamido]acetamido)-2,2-dimethyl-3-(5-tetrazolyl)penam

To a stirred solution of 0.80 g. (2.7 mmole) of 6-(2-aminoacetamido)-2,2-dimethyl-3-(5-tetrazolyl)penam and 0.453 g. (5.4 mmole) of sodium bicarbonate in 21 ml. of water and 15 ml. of acetone at 0°–5° C. is added 0.32 ml. (2.8 mmole) of benzoyl chloride. Stirring is continued for a further 20 minutes at ca. 0° C., and then the acetone is removed in vacuo. The aqueous residue is extracted with ethyl acetate and the extracts are discarded. The pH of the aqueous phase is adjusted to 2.0, and the product is extracted into ethyl acetate. The solvent is dried ($Na_2SO_4$), and then concentrated in vacuo to give 150 mg. (37% yield) of the title compound, m.p. 85°–93° C. IR (KBr disc): 1785 $cm^{-1}$ (β-lactam) and 1695 $cm^{-1}$ (amide I). NMR (in $D_2O$): 7.90 ppm (m,2H), 7.50 ppm (m,3H), 5.82 ppm (s,1H), 5.58 ppm (s,1H), 5.19 ppm (s,1H), 4.25 ppm (m,2H), 1.67 ppm (s,3H), 1.67 ppm (s,1H).

EXAMPLE XCV 6-(2-[2-Bromoacetamido]-2-phenylacetamido)-2,2-dimethyl-3-(5-tetrazolyl)penam To a stirred slurry of 4.27 g. (10 mmole) of 6-(2-amino-2amino-2-phenylacetamido)-2,2-dimethyl-3-(5-tetrazolyl)penam in 25 ml. of water, at 0° C., is added 1.39 g. (10 mmole) of bromoacetic acid in 6 ml. of water. The pH is adjusted to 6.0, and then 1.9 g. (10 mmole) of 1-ethyl-3-(dimethylaminopropyl)carbodimide hydrochloride in 9 ml. of water is added. The mixture is stirred for 3 hours at pH 6. At this point, the pH is raised to 7.0, and the reaction mixture is washed with ethyl acetate. The pH is then lowered to 2.0, and the product is extracted into ethyl acetate. The dried extracts are concentrated to dryness in vacuo to give 2.0 g. (40% yield) of the title compound, m.p. 128°–135° C. IR (KBr disc): 1800 $cm^{-1}$ (β-lactam) and 1653 $cm^{-1}$ (amide I). NMR (in DMSO-$d_6$/$D_2O$): 7.43 ppm (s,5H), 5.73 ppm (s,1H), 5.63 ppm (m,2H), 5.23 ppm (s,1H), 4.02 ppm (s,2H), 160 ppm (s,3H), 1.00 ppm (s,3H).

EXAMPLE XCVI 6-(2-[2-(4-Pyridylthio)acetamido]-2-phenylacetamido)-2,2-dimethyl-3-(5-tetrazolyl)penam To a stirred solution of 644 mg. of 6-(2-[2-bromoacetamido]-2-phenylacetamido)-2,2-dimethyl-3-(5-tetrazolyl)penam in 15 ml. of N,N-dimethylformamide is added 45 mg. of 4-mercaptopyridine followed by 0.19 ml. of triethylamine. Stirring is continued for 3 hours at 25° C., and then the reaction solution is added dropwise into 200 ml. of vigorously stirred chloroform. The precipitate is removed by filtration, and the filtrate is added dropwise with stirring to 400 ml. of hexane. This causes the product to precipitate. After being slurried with methylene chloride, it weighs 228 mg. (33% yield), m.p. 182°–198° C. (dec.). IR (KBr disc): 1780 $cm^{-1}$ (β-lactam) and 1667 $cm^{-1}$ (amide I). NMR (DMSO-$d_6$/$D_2O$): 8.33 ppm (d,4H), 7.33 (s,5H), 5.60 ppm (m,3H), 5.15 ppm (s,1H), 3.68 ppm (s,2H), 1.47 ppm (s,3H), 1.00 ppm (s,3H).

EXAMPLE XCVII 6-(2-[2-($\Delta^1$-Imidazolin-2-ylthio)acetamido]-2-phenylacetamido)-2,2-dimethyl-3-(5-tetrazolyl)penam The title compound is obtained in 73% yield by replacing the 4-mercaptopyridine of Example XCVI with ethylene thiourea. The product has m.p. 166°–175° C. (dec.). IR (KBr disc): 1785 $cm^{-1}$ (β-lactam), 1667 $cm^{-1}$ (amide I). NMR (in $D_2O$): 7.37 ppm (s,5H), 5.65 ppm (s,1H), 5.53 ppm (m,2H), 5.23 ppm (s,1H), 3.62 ppm (s,2H), 3.50 ppm (m,4H), 1.42 ppm (s,3H), 0.87 ppm (s,3H).

EXAMPLE XCVIII 6-(D-2-[2-Chloroacetamido]-2-phenylacetamido)-2,2-dimethyl-3-(5-tetrazolyl)penam To a stirred solution of 2.02 g. of 6-(D-2-amino-2-phenylacetamido)-2,2-dimethyl-3-(5-tetrazol-5-yl)penam and 1.5 ml. of t riethylamine, in 25 ml. of dichloromethane, is added, dropwise, 0.48 ml. of chloroacetyl chloride, at 0° C. Stirring is continued for a further 2 hours at 0° C., and then the solvent is removed by evaporation in vacuo. The residue is stirred with chloroform and recovered by filtration. This affords 1.16 g (48% yield) of the title compound, m.p. 142°–146° C. IR(KBr disc): 1780 and 1650 $cm^{-1}$. NMR (DMSO-$d_6$/$D_2O$): 7.47 ppm (m, 5H), 5.77 ppm (s, 1H), 5.67 ppm (m, 2H), 5.25 ppm (s, 1H), 4.25 ppm (s, 2H), 1.63 ppm (s, 3H) and 1.02 ppm (s, 3H).

EXAMPLE IC 6-(D-2-[2-Chloroacetamido]-2-[2-furyl]acetamido)-2,2-dimethyl 3-(5-tetrazolyl)penam To a solution of 10 drops of N-methylmorpholine in 40 ml. of acetone, cooled to −50° C., is added 0.30 ml. of ethyl chloroformate (3.2 mmole). After stirring 5 minutes at −50° C., a solution of 0.696 g. (3.2 mmole) of N-chloroacetyl-2-[2-furyl]glycine [$\alpha_D$ = −170° ethanol] and 0.44 ml. of triethylamine (3.2 mmol), in 10 ml. of acetone, is added. The resulting solution is stirred 10 minutes at −50° C. and then a solution prepared by suspending 0.72 g. (3 mmole) of 6-amino-2,2-dimethyl-3-(5-tetrazolyl)penam in a mixture of 12 ml. of water and 8 ml. of acetone and adjusting the pH to 7.0, is added in one portion. The cooling bath is removed, and the solution is allowed to warm to room temperature over a 45 minute period with stirring. The acetone is removed using a rotary evaporator and an equal volume of ethyl acetate is added to the aqueous layer. The pH is adjusted to 2.0, and the ethyl acetate layer is separated. The aqueous layer is extracted with ethyl acetate (2×50 ml.) and the combined organic layers are washed with water brine, and dried ($Na_2SO_4$). Concentration in vacuo gives an oily solid, which is washed with dichloromethane and dried to give 590 mg. (45% yield) of the title compound as a white solid, mp 149°-151° C. IR (KBr disc): 1785 and 1667 $cm^{-1}$. NMR (DMSO-$d_6$): 7.57 ppm (m, 1H), 6.35 ppm (m, 2H), 5.77 ppm (d, 1H), 5.60 ppm (m, 2H), 5.17 ppm (s, 1H), 4.13 ppm (m, 2H), 1.60 ppm (s, 3H) and 1.03 ppm (s, 3H).

EXAMPLE C

6-(D-2-[N,N'-dimethylamidinothio)acetamido]-2-phenylacetamido)-2,2-dimethyl-3-(5-tetrazolyl)penam To a stirred solution of 300 mg. of sodium iodide in 30 ml. of acetone, is added a solution of 900 mg. of 6-(D-2-[2-chloroacetyl]-2-phenylacetamido)-2,2-dimethyl-3-(5-tetrazolyl)penam and 0.3 ml. of triethylamine in 20 ml. of acetone. A solution of 208 mg. of N,N'-dimethylthiourea in 10 ml. of acetone is added, and then the resulting reaction mixture is heated at 55° C. for 8 hours. At this point, the mixture is cooled to 25° C. and the precipitate is removed by filtration to give 390 mg. (37% yield) of the title compound, m.p. 240°-250° C. IR (KBr disc): 1775 and 1667 $cm^{-1}$. NMR (DMSO-$d_6$/$D_2O$): 7.4 ppm (m, 5H), 5.8 ppm (s, 1H), 5.68 ppm (m, 2H), 5.16 ppm (s, 1H), 4.2 ppm (s, 2H), 2.97 ppm (s, 6H), 1.50 ppm (s, 3H) and 0.90 ppm (s, 3H).

EXAMPLE CI

Using the procedure of Example C, but replacing the N,N'-dimethylthiourea with the appropriate reagent, the following compounds are prepared.

EXAMPLE CII

6-(D-2-[3-(2-[Guanylthio]acetyl)ureido]-2-phenylacetamido)-2,2-dimethyl-3-(5-tetrazol-5-yl)penam To a stirred solution of 225 mg. of sodium iodide in 7.5 ml. of acetone is added, with stirring, at 25° C., 865 mg. of 6-(D-2-[3-(2-chloroacetyl)ureido]-b 2-phenylacetamido)-2,2-dimethyl-3-(5-tetrazolyl)penam, followed by 114 mg. of thiourea. Stirring is continued for 24 hours, and then the precipitate which has formed is removed by filtration. This affords 720 mg. (92% yield) of the title compound, mp 193°-211° C. (dec.). IR(KBr disc): 1780 and 1660 $cm^{-1}$.

EXAMPLE CIII

6-(D-2-[3-(2-[N,N'-diethylguanylthio]acetyl)ureido]-2-phenyl acetamido)-2,2-dimethyl-3-(5-tetrazolyl)penam The title compound is prepared in 31.5% yield by repeating the procedure of Example CII, but using N,N'-diethylthiourea in place of thiourea. IR(KBR disc): 1780 and 1670 $cm^{-1}$.

EXAMPLE CIV

6-(D-2-Methanesulfonamido-2-phenylacetamido)-2,2-dimethyl-3-(5-tetrazolyl)penam The pH of a stirred solution of 1.42 g. of 6-(D-2-amino-2-phenylacetamido)-2,2-dimethyl-3-(5-tetrazolyl)penam in 6 ml. of water and 6 ml. of tetrahydrofuran is adjusted to 7.8 (6 N sodium hydroxide). To this solution is then added 5.70 mg. of methanesulfonyl chloride, and stirring is continued for 1 hour with 6 N sodium hydroxide being added as necessary to maintain the pH at 7.2. At this point, the tetrahydrofuran is removed by evaporation in vacuo, and the aqueous residue is washed with ethyl acetate. The pH is then lowered to 2.0, and the product is extracted into ethyl acetate. The ethyl acetate is washed successively with 6 N hydrochloric acid and water, and then dried using anhydrous sodium sulfate. Evaporation of the solvent in vacuo gives the crude product. This crude product is

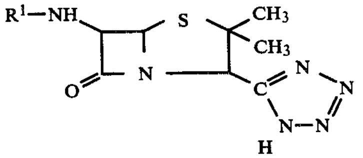

| $R^1$ | mp (°C.) | Yield (%) | IR ($cm^{-1}$) | NMR (DMSO-$d_6$) (ppm) |
|---|---|---|---|---|
| 2-(2-[pentamethyleneamidinothio] acetamido)-2-phenylacetyl | 190–210 | 52 | 1770, 1667 | 7.4 (m,5H), 5.8(s,1H), 5.61(d,1H),5.50(d,1H) 5.1 (s,1H), 4.07 (s,2H), 3.69 (m,4H), 1.67 (m,4H), 1.55 (s,3H), 0.93 (s,3H). |
| 2-(2-[2-benzimidazolylthio]-acetamido)-2-phenylacetyl | 150–190 | 62 | 1770, 1667 | 7.36 (m,9H), 5.76 (s,1H), 5.56 (m,2H), 5.10 (s,1H), 4.15 (s,2H), 1.57 (s,3H), 0.9 (s,3H) |
| 2-(2-[N,N'-diethylamidinothio]-acetamido)-2-phenylacetyl | 172–178 | 88 | 1770, 1667 | 7.50 (m,5H), 5.80 (s.1H), 5.60 (m,2H), 5.13 (s,1H), 3.97 (s,2H), 3.47 (q,4H), 1.60 (s,3H), 1.20 (t,6H), 0.97 (s,3H) |
| 2-(2-[N,N'-di-n-butylamidino-thio]acetamido)-2-phenylacetyl | 155–170 | 41 | 1775, 1667 | 7.35 (m,5H), 5.80 (d,1H), 5.55 (m,2H), 5.05 ppm (s,1H), 4.17 (s,2H), 3.40 (m,4H), 1.56 (s,3H), 1.43 (m,8H), 0.96 (m,6H), 0.97 (s,3H) |
| 2-(2-[4-oxo-$\Delta^2$-imidazolin-2-yl-thio]acetamido)-2-phenylacetyl | | 50 | 1785, 1667 | 7.4(m,5H), 5.75(d,1H), 5.54 (m,2H), 5.10 (s,1H), 4.18 (s,2H), 3.93 (s,2H), 1.57 (s,3H), 0.97 (s,3H). |
| 2-(2-[amidinothio]acetamido)-2-phenylacetyl | 177–185 | 25 | 1780, 1670 | 7.40 (m,5H, 5.77 (d,1H), 5.55 (m,2H), 5.10 (s,1H), 3.90 (s,2H), 1.57 (s,3H), 0.97 (s,3H). |
| 2-(2-[2-imidazolylthio]acet-amido)-2-phenylacetyl | | 67 | | 7.4 (m,5H), 7.2 (m,2H), 5.74 (s,1H), 5.63 (m,2H), 5.2 (s.1H), 3.89 (s,2H), 1.55 (s,3H), 0.97 (s,3H) |

dissolved in the minimum amount of ethyl acetate, and then the solution is added dropwise with stirring to 200 ml. of hexane. The solid which precipitates is filtered off, giving 675 mg. (45%) of the title compound, m.p. 117°-48° C. IR (Nujol mull): 1785 $cm^{-1}$ (β-lactam). NMR (in DMSO-$d_6$): 9.45-9.15 ppm (m, 1H), 8.05 ppm (d, 1H), 7.60-7.10 ppm (m, 5H), 5.60-5.15 ppm (m, 4H), 2.75 ppm (s, 3H), 1.60 ppm (s, 3H), and 1.00 ppm (s, 3H).

EXAMPLE CV

Reaction of either 6-(D-2-amino-2-phenylacetamido)-2,2-dimethyl-3-(5-tetrazolyl)penam or 6-(D-2-[2-aminoacetamido]-2-phenylacetamido)-2,2-dimethyl-3-(5-tetrazolyl)penam with the appropriate sulfonyl chloride, according to the procedure of Example CIV provides the following congeners:

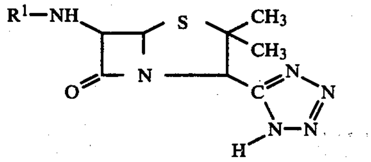

| $R^1$ | Yield (%) | Melting Point* (°C.) | Infrared Spectrum ($cm^{-1}$) | NMR Spectrum (DMSO-$d_6$;ppm) |
|---|---|---|---|---|
| 2-(propanesulfonamido)-2-phenylacetyl | 63 | 100-130 | 1780 | 9.40-9.20(m,1H), 8.10 (d,1H), 7.65-7.25 (m,5H), 5.70-5.20(m,4H), 2.80(t,2H), 1.80-1.40(m,5H), 1.05-0.70(m,6H). |
| 2-(4-methoxybenzenesulfonamido)-2-phenylacetyl | 39 | 130-155 | 1790 | 9.25(d,1H), 8.45(d,1H), 7.70(d,2H), 7.50-7.10(m,5H), 7.00(d,2H), 5.60-5.15(m,4H), 3.80(s,3H), 1.55(s,3H), 1.00(s,3H). |
| 2-(2-naphthalenesulfonamido)-2-phenylacetyl | 50 | 70-105 | 1780 | 9.20(d,1H), 8.80(d,1H), 8.40-7.05(m,7H), 5.55-5.50(m,4H), 1.50(s,3H), 0.95(s,3H). |
| 2-(2-thiophenesulfonamido)-2-phenylacetyl | 35 | 127-161 | 1790 | 9.30(d,1H), 8.95(d,1H), 7.90-7.00(m,8H), 5.70-5.20 (m,4H), 1.60(s,3H), 1.00(m,6H). |
| 2-(ethanesulfonamido)-2-phenylacetyl | 52 | 126-145 | 1785 | 9.40-9.10(m,1H), 8.10(d,1H), 7.70-7.20(m,5H), 5.70-5.20(m,4H), 2.90(q,2H), 1.60(s,3H), 1.10(s,3H). |
| 2-(4-chlorobenzenesulfonamido)-2-phenylacetyl | 62 | 135-149 | 1780 | 9.30(d,1H), 8.90(d,1H), 7.85-7.10(m,9H), 5.60-5.15 (m,4H), 1.60(s,3H), 1.00(s,3H). |
| 2-(4-nitrobenzenesulfonamido)-2-phenylacetyl | 68 | 135-154 | 1790 | 9.35-9.10(m,2H), 8.35(d,2H), 8.00(d,2H), 7.50-7.10 (m,5H), 5.60-5.20(m,4H), 1.60(s,3H), 1.00(s,3H). |
| 2-(benzenesulfonamido)-2-phenylacetyl- | 74 | 133-147 | 1790 | 9.30(d,1H), 8.75(d,1H), 7.90-7.05(m,10H), 5.60-5.20 (m,4H), 1.60(s,3H), 1.00(s,3H). |
| 2-(α-toluenesulfonamido)-2-phenylacetyl | 50 | 117-145 | 1780 | 9.15 -9.05(m,1H), 8.15(d,1H), 7.65-7.25(m,10H), 5.70-5.20(m,4H), 1.60(s,3H), 1.05(s,3H). |
| 2-(2-[methanesulfonamido]acetamido)-2-phenylacetyl | 37 | 93-125 | 1780 | 9.50-9.25(m,1H), 8.60(d,1H), 7.70-7.20(m,5H), 5.90-5.50(m,3H), 5.25(s,1H), 3.75(d,2H), 2.90 (s,3H), 1.60(s,3H), 1.00(s,3H). |
| 2-(2-[benzenesulfonamido]acetamido)-2-phenylacetyl | 56 | 120-144 | 1790 | 9.60-9.30(m,1H), 8.60(d,1H), 8.20-7.20(m,10H), 5.80-5.50(m,3H), 5.25)s,1H), 3.60(d,2H), 1.60 (s,3H), 1.00(s,3H). |
| 2-(2-[α-toluenesulfonamido]-acetamido)-2-phenylacetyl | 29 | 130-152 | 1780 | 9.60-9.30(m,1H), 8.60(d,1H), 7.70-7.20(m,10H), 5.90-5.50(m,2H), 5.25(s,1H), 5.00(s,1H), 4.40 (s,2H), 3.70(d,2H), 1.60(s,3H), 1.00(s,3H). |
| 2-(2-[2-thiophenesulfonamido]acetamido)-2-phenylacetyl | 42 | 12[illegible]-150 | 1780 | 9.60-9.20(m,1H), 8.55(d,1H), 8.25(t,1H), 7.95 (d,1H), 7.70-7.19(m,7H), 5.90-5.50(m,3H), 5.25 (s,1H), 3.70(d,2H), 1.60(s,3H), 1.00(s,3H). |

*with decomposition

EXAMPLE CVI

6-(D-2-[Propanesulfonamido]-2-[p-hydroxyphenyl-]acetamido-)-2,2-dimethyl-3-(5-tetrazolyl)penam The title compound is prepared in 38% yield from 6-(D-2-amino-2-[p-hydroxyphenyl]acetamido)-2,2-dimethyl-3-(5-tetrazolyl)penam and propanesulfonyl chloride, using the procedure of Example CIV. The product has m.p. 115°-157° C. (dec.). IR (mujol mull): 1780 $cm^{-1}$ (β-lactam). NMR (in DMSO-$d_6$): 9.20-8.90 ppm (m, 1H), 7.90 ppm (d, 1H), 7.30 ppm (d, 2H), 6.70 ppm (d, 2H), 5.70-5.00 ppm (m, 4H), 2.80 ppm (t, 2H), 1.90-1.30 ppm (m, 5H), 1.10-0.65 ppm (m, 6H).

EXAMPLE CVII

6-(D-2-[Benzenesulfonamido]-2-[p-hydroxyphenyl-]acetamido)-2,2-dimethyl-3-(5-tetrazolyl)penam The title compound is prepared in 53% yield from 6-(D-2-amino-2-[p-hydroxyphenyl]acetamido)-2,2-dimethyl-3-(5-tetrazolyl)penam and benzenesulfonyl chloride, using the procedure of Example CIV. The product has m.p. 152°-165° C. (dec.). IR (nujol mull): 1780 $cm^{-1}$ (β-lactam). NMR (in DMSO-$d_6$): 9.10 ppm (d, 1H), 8.50 ppm (d, 1H), 7.90-7.40 ppm (m, 5H), 7.10 ppm (d, 2H), 6.55 ppm (d, 2H), 5.60-5.10 ppm (m, 4H), 1.55 ppm (s, 3H), 1.00 ppm (s, 3H).

EXAMPLE CVIII

6-(2-D-[2-Benzamidoacetamido]-2-phenylacetamido)-2,2-dimethyl-3-(5-tetrazolyl)penam To a stirred solution of 1.29 g. of 6-(2-D-[2-aminoacetamido]-2-phenylacetamido)-2,2-dimethyl-3-(5-tetrazolyl)penam and 1.3 ml. of triethylamine in 15 ml. of dimethylformamide, is added 0.4 ml. of benzoyl chloride. Stirring is continued for a further 30 minutes, and then the reaction mixture is filtered. The filtrate is added dropwise to 300 ml. of ether, which causes a gummy solid to precipitate. The ether is removed by decantation, and the solid is partitioned between ethyl acetate and water. The pH of the aqueous phase is adjusted to 2.0 (dilute hydrochloric acid), and the ethyl acetate layer is removed and combined with a further ethyl acetate extract of the acidified aqueous phase. The combined extracts are washed with water, followed by brine, and then dried using anhydrous sodium sulfate. Evaporation of the solvent in vacuo gives a gum, which is redissolved in 30 ml. of ethyl acetate, and then the solution is added dropwise to 200 ml. of hexane. The white solid which precipitates is filtered off, giving 0.85 g. of the title compound, m.p. 150° C. (dec.). IR (KBr disc): 1780 $cm^{-1}$ (β-lactam). NMR (DMSO-$d_6$): 9.40-9.20 ppm (m, 1H), 8.90-8.40 ppm (m, 2H), 8.00-7.10 ppm (s, 12H), 5.90-5.40 ppm (m, 3H), 5.25 ppm (s, 1H), 4.00 ppm (d, 2H), 1.60 ppm (s, 3H) and 1.00 ppm (s, 3H).

EXAMPLE CIX

Following the procedure of Example CVIII, and replacing the benzoyl chloride used therein by the appropriate acid chloride, the following congeners are produced:

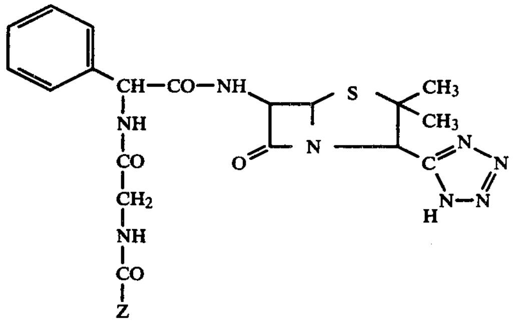

| Z | Yield (%) | Melting Point* (°C.) | Infrared Spectrum ($cm^{-1}$) | NMR Spectrum DMSO-$d_6$ (ppm) |
|---|---|---|---|---|
| methyl | 59 | 135-142 | 1780 | 9.3 (d,1H), 8.6 (d,1H), 8.1 (t,1H), 7.4 (s,5H), 6.4-5.4 (m,9H), 5.2 (s,1H), 3.85 (d,2H), 1.85 (s,3H), 1.6 (s,3H), 1.0 (s,3H) |
| ethyl | 58 | 148-153 | 1790 | 9.3 (d,1H), 8.5 (d,1H), 8.0 (t,1H), 7.4 s,5H), 5.9-5.5 (m,3H), 5.25 (s,1H), 3.8 (d, 2H), 2.18 (q,2H), 1.0 (s,3H), 1.18-0.8 (m,6H). |
| p-chlorophenyl | 67 | 180-185 | 1790 | 9.4-9.2 (m,1H), 9.0-8.4 (m,2H), 8.0-7.2 (m, 9H), 5.85-5.45 (m,3H), 5.2 (s,1H), 4.0 (d, 2H), 1.6 (D,3H), 1.0 (s,3H). |
| p-nitrophenyl | 67 | 155-164 | 1780 | 9.6-8.0 (m,7H), 7.4 (s, 5H), 5.9-5.4 (m, 3H), 5.2 (s, 1H), 4.05 (d, 2H), 1.6 (s, 3H), 1.0 (s,3H) |
| p-methoxyphenyl | 54 | 151-158 | 1780 | 9.55-9.2 (m, 1H), 8.7-8.4 (m, 2H), 7.9 (d, 2H), 7.6-7.2 (m, 5H), 5.05 (d, 2H), 5.9-5.4 (m, 3H), 5,2 (s, 1H), 4.0 (d, 2H), 3.8 (s, 3H), 1.6 (s,3H), 10 (s, 3H). |
| n-propyl | 60 | 120-132 | 1785 | 9.5-9.2 (d, 1H), 8.6-8.35 (d, 1H), 8.2-7.9 (m, 1H), 7.45 (s, 5H), 5.9-5.9 (m,3H), 5.3 (s, 1H), 3.85 (d, 2H), 2.3-1.95 (m, 2H), 1.8-1.3 (m, 5H), 1.1-0.75 (m,6H) |
| ethoxy | 40 | 131-138 | 1780 | 9.5-9.2 (m, 1H), 8.6-8.35 (m, 1H), 7.7-7.2 (m, 6H), 5.9-5.5 (m, 3H), 5.25 (s, 1H), 4.2-3.6 (m, 4H), 1.6 (s, 3H) 1.30-0.9 (m, 6H) |
| benzyloxy | 65 | 123-128 | 1780 | 9.0-8.8 (m, 1H), 8.1 (d, 1H), 7.3 (s, 10H), 7.1-6.7 (m, 1H) 5.9-5.45 (m, 3H), 5.15 (s, 1H), 5.1 (s, 2H), 3.85 (d, 2H) 1.65 (s, 3H), 1.05 (s, 3H). |

*with decomposition

EXAMPLE CX

Using the procedure of Example CVIII, the following compounds are prepared by the acylation of 6-amino-2,2-dimethyl-3-(5-tetrazolyl)penam, 6-(D-2-amino-2-phenylacetamido)-2,2-dimethyl-3-(5-tetrazolyl)penam or 6-(D-2-[3-aminopropionamido]-2-phenylacetamido)-2,2-dimethyl-3-(5-tetrazolyl)penam with the appropriate acid chloride.

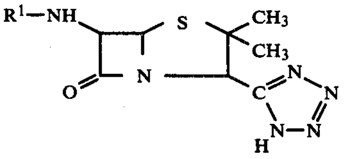

| $R^1$ | Yield (%) | IR ($cm^{-1}$) | NMR (DMSO-$d_6$) (ppm) |
|---|---|---|---|
| 2-(phenylthio)acetyl | 31 | 1780 | 1.10 (s,3H), 1.70 (s,3H), 3.85 (s,2H), 5.25-5.80 (m,3H), 7.10-7.50 (m,6H), 9.10 (d,1H) |
| D-2-(2-[phenylthio]acetamido)-2-phenylacetyl | 22 | 1785 | 1.05 (s,3H), 1.60 (s,3H), 3.80 (s,2H), 5.10-6.00 (m,5H) 7.10-7.60 (m,10H), 8.8-9.10 (m,1H), 9.30-9.60 (m,1H) |
| 2-(ethylthio)acetyl | 45 | 1785 | 0.80-1.30 (m,6H), 1.60 (s,3H), 2.30-2.80 (m.2H + DMSO), 3.20 (s,2H), 5.10-6.10 (m,4H), 8.8 (d,1H) |

-continued

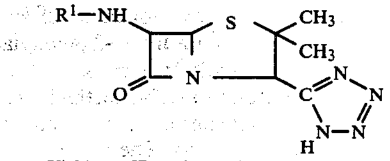

| $R^1$ | Yield (%) | IR ($cm^{-1}$) | NMR ($DMSO-d_6$) (ppm) |
|---|---|---|---|
| D-2-(2-[ethylthio]acetamido)-2-phenylacetyl | 59 | 1785 | 0.80–1.30 (m,6H), 1.55 (s,3H), 2.30–2.80 (m,2H + DMSO), 3.20 (s,2H), 5.10–5.80 (m,4H), 6.00–7.00 (m,1H), 7.10–7.60 (m,5H), 8.60 (d,1H), 9.10–9.50 (m,1H) |
| 3-(methoxycarbonyl)-butyryl | 46 | 1785 | 1.05 (s,3H), 1.50–2.05 (m,5H), 2.10–2.65 (m,4H + DMSO), 3.60 (s,3H), 5.20–6.00 (m,4H), 8.90 (d,1H) |
| D-2-(3-[methoxycarbonyl]-butyramido)-2-phenylacetyl | 68 | 1790 | 0.80–1.40 (m,5H), 1.50–2.10 (m,5H), 2.20–2.80 (m,2H + DMSO), 3.65 (2,3H), 5.20–5.80 (m,4H), 7.20–7.60 (m,5H), 8.60 (d,1H), 9.20–9.50 (m,1H) |
| 2-(ethoxycarbonyl)acetyl | 31 | 1785 | 0.80–1.40 (m,6H), 1.65 (s,3H), 3.40 (s,2H), 4.10 (q,2H), 5.20–5.75 (m,4H), 9.10 (d,1H) |
| D-2-(2-[ethoxycarbonyl)-acetamido)-2-phenyl acetyl | 31 | 1775 | 0.90–1.40 (m, 6H), 1.65 (s,3H), 3.45 (s,2H), 4.20 (q,2H), 4.40–6.00 (m,$H_2O$+5H), 5.72–7.75(m,5H), 9.00 (d,1H), 9.30–9.70 (m,1H) |
| 2-(benzylthio)acetyl | 41 | 1780 | 1.05 (s,3H), 1.70 (s,3H), 3.20 (s,2H), 3.85 (s,2H), 5.25–5.80 (m,3H), 7.20–7.50 (m,6H), 8.95 (d,1H) |
| D-2-(2-[benzylthio]acetamido)-2-phenylacetyl | 39 | 1780 | 1.00 (s,3H), 1.60 (s,3H), 3.25 (s,2H), 3.80 (s,2H), 5.20–5.90 (m,4H), 7.00–7.80 (m,11H), 8.80 (d,1H), 9.30–9.70 (m,1H) |
| D-2-(3-benzamido)-propionamido)-2-phenyl-acetyl | 43 | 1780 | 1.05 (s,3H), 1.6 (s,3H), 2.3–2.8 (m,2H), 3.2–3.8 (2H,m) 5.3 (s,1H), 5.4–6.0 (m,3H), 7.1–7.65 (m,10H), 7.7–8.0 (m,1H), 8.3–8.9(m,2H), 9.2–9.5 (m,1H) |
| D-2-(3-[4-chlorobenzamido]propionamido)-2-phenyl-acetyl | 63 | 1785 | 1.05 (s,3H), 1.6 (s,3H), 2.3–2.8 (m,2H), 3.0–3.8 (m,2H), 5.25 (s,1H), 5.45–5.95 (m,3H), 7.0–8.1 (m,10H), 8.35–8.8 (m,2H), 9.1–9.45 (broad hump 1H) |
| D-2-(3-[3-chlorobenzamido]propionamido)-2-phenyl-acetyl | 57 | 1785 | 1.05 (s,2H), 1.6 (s,3H), 2.25–2.7 (m,2H), 3.2–3.7 (m,2H) 5.25 (m,1H), 5.45–5.9 (m,3H), 7.2–8.0 (m,9H), 8.45–8.8 (m,2H), 9.2 (d,1H) |
| D-2-(3-[2-furnancarboxamido]-propionamido)-2-phenylacetyl | 34 | 1780 | 1.05 (s,3H), 1.6 (s,3H), 2.2–2.7 (m,2H), 3.1–3.7 (m broad2-H) 5.25 (s,1H), 5.4–5.95 (m,3H), 6.55–6.7 (m,1H), 7.0–7.75 (G,7H), 7.8 (s,1H), 8.1–8.4 (m,1H), 8.65 (d,1H), 9.05–9.35 (m,1H) |
| D-2-(3-acetamidopropionamido)-2-phenylacetyl | 33 | 1780 | 1.05 (s,3H), 1.65 (s,3H), 2.2–2.65 (m,3H), 3.1–3.6 (m,2H), 5.25 (s,1H), 5.4–6.0 (m,3H), 7.2–7.7 (m,5H), 7.7–8.0 (m,1H), 8.6 (s,1H), 9.2 (d,1H) |

EXAMPLE CXI

Reaction of the appropriate 6-(2-substituted-2-aminoacetamido)-2,2-dimethyl-3-(5-tetrazolyl)penam or 6-(2-substituted-2-[2-aminoacetamido]acetamido)-2,2-dimethyl-3-(5-tetrazolyl)penam with the requisite acid chloride, according to the procedure of Example CVIII, affords the following congeners:

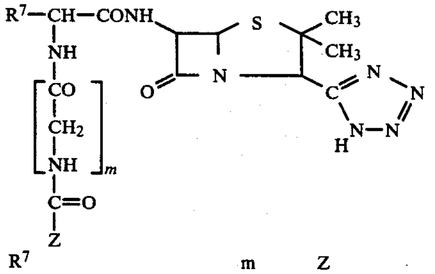

| $R^7$ | m | Z |
|---|---|---|
| isopropyl | 0 | methyl |
| isopropyl | 0 | phenyl |
| isopropyl | 0 | p-chlorophenyl |
| isopropyl | 0 | 2-thienyl |
| phenyl | 0 | propyl |
| phenyl | 0 | isobutyl |
| phenyl | 0 | n-hexyl |
| phenyl | 0 | m-tolyl |
| phenyl | 0 | p-methoxyphenyl |
| p-hydroxyphenyl | 0 | p-bromophenyl |
| p-hydroxyphenyl | 0 | 2-furyl |

-continued

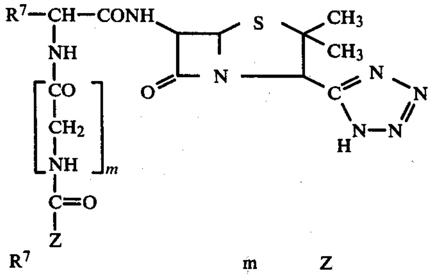

| $R^7$ | m | Z |
|---|---|---|
| m-methoxyphenyl | 0 | 4-pyridyl |
| o-tolyl | 0 | p-fluorophenyl |
| m-bromophenyl | 0 | 3,4-dichlorophenyl |
| 2-thienyl | 0 | p-n-hexyloxyphenyl |
| 3-thienyl | 0 | phenyl |
| 2-furyl | 0 | 3-thienyl |
| p-(hydroxymethyl)phenyl | 0 | 2-furyl |
| phenyl | 1 | n-butyl |
| phenyl | 1 | 2-pyridyl |
| phenyl | 1 | m-bromophenyl |
| p-hydroxyphenyl | 1 | 2-thienyl |
| p-hydroxyphenyl | 1 | methyl |

EXAMPLE CXII

6-(2-[3-Phenylureido]-2-[p-hydroxphenyl]acetamido)-2,2-dimethyl-3-(5-tetrazolyl)penam To a stirred solution of 0.78 g. (0.002 mole) of 6-(2-amino-2-[p-hydroxyphenyl]acetamido)-2,2-dimethyl-3-(5-tetrazolyl)penam in 40 ml. of 1:1 acetone-water, the pH of which has been adjusted to 6.0 by the addition of sodium bicarbonate solution, is added 0.238 g. (0.002 mole) of phenyl isocyanate, at ambient temperature. Stirring is continued at ambient temperature for a further 30 minutes, and then 50 ml. of ethyl acetate is added. The pH of the aqueous phase is lowered to 1.5 with 1 N hydrochloric acid, and then the organic layer is removed, dried and evaporated to dryness in vacuo. The residue is re-dissolved in a small volume of ethanol, to which 0.2 ml. of triethylamine is then added. The resulting solution is added dropwise to 200 ml. of ether, with vigorous stirring, and then the solid which precipitates is filtered off. This affords 0.8 g. (66% yield) of 6-(2-[3-phenylureido]-2-[p-hydroxyphenyl]acetamido)-2,2-dimethyl-3-(5-tetrazolyl)penam as its triethylamine salt, m.p. 165°-170° C. (dec.). The infrared spectrum of the product (KBr disc) shows absorptions at 1790 $cm^{-1}$ (β-lactam) and 1670 $cm^{-1}$ (amide I). The NMR spectrum ($DMSO-d_6/D_2O$) shows absorptions at 7.60-6.70 ppm (multiplet, 9H, aromatic hydrogens), 5.80-5.50 ppm (multiplet, 3H, C-5 and C-6 hydrogens, and side-chain methine hydrogen), 5.05 ppm (singlet, 1H, C-3 hydrogen), 3.05 ppm (quartet, 6H, N—$CH_2CH_3$), 1.55 ppm (singlet, 3H, C-2 methyl hydrogen), 1.10 ppm (triplet, 9H, N-$CH_2CH_3$) and 0.95 ppm (singlet, 3H, C-2 methyl hydrogens).

The MIC of the title compound against *Strep. pyogenes* is <0.1 μg./ml.

EXAMPLE CXIII

Using the procedure of Example CXII, and reacting either 6-(2-amino-2-phenylacetamido)-2,2-dimethyl-3-(5-tetrazolyl)penam or 6-(2-amino-2-[p-hydroxyphenyl]acetamido)-2,2-dimethyl-3-(5-tetrazolyl)penam with the appropriate isocyanate, the following compounds are prepared. The compounds are isolated as their triethylamine salts.

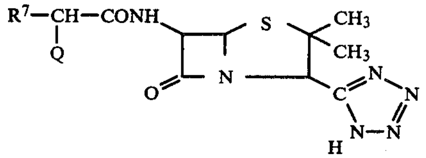

| $R^7$ | Q | Yield (%) | m.p. (°C.) | Infrared Spectrum ($cm^{-1}$) | NMR Spectrum ($DMSO-d_6/D_2O$; ppm) |
|---|---|---|---|---|---|
| $C_6H_5$ | p-$CH_3OC_6H_4NHCONH$ | 64 | 148-52 | 1785, 1670, 1615, 1550, 1515 | 7.65-7.15(m,7H), 6.85(d,2H), 5.75-5.40(m,3H) 5.05(s,1H), 3.7(s,3H), 3.05(q,6H), 1.55(s, 3H), 1.15(t,9H), 0.95(s,3H). |
| $C_6H_5$ | p-$ClC_6H_4NHCONH$ | 75 | 148-55 | 1785, 1680, 1660, 1550, 1495 | 7.75-7.20(m,9H), 5.85-5.45(m,3H), 5.05(s,1H), 3.05 (q,6H), 1.55(s,3H), 1.15(t,9H), 0.95(s,3H). |
| $C_6H_5$ | p-$CH_3C_6H_4NHCONH$ | 79 | 152-55 | 1785, 1680, 1615, 1550, 1505 | 7.60-6.95(m,9H), 5.80-5.50(m,3H), 5.10(s,1H), 3.05(q,6H), 2.15(s,3H), 1.60(s,3H), 1.10(t, 9H, 0.95(s,3H). |
| $C_6H_5$ | $C_6H_5HNCONH$ | 79 | 150-55 | 1785, 1670, 1600, 1550, 1505 | 7.75-6.85(m,10H), 5.80-5.45(m,3H), 5.10(s,1H), 3.10(q,6H), 1.60(s,3H), 1.15(t,9H), 0.95(s,3H), |
| $C_6H_5$ | $CH_3NHCONH$ | 45 | 112-20 | 1785, 1655, 1565, 1505 | 7,45(s,5H), 5.70-5.40(m,3H), 5.1(s,1H), 3.1(q, 6H), 2.60(d,3H), 1.60(s,3H), 1.20(t,9H), 0.95 (s,3H). |
| p-$HOC_6H_4$ | p-$CH_3OC_6H_4NHCONH$ | 63 | 1785, 1670, 1655, | 7.60-7.20(m,4H), 7.55-6.75(m,4H), 5.85-5.40(m, 1615, 1550, 1515 | 3H), 5.05(s,1H), 3.70(s,3H), 3.10(q,6H), 1.60 (s,3H), 1.20(t,9H), 0.95(s,3H). |
| p-$HOC_6H_4$ | p-$ClC_6H_4NHCONH$ | 39 | 170 | 1785, 1680, 1600, 1550, 1520, 1505 | 7.65-6.75(m,8H), 5.75-5.45(m,3H), 5.05(s,1H), 3,10(q,6H), 1.55(s,3H), 1.15(t,9H), 0.95(s,3H). |

EXAMPLE CXIV

6-(2-[3-(2-[p-Chlorophenyl]acetimidoyl-)ureido]acetamido)-2,2-dimethyl-3-(5-tetrazolyl)penam To a stirred solution of 480 mg. of 6-amino-2,2-dimethyl-3-(5-tetrazolyl)penam and 404 mg. of triethylamine, in 6 ml. of N,N-dimethylformamide, is added 650 mg. of 2-(3-[2-(p-chlorophenyl)acetimidoyl]ureido)acetyl chloride hydrochloride. Stirring is continued for 1 hour, and then the reaction mixture is filtered. The filtrate is added to 300 ml. of ether, and the solid which precipitates is filtered off. The solid is washed thoroughly with methylene chloride, and dried, giving 585 mg. of the title compound, m.p. 150°-162° C. IR spectrum (Nujol mull): 1780 $cm^{-1}$ (β-lactam). NMR spectrum ($DMSO-d_6$): 8.90 ppm (d, 1H), 8.00-7.20 ppm (m, 8H), 5.80-5.20 ppm (m, 3H), 4.10-3.60 ppm (m, 4H), 1.65 ppm (s, 3H), 1.10 ppm (s, 3H).

EXAMPLE CXV

Using the procedure of Example CXIV and reacting either 6-amino-2,2-dimethyl-3-(5-tetrazolyl)penam or 6-(D-2-amino-2-phenylacetamido)-2,2-dimethyl-3-(5-tetrazolyl)penam with the appropriate acid chloride hydrochloride the following compounds are produced.

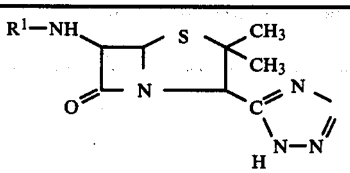

| R[1] | Yield (%) | Melting Point* (° C.) | Infrared Spectrum ($cm^{-1}$) | NMR Spectrum (DMSO-$d_6$; ppm) |
|---|---|---|---|---|
| 2-(3-[benzimidoyl]ureido)-acetyl | 81 | 153–164 | 1780 | 8.90(d,1H), 8.70-7.20(m,9H), 5.80-5.20(m,3H), 4.10-3.70(m,2H), 1.65(s,3H), 1.10(s,3H). |
| 2-(3-[p-methoxybenzimidoyl]-ureido)acetyl | 71 | 162–168 | 1775 | 8.80(d,1H), 8.05-6.20(m,8H), 5.75-5.15(m,3H), 4.05-3.70(m,5H), 1.65(s,3H), 1.05(s,3H). |
| 2-(2-[3-(2-[p-chlorophenyl]-acetimidoyl)ureido]acet-amido)-2-phenylacetyl | 50 | 160–169 | 1780 | 9.40-9.20(m,1H), 8.80(d,1H), 8.40-7.10(m,13H), 5.90-5.15(m,4H), 4.05-3.70(m,4H), 1.55(s,3H), 1.00(s,3H). |
| 2-(2-[3-(benzimidoyl)ureido]-acetamido)-2-phenylacetyl | 45 | 160–166 | 1775 | 9.40(d,1H), 8.60(d,1H), 8.10-6.00(m,14H), 5.90-5.10(m,4H), 4.00-3.60(m,2H), 1.55(s,3H), 1.00 (s,3H). |
| 2-(2-[3-(p-methoxybenzimi-doyl)ureido]acetamido-2-phenylacetyl | 64 | 168–174 | 1775 | 9.40(d,1H), 8.70(d,1H), 8.10-6.30(m,13H), 6.00-5.10(m,4H), 4.10-3.70(m,5H), 1.55(s,3H), 1.00 (s,3H). |

≢*with decomposition

EXAMPLE CXVI 6-(3-Phenylureido)-2,2-dimethyl-3-(5-tetrazolyl)penam

To a stirred slurry of 724 mg. of 6-amino-2,2-dimethyl-3-(5-tetrazolyl)penam in 10 ml. of methylene chloride is added 1.3 ml. of triethylamine. The mixture is stirred for 40 minutes, and then filtered. To the filtrate is added 0.35 ml. of phenyl isocyanate. Stirring is continued for a further 45 minutes, and then the reaction mixture is cooled in an ice-bath for 30 minutes. The solid which precipitates is filtered off, washed with ether, and dried, giving 935 mg. of the title compound as its triethylamine salt, m.p. 110°-120° C. IR spectrum (Nujol mull): 1775 $cm^{-1}$ (β-lactam), 1700 $cm^{-1}$, 1600 $cm^{-1}$ and 1550 $cm^{-1}$. NMR spectrum (DMSO-$d_6$): 9.00 ppm (s, 1H), 7.50–6.70 ppm (m, 7H), 5.65 ppm (m, 2H), 5.10 ppm (s, 1H), 3.10 ppm (q, 6H), 1.80 ppm (s, 3H), 1.18 ppm (t, 9H), 1.00 ppm (s, 3H).

In like manner, using ethyl isocyanate, there is obtained a 70% yield of 6-(3-ethylureido)-2,2-dimethyl-3-(5-tetrazolyl)penam triethylamine salt, m.p. 80°-90° C. IR spectrum (KBr disc): 1785 $cm^{-1}$ (β-lactam), 1668 $cm^{-1}$ and 1570 $cm^{-1}$. NMR spectrum (DMSO-$d_6$): 7.80 ppm (m, 1H), 6.50 ppm (m, 2H), 5.60 ppm (m, 2H), 5.10 ppm (s, 1H), 3.10 ppm (q, 8H), 1.60 ppm (s, 3H), 1.40–0.70 ppm (m, 15H).

EXAMPLE CXVII 6-(D-2-Allophanamido-2-phenylacetamido)-2,2-dimethyl-3-(5-tetrazolyl)penam To a stirred solution of 1.12 g. (3 mmole) of 6-(D-2-amino-2-phenylacetamido)-2,2-dimethyl-3-(5-tetrazolyl)penam and 0.485 ml. of triethylamine in 6 ml. of water is added portionwise, during 10 minutes, 0.512 g. (3.5 mmole) of N-methyl-N-nitrosobiuret. Stirring is continued for a further 2 hours, and then the pH is adjusted to 2.0. The product is extracted into ethyl acetate, and then the extract is treated with 0.42 ml. (3.0 mmole) of triethylamine and then evaporated to dryness in vacuo. This affords 1.4 g. (84% yield) of the title compound as its triethylamine salt. IR (KBr disc): 1785, 1695 and 1540 $cm^{-1}$. NMR (in $CDCl_3$): 9.4–8.4 ppm (m), 8.3 ppm (s), 7.7–7.1 ppm (m), 7.1–6.7 ppm (m), 5.9–5.3 ppm (m), 5.3–5.0 ppm (d), 4.5–4.1 ppm (d), 1.6 ppm (s), 1.0 ppm (s).

EXAMPLE CXVIII 6-(3-Aminomethyl-2-phenylisocrotonamido)-2,2-dimethyl-31 -(5-tetrazolyl)penam To a stirred solution of 720 mg. (3 mmole) of 6-amino-2,2-dimethyl-3-(5-tetrazolyl)penam and 0.84 ml. (6 mmole) of triethylamine is 15 ml. of methylene chloride, at −20° C., is added 706 mg. (3 mmole) of 3-azidomethyl-2-phenylisocrotonoyl chloride (The Journal of Antibiotics, Tokyo, 24, 626 [1971]) dissolved in 5 ml. of methylene chloride. The cooling is removed, and the reaction mixture is stirred as it warms to room temperature and then for a further 15 minutes. The pH of the reaction mixture is then adjusted to 7.8, and it is extracted with ethyl acetate. The ethyl acetate is discarded, and the pH of the residual aqueous phase is lowered to 2.5. It is then re-extracted with ethyl acetate, and to this second extract is added 3 mmoles of sodium 2-ethylhexanoate. The solvent is then removed by evaporation in vacuo leaving a gummy solid (1.12 g.).

The above solid is dissolved in 35 ml. of water, and 500 mg. of 10% palladium-on-carbon is added. The mixture is then hydrogenated in a Parr hydrogenator, under 20 p.s.i. pressure, at 25° C., for 16 hours. At this point, the catalyst is removed by filtration, and the filtrate is acidified to pH 2.0. It is filtered, and the pH of the filtrate is raised to 5.7. The filtrate is lyophilized, to produce 900 mg. (87% yield) of the title compound. IR (KBr disc): 1770 $cm^{-1}$ (β-lactam).

EXAMPLE CXIX 6-(D-2-[2-(Benzamidino)acetamido]-2-phenylacetamido)-2,2-dimethyl-3-(5-tetrazolyl)penam A mixture of 1.72 of g. of 6-(D-2-[2-aminoacetamido]-2-phenylacetamido-2,2-dimethyl-3-(5-tetrazolylbenam, 0.66 g. of ethyl benzimidate and 20 ml. of N,N-dimethylformamide is stirred for 1 hour at 25° C. The filtered reaction mixture is then added dropwise with stirring to a large excess of chloroform, and the solid which precipitates is filtered off. This affords 0.93 g. (43% yield) of the title compound, m.p. 198° C. (dec.). IR (KBr disc): 1770 $cm^{-1}$ (β-lactam). NMR (DMSO-$d_6$):

9.35–9.00 ppm (m, 2H), 8.00–7.15 (m, 12H), 5.95 ppm (d, 2H), 5.55. 5.30 ppm (m, 2H), 5.00 ppm (s, 1H), 4.35 ppm (s, 2H), 1.50 ppm (s, 3H) and 0.90 ppm (s, 3H).

EXAMPLE CXX

Following the procedure of Example CXIX, and reacting 6-(D-2-[2-aminoacetamido]-2-phenylacetamido)-2,2-dimethyl-3-(5-tetrazolyl)penam with the appropriate imidate ester, the following compounds are prepared:

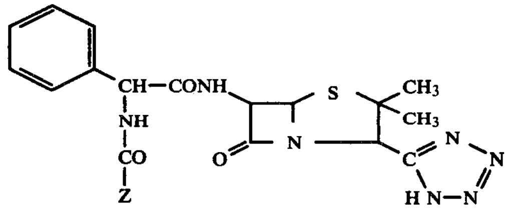

| Z | Yield (%) | Melting Point* (°C.) | Infrared Spectrum ($cm^{-1}$) | NMR Spectrum (DMSO-$d_6$; ppm) |
|---|---|---|---|---|
| 4-pyridinecarboxamidomethyl | 60 | 193 | 1770 | 9.1-8.7(m,4H), 7.9-7.2(m,7H), 6.4-4.7(m,11H), 4.3(s,2H), 1.5(s,3H), 0.9(s,3H). |
| 3,5-dibromobenzamidinomethyl | 32 | 195 | 1775 | 9.3-8.8(m,2H), 8.2-7.1(m,8H), 5.95-5.3(m,3H), 4.95(s,1H), 4.24(s,2H), 1.5(s,3H), 0.9(s,3H). |
| 2-thiopnenecarboxamindinomethyl | 35 | 185 | 1770 | 9.45-8.9(m,2H), 8.15-7.9(m,2H), 7.7-7.2(m, 6H), 6.0-5.4(m, 3H), 5.05(s,1H), 4.22(s,2H), 1.5(s,3H), 0.9(s,3H). |
| acetamidinomethyl | 69 | 185 | 1775 | 9.6-8.6(m,5H), 7.75-7.15(m,5H), 6.0-5.3(m,3H), 5.0(s,1H), 4.14(s,2H), 2.22(s,3H), 1.55(s,3H), 0.92(s,3H). |
| 4-pyridinecarboxamidinomethyl N-oxide | 22 | 200 | 1775 | 9.7-9.3(m,2H), 8.42(d,2H), 7.8(d,2H), 7.2(s,5H), 6.0-5.3 (m,3H), 5.05(s,1H), 4.2(s,2H), 1.55(s,3H), 0.95(s,3H). |
| (2-[p-chlorophenyl]-acetamidino)methyl | 45 | 192 | 1770 | 9.8-8.7(m,4H), 7.7-7.1(m,10H), 5.9-5.2(m,3H), 4.95(s,1H), 4.4-3.0(m,6H), 1.5(s,3H), 0.9(s,3H). |
| p-nitrobenzamidinomethyl | 82 | 197 | 1770 | 9.4-8.9(m,2H), 8.5(d,2H), 8.1(d,2H), 8.0-6.6(m,8H), 5.9(d, 1H), 5.65-5.4(m,2H), 5.05(s,1H), 4.35(s,2H), 1.55(s,3H), 0.9(s,3H). |
| m-sulfamoylbenzamidinomethyl | 51 | 180–185 | 1780 | 8.35-7.5(m,9H), 5.85(d,2H), 5.55(m,2H), 5.02(s,1H), 4.35 (m,2H), 1.50(s,3H), 0.95(s,3H). |
| m-cyanobenzamidinomethyl | 75 | 180–185 | 1785 | 8.4-7.45(m,9H), 5.85(d,1H), 5.5(m,2H), 5.02(s,1H), 4.3(m, 2H), 1.5(s,3H), 0.9(s,3H). |
| 2-benzimidazolecarboxamidinomethyl (triethylamine salt) | 59 | 126–140 | 1785 | 8.0-7.2(m,9H), 5.9(d,1H), 5.55(mm2H), 5.0(s,1H), 4.1(s,2H), 3.0(q,6H), 1.5(s,3H), 1.18(t,9H), 0.9(s,3H). |
| 2-pyrimidinecarboxamidinomethyl | 49 | 149–169 | 1785 | 9.3(s,1H), 8.85(m,2H), 7.35(m,5H), 5.8(d,1H), 5.5(m,2H), 5.03(s,1H), 4.25(m,2H), 1.5(s,3H), 0.9(s,3H). |
| 3-cyano-5-iodobenzamidinomethyl | 58 | | 1780 | 8.55(m,3H), 7.6(m,5H), 5.9(d,1H), 5.6(m,3H), 5.03(s,1H), 4.2(m,2H, 1.55(s,3H), 0.9(s,3H). |
| 2-quinoxalinecarboxamidonomethyl | 53 | | 1785 | 9.8(s,1H), 8.2(m,4H), 7.5(m,5H), 5.95(d,1H), 5.6(m,2H), 5.1(s,1H), 4.3(m,2H), 1.55(s,3H), 0.95(s,3H). |
| m-carbamoylbenzamidinomethyl | 81 | | 1785 | 8.6-7.25(m,9H), 5.95(d,1H), 5.56(m,2H), 5.05(s,1H), 4.4(m,2H), 1.55(s,3H), 0.9(s,3H). |
| 2-pyrrolecarboxamidinomethyl | 83 | | 1785 | 7.3(m,7H), 6.3(m,1H), 5.85(d,1H), 5.5(m,2H), 5.0(s,1H), 4.25(m,2H), 1.55(s,3H), 0.9(s,3H). |
| 2-benzthiazolecarboxamidinomethyl | 54 | 212–15 | 1770<br>1667 | 0.95 (s,3H), 1.55(s,3H), 3.95(b,2H), 5,1 (s,1H), 5.4-5.95 (c,3H), 7.5 (b,7H), 8.2 (b,2H) |
| 3,5-disulfamoylbenzamidinomethyl | 31 | 185–92 | 1770<br>1667 | 0.95 (s,3H), 1.55 (s,3H), 4.1 (b,2H), 5.1 (s,1H), 5.45-5.95 (c,3H), 7.5 (b,5H), 8.5 (b,3H) |
| 3-sulfamoyl-5-bromobenzamidinomethyl | 78 | 196–200 | 1786<br>1681 | 0.95 (s,3H), 1.55 (s,3H), 4.25 (b,2H), 5.1 (s,1H), 5.6 (c,2H), 5.85 (s,1H), 7.5 (b,5H), 8.1 (b,2H), 8.6 (b,1H) |
| 3-sulfamoyl-5-chlorobenzamidinomethyl | 71 | 197–200 | 1770<br>1667 | 0.95 (s,3H), 1.55 (s,3H), 4.4 (b,2H), 5.05 (s,1H), 5.55 (c,2H), 5.8 (s,1H), 7.5 (b,5H), 8.0 (6,2H), 8.4 (b,1H) |
| 3-chloro-5-cyanobenzamidinomethyl | 73 | 203 | 1786<br>1681 | 0.95 (s,3H), 1.55 (s,3H), 4.25 (b,2H), 5.05 (s,1H), 5.5 (c,2H), 5.85 (s,1H), 7.4 (b,5H), 8.25 (b,3H) |
| 2-benzoxazolecarboxamidinomethyl | 73 | 199 | 1786<br>1667 | 0.95 (s,3H), 1.55 (s,3H), 4.3 (b,2H), 5,.1 (s,1H), 5.55 (c,2H), 5.8 (s,1H), 7.2-8.2 (c,9H) |

*with decomposition

EXAMPLE CXXI

Reaction of the appropriate compound of formula I or II, wherein $R^2$ and $R^3$ are each hydrogen and $R^1$ is of formula V, wherein n is 1 and Q is amino, with the requisite ethyl imidate, according to the procedure of Example CXIX, produces the following compounds

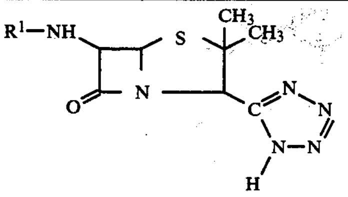

| R[1] | Yield % | Melting Point* (0° C.) | Infrared Spectrum ($cm^{-1}$) | NMR Spectrum (DMSO-$d_6$/$D_2O$; ppm) |
|---|---|---|---|---|
| 2-(3,5-dimethylbenz-amidino)acetyl | 31 | 170–186 | 1775 | 7.35 (s, 3H), 5.77 (d, 1H), 5.60 (d, 1H), 5.20 (s, 1H), 4.34 (s, 2H) 2.37 (s, 6H), 1.67 (s, 3H), 1.01 (s, 3H). |
| 2-(4-pyridinecarbox-amidino)acetyl | 24 | 170–182 | 1785,1680 | 8.40 (d, 2H), 7.70 (d, 1H), 5.83 (d, 1H), 5.67 (d, 1H),5.30 (s, 1H), 4.50 (s, 2H), 1.67 (s, 3H) 1.01 (s, 3H). |
| 2-(acetamidinoacetyl) | 69 | 118–127 | 1770,1680 | 5.83 (d, 1H), 5.67 (d, 1H), 5.30 (s, 1H), 4.33 (s, 2H), 2.40 (s, 3H), 1.67 (s, 3H), 1.01 (s, 3H). |
| 2-(2-thiophenecarbox-amidino)acetyl | 67 | 175–180 | 1780 | 8.03 (m, 2H), 7.34 (m, 1H), 5.78 (d, 1H), 5.60 (d, 1H) 5.19 (s, 1H), 4.35 (s, 2H), 1.67 (s, 3H), 1.01 (s, 3H) |
| 2-(4-pyridiencarbox-amidino)-3-phenyl-propionyl | 58 | 172 | 1780,1680 | |
| 2-(4-pyridinecarbox-amidino)-3-methyl-butyryl | 38 | | 1785,1680 | 8.40 (d, 2H), 7.77 (d, 2H), 5.76 (d, 1H), 5.56 (d, 1H) 5.19 (s, 1H), 4.33 m, 1H), 2.30 (m, 1H), 1.60 (s, 3H) 1.01 (s, 3H). |

*decomposition

EXAMPLE CXXII

Using the procedure of Example CXIX, and reacting 6-(D-2-[3-aminopropionamido]-2-phenylacetamido)-2,2-dimethyl-3(5-tetrazolyl)penam with the appropriate ethyl imidate, the following compounds are prepared:

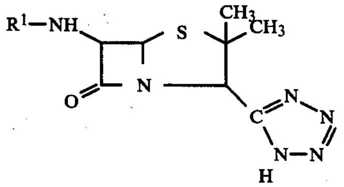

| R[1] | Yield (%) | IR ($cm^{-1}$) | NMR(DMSO-$d_6$) (ppm) |
|---|---|---|---|
| D-2-(3-[4-pyridinecar boxamidino]propionam-ido)-2-phenylacetyl | 63 | 1765 | 0.9 (s,3H), 1.55 (s,3H), 2.5–3.0 (m,2H), 3.45–4.0 (m,2H), 5.0 (s,1H), 5.3–5.6 (m,2H), 5.85 (s,1H), 7.0–8.0 (m,11H), 8.6–9.3 (m,4H) |
| D-2-(3-pyridine-1-oxide-4-carboxamidino]pro-pionamido)-2-phenylacetyl | 82 | 1770 | DMSO-$D_6$:δ0.9 (s,3H), 1.55 (s,3H),2.4–3.0 (m,2H), 3.35–3.9 (m,2H), 5.05 (s,1H), 5.35–5.65 (m,2H), 5.85 (d,1H), 6.4–8.1 (m,12H), 8.45(d,2H), 8.7–9.1 (m,2H). DMSO-$D_6$+$D_2O$: δ0.95 (s,3H), 1.5(s,3H), 2.4–3.0 (m,2H), 3.4–4.0(m,2H), 5.1 (s,1H), 7.45 (s,5H), 7.8 (d,2H), 8.45 (d,2H) |
| D-2-(3-[2-thienylcarb-oxamidino]propionam-ido)-2-phenylacetyl | 78 | 1775 | DMSO-$D_6$:δ0.95 (s,3H), 1.55 (s,3H), 2.4–3.0 (m,2H), 3.4–4.0 (m,2H), 5.05 (s,1H), 5.25–5.65 (m,2H), 5.85 (d,1H), 7.1–7.65 m7-8H), 7.9–8.25 (m,2H), 7.0–9.7 (Broad & m4-5H) DMSO $D_6$+$D_2O$:δ0.95 (s,3H), 1.55 (s,3H), 2.4–3.0 (m,2H), 3.5–4.05 (m,2H), 5.2 (s,1H), 5.45–5.9 (m,3H), 7.2–7.7 (m,6H), 7.8–8.25 (m,2H) |
| D-2-(3-benzamidino-propionamido)-2-phenylacetyl | 74 | 1765 | DMSO-$D_6$:δ0.9 (s,3H), 1.55 (s,3H), 2.4–2.95 (m,2H), 3.3–3.9 (m,2H), 5.05 (s,1H), 5.3–5.6 (m,2H), 5.85 (d,1H), 7.2–8.0 (11H) 8.6–10.0 (4-5H) |
| D-2-(3-[3,5-dibromobenzam-idino]propionamido)-2-phenylacetyl | 82 | 1770 | 1.5 (s,3H), 2.45–2.9(m,2H), 3.3–3.8(m,2H), 4.95 (s,1H), 5.3–5.5 (m,2H), 5.8 (d,1H), 7.1–7.7 (m6-7H); 7.8–8.3 (m,3H), 8.8–9.3 (m,2H) |
| D-2-(3-acetamidinopropionamido)-2-phenylacetyl | 70 | 1770 | 0.95 (s,3H), 1.55 (s,3H), 2.15 (s,3H), 2.25–2.8 (m,2H), 3.1–3.7 (m,2H), 5.05 (s,1H), 5.3–5.65 (m,2H), 5.85 (d,1H), 7.0–7.7 (m,5H), 8.0–10.0 (5-6H) |
| D-2-(3-[3,4-dichlorobenz-amidino]propionamido)-2-phenyl-acetyl | 81 | 1770 | 0.95 (s,3H), 1.55 (s,3H), 2.5–3.0 (m,2H) 3.35–3.9 (m,2H), 5.0 (s,1H), 5.25–5.65 (m,2H), 5.85 (d,1H), 6.8–9.4 (m, 12-13H), |
| D-2-(3-[4-chlorophenyl]acet-amidinopropionamido)-2- | 86 | 1700 | 0.95 (s,3H), 1.55 (s,3H), 2.4–2.9 (m,2H), 3,2–4.0 m,4H), 5.05 (s,1H), 5.8 (d,1H), 7.1–7.7 (m,10H). |

-continued

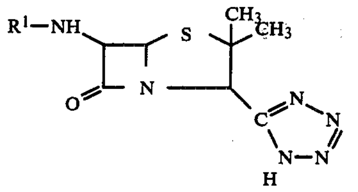

| $R^1$ | Yield (%) | IR ($cm^{-1}$) | NMR($DMSO-d_6$) (ppm) |
|---|---|---|---|
| phenylacetyl | | | |

EXAMPLE CXXIII

Reaction of the appropriate 6-(2-substituted-2-aminoacetamido)-2,2-dimethyl-3-(5-tetrazolyl)penam or 6-(2-substituted-2-[2-aminoacetamido]acetamido)-2,2-dimethyl-3-(5-tetrazolyl)penam with the appropriate imidate ester, according to the procedure of Example CXIX produces the following congeners:

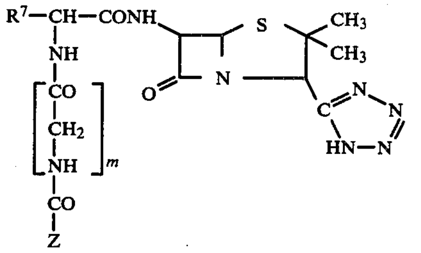

| $R^7$ | m | Z |
|---|---|---|
| methyl | 0 | acetamidinomethyl |
| methyl | 0 | benzamidinomethyl |
| methyl | 0 | p-chlorobenzamidinomethyl |
| isopropyl | 0 | m-bromobenzamidinomethyl |
| isopropyl | 0 | p-methoxybenzamidinomethyl |
| isopropyl | 0 | 3,5-dichlorobenzamidinomethyl |
| isopropyl | 0 | 2-furancarboxamidinomethyl |
| isopropyl | 0 | 4-pyridinecarboxamidinomethyl |
| phenyl | 0 | m-methoxybenzamidinomethyl |
| phenyl | 0 | p-fluorobenzamidinomethyl |
| phenyl | 0 | p-methylbenzamidinomethyl |
| phenyl | 0 | m-methylthiobenzamidinomethyl |
| p-hydroxyphenyl | 0 | 2-benzimidazolecarboxamidino-methyl |
| p-hydroxyphenyl | 0 | benzamidinomethyl |
| p-(hydroxymethyl)phenyl | 0 | benzamidinomethyl |
| 2-thienyl | 0 | 4-pyridinecarboxamidinomethyl |
| 2-thienyl | 0 | 2-thiophenecarboxamidinomethyl |
| 3-thienyl | 0 | benzamidinomethyl |
| 2-furyl | 0 | 3,5-dichlorobenzamidinomethyl |
| 3-chloro-4-hydroxy-phenyl | 0 | 4-pyridinecarboxamidinomethyl |
| p-methoxyphenyl | 0 | benzamidinomethyl |
| m-tolyl | 0 | 3-pyridinecarboxamidinomethyl |
| phenyl | 0 | propanecarboxamidinomethyl |
| phenyl | 0 | butanecarboxamidinomethyl |
| p-hydroxyphenyl | 0 | hexanecarboxamidinomethyl |
| m-butoxyphenyl | 0 | benzamidinomethyl |
| methyl | 1 | acetamidinomethyl |
| methyl | 1 | benzamidinomethyl |
| isopropyl | 1 | 4-pyridinecarboxamidinomethyl |
| phenyl | 1 | butanecarboxamidinomethyl |
| phenyl | 1 | 3,5-dichlorobenzamidinomethyl |
| phenyl | 1 | 2-thiophenecarboxamidinomethyl |
| p-hydroxyphenyl | 1 | benzamidinomethyl |
| p-chlorophenyl | 1 | 4-pyridinecarboxamidinomethyl |

EXAMPLE CXXIV

6-(D-2-[2-(4-Pyridinecarboxamidino)acetamido]-2-[p-hydroxyphenyl]acetamido)-2,2-dimethyl-3-(5-tetrazolyl)penam The title compound is prepared in 80% yield from 6-(D-2-[2-aminoacetamido]-2-[p-hydroxyphenyl]acetamido)-2,2-dimethyl-3-(5-tetrazolyl) penam and ethyl 4-pyridinecarboximidate, using the procedure of Example CXIX. The product has m.p. 195° C. (dec.). IR (KBr disc): 1775 $cm^{-1}$. NMR ($DMSO-d_6$): 9.3–8.8 ppm (m, 4H), 8.8–7.0 ppm (m, 4H), 7.75 ppm (d, 2H), 7.25 ppm (d, 2H), 6.75 ppm (d, 2H), 5.85–5.45 ppm (m, 3H), 5.05 ppm (s, 1H), 4.35 ppm (s, 2H), 1.5 ppm (s, 3H), 0.95 ppm (s, 3H).

EXAMPLE CXXV

6-(D-2-[2-(3-Ethylureido)acetamido]-2-phenylacetamido)-2,2-dimethyl-3-(5-tetrazolyl)penam A mixture of 1.29 g. of 6-(D-2-[2-aminoacetamido]-2-phenylacetamido)-2,2-dimethyl-3-(5-tetrazolyl)penam, 0.23 g. of ethyl isocyanate and 15 ml. of N,N-dimethylformamide is stirred at room temperature for 45 minutes. The filtered reaction mixture is then added dropwise with stirring to 300 ml. of ether, and the precipitate which forms is filtered off. The solid is partitioned between water and ethyl acetate, and the pH is adjusted to 8.0. The ethyl acetate is removed and discarded. The pH of the aqueous phase is adjusted to 2.0, and the product is extracted into ethyl acetate. The washed (water) and dried ($Na_2SO_4$) ethyl acetate is concentrated to small volume and the product crystallizes out. It is filtered off. The yield of the title compound is 0.74 g. (49%), m.p. 162° C. (dec.). IR (KBr disc): 1785 $cm^{-1}$ ($\beta$-lactam). NMR ($DMSO-d_6/CDCl_3$): 9.3–9.1 ppm (s,1H), 8.3 ppm (d,1H), 7.65–7.2 ppm (m,5H), 6.3–5.5 ppm (m,5H), 5.2 ppm (s,1H), 3.8 ppm (d,2H), 3.3–2.9 ppm (m,2H), 1.65 ppm (s,3H), 1.2–0.9 ppm (m,6H).

EXAMPLE CXXVI

Reaction of 6-(D-2-[2-aminoacetamido]-2-phenylacetamido)-2,2-dimethyl-3(5-tetrazolyl)penam with the appropriate isocyanate, according to the procedure of Example CXXV, provides the following compounds.

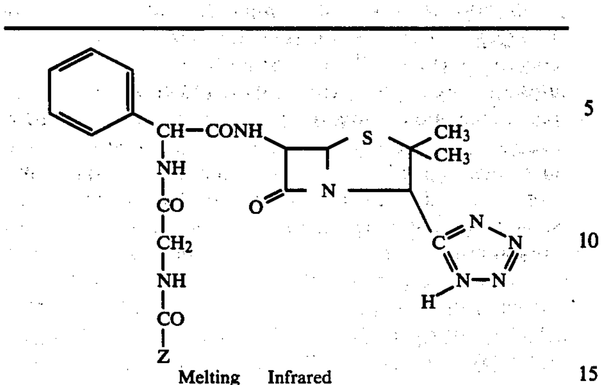

| Z | Yield (%) | Melting Point* (°C.) | Infrared Spectrum ($cm^{-1}$) | NMR Spectrum (DMSO-$d_6$; ppm) |
|---|---|---|---|---|
| anilino | 38 | 158 | 1780 | 9.3-9.0(m,1H), 8.7-8.4(m,1H, 7.7-6.9(m. 10H), 6.6-6.3(m,1h), 5.9-5.45(m,3H), 5.2 (s,1H), 3.95(d,2H), 1.65(s,3H), 1.05(s,3H). |
| methyl-amino | 33 | 154 | 1785 | 9.25-9.05(m,1H), 8.15 (d,1H), 7.6-7.15(m,5H), 6.3-5.2(m,5H), 5.15(s, 1H), 3.8(d,2H), 2.65 (d,3H), 1.6(s,3H), 1.05(s,3H). |

*with decomposition

EXAMPLE CXXVII 6-(D-2-[2-Phenoxyacetamido]-2-[4-hydroxyphenyl-]acetamido)-2,2-dimethyl-3-(5-tetrazol-5-yl)penam To a stirred mixture of 1.0 g. of 6-(D-2-amino-2-[4-hydroxyphenyl]acetamido)-2,2-dimethyl-3-(5-tetrazol-5-yl)penam, and 0.91 ml. of triethylamine, in 20 ml. of methylene chloride, is added 3 ml. of N,N-dimethylformamide. This solution is then cooled to 0° C., and a solution of 0.375 g. of phenoxyacetyl chloride in 10 ml. of methylene chloride is added dropwise. The mixture is stirred for 30 minutes after the end of the addition, and then the solvent is removed by evaporation in vacuo. The residue is dissolved in water. The aqueous solution is extracted with ethyl acetate and then acidified to pH 2.4. The aqueous phase is again extracted with ethyl acetate, and the latter extract is dried using anhydrous sodium sulfate. Removal of the solvent by evaporation in vacuo leaves 0.91 g. of crude product. The crude product is purified by chromatography using Sephadex LH-20 as adsorbant, and eluting with water. The yield of purified product is 0.33 g. (30%), mp 180°-192° C. (dec.). IR (KBr disc): 1786, 1667, 1613 and 1515 $cm^{-1}$. NMR ($CDCl_3$/DMSO-$d_6$): 9.13 ppm (d, J=7Hz, 1H), 8.58 ppm (d, J=8Hz, 1H), 7.00-7.60 ppm (m, 9H), 5.90 ppm (d, J=8Hz, 1H), 5.60 ppm (m, 2H), 5.03 ppm (s, 1H), 4.65 ppm (s, 2H), 1.57 ppm (s, 3H) and 0.97 ppm (s, 3H).

EXAMPLE CXXVIII 6-(D-2-Phthalimido-2-phenylacetamido)-2,2-dimethyl-3-(5-tetrazolyl)penam To a stirred solution of 1.07 g. of 6-(D-2-amino-2-phenylacetamido)-2,2-dimethyl-3-(5-tetrazolyl)penam and 1.03 ml. of triethylamine, in 20 ml. of methylene chloride, is added, at 0° C., a solution of phthalic anhydride in 10 ml. of methylene chloride. The mixture is stirred at ambient temperature for 1.5 hours, and then the solvent is removed by evaporation in vacuo. The residue is dissolved in water at pH 7.8, and the water is washed with ethyl acetate. The pH of the aqueous phase is then lowered to 2.0 and the product is extracted into ethyl acetate. The latter ethyl acetate is washed with water, dried using anhydrous sodium sulfate, and evaporated in vacuo. This affords 1.2 g. (92% yield) of the title compound, mp 185°-197° C. (dec.). IR (KBr disc): 1795, 1724 and 1639 $cm^{-1}$. NMR ($CDCl_3$/DMSO-$d_6$): 8.67 ppm (m, 3H), 8.25 ppm (d, J=8Hz, 1H), 7.50 ppm (m, 9H), 5.98 ppm (d, J=8Hz, 1H), 5.65 ppm (m, 2H), 5.28 ppm (s, 1H), 1.67 ppm (s, 3H) and 1.10 ppm (s, 3H).

EXAMPLE CXXIX 6-(D-2-[3-Phenylthiouredio]-2-phenylacetamide)-2,2-dimethyl-3-(5-tetrazol)penam To a stirred solution of 910 mg. of 6-(D-2-amino-2-phenylacetamido)-2,2-dimethyl-3-(5-tetrazolyl)penam, and 0.61 ml. of triethylamine, in 20 ml. of methylene chloride, is added 0.27 ml. of phenyl isothiocyanate. Stirring is continued for 2 hours at ambient temperature, and then the solvent is removed by evaporation in vacuo. The residue is dissolved in water at pH 7.8, and the water is washed with ethyl acetate. The pH of the aqueous phase is then lowered to 2.0 and the product is extracted into ethyl acetate. The latter ethyl acetate is washed with water, dried using anhydrous sodium sulfate, and evaporated in vacuo. This affords 707 mg. (64% yield) of the title compound mp 150°-167° C. (dec.). IR (KBr disc: 1786, 1681 and 1515 $cm^{-1}$. NMR ($CDCl_3$/DMSO-$d_6$): 9.17 ppm (s, 1H), 8.27 ppm (m, 1H), 7.97 ppm (d, J=7Hz, 1H), 7.4 ppm (m, 10H), 6.3 ppm (d, J=7Hz, 1H), 5.63 ppm (m, 2H), 5.27 ppm (s, 1H), 1.6 ppm (s, 3H) and 1.1 ppm (s, 3H).

EXAMPLE CXXX 6-(D-2-[3-Guanylureido]-2-phenylacetamido)-2,2-dimethyl-3-(5-tetrazolyl)penam To a stirred solution of 0.5 g of guanylsemicarbazide dihydrochloride (U.S. Pat. No. 3,579,514) in 5 ml. of water, is added dropwise, 0.184 g. of sodium nitrite in 2 ml. of water, at ca. 0° C. The resulting solution is stirred for 10 minutes at ca. 0° C. A second solution is then prepared from 1.14 g. of 6-(D-2-amino-2-phenylacetamido)-2,2-dimethyl-3-(5-tetrazolyl)penam, 20 ml. of water, 6 ml. of dioxane and sufficient triethylamine to bring the pH to 8.0. The pH of the second solution is then lowered to 7.5, and the first solution is added dropwise at ca. 0° C. The resulting reaction mixture is stirred for 45 minutes. To it is then added a solution prepared from 0.95 g. of sodium nitrite, 0.25 g. of guanylsemicarbazide dihydrochloride and 3 ml. of water. Stirring is continued for a further 45 minutes, and then the reaction mixture is lyophilized. The residue is extracted with chloroform. The insoluble material is then suspended in 20 ml. of water, the pH of which is then adjusted to 5.0. The solid is filtered off and dried, to give 0.87 g. (71% yield) of the title compound, m.p. 192°-194° C. (dec.). IR (KBr disc: 1785 $cm^{-1}$ (β-lactam). NMR (in DMSO-$d_6$): 7.55 ppm (m, 5H), 5.85-5.55 ppm (m,3H), 5.10 ppm (s,1H), 1.55 ppm (s,3H), 0.95 ppm (s,3H).

In like manner, starting from 6-(D-2-amino-2-[4-hydroxyphenyl]acetamido)-2,2-dimethyl-3-(5-tetrazolyl)penam, there is prepared a 94% yield of 6-(D-2-[3-guanylureido]-2-[4-hydroxyphenyl]acetamido)-2,2- dimethyl-3-(5-tetrazolyl)penam, m.p. 186°-199° C. IR(KBr disc): 1783, 1695 and 1667 $cm^{-1}$. NMR ($DMSO-d_6/D_2O$): 0.95 (s,3H), 1.55 (s,3H), 5.1 (s,1H), 5.4-5.8 (m,3H), 6.8 (d,2H), 7.35 (d,2H).

EXAMPLE CXXXI

Following the procedure of Example CXXX and reacting the appropriate 6-(2-amino-2-substituted-acetamido)-2,2-dimethyl-3-(5-tetrazolyl)penam with diazotized guanylsemicarbazide, the following compounds are prepared.

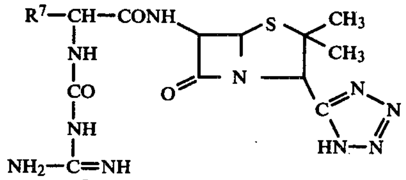

| $R^7$ |
|---|
| methyl |
| isopropyl |
| cyclopentyl |
| 3-cyclohexenyl |
| 1,4-cyclohexadienyl |
| m-hydroxyphenyl |
| p-chlorophenyl |
| o-fluorophenyl |
| 3,4-dichlorophenyl |
| p-methoxyphenyl |
| p-tolyl |
| 3,4-dimethoxyphenyl |
| 2-thienyl |
| 3-thienyl |
| 2-furyl |
| 3-pyridyl |
| 3-chloro-4-hydroxyphenyl |

EXAMPLE CXXXII

6-(D-2-Ureido-2-phenylacetamido)-2,2-dimethyl-3-(5-tetrazolyl)penam

A mixture of 0.5 g. of 2-(D-2-amino-2-phenylacetamido)-2,2-dimethyl-3-(5-tetrazolyl)penam and 94 mg. of potassium cyanate in 10 ml. of water is heated rapidly to 80° C., and then cooled rapidly to 25° C. The reaction mixture is stirred at ambient temperature for 18 hours, and then filtered. The filtrate is acidified to pH 2.0, and the solid which precipitates is filtered off. It is dissolved in a small volume of ethanol, to which 0.067 ml. of triethylamine is added, and then this solution is poured into 100 ml. of ether. The solid which precipitates is filtered off, giving 0.23 g. (38% yield) of the title compound as its triethylamine salt, m.p. 138°-150° C. (dec.). IR (KBr disc): 1785 $cm^{-1}$ (β-lactam) and 1670 $cm^{-1}$ (amide I). NMR (in $DMSO-d_6/D_2O$): 7.45 ppm (m,5H), 5.80-5.40 ppm (m,3H), 5.10 ppm (s,1H), 3.10 ppm (q,6H), 1.60 ppm (s,3H), 1.20 ppm (t,9H), 0.95 ppm (s,3H).

EXAMPLE CXXXIII

6-(D-2-Sulfamoyl-2-phenylacetamido)-2,2-dimethyl-3-(5-tetrazolyl)penam

A suspension of 1.5 g. of 2-sulfamoyl-2-phenylacetic acid in 15 ml. of thionyl chloride is heated under reflux for 30 minutes, and then the thionyl chloride is removed by evaporation in vacuo. To the residue is added 50 ml. of benzene and the mixture is evaporated to dryness in vacuo again. The residue is then dissolved in 30 ml. of acetone, and added dropwise, with stirring, at 0° C., to a solution of 0.84 g. of 6-amino-2,2-dimethyl-3-(5-tetrazolyl)penam in 25 ml. of water and 3.5 ml. of 1N sodium hydroxide. During the addition, and for 30 minutes afterwards, the pH is maintained at 6.0-6.2. At this point, the reaction mixture is adjusted to pH 2.0, and the product is extracted into ethyl acetate. The ethyl acetate is dried using anhydrous sodium sulfate, and then it is evaporated to dryness in vacuo. The residue is dissolved in methylene chloride containing 4.9 ml. of triethylamine. The solvent is again evaporated to dryness in vacuo, giving 1.1 g. (58% yield) of the title compound as its triethylamine salt, m.p. 129°-139° C. (dec.). IR (KBr disc): 1770 $cm^{-1}$ (β-lactam). NMR ($DMSO-d_6/D_2O$): 7.60 ppm (m,5H), 5.90-5.40 ppm (m,3H), 5.05 ppm (s,1H), 1.55 ppm (s,3H), 0.95 ppm (s,3H).

Preparation of 2-sulfamoyl-2-phenylacetic acid is described in British Pat. No. 1,067,965.

EXAMPLE CXXXIV

6-(D-2-[2-Guanylacetamido]-2-phenylacetamido)-2,2-dimethyl-3-(5-tetrazolyl)penam To a stirred solution of 405 mg. of p-nitrophenol in 10 ml. of N,N-dimethylformamide is added 620 mg. of dicyclohexylcarbodiimide followed by 410 mg. of 2-guanylacetic acid hydrochloride. Stirring is continued for 4 hours, and then to this solution is added a solution of 948 mg. of 6-(D-2-amino-2-phenylacetamido)-2,2-dimethyl-3-(5-tetrazolyl)penam triethylamine salt in 10 ml. of N,N-dimethylformamide. Stirring is continued overnight, and then the filtered reaction mixture is poured into 300 ml. of ether. A gummy precipitate forms, and the excess solvent is removed by decantation. The gummy material is then slurried in 300 ml. of methylene chloride containing 1 ml. of triethylamine. This affords, after filtration, 0.4 g. (44% yield) of the title compound, m.p. 172°-176° C. (dec.). IR (KBr disc): 1780 $cm^{-1}$ (β-lactam). NMR (in $DMSO-d_6/D_2O$): 7.45 ppm (m,5H), 5.85 ppm (d,1H), 5.55 ppm (m,2H), 5.05 ppm (s,1H), 2.70 ppm (m,4H), 1.55 ppm (s,3H), 0.95 ppm (s,3H).

The 2-guanylacetic acid hydrochloride used in this Example is prepared from ethyl 2-cyanoacetate in a manner analogous to that described for the preparation of 3-guanylpropionic acid hydrochloride.

EXAMPLE CXXXV

6(D-2-[p-Guanidinobenzamido]-2-phenylacetamido)-2,2-dimethyl-3-(5-tetrazolyl)penam A mixture of 2.15 g. of p-guanidinobenzoic acid hydrochloride and 75 ml. of thionyl chloride is heated under reflux for 18 hours. It is then cooled to 25° C., and concentrated to dryness in vacuo. The residue is washed thoroughly with ethylene dichloride. This affords 1.7 g. of p-guanidinobenzoyl chloride hydrochloride.

To a stirred solution of 0.854 g. of 6-(D-2-amino-2-phenylacetamido)-2,2-dimethyl-3-(5-tetrazolyl)penam trihydrate and 0.54 ml. of triethylamine in 10 ml. of N,N-dimethylformamide is added, at 0° C., 0.468 g. of p-guanidinobenzoyl chloride hydrochloride. Stirring is continued for 30 minutes, and then a further 0.14 ml. of triethylamine and 0.124 g. of p-guanidinobenzoyl chloride hydrochloride is added. After being stirred for a further 30 minutes, the reaction mixture is filtered and the filtrate is added dropwise to 300 ml. of ether. The solid which precipitates is filtered off, and washed thoroughly with methylene chloride containing triethylamine. This affords 0.8 g. (75% yield) of the title compound, m.p. 196°-200° C. IR (KBr disc): 1770 $cm^{-1}$ (β-lactam). NMR (in DMSO-$d_6$/$D_2O$): 8.25-7.20 ppm (m,9H), 6.00 ppm (d,1H), 5.50 ppm (m,2H), 5.05 ppm (s,1H), 1.50 ppm (s,3H), 0.95 ppm (s,3H).

The preparation of p-guanidinobenzoic acid is described in *Rec. Trav. Chim. Pay-Bas,* 72, 643 (1952).

EXAMPLE CXXXVI

Reaction of 6-(D-2-amino-2-phenylacetamido)-2,2-dimethyl-3-(5-tetrazolyl)penam or 6-(D-2-amino-2-[4-hydroxyphenyl]acetamido)-2,2-dimethyl-3-(5-tetrazolyl)penam with the appropriate acid chloride hydrochloride, according to the procedure of Example CXXXV, provides the following congeners. Acid chloride hydrochlorides are prepared from the corresponding acids by the method of Hardcastle et al., *Journal of Organic Chemistry,* 31, 897 (1966).

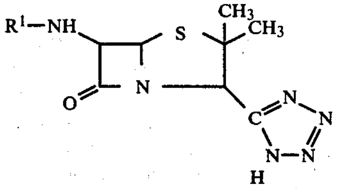

| $R^1$ | Yield (%) | Melting Point* (°C.) | Infrared Spectrum ($cm^{-1}$) | NMR Spectrum (ppm; DMSO-$d_6$/$D_2O$) |
|---|---|---|---|---|
| D-2-(2-guanidinoacetamido)-2-phenylacetyl | 77 | 166-176 | 1780 | 7.80-7.25(m.5H), 5.85(d,1H), 5.55(m,2H), 5.10 (s,1H), 4.00(m, 2H), 1.50(s,3H), 0.95 (s,3H), |
| D-2-(2-[$\Delta^1$-imidazolin-2-ylamino]acetamido)-2-phenylacetyl | 37 | 170-177 | 1785 | 7.40(m,5H), 5.85(d,1H), 5.55(m,2H), 5.05(s,1H), 4.05(m,2H), 3.65(m,4H), 1.50(s,3H), 0.95(s,3H), |
| D-2-(2-[4-guanidinophenyl]-acetamido)-2-phenylacetyl | 53 | 196-200 | 1780 | 7.80-7.05(m,9H), 5.80(d,1H), 5.45(m,2H), 5.05(s,1H), 3.6(s, 2H), 1.50(s,3H), 0.90(s,3H), |
| D-2-(3-guanylpropionamido)-2-phenylacetyl | 25 | 180-186 | 1785 | 7.45(m,5H), 5.85(d,1H), 5.55(m,2H), 5.05(s,1H), 2.70(m,4H), 1.55(s,3H), 0.95(s,3H), |
| D-2-(2-[(N-methylguanyl)-amino]acetamido)-2-phenylacetyl | 79 | 200-208 | 1772 | 9.70-9.05(m,2H), 8.00-7.10(m,10H), 5.95(d,1H), 5.60-5.30 (m,2H), 5.00(s,1H), 4.00(s,2H), 2.75(s,3H), 1,50(s,3H), 0.90 (s,3H), |
| D-2-(2-[3-(guanyl)ureido]-acetamido)-2-phenylacetyl | 54 | 166-176 | 1785 | 7.45(m,5H), 5.80(d,1H), 5,50(m,2H), 5.05(s,1H), 3,85(m,2H),. 1.55(s,3H), 0.95(s,3H), |
| D-2-(2-[3-(N-methylguanyl)-ureido[acetamido)-2-phenylacetyl | 85 | 168-171 | 1786 1667 | 0.95(s,3H), 1.55(s,3H), 2.9(s,3H), 3.85(m,2H), 5.1(s,1H), 5.4-5.95(m,3H), 7.5 (m,5H), |
| D-2-(2-[3-(N-ethylguanyl)-ureido]acetamido)-2-phenylacetyl | 60 | 165-175 | 1783 1667 | 0.95(s,3H), 1.2(m,3H), 1,55(s,3H), 3.3(m,2H), 3,95(m,2H), 5.15 (s,1H), 5.5-5,85 (m,3H), 7.5(m,5H), |
| D-2-(2-[3-(N-benzylguanyl)-ureido]acetamido)-2-phenylacetyl | 58 | 165-169 | 1786, 1681 1626 | 0.95(s,3H), 1.55(s,3H), 3.85(m,2H), 4.5(m,2H), 5.1(s,1H), 5.4-5.8(m,3H), 7.4(m,10H), |
| D-2-(2-[3-(N-p-chlorobenzyl-guanyl)ureido]acetamido)-2-phenylacetyl | 59 | 178-190 | 1786, 1681, 1626 | 0.95(s,3H), 1.55(s,3H), 3.9(m,2H), 4.5(m,2H), 5.15 (s,1H), 5.4-5.85 (m,3H), 7.5(m,9H), |
| D-2-(2-[3-(N-[cyclohexylmethyl]guanyl)ureido]acetamido)-2-phenylacetyl | 68 | 178-185 | 1786, 1681 | 0.95(s,3H), 1.55(m,14H), 3.1(m,2H), 3.9(m,2H), 5.15(s,1H), 5.4-5.8(m,3H), 7.45(m,7H), 8.6(m,2H) |
| D-2-(2-[3-(guanyl)ureido]-acetamido)-2-(4-hydroxyphenyl)acetyl | 62 | 182-188 | 1786, 1695, 1667 | 0.95 (s,3H), 1.55 (s,3H), 3.8 (m,2H), 5.05 (s,1H), 5.4-5.8 (m,3H), 6.8 (d,2H), 7.3 (d,2H). |

*with decomposition

The acid chloride hydrochlorides used in this Example are prepared from the corresponding acids, using thionyl chloride. 2-(Guanylureido)acetic acid is prepared by the method of Frankel and Sheradsky, *J. Chem. Soc.* (London), C, 2698 (1967); 2-(p-guanidinophenyl)acetic acid is prepared by the method of Leanza et al., *Nature,* 207, 1395 (1965); and 3-guanylpropionic acid is prepared by the method of McElvain and Schroeder, *J. Amer. Chem. Soc.,* 71, 40 (1949).

EXAMPLE CXXXVII

Following the procedure of Example CXXXV and reacting the appropriate 6-(2-amino-2-substituted-acetamido)-2,2-dimethyl-3-(5-tetrazolyl)penam with 2-guanidinoacetyl chloride hydrochloride, the following compounds are prepared:

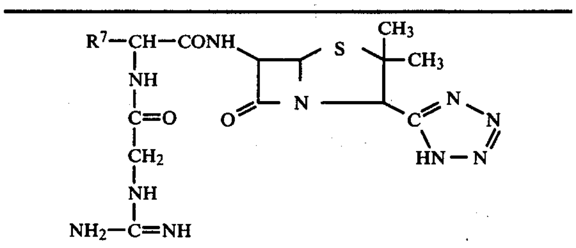

$R^7$ methyl
isopropyl
allyl
cyclohexyl
3-cyclohexenyl
1,4-cyclohexadienyl
p-hydroxyphenyl
p-chlorophenyl
m-methoxyphenyl
o-fluorophenyl
3,4-dichlorophenyl -continued

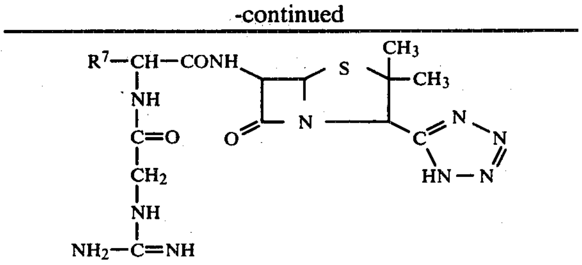

| $R^7$ |
|---|
| p-tolyl |
| 3-chloro-4-hydroxyphenyl |
| 2-thienyl |
| 3-thienyl |
| 2-furyl |
| 3-pyridyl |
| 5-tetrazolyl |
| 5-ethyl-2-thienyl |

EXAMPLE CXXXVIII

6-(D-2-[3-(2-Furoyl)ureido]-2-phenylacetamido)-2,2-dimethyl-3-(5-tetrazolyl)penam To a stirred suspension of 5.0 g. of 6-(D-2-amino-2-phenylacetamido)-2,2-dimethyl-3-(5-tetrazolyl)penam in 50 ml. of methylene chloride is added 2.72 g. of triethylamine. After 10 minutes, the solution is dried ($Na_2SO_4$), and then it is concentrated to dryness in vacuo giving the triethylamine salt of 6-(D-2-amino-2-phenylacetamido)-2,2-dimethyl-3-(5-tetrazolyl)penam.

To 948 mg. of the above triethylamine salt, in 10 ml. of methylene chloride, at 0° C., is added 274 mg. of 2-furoyl isocyanate dissolved in a small volume of methylene chloride. After 10 minutes, the solvent is removed in vacuo. The residue partitioned between ethyl acetate and water, and the pH is adjusted to 7.7. The ethyl acetate is removed and discarded. The pH of the remaining aqueous phase is adjusted to 2.5 and the product is extracted into ethyl acetate. The ethyl acetate is washed with water, followed by brine, and then it is evaporated to dryness in vacuo. The residue is dissolved in methylene chloride containing 145 mg. of triethylamine and again the solution is evaporated to dryness in vacuo. This affords 930 mg. (76% yield) of the title compound or its triethylamine salt, mp. 90°–115° C. (dec.). IR (KBr disc): 1778 $cm^{-1}$ ($\beta$-lactam). NMR (in $CDCl_3$): 8.2–7.2 (m), 6.5 (m), 6.0–5.4 (m), 1.7 (s), 1.1 (s).

EXAMPLE CXXXIX

Using the procedure of Example CXXXVIII, and reacting either 6-amino-2,2-dimethyl-3-(5-tetrazolyl)penam or 6-(D-2-amino-2-phenylacetamido)-2,2-dimethyl-3-(5-tetrazolyl)penam with the appropriate-acyl isocyanate, acyl isothiocyanate or sulfonyl isocyanate, the following compounds are prepared

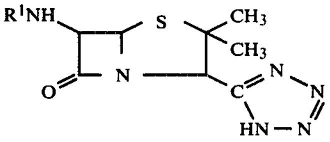

| $R^1$ | Yield (%) | Infrared Spectrum ($cm^{-1}$) | NMR Spectrum ($CDCl_3$; ppm) |
|---|---|---|---|
| *2-(3-acetylureido)-2-phenylacetyl | 98 | 1785, 1680, 1495 | 7.4(s), 6.0–5.4(m), 5.3(s), 2.1(m), 1.6(s), 1.1(s), |
| *2-(3-butyrylureido)-2-phenylacetyl | | 1770, 1695 | 7.2(s,5H), 5.8(m,3H), 5.2(s,1H), 2.2(m,2H), 1.4(s,3H), 0.9(s,3H). |
| *2-(3-[chloroacetyl]ureido)-2-phenylacetyl | 84 | 1770, 1695, 1530 | 7.8–7.3(m,5H), 6.0–5.5(m,4H), 5.3(s,1H), 4.3(s,2H), 1.5(s,3H), 1.1(s,3H). |
| *2-(3-[3-pyridylcarbonyl]-ureido)-2-phenylacetyl | 88 | 1785, 1695, 1495 | 9.0–8.0(m,3H), 7.7–7.3(s,6H), 6.0–5.3(n,3H), 1.6(s,3H), 1.2(s,3H). |
| *2-(3-benzoylureido)-2-phenylacetyl | 48 | 1785, 1670, 1540, 1515, 1480 | 8.6–7.3(m,10H), 6.3–5.7(m.2H), 5.4(s,2H), 1.6(s,3H), 1.1(s,3H). |
| *2-(3-[3,5-dibromobenzoyl]-ureido)-2-Phenylacetyl | 49 | 1770, 1670, 1560, 1490 | 8.3–7.3(m,8H), 6.1–5.4(m,3H), 5.3(s,1H), 1.6(s,3H), 1.1(s,3H). |
| *2-(3-[4-pyridylcarbonyl]-ureido)-2-phenylacetyl | 68 | 1785, 1670, 1505 | 9.0–7.3(m,9H), 6.0–5.3(m,4H), 1.5(s,3H), 1.0(s,3H). |
| *2-(3-propionylureido)-2-phenylacetyl | 80<br>8-1540 | 1770, 1695, 1.3-1.0(m,6-H). | 7.7–7.3(m,5H), 6.5(m,2H), 6.0–5.3(m,5H), 1.5(s,3H), |
| *2-(3-[cyclopropylcarbonyl]-ureido)-2-phenylacetyl | 83 | 1770, 1695 | 7.4(s,5H), 5.8∝5.2(s,4H), 1.4(s,4H), 0.9(s,7H). |
| *2-(3-[1-adamantylcarbonyl]-ureido)-2-phenylacetyl | 76 | 1785, 1680 | 7.2(s,5H), 5.8–5.2(s,4H), 1.4(s,3H), 0.9(s,3H). |
| *2-(3-benzoylthioureido)-2-phenylacetyl | 79 | 1770, 1680, 1480 | 7.7–7.2(s), 6.0–5.3(m), 2.05(s), 1.6(s), 1.1(s). |
| *2-(3-[2-furoyl]thioureido)-2-phenylacetyl | 73 | 1770, 1680, 1590, 1515 | 7.7–7.0(m), 6.6(m), 6.0–5.4(m), 5.3(s), 2.1(s), 1.6 (s), 1.1(s). |
| 2-(3-[p-toluenesulfonyl]-ureido)-2-phenylacetyl | 70 | 1800, 1600 | 7.9(d,2H), 7.4(m,8H), 5.5(m,3H), 5.2(s,1H), 2.4(s,3H), 1.6(s,3H), 1.05(s,3H). |
| 3-acetylureido | 58 | 1790, 1695 | 10.45(s,1H), 9.35(d,1H), 5.8(m,2H), 5.35(s,1H), 2.1(s,3H), 1.7(s,3H), 1.15(s,3H), |
| 3-(2-furoyl)ureido | 60 | 1795, 1695 | 9.33(m,2H), 7.5(m,3H), 6.6(m,2H), 5.8(m,2H), 5.45(s,1H), 1.8(s,3H), 1.2(s,3H), |
| 3-(p-toluenesulfonyl)-ureido | 91 | 1795, 1695 | 7.7(q,4H), 7.1(d,1H), 5.8–5.4(m,2H), 5.3(s,1H), 2.4(s,3H), 1.7(s,3H), 1.07(s,3H). |
| **2-(3-[2-phenylacetyl]-ureido)-2-phenylacetyl | 82 | 1770, 1685 | 7.7–6.9(m,10H), 5.8–5.2(m,4H), 2.0(m,2H), 1.6–0.2(m,10H). |

-continued

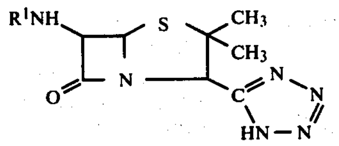

| $R^1$ | Yield (%) | Infrared Spectrum ($cm^{-1}$) | NMR Spectrum ($CDCl_3$; ppm) |
|---|---|---|---|
| **2'-(3-[benzyloxycarbonyl]-ureido)-2-phenylacetyl | 50 | 1770, 1730 1680 | 7.8-6.8(m,10H), 5.9-5.2(m,4H), 2.0(s,1H), 1.9-1.0(m,15H). |
| **2-(3-[acetyl]thioureido)-2-phenylacetyl | 79 | 1760, 1660 | 7.7-7.1(m,5H), 5.8-5.3(m,4H), 2.1(m,4H), 1.5(s,3H), 1.0(s,3H), |
| **2-(3-[3-methyl-5-isoxazolylcarbonyl]ureido)-2-phenylacetyl | 64 | 1770, 1695 | 7.8-7.2(m,6H), 7.0(s,1H), 5.7 (m,4H), 5.3(s,1H), 2.4(s,3H) 2.2(s,1H), 1.5(s,3H), 1.0(s,3H), |

*This compound is isolated as its triethylamine salt.
**This compound is isolated as its sodium salt

EXAMPLE CXL

Using the procedure of Example CXXXVIII, and reacting 6-(2-amino-2-substituted-acetamido)-2,2-dimethyl-3-(5-tetrazolyl)penam or 6-(2-[2-aminoacetamido]-2-substituted-acetamido)-2,2-dimethyl-3-(5-tetrazolyl)penam with the appropriate acyl isocyanate, provides the following compounds

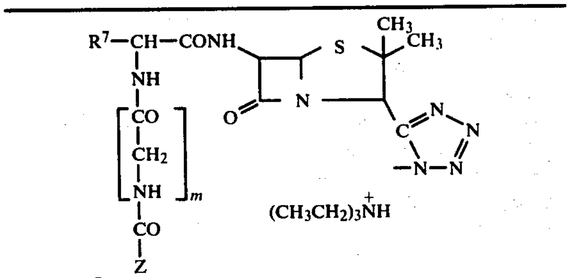

| $R^7$ | Z | m |
|---|---|---|
| methyl | 2-furancarboxamido | 0 |
| methyl | benzamido | 0 |
| isopropyl | acetamido | 0 |
| isopropyl | 2-furancarboxamido | 1 |
| phenyl | p-chlorobenzamido | 0 |
| phenyl | m-bromobenzamido | 0 |
| phenyl | 0-fluorobenzamido | 0 |
| phenyl | 3,4-dichlorobenzamido | 0 |
| phenyl | p-methoxybenzamido | 0 |
| phenyl | m-n-butoxybenzamido | 0 |
| phenyl | 3,4-dimethoxybenzamido | 0 |
| phenyl | p-isopropylbenzamido | 0 |
| p-hydroxyphenyl | 2-furancarboxamido | 0 |
| p-hydroxyphenyl | benzamido | 0 |
| p-chlorophenyl | propionamido | 0 |
| m-methoxyphenyl | 3,4-dichlorobenzamido | 0 |
| p-tolyl | 2-thiophenecarboxamido | 0 |
| 3,5-dichlorophenyl | 3-thiophenecarboxamido | 0 |
| 3-chloro-4-hydroxyphenyl | 2-furancarboxamido | 0 |
| 3-chloro-4-hydroxyphenyl | benzamido | 0 |
| 2-thienyl | 2-furancarboxamido | 0 |
| 2-thienyl | benzamido | 0 |
| 3-thienyl | p-chlorobenzamido | 0 |
| 3-thienyl | n-butyramido | 0 |
| 2-furyl | 3-furancarboxamido | 0 |
| 3-furyl | p-iodobenzamido | 0 |
| 3-pyridyl | benzamido | 0 |
| 1,4-cyclohexadienyl | 2-furancarboxamido | 0 |
| methyl | benzamido | 1 |
| phenyl | 2-furancarboxamido | 1 |
| p-hydroxyphenyl | 3,5-dichlorobenzamido | 1 |
| 3-chloro-4-hydroxyphenyl | benzamido | 1 |
| 2-thienyl | 2-furancarboxamido | 1 |
| 3-thienyl | benzamido | 1 |

-continued

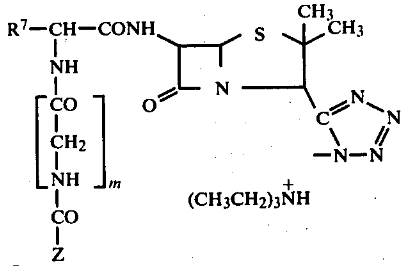

| $R^7$ | Z | m |
|---|---|---|
| 3-chloro-4-hydroxyphenyl | acetamido | 0 |
| p-chlorophenyl | propionamido | 0 |
| 2-thienyl | n-butyramido | 0 |
| 3-furyl | | |
| isopropyl | n-hexanoyl | 0 |
| phenyl | isobutyramido | 0 |
| phenyl | acetamido | 1 |
| p-hydroxyphenyl | propionamido | 1 |

EXAMPLE CXLI

6-(D-2-[4-Aminobenzamido]-2-phenylacetamido)-2,2-dimethyl-3-(5-tetrazolyl)penam A solution is prepared by suspending 1.05 g. of 6-(D-2-[4-nitrobenzamido]-2-phenylacetamido)-2,2-dimethyl-3-(5-tetrazolyl)penam in 50 ml. of water, and adjusting the pH to 7.3 using sodium bicarbonate solution. To this solution is then added 1.0 g. of 10% palladium on carbon, and the mixture is shaken under an atmosphere of hydrogen, at a pressure of ca. 40 psi, until hydrogen uptake ceases. The spent catalyst is removed by filtration, and the aqueous solution is lyophilized. This affords 0.91 g. of crude product. A portion of the crude product is purified further by column chromatography using Sephadex LH-20 and eluting with water. The purified product has mp 260°-272° C. IR(KBR disc): 1770 and 1626 $cm^{-1}$. NMR ($D_2O$): 7.6-7.0 ppm (m, 7H), 6.5 ppm (d, J=9 Hz, 2H), 5.6-5.4 ppm (m, 3H), 5.2 ppm (s, 1H), 1.4 ppm (s, 3H) and 0.88 ppm (s, 3H).

EXAMPLE CXLII

6-(D-2-[2-(4-Aminophenyl)acetamido]-2-phenylacetamido)-2,2-dimethyl-3-(5-tetrazolyl)penam The title compound is prepared in 23% yield by hydrogenation of 6-(D-2-[2-(4-nitrophenyl)acetamido]-2-phenylacetamido)-2,2-dimethyl-3-(5-tetrazolyl)penam, using the procedure of Example CXLI. The product has mp 260°–270° C. (dec.). IR(KBr disc): 1770, 1653 and 1515 $cm^{-1}$. NMR ($O_2O$): 7.6–6.8 ppm (m), 5.6 ppm (m), 5.2 ppm (s), 3.4 ppm (s), 1.3 (s) and 0.8 (s).

EXAMPLE CXLIII

6-(L-2-Hydroxy-2-phenylacetamido)-2,2-dimethyl-3-dimethyl-3-(5-tetrazolyl)penam A mixture of 0.152 g of L-mandelic acid, 0.115 g of N-hydroxysuccinimide and 0.206 g of N,N-dicyclohexycarbodiimide in 10 ml of tetrahydrofuran in a 25 ml flask, is stirred at ambient temperature overnight. In a separate flask, 0.216 g of 6-amino-2,2-dimethyl-3-(5-tetrazolyl)penam and 0.23 ml of triethylamine in 10 ml of chloroform and 10 ml of methylene chloride is stirred overnight. The mixture in the first flask is then filtered, and the filtrate is added slowly to the second flask. The resultant mixture is stirred for 4 hours at ambient temperature. The solvents are then removed by evaporation in vacuo, and the residue is partitioned between ethyl acetate and water. The pH is adjusted to 4.7 (1 N sodium hydroxide), and then the organic phase is withdrawn and discarded. The pH of the aqueous phase is then reduced to 2.0 (5% hydrochloric acid), and the product is extracted with ethyl acetate. The solvent is washed with dilute hydrochloric acid followed by brine, dried using anhydrous sodium sulfate, and then it is added dropwise with stirring to 400 ml of hexane. The precipitate which forms is filtered off, giving 170 mg of 6-(L-2-hydroxy-2-phenylacetamido)-2,2-dimethyl-3-(5-tetrazolyl)penam. NMR (in DMSO-$d_6$): 8.16 ppm (broad singlet, 1H, O<u>H</u>), 7.47–7.04 ppm (multiplet, 6H, aromatic protons and N<u>H</u>), 5.73-5.50 ppm (multiplet, 2H, C-5 and C-6 hydrogens), 5.31 and 5.07 ppm (2 singlet, 2H, C-3 hydrogen and side-chain methine hydrogen), 1.67 and 1.10 ppm (2 singlets, 6H, C-2 methyl hydrogens).

EXAMPLE CXLIV

6-(D-2-Hydroxy-2-phenylacetamido)-2,2-dimethyl-3-(5-tetrazolyl)penam

The procedure of Example CXLIII is repeated, except that the L-mandelic acid used therein is replaced by an equivalent amount of D-mandelic acid. This affords a 77% yield of the title compound. NMR (in DMSO-$d_6$): 8.40–8.20 ppm (broad doublet, 1H, N<u>H</u>), 7.48–7.18 ppm (multiplet, 6H, aromatic hydrogens and O<u>H</u>), 5.31 and 5.07 ppm (2 singlets, 2H, C-3 hydrogen and side-chain methine hydrogen), 1.65 and 1.07 ppm (2 singlets, 6H, C-2 methyl hydrogens).

EXAMPLE CXLV

6-(2-Carboxy-2-phenylacetamido)-2,2-dimethyl-3-(5-tetrazolyl)penam

To a stirred solution of 150 mg of 6-amino-2,2-dimethyl-3-(5-tetrazolyl)penam in 5 ml of water is added dropwise dilute sodium hydroxide to give a pH of 6.1. To this solution is then added 150 mg of phenylamalonic acid, followed by 120 mg of 1-ethyl-3-(3-dimethylaminoprop-1-yl)carbodiimide. The solution is stirred for a further 3.5 hours, during which time the pH is maintained in the range from 6.1 to 6.3 by the dropwise addition of dilute hydrochloric acid. At this point, the pH is raised to 7.3 by the addition of saturated sodium bicarbonate solution, and the reaction mixture is extracted with ethyl acetate. The extract is discarded. The aqueous phase is then acidified to pH 2 using dilute hydrochloric acid, and it is again extracted with ethyl acetate (two 30-ml portions). The latter extract is dried, and concentrated to a volume of about 25 ml. To this solution is then added a solution of 180 mg of sodium 2-ethylhexanoate in 1.25 ml of ethyl acetate. The precipitate which forms is filtered off to give 176 mg of the disodium salt of 6-(2-carboxy-2-phenylacetamido)-2,2-dimethyl-3-(5-tetrazolyl)penam. The infrared spectrum of the product (KBr disc) shows absorptions at 1765 $cm^{-1}$ ($\beta$-lactam carbonyl), 1670 $cm^{-1}$ (amide I band) and 1600 $cm^{-1}$ (carboxylate carbonyl). The NMR spectrum (in $D_2O$) shows absorptions at 7.40 ppm (broad singlet, aromatic hydrogens), 5.70 ppm (doublet, C-5 hydrogen), 5.50 ppm (doublet, C-6 hydrogen), 5.25 ppm (2 singlets, C-3 hydrogen), 1.50 ppm (2 singlets, C-2 methyl hydrogens) and 0.95 ppm (2 singlets, C-2 methyl hydrogens).

EXAMPLE CXLVI

Following the procedure of Example CXLV, and replacing the phenylmalonic acid used therein by an equimolar amount of the appropriate 2-substituted malonic acid, there is produced 6-(2-carboxy-2-[2-furyl]acetamido)-2,2-dimethyl-3-(5-tetrazolyl)penam, 6-(2-carboxyvaleramido)-2,2-dimethyl-3-(5-tetrazolyl)penam, 6-(2-carboxy-2-[p-chlorophenyl]acetamido-2,2-dimethyl-3-(5-tetrazolyl)penam, 6-(2-carboxy-2-[p-tolyl]acetamido-2,2-dimethyl-3-(5-tetrazolyl)penam, 6-(2-carboxy-2-[1,4-cyclohexadienyl]acetamido-2,2-dimethyl-3-(5-tetrazolyl)penam, 6-(2-carboxy-2-cyclohexylacetamido)-2,2-dimethyl-3-(5-tetrazolyl)penam and 6-(2-carboxy-b 3-phenylpropionamido)-2,2-dimethyl-3-(5-tetrazolyl)penam, respectively.

EXAMPLE CXLVII

6-(2-Carboxy-2-[2-thienyl]acetamido)-2,2-dimethyl-3-(5-tetrazolyl)penam

To a stirred suspension of 370 mg (0.002 mole) of 2-(2-thienyl)malonic acid (Netherlands Pat. No. 6805524) in 4 ml. of water is added 480 mg. (0.002 mole) of 6-amino-2,2-dimethyl-3-(5-tetrazolyl)penam, and then the pH is adjusted to 6.5 using 20% sodium hydroxide. The resulting clear solution is cooled to 0° C. and 384 mg. (0.002 mole) of 1-ethyl-3-(3-dimethylaminopropyl)carbodiimide hydrochloride is added. The solution is stirred for 3.5 hours at 0° C., with the pH maintained between 6 and 7 using 1 N hydrochloric acid. At this point, the pH of the solution is then lowered to 2.0 and the mixture is extracted with ethyl acetate. The extracts are combined, dried and then concentrated to ca. 15 ml. To this solution is added a solution of 665 mg (0.040 mole) of sodium 2-ethylhexanoate in 2.6 ml., and then the solid which precipitates is filtered off, and dried, to give 462 mg. (51% yield) of 6-(2-carboxy)-2-[2-thienyl]acetamido)-2,2-dimethyl-3-(5-tetrazolyl)penam as it disodium salt. The infrared spectrum of the product (KBr disc) shows absorption bands at 1780 $cm^{-1}$ ($\beta$-lactam), 1670 $cm^{-1}$ (amide I), 1615 $cm^{-1}$ (carboxylate) and 1560 $cm^{-1}$ (amide II). The NMR spectrum (in $D_2O$) shows absorptions at 7.50–7.1 ppm (multiplet, thienyl hydrogens), 5.90 ppm (doublet of doublets, C-6 hydrogen), 5.65 ppm (doublet, C-5 hydrogen), 5.40 ppm (doublet, C-3 hydrogen), 1.68 ppm (doublet, C-2 methyl hydrogens) and 1.00 ppm (doublet, C-2 methyl hydrogens).

EXAMPLE CXLVIII 6-(2-Carboxy-2-[3-thienyl]acetamido)-2,2-dimethyl-3-(5-tetrazolyl)penam Reaction of 500 mg. (2.69 mmole) of 2-(3-thienyl)malonic acid (British Pat. No. 1,125,557) with 645 mg. (2.69 mmole) of 6-amino-2,2-dimethyl-3-(5-tetrazolyl)penam, according to the procedure of Example CXLVII, affords 810 mg. (67% yield) of 6-(2-carboxy-2-[3-thienyl]acetamido)-2,2-dimethyl-3-(5-tetrazolyl)penam as its disodium salt. The infrared spectrum of the product KBr disc) shows absorptions at 1775 $cm^{-1}$ (β-lactam), 1670 $cm^{-1}$ (amide I), 1620 $cm^{-1}$ (carboxylate) and 1525 $cm^{-1}$ (amide II). The NMR spectrum ($D_2O$) shows absorptions at 7.80-7.00 ppm (multiplet, thienyl hydrogens), 5.88 ppm (doublet, C-6 hydrogen), 5.65 ppm (doublet of doublets, C-5 hydrogen), 5.40 ppm (doublet, C-3 hydrogen), 1.60 ppm (doublet, C-2 methyl hydrogens) and 1.00 ppm (doublet, C-2 methyl hydrogens).

EXAMPLE CIL 6-(2-Sulfo-2-phenylacetamido)-2,2-dimethyl-3-(5-tetrazolyl)penam

To a stirred of 240 mg. of 6-amino-2,2-dimethyl-3-(5-tetrazolyl)penam in 5 ml. of methylene chloride is added 0.254 ml of triethyl amine. This is stirred for a further 45 minutes, and then it is cooled to about 0° C. To it is then added a solution, in 6 ml. of methylene chloride, of 389 mg. of the mixed carbonic-carboxylic anhydride formed by reacting the bis-triethylamine salt of 2-sulfo-2-phenylacetic acid with one equivalent of ethyl chloroformate (Nicolaus, et al., *Annali di Chimica* [*Rome*], 53, 14 [1963]). The reaction mixture is then stirred at about 0° C. for a further 1.5 hours after the addition of the anhydride solution. At this point, the reaction mixture is filtered and then a solution of 288 mg of sodium 2-ethylhexanoate in ethyl acetate is added. The precipitate which forms is filtered off, giving the crude product as its disodium salt. The crude product is purified by dissolving it in water and adding the solution to a column of 25 g of Sephadex LH-20 (Pharmacia Fine Chemicals, Inc.) made up in water. The column is eluted with water, taking fractions, and the composition of the fractions is assayed by thin-layer chromatography. The fractions containing the pure product are combined and lyophilized, giving 117 mg. of the disodium saalt of 6-(2-sulfo-2-phenylacetamido)-2,2-dimethyl-3-(5-tetrazolyl) penam. The infrared spectrum (KBr disc) of the product shows absorptions at 1765 $cm^{-1}$ (β-lactam carbonyl) and 1660 $cm^{-1}$ (amide I band). The NMR spectrum (in $D_2O$) shows absorptions at 7.60–7.20 ppm (multiplet, aromatic hydrogens), 5.70 and 5.50 ppm (2 multiplets, C-5 and C-6 hydrogens), 5.20 ppm (multiplet, methine hydrogen), 5.00 ppm (singlet, C-3 hydrogen), 1.50 ppm (2 singlets, C-2 hydrogens) and 0.95 ppm (2 singlets, C-2 methyl hydrogens).

EXAMPLE CL 6-(2-[5-Indanyloxycarbonyl]-2-phenylacetamido)-2,2-dimethyl-3-(5-tetrazolyl)penam Reaction of 592 mg. (2.0 mmole) of 5-indanyl 2-phenylmalonate with 480 mg. (2.0 mmole) of 6-amino-2,2-dimethyl-3-(5-tetrazolyl)penam, according to the procedure of Example CXLVII affords 680 mg. (63% yield) of 6-(2-[5-indanyloxycarbonyl]-2-phenylacetamido)-2,2-dimethyl-3-(5-tetrazolyl)penam as its sodium salt. The infrared spectrum (KBr disc) of the product shows absorption bands at 1780 $cm^{-1}$ (β-lactam), 1705 $cm^{-1}$ (ester), 1680 $cm^{-1}$ (amide I) and 1565 $cm^{-1}$ (amide II). The NMR spectrum ($D_2O$) shows absorption bands at 7.80–6.80 ppm (multiplet, aromatic hydrogens), 5.70 ppm (multiplet, C-5 and C-6 hydrogens), 5.25 ppm (doublet, C-3 hydrogen), 2.60–2.00 ppm (multiplet, C-1 and C-3 indanyl hydrogens), 2.00-1.80 ppm (multiplet, C-2 indanyl hydrogens), 1.35 ppm (doublet, C-2 methyl hydrogens) and 0.90 ppm (doublet, C-2 methyl hydrogens).

EXAMPLE CLI 6-(2-Phenoxycarbonyl-2-phenylacetamido)-2,2-dimethyl-3-(5-tetrazolyl)penam A stirred solution of 1.80 g. of phenyl chlorocarbonyl ketene (U.S. Pat. No. 3,679,801) in 20 ml. of chloroform is cooled to −40° C., and then 0.94 g of phenol is added. Stirring is con tinued at −40° C. for a further 20 minutes, and then a solution of 2.40 g. of 6-amino-2,2-dimethyl-3-(5-tetrazolyl)penam and 1.40 ml of triethylamine in 50 ml. of chloroform is added dropwise. The cooling bath is removed, and the mixture is stirred for a further 30 minutes. The mixture is filtered, and the chloroform is evaporated in vacuo to give crude 6-(2-phenoxycarbonyl-2-phenylacetamido)-2,2-dimethyl-3-(5-tetrazolyl)penam, as its triethylamine salt.

EXAMPLE CLII

The procedure of Example CLI is repeated except that the phenyl chlorocarbonyl ketene used therein is replaced by an equimolar amount of p-chlorophenyl chlorocarbonyl ketene, 2-furyl chlorocarbonyl ketene and 3-thienyl chlorocarbonyl ketene, respectively. There is produced:

6-(2-phenoxycarbonyl-2-[p-chlorophenyl]acetamido)-2,2-dimethyl-3-(5-tetrazolyl)penam,
6-(2-phenoxycarbonyl-2-[2-furyl]acetamido)-2,2-dimethyl-3-(5-tetrazolyl)penam, and
6-(2-phenoxycarbonyl-2-[3-thienyl]acetamido)-2,2-dimethyl-3-(5-tetrazolyl)penam,
respectively.

When the procedure of Example CLI is repeated, and the phenol used therein is replaced by an equimolar amount of the appropriate substituted phenol, the products are:

6-(2-[m-methoxyphenoxycarbonyl]-2-phenylacetamido)-2,2-dimethyl-3-(5-tetrazolyl)penam,
6-(2-[-methylphenoxycarbonyl]-2-phenylacetamido)-2,2-dimethyl-3-(5-tetrazolyl)penam,
6-(2-[5-indanyloxycarbonyl]-2-phenylacetamido)-2,2-dimethyl-3-(5-tetrazolyl)penam,
6-(2-[p-nitrophenoxycarbonyl]-2-phenylacetamido)-2,2-dimethyl-3-(5-tetrazolyl)penam,
6-(2-[m-bromophenoxycarbonyl]-2-phenylacetamido)-2,2-dimethyl-3-(5-tetrazolyl)penam,
6-(2-[o-fluorophenoxycarbonyl]-2-phenylacetamido)-2,2-dimethyl-3-(5-tetrazolyl)penam
6-(2-[p-cyanophenoxycarbonyl]-2-phenylacetamido)-2,2-dimethyl-3-(5-tetrazolyl)penam, and
6-(2-[3,4-dichlorophenoxycarbonyl]-2-phenylacetamido)-2,2-dimethyl-3-(5-tetrazolyl)penam.

EXAMPLE CLIII 6-(2-carbamoyl-2-phenylacetamido)-2,2-dimethyl-3-(5-tetrazolyl)penam To a stirred solution of 523 mg. (0.001 mole) of 6-(2-[p-nitrophenoxycarbonyl]-2-phenylacetamido)-2,2-dimethyl-3-(5-tetrazolyl)penam and 101 mg of triethylamine in 50 ml. of chloroform is added 1 ml of a 1 M solution of ammonia in methanol, at −30° C. Stirring is continued for 4 hours without external cooling and then evaporation in vacuo leaves the crude product as its triethylamine salt.

EXAMPLE CLIV 6-(D-2-sulfoamino-2-phenylacetamido)-2,2-dimethyl-3-(5-tetrazolyl)penam To a stirred suspension of 2.13 g. (0.005) mole of 6-(D-2-amino-2-phenylacetamido)-2,2-dimethyl-3-(5-tetrazolyl)penam in 50 ml. of methylene chloride is added 0.84 ml. (0.006 mole) of triethylamine. The mixture is stirred until most of the solid dissolves. To this solution is then added approximately 2 g. of pulverized Linde 4 A molecular sieves, and stirring is continued for an additional one hour. The molecular sieves are removed by filtration, and the filtrate is cooled to 0° C. To this cooled solution is added, portionwise, over 5 minutes, 0.84 g. (0.006 mole) of trimethylaminesulfur trioxide complex. The solution is stirred at 0° C. for 5 minutes, and then at ambient temperature for 2.5 hours. A solution of 2.5 g. of sodium 2-ethylhexanoate in 10 ml. of 1-butanol is then added. The resulting precipitate is filtered, dissolved in 20 ml. of water and cooled to 0° C. The pH of the reaction is adjusted to 5.0 (glacial acetic acid) and the resulting cloudy solution is stirred for 1 hour. After filtration through diatomaceous earth, the filtrate is added dropwise with stirring to 700 ml. of cold (0° C.) acetone. The resulting precipitate is collected, and dried, to yield 1.80 g. (65.3% yield) of 6-(D-2-sulfoamino-2-phenylacetamido)-2,2-dimethyl-3-(5-tetrazolyl)penam as its disodium salt. The infrared spectrum (KBr disc) shows absorptions at 1770 $cm^{-1}$ (β-lactam), 1660 $cm^{-1}$ (amide I) and 1550 $cm^{-1}$ (amide II). The NMR spectrum ($D_2O$) shows absorptions at 7.46 ppm (S, 5H aromatic hydrogens), 5.64 ppm (q, 2H, C-5 and C-6 hydrogens), 5.33 ppm) S, 1H, methine hydrogen), 5.10 ppm (S, 1H, C-3 hydrogen), 1.58 ppm (S, 3H, C-2 methyl hydrogens) and 1.00 ppm (S, 3H, C-2 methyl hydrogens). $[\alpha]_D^{25} = 108°$ ($H_2O$).

Analysis—Calcd. for $C_{16}H_{17}N_7O_5S_2Na_2$ (percent): C, 34.85; H, 4.20; N, 17.78; S, 11.63. Found: (Percent): C, 35.02; H, 4.31; N, 17.82; S, 11.91.

EXAMPLE CLV

Reaction of the appropriate 6-(2-amino-2-substituted-acetamido)-2,2-dimethyl-3-(5-tetrazolyl)penam with the sulfur trioxide-trimethylamine complex, according to the procedure of Example CLIV provides the following compounds:

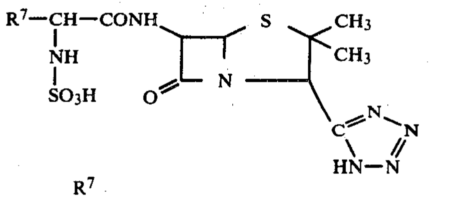

| $R^7$ |
|---|
| methyl |
| isopropyl |
| cyclopentyl |
| 3-cyclohexenyl |
| 1,4-cyclohexadienyl |
| benzyl |
| p-chlorobenzyl |
| p-hydroxyphenyl |
| m-methoxyphenyl |
| m-bromophenyl |
| o-fluorophenyl |
| p-tolyl |
| 3-chloro-4-hydroxyphenyl |
| 3,4-dichlorophenyl |
| 3,4-dimethoxyphenyl |
| 2-thienyl |
| 3-thienyl |
| 2-furyl |
| 3-pyridyl |

EXAMPLE CLVI 6-(D-2-[Carboxymethoxy]acetamido-2-phenylacetamido)-2,2-dimethyl-3-(5-tetrazolyl)penam To a stirred solution of 2.59 g. (6.0 mmole) of 6-(D-2-amino-2-phenylacetamido)-2,2-dimethyl-3-(5-tetrazolyl)penam trihydrate and 1.70 ml. (12.2 mmole) of triethylamine in 70 ml. of methylene chloride, at 0°–5° C., is added a solution of 1.40 g. (12.0 mmole) of diglycolic anhydride in 30 ml. of methylene chloride. The solution is stirred at 0°–5° C. for 1 hour and then it is extracted with 200 ml. of 10% sodium bicarbonate solution. The pH of the aqueous phase is adjusted to 2.0 and the product is extracted into ethyl acetate. The solvent is dried ($MgSO_4$), and then concentrated in vacuo, to give 820 mg. (28% yield) of the title compound. IR (KBr disc): 1780 $cm^{-1}$ (β-lactam) and 1650 $cm^{-1}$ (amide I). NMR (in DMSO-$d_6$): 7.41 ppm (m, 5H), 5.55–5.90 ppm (m, 3H), 5.24 ppm (S, 1H), 4.17 ppm (S, 2H), 4.10 ppm (s, 2H), 1.57 ppm (s, 3H), 0.99 (s, 3H).

EXAMPLE CLVII 6-(D-2-[4-Carboxy-2,3-propionamido]-2-phenylacetamido)-2,2-dimethyl-3-(5-tetrazol-5-yl)penam The title compound is prepared in 73% yield from 6-(D-2-amino-2-phenylacetamido)-2,2-dimethyl-3-(5-tetrazolyl)penam and epoxysuccinic anhydride, using the method of Example CLVI. IR. (KBr disc): 1790 $cm^{-1}$ (β-lactam) and 1665 $cm^{-1}$ (amide I). NMR (in DMSO-$d_6$): 7.42 ppm (m, 5H), 5.55–5.85 ppm (m, 3H), 5.27 ppm (s, 1H), 3.87 ppm (s, 2H), 1.60 ppm (s, 3H), 1.02 ppm (s, 3H).

EXAMPLE CLVIII 6-(2-[2-(Carboxymethyl)phenyl]acetamido)-2,2-dimethyl-3-(5-tetrazolyl)penam An ice-bath cooled, stirred mixture of 1.94 g (10 mmol) of o-phenylenediacetic acid, and 60 ml. of water is adjusted to pH 5.5 by the careful addition of 6 N sodium hydroxide. The resulting solution is treated with 1.92 g (10 mmol) of 1-(3-dimethylaminopropyl)-3-ethylcarbodiimide hydrochloride and stirring is continued for 30 minutes, with the pH being maintained at 5.5 by the addition of 6.0 N hydrochloric acid. A solution consisting of 2.4 g. (10 mmol) of 6-amino-2,2-dimethyl-3-(5-tetrazolyl)penam and 30 ml. of water (adjusted to pH 7) is added to the first mentioned solution and stirring and cooling is continued for an hour. The aqueous solution is washed three times with 30 ml. portions of ethyl acetate, and is then adjusted to pH 2.5 with 6 N hydrochloric acid. This solution is extracted twice with 40 ml. portions of ethyl acetate, and the combined extracts are washed with 50 ml. of water. After being dried over anhydrous sodium sulfate, the extract is evaporated under reduced pressure to furnish a colorless foam: yield 3 g. The foam is dissolved in 50 ml. of ethyl acetate and then it is treated with 2.4 g. (14.5 mmol) of sodium 2-ethylhexanoate in 30 ml. of ethyl acetate. The title compound precipitates as the sodium salt: yield 3.4 g (74%) IR (KBr) 1770, 1667, and 1587 $cm^{-1}$ NMR ($D_2O$): 7.25 ppm (s, 4H), 5.70 (d, 1H), 5.40 (d, 1H), 5.25 (s, 1H), 3.70 (s, 2H), 3.60 (s, 2H), 1.50 (s, 3H), 1.00 (s, 3H).

EXAMPLE CLIX 6-(2-Acetyl-2-phenylacetamido)-2,2-dimethyl-3-(5-tetrazolyl)penam To a solution of 700 mg (3.92 mmoles) of 1-carboxy-1-phenyl-2-propanone in 35 ml. of dry tetrahydrofuran is added 453 mg (3.92 mmoles) of N-hydroxysuccinimide (dissolved in a small portion of dry tetrahydrofuran), followed by 811 mg. (3.92 mmoles) of dicyclohexylcarbodiimide dissolved in a small portion of dry tetrahydrofuran. The reaction mixture is allowed to stir at room temperature for approximately three hours. The reaction mixture is then filtered and the yellow filtrate is added dropwise, with stirring, to a cooled (0° C.) solution of 720 mg. (3 mmoles) of 6-amino-2,2-dimethyl-3-(5-tetrazolyl)penam and 606 mg. of triethylamine in 15 ml. of methylene chloride. The resulting solution is stirred for 45 minutes, and then the solvent is removed by evaporation in vacuo. To the residue is added 50 ml. of water and 50 ml. of ethyl acetate, and the pH is adjusted to 7.8 using sodium bicarbonate solution. The ethyl acetate layer is removed and discarded. To the aqueous phase is added a further quantity of ethyl acetate and the pH is adjusted to 2.5.

The ethyl acetate is removed, washed with water, washed with sodium chloride solution, and then dried using anhydrous sodium sulfate. To the dried solution is added 0.42 ml. (3 mmole) of triethylamine, and then the solvent is removed giving the title compound as its triethylamine salt. The yield is 540 mg. (36%). IR ($CHCl_3$ solution): 1780 $cm^{-1}$. NMR ($CDCl_3$): 7.6-7.2 ppm (m, 5H), 6.0-5.6 (m, 4H), 5.4 ppm (s, 1H), 3.4-3.1 ppm (q, 6H), 2.2 ppm (s, 3H), 1.8 ppm (s, 3H), 1.6-1.3 (m, 9H) and 1.0 ppm (s, 3H).

EXAMPLE CLX 6-(D-2-[2-carboxy-3-(2-thienyl)acrylamido]-2-phenylacetamido)-2,2-dimethyl-3-(5-tetrazolyl)penam To 20 ml. of water at ca. 0° C., is added 0.99 g. (5 mmole) of (2-thienyl)methylenemalonic acid followed by 1.86 g. (5 mmole) of 6-(D-2-amino-2-phenylacetamido)-2,2-dimethyl-3-(5-tetrazolyl)penam, and the pH raised to 7.7. When a clear solution is obtained, the pH is lowered to 6.0, and 0.96 g. (5 mmole) of 1-ethyl-3-(3-dimethylaminopropyl)carbodiimide is added. The mixture is stirred at ca. 0° C. for 3 hours, with the pH being maintained at 6.0 by the addition of 6 N hydrochloric acid. At this point, the pH is again raised to 7.7, and the reaction mixture is extracted with ethyl acetate. The extracts are discarded, and the residual aqueous phase is acidified to pH 2.6. The product is extracted into ethyl acetate, and then the extract is treated with 1.4 ml. (10 mmole) of triethylamine. The solvent is removed by evaporation in vacuo, which affords 1.8 g. (55% yield) of the title compound as its triethylamine salt. IR ($CHCl_3$ solution): 1780, 1660 and 1600 $cm^{-1}$. NMR (in $CDCl_3$): 11.6-10.9 ppm (s,1H), 8.5 ppm (s,1H), 7.8-6.9 ppm (m,9H), 5.9-5.3 ppm (m,4H), 1.6 ppm (s,3H), 1.0 ppm (s,3H).

In like manner, starting with (p-chlorophenyl)methylenemalonic acid, there is prepared, in 71% yield, 6-(D-2-[2-carboxy-2-(p-chlorophenyl)acrylamido]-2-phenylacetamido)-2,2-dimethyl-3-(5-tetrazolyl)penam triethylamine salt. IR (KBr disc): 1780, 1670 and 1600 $cm^{-1}$. NMR (in $CDCl_3$): 10.5-9.0 ppm (m,1H), 8.1-7.1 ppm (m,10H), 5.9-5.3 ppm (m,4H), 1.6 ppm (s,3H), 1.1 ppm (s,3H).

EXAMPLE CLXI 6-(2,2-Dimethyl-5-oxo-4-phenyl-1-imidazolidinyl)-2,2-dimethyl-3-(5-tetrazolyl)penam A mixture of 1.0 g (2.34 mmole) of 6-(D-2-amino-2-phenylacetamido)-2,2-dimethyl-3-(5-tetrazolyl)penam, 0.654 ml (4.86 mmole) of triethylamine and 100 ml of anhydrous acetone is stirred at ca. 25° C. for 24 hours. At this point, the solvent is removed by evaporation in vacuo, leaving 1.10 g of 6-(2,2-dimethyl-5-oxo-4-phenyl-1-imidazolidinyl)-2,2-dimethyl-3-(5-tetrazolyl)penam, as its triethylamine salt. The infrared spectrum (KBr disc) shows absorptions at 1786 $cm^{-1}$ ($\beta$-lactam) and 1709 $cm^{-1}$. The NMR spectrum (DMSO-$d_6$/$D_2O$) shows absorptions at 7.76-7.15 ppm (multiplet, 5H, aromatic hydrogens), 5.22 ppm (singlet, 1H, imidazolidine methine hydrogen) 5.78 and 5.10 ppm (two doublets, 2H, J=4 Hz, C-5 and C-6 hydrogens), 4.69 ppm (singlet, 3H, C-3 hydrogen), 3.10 ppm (quarter, 6H, J=8 Hz, N—$C\underline{H}_2$—$CH_3$), 1.62 ppm (singlet, 3H, imidazolidine methyl hydrogens), 1.50 ppm (singlet, 3H, C-2 methyl hydrogens), 1.40 ppm (singlet, 3H, imidazolidine methyl hydrogens), 1.21 ppm (triplet, 9H, J=8 Hz, N—$CH_2$—$C\underline{H}_3$) and 0.98 ppm (singlet, 3H, C-2 methyl hydrogens).

EXAMPLE CLXII 6-(2,2-Dimethyl-5-oxo-4-[p-hydroxyphenyl]-1-imidazolidinyl)-2,2-dimethyl-3-(5-tetrazolyl)penam Reaction of 6-(D-2-amino-2-[p-hydroxyphenyl]-2-phenylacetamido)-2,2-dimethyl-3-(5-tetrazolyl)penam, with acetone and triethylamine, according to the procedure of Example CLXI affords 6-(2,2-dimethyl-5-oxo-4-[p-hydroxyphenyl]-1-imidazolidinyl)-2,2-dimethyl-3-(5-tetrazolyl)penam as its triethylamine salt. The infrared spectrum (KBr disc) shows absorption bands at 1786 $cm^{-1}$ ($\beta$-lactam) and 1686 $cm^{-1}$. The NMR spectrum (DMSO-$d_6$/$D_2O$) shows absorptions at 6.82 and 7.35 ppm (quartet, 4H, aromatic hydrogens), 5.16 ppm (singlet, 1H, imidazolidine methine hydrogen), 5.71 and 5.07 ppm (two doublets, 2H, J=4 Hz, C-5 and C-6 hydrogens), 4.52 ppm (singlet, 3H, C-3 hydrogen), 3.07 ppm (quartet, 6H, J=8 Hz, N—$C\underline{H}_2$—$CH_3$), 1.60 ppm (singlet, 3H, imidazolidine methyl hydrogens), 1.43 ppm (singlet, 3H, C-2 methyl hydrogen), 1.36 ppm (singlet, 3H, imidazolidine methyl hydrogens), 1.16 ppm (triplet, 9H, J=8 Hz, N—$CH_2$—$C\underline{H}_3$) and 0.97 ppm (singlet, 3H, C-2 methyl hydrogens).

EXAMPLE CLXIII

Following the procedure of Example CLXI, and reacting the appropriate 6-(2-amino-2-substituted-acetamido)-2,2-dimethyl-3-(5-tetrazolyl)penam with the requisite aldehyde or ketone, the following compounds are prepared:

6-(2,2-dimethyl-5-oxo-4-[p-fluorophenyl]-1-imidazolidinyl)-2,2-dimethyl-3-(5-tetrazolyl)penam,
6-(2,2-dimethyl-5-oxo-4-[o-chlorophenyl]-1-imidazolidinyl)-2,2-dimethyl-3-(5-tetrazolyl)penam,
6-(2,2-dimethyl-5-oxo-4-[m-bromophenyl]-1-imidazolidinyl)-2,2-dimethyl-3-(5-tetrazolyl)penam,
6-(2,2-diethyl-5-oxo-4-[m-hydroxyphenyl]-1-imidazolidinyl)-2,2-dimethyl-3-(5-tetrazolyl)penam,
6-(2-ethyl-5-oxo-4-[p-hydroxyphenyl]-1-imidazolidinyl)-2,2-dimethyl-3-(5-tetrazolyl)penam,
6-(2,2-dimethyl-5-oxo-4-[m-tolyl]-1-imidazolidinyl)-2,2-dimethyl-3-(5-tetrazolyl)penam,
6-(2,2-dimethyl-5-oxo-4-[p-amyloxyphenyl]-1-imidazolidinyl)-2,2-dimethyl-3-(5-tetrazolyl)penam,
6-(2,2-dimethyl-5-oxo-4-[m-butoxyphenyl]-1-imidazolidinyl)-2,2-dimethyl-3-(5-tetrazolyl)penam,
6-(2,2-dimethyl-5-oxo-4-[p-methoxyphenyl]-1-imidazolidinyl)-2,2-dimethyl-3-(5-tetrazolyl)penam,
6-(2-ethyl-2-methyl-5-oxo-4-[p-n-hexyloxyphenyl]-1-imidazolidinyl)-2,2-dimethyl-3-(5-tetrazolyl)penam,
6-(2,2-dimethyl-5-oxo-4-[p-isopropylphenyl]-1-imidazolidinyl)-2,2-dimethyl-3-(5-tetrazolyl)penam,
6-(2,2-dimethyl-5-oxo-4-[p-methylthiophenyl]-1-imidazolidinyl)-2,2-dimethyl-3-(5-tetrazolyl)penam,
6-(2,2-dimethyl-5-oxo-4-cyclopropyl-1-imidazolidinyl)-2,2-dimethyl-3-(5-tetrazolyl)penam,
6-(2,2-dimethyl-5-oxo-4-cyclopentyl-1-imidazolidinyl)-2,2-dimethyl-3-(5-tetrazolyl)penam,
6-(2,2-dimethyl-5-oxo-4-cyclohexyl-1-imidazolidinyl)-2,2-dimethyl-3-(5-tetrazolyl)penam,
6-(2,2-dimethyl-5-oxo-4-cycloheptyl-1-imidazolidinyl)-2,2-dimethyl-3-(5-tetrazolyl)penam,
6-(2,2-dimethyl-5-oxo-4-[2-thienyl]-1-imidazolidinyl)-2,2-dimethyl-3-(5-tetrazolyl)penam,
6-(2,2-dimethyl-5-oxo-4-[3-thienyl]-1-imidazolidinyl)-2,2-dimethyl-3-(5-tetrazolyl)penam,
6-(2,2-dimethyl-5-oxo-4-[2-furyl]-1-imidazolidinyl)-2,2-dimethyl-3-(5-tetrazolyl)penam,
6-(2,2-dimethyl-5-oxo-4-[3-furyl]-1-imidazolidinyl)-2,2-dimethyl-3-(5-tetrazolyl)penam,
6-(2,2-dimethyl-5-oxo-4-[3-pyridyl]-1-imidazolidinyl)-2,2-dimethyl-3-(5-tetrazolyl)penam, and
6-(2,2-dimethyl-5-oxo-4-[5-ethyl-2-thienyl]-1-imidazolidinyl)-2,2-dimethyl-3-(5-tetrazolyl)penam,
6-(2,2-dimethyl-5-oxo-4-[4-isothiazolyl]-1-imidazolidinyl)-2,2-dimethyl-3-(5-tetrazolyl)penam,
6-(2,2-dimethyl-5-oxo-4-[3-isothiazolyl]-1-imidazolidinyl)-2,2-dimethyl-3-(5-tetrazolyl)penam,
6-(2,2-dimethyl-5-oxo-4-[3-chloro-4-hydroxyphenyl]-1-imidazolidinyl)-2,2-dimethyl-3-(5-tetrazolyl(penam,
6-(2,2-dimethyl-5-oxo-4-[3,4-dimethoxyphenyl]-1-imidazolidinyl)-2,2-dimethyl-3-(5-tetrazolyl)penam,.
6-(2,2-dimethyl-5-oxo-4-[3-methyl-4-methoxyphenyl]-1-imidazolidinyl)-2,2-dimethyl-3-(5-tetrazolyl)penam.

EXAMPLE CLXIV

6-(5-Oxo-4-phenyl-1-imidazolidinyl)-2,2-dimethyl-3-(5-tetrazolyl)penam

To a stirred suspension of 1.0 g. (2.26 mole) of 6-(D-2-amino-2-phenylacetamido)-2,2-dimethyl-3-(5-tetrazolyl)penam trihydrate in 15 ml. of water is added 151 μl. (2.53 mmole) of 2-aminoethanol followed by 342 μl. (4.6 mmole) of 37% aqueous formaldehyde. The suspension is stirred for 7 hours, and then it is lyophilized to give 0.96 g. (92% yield) of the title compound, as its ethanolamine salt. IR (KBr disc): 1773 $cm^{-1}$ (β-lactam) and 1681 $cm^{-1}$ (amide I). NMR (in DMSO-$d_6$): 8.75 ppm (multiplet, 2H), 7.30 ppm (singlet, 5H), 6.00–5.60 ppm and 4.90–4.40 ppm (multiplets, 4H), 4.00–3.20 ppm (multiplet, 4H), 1.70 ppm and 1.06 ppm (2 singlets, 6H).

EXAMPLE CLXV

6-(5-Oxo-4-[p-hydroxyphenyl]-1-imidazolidinyl)-2,2-dimethyl-3-(5-tetrazolyl)penam The procedure of Example CLXIV is repeated, except that the 6-(D-2-amino-2-phenylacetamido)-2,2-dimethyl-3-(5-tetrazolyl)penam trihydrate used therein is replaced by an equivalent amount of 6-(D-2-amino-2-[p-hydroxyphenyl]acetamido)-2,2-dimethyl-3-(5-tetrazolyl)penam trihydrate. This affords 0.96 g. (92% yield) of the title compound as its ethanolamine salt. IR (KBr disc): 1776 $cm^{-1}$ (β-lactam) and 1675 $cm^{-1}$ (amide I). NMR (in DMSO-$d_6$): 8.52 ppm (multiplet, 2H), 7.14 ppm (multiplet, 4H), 5.90–5.00 ppm and 4.80–4.40 ppm (multiplets, 4H), 3.80–3.00 ppm (multiplet, 4H), 1.67 ppm and 1.06 ppm (2 singlets, 6H).

EXAMPLE CLXVI

Following the procedure of Example CLXIV, and reacting the appropriate 6-(2-amino-2-substituted-acetamido)-2,2-dimethyl-3-(5-tetrazolyl)penam with the requisite aldehyde, the following compounds are prepared:

6-(5-oxo-4-[p-chlorophenyl]-1-imidazolidinyl)-2,2-dimethyl-3-(5-tetrazolyl)penam,
6-(2-methyl-5-oxo-4-[3-chloro-4-hydroxyphenyl]-1-imidazolidinyl)-2,2-dimethyl-3-(5-tetrazolyl)penam,
6-(5-oxo-4-[p-n-hexylphenyl]-1-imidazolidinyl)-2,2-dimethyl-3-(5-tetrazolyl)penam,
6-(2-methyl-5-oxo-[m-n-propylthiophenyl]-1-imidazolidinyl)-2,2-dimethyl-3-(5-tetrazolyl)penam and
6-(2-ethyl-5-oxo[p-n-hexylthiophenyl]-1-imidazolidinyl)-2,2-dimethyl-3-(5-tetrazolyl)penam,
6-(5-oxo-4-[2-thienyl]-1-imidazolidinyl)-2,2-dimethyl-3-(5-tetrazolyl)penam and
6-(5-oxo-4-[3-thienyl]-1-imidazolidinyl)-2,2-dimethyl-3-(5-tetrazolyl)penam,
respectively

EXAMPLE CLXVII

6-([Hexahydro-1-azepinyl]methyleneamino)-2,2-dimethyl-3-(5-tetrazolyl)penam

To a stirred solution of 1.2 g (5 mmoles) of 6-amino-2,2-dimethyl-3-(5-tetrazolyl)penam, 1.0 g (10 mmole) of triethylamine and 30 ml of dichloromethane, cooled to 0° C., is added 0.54 g (5 mmole) of chlorotrimethylsilane. After 15 minutes, 0.86 (5 mmole) of 1-(dimethoxymethyl)hexahydroazepine (British Pat. No. 1,293,590) is added, and stirring is continued for a further 1 hour.

The volatile components are removed by evaporation in vacuo, and then the residue is extracted with 25 ml of acetone. The insoluble material is filtered off, and the acetone is evaporated in vacuo to a yellow foam, which changes to a white powder on trituration with ether. This affords 1.44 g (82% yield) of 6-([hexahydro-1-azepinyl]methyleneamino)-2,2-dimethyl-3-(5-tetrazolyl)penam. The infrared spectrum of the product (KBr disc) shows absorption bands at 1795 $cm^{-1}$ (β-lactam), 1706 $cm^{-1}$ and 1645 $cm^{-1}$. The NMR spectrum ($CDCl_3$) shows absorption bands at 8.00 ppm (singlet, 1H, N—C$\underline{H}$=N), 5.90 and 5.60 ppm (two doublets, 2 H, J=4 Hz, C-5 and C-6 hydrogens), 5.40 ppm (singlet, 1H, C-3 hydrogen), 3.90–3.50 (multiplet, 4H, $CH_2$—N—C$\underline{H}_2$), 2.00–1.50 ppm (multiplet, 11H, C-2 methyl hydrogens and [C$\underline{H}_2$]$_4$) and 1.20 ppm (singlet, 3H, C-2 methyl hydrogens). Examination of the product by thin-layer chromatography (0.2 M NaOAc: acetone; 1:6) showed a single spot ($R_f$0.23).

EXAMPLE CLXVIII

6-([Dimethylamino]methyleneamino)-2,2-dimethyl-3-(5-tetrazolyl)penam

Reaction of N,N-dimethylformamide dimethyl acetal with 6-amino-2,2-dimethyl-3-(5-tetrazolyl)penam, according to the procedure of Example CLXVII on a 5 mmole scale produces 1.47 g (89% yield) of product. The product is a 3:1 complex of 6-([dimethylamino]methyleneamino)-2,2-dimethyl-3-(5-tetrazolyl)penam with triethylamine. The infrared spectrum of the product (KBr disc) shows absorption bands at 1780 $cm^{-1}$ (β-lactam), 1710 $cm^{-1}$ and 1640 $cm^{-1}$. The NMR spectrum shows absorptions at 8.00 ppm (singlet, 1H, N—C$\underline{H}$=N), 5.80 and 5.50 ppm (two doublets, 2H, J=4 Hz, C-5 and C-6 hydrogens), 5.30 ppm (singlet, 1H, C-3 hydrogen), 3.40–3.00 ppm (multiplet, 8H, N(C$\underline{H}_3$)$_2$ and N—C$\underline{H}_2$—$CH_3$), 1.70 ppm (singlet, 3H, C-2 methyl hydrogens, 1.30 ppm (triplet 3H, N—$CH_2$—C$\underline{H}_3$), 1.70 ppm (singlet, 3H, C-2 methyl hydrogens). When examined by thin-layer chromatography (0.2 M NaOAc: acetone; 1:6), showed a single spot ($R_f$0.26).

EXAMPLE CLXIX

6-(D-2-[Dimethylaminomethyleneamino]-2-phenylacetamido)-2,2-dimethyl-3-(5-tetrazolyl)penam To a stirred solution of 3.73 g. (10 mmole) of 6-(D-2-amino-2-phenylacetamido)-2,2-dimethyl-3-(5-tetrazolyl)penam and 2.02 g. (20 mmole) of triethylamine in 50 ml. of methylene chloride, at 0° C., is added 1.08 g. (10 mmole) of trimethylsilyl chloride. Stirring is continued for 20 minutes at 0° C., and then 1.2 g. (10 mmole) of N,N-dimethylformamide dimethyl acetal acetal is added. Stirring is continued for a further 2 hours, and then 2 ml. of methanol is added. The solvents are removed by evaporation in vacuo, and acetone is added to the residue. After filtration, the filtrate is evaporated to dryness. This latter residue is dissolved in 25 ml. of methylene chloride containing 1.4 ml. of triethylamine, and then the solution is added dropwise with stirring to 400 ml. of ether. The solid which precipitates is filtered off, giving 4.83 g. (90% yield) of the title compound as its triethylamine salt. IR (KBr disc): 1786, 1710 and 1652 $cm^{-1}$. NMR (in $D_2O$): 7.8 ppm (s, 1H), 7.6 ppm (s, 5H), 6.0 ppm (d, 2H), 5.8 ppm (d, 2H), 5.5 ppm (s, 1H), 5.4 ppm (s, 1H), 3.3 ppm (q, 6H), 3.2 ppm (s, 6H), 1.8 ppm (s, 3H), 1.4 ppm (t, 9H), and 1.2 ppm (s, 3H).

EXAMPLE CLXX

6-(D-2-[2-(Hexahydro-1-azepinyl]methyleneamino)acetamido]acetamido)-2-dimethyl-3-(5-tetrazolyl)penam A procedure analogous to that of Example CLXIX is used to obtain the title compound from the reaction 1.07 g. (2.5 mmol) of 6-D-[2-(2-aminoacetamido)-2-phenylacetamido]-2,2-dimethyl-3-(5-tetrazolyl)penam and 0.43 g. (2.5 mmol) of 1-(dimethoxymethyl)hexahydroazepine. The product is isolated as its triethylamine salt: yield 0.68 g (43%); IR (KBr) 1780 and 1695 $cm^{-1}$; NMR ($D_2O$) 8.05 ppm (s, 1H), 7.75 (s, 5H), 6.0–5.6 (m, 2H), 5.50 (s, 1H), 4.50 (s, 2H), 4.20 (s, 1H), 4.05–3.65 (m, 4H), 3.4 (q, 6H), 2.35–1.75 (m, 8H), 1.70 (m, 8H), 1.70 (s, 3H), 1.55 (t, 9H), 1.10 (s, 3H).

EXAMPLE CLXXI

6-(D-2-[Dimethylaminomethyleneamino]-2-[p-hydroxyphenyl]acetamido)-2,2-dimethyl-3-(5-tetrazolyl)penam To a stirred solution of 1.95 g. (5 mmole) of 6-(D-2-amino-2-[p-hydroxyphenyl]acetamido)-2,2-dimethyl-3-(5-tetrazolyl)penam and 0.5 g. (5 mmole) of triethylamine in 12 ml. of methylene chloride, at 0° C., is added 0.6 g. of N,N-dimethylformamide dimethyl acetal. Stirring is continued for 1 hour at 0° C., and then the reaction mixture is poured into 100 ml. of ether. This causes a gummy solid to precipitate. The solvent is decanted from the solid, and then the solid is dissolved in 50 ml. of methylene chloride and 2 ml. of triethylamine. The solution is treated with activated charcoal, filtered, and then added dropwise to 100 ml. of ether. The solid which precipitates is redissolved in methylene chloride containing triethylamine, again treated with activated charcoal, and again added dropwise with stirring to ether. The solid which precipitates is filtered off, giving 450 mg. (17% yield) of the title compound as its triethylamine salt. IR (KBr disc): 1786, 1715 and 1652 $cm^{-1}$. NMR (in $D_2O$-$NaHCO_3$): 7.7 ppm (s, 1H), 7:3 ppm (d, 2H), 6.9 ppm (d, 2H), 5.8 ppm (d, 1H), 5.5 ppm (d, 1H), 5.3 ppm (2s, 2H), 3.2 ppm (q, 6H), 3.1 ppm (s, 6H), 1.3 ppm (t, 9H), 1.0 ppm (s, 3H).

In like manner, starting with 6-(D-2-[2-aminoacetamido]-2-phenylacetamido)-2,2-dimethyl-3-(5-tetrazolyl)penam, there is prepared a 29% yield of a 2:1 complex of 6-(D-2-[2-(dimethylaminomethyleneamino)acetamido]-2-phenylacetamido)-2,2-dimethyl-3-(5-tetrazolyl)penam-triethylamine. IR (KBr disc): 1780, 1715 and 1667 $cm^{-1}$. NMR (in $D_2O$): 7.9 ppm (s, 1H), 7.5 ppm (s, 5H), 5.6 ppm (s, 1H), 5.7 ppm (d, 1H), 5.5 ppm (d, 1H), 5.3 ppm (s, 1H), 4.3 ppm (s, 2H), 3.3 ppm (s, 3H), 3.2 ppm (s, 3H), 3.2 (q, 3H), 1.5 ppm (s, 3H), 1.3 ppm (t, 4.5H) and 1.0 ppm (s, 3H).

EXAMPLE CLXXII

6-(2-Phenylacetamido)-2,2-dimethyl-3-(1-[pivaloyloxymethyl]tetrazol-5-yl)penam and 6-(2-Phenylacetamido)-2,2-dimethyl-3-(2-[pivaloyloxymethyl]tetrazol-5-yl)penam To a stirred suspension of 10.0 g. (0.0264 mole) of 6-(2 sodium salt, in 105 ml. of acetone, is added 2.6 ml. of 25% aqueous sodium iodide, followed by 4.35 g. (0.0290 mole) of chloromethyl pivalate. The mixture is refluxed for 4.5 hours, and then it is cooled to ambient temperature. To the mixture is then added 100 ml. of water, and the resulting suspension is extracted with ethyl acetate. The extracts are dried and evaporated to give 6.3 g. of white foam. The MIC of this mixture of the title compounds against *Strep. pyogenes* in 0.2 μg/ml.

The white foam is re-dissolved in a small volume of 80:20 chloroform-ethyl acetate and absorbed on a column of 180 g. of chromatographic grade silica gel. The column is then eluted with 80:20 chloroform-ethyl acetate taking fractions. Each fraction consists of 700 drops of solvent. Fractions 55–95 are combined and evaporated in vacuo to give 2.03 g. of 6-(2-phenylacetamido)-2,2-dimethyl-3-(2-[pivaloyloxymethyl]tetrazol-5-yl)penam. IR (KBr disc) 1785, 1760, 1670 and 1515 $cm^{-1}$. NMR (DMSO-$d_6$/$D_2O$): 7.50 (s, 5H), 6.70 (s, 2H) 6.00-5.60 (m, 2H), 3.85 (s, 2H), 1.65 (s, 3H), 1.36 (s, 9H) and 1.20 (s, 3H) ppm. Fractions 100–164 are combined and evaporated in vacuo to give 0.80 g. of 6-(2-phenylacetamido)-2,2-dimethyl-3-(1-[pivaloyloxymethyl]tetrazol-5-yl)penam. IR (KBr disc): 1780, 1760, 1670 and 1515 $cm^{-1}$. NMR (DMSO-$d_6$($D_2O$): 7.50 (s, 5H) 6.80 (s, 2H), 6.50 (s, 2H), 5.60 (s, 1H), 3.85 (s, 2H), 1.75 (s, 3H), 1.36 (s, 9H) and 1.34 (s, 3H) ppm.

Reaction of 6-(2-phenylacetamido)-2,2-dimethyl-3-(5-tetrazolyl)penam sodium salt with 1-acetoxyethyl chloride, according to the above procedure, produces 6-(2-phenylacetamido)-2,2-dimethyl-3-(1[2]-[1-acetoxyethyl]tetrazol-5-yl)penam as a mixture of isomers, m.p. 55°–70° C., yield 28%. IR (KBr disc): 1780, 1770, 1670 and 1515 $cm^{-1}$. NMR ($CDCl_3$): 7.20 (s, 6H), 6.25 (m, 1H), 5.75–5.40 (m, 2H), 5.20 (s, 1H), 3.60 (s, 2H), 2.00 (m, 6H), 1.45 (s, 3H) and 0.95 (s, 3H) ppm.

In like manner, reaction of 6-(2-phenylacetamido)-2,2-dimethyl-3-(5-tetrazolyl)penam sodium salt with 3-bromophthalide, according to the above procedure, produces 6-(2-phenylacetamido)-2,2-dimethyl-3-(1[2]-[3-phthalidyl]tetrazol-5-yl)penam as a mixture of isomers, m.p. 70°–85° C., yield 91%. IR (KBr disc): 1785, 1675 and 1500 $cm^{-1}$. NMR ($CDCl_3$): 8.05-7.10 (m, 9H), 6.55-6.20 (m, 2H), 5.80 (m, 2H), 5.20 (m, 1H), 3.60 (s, 2H), 1.60 (s, 3H) and 1.00 (s, 3H) ppm.

EXAMPLE CLXXIII

Reaction of the appropriate 6-acylamino-2,2-dimethyl-3-(5-tetrazolyl)penam with the requisite alkanoyloxyalkyl chloride or with 3-bromophthalide, according to the procedure of Example CLXXII, provides the following congeners. In each case, the product is a mixture of monoalkylated compounds, in which the alkanoyloxyalkyl or phthalidyl substituent is located at either the 1- or the 2-position of the tetrazole ring.

6-acetamido-2,2-dimethyl-3-(1[2]-acetoxymethyltetrazol-5-yl)penam,
6-propionamido-2,2-dimethyl-3-(1-[2]-isobutyryloxymethyltetrazol-5-yl)penam,
6-(2-phenylacetamido)-2,2-dimethyl-3-(1[2]-propionyloxymethyltetrazol-5-yl)penam,
6-(2-phenoxyacetamido)-2,2-dimethyl-3-(1[2]-n-hexanoyloxymethyltetrazol-5-yl)penam,
6-(2-cyclohexanecarboxamido)-2,2-dimethyl-3-(1[2]-pivaloyloxymethyltetrazol-5-yl)penam,
6-(2-p-chlorophenylacetamido)-2,2-dimethyl-3-(1[2]-acetoxymethyltetrazol-5-yl)penam,
6-(2-m-methoxyphenylacetamido)-2,2-dimethyl-3-(1[2]-propionyloxymethyltetrazol-5-yl)penam,
6-(2-[3-chloro-4-hydroxyphenyl]acetamido)-2,2-dimethyl-3-(1[2]-pivaloyloxymethyltetrazol-5-yl)penam
6-(2-[2-thienyl]acetamido)-2,2-dimethyl-3-(1-[2]-acetoxymethyltetrazol-5-yl)penam
6-(3-furancarboxamido)-2,2-dimethyl-3-(1-[2]-n-butyryloxymethyltetrazol-5-yl)penam,
6-(2-phenylpropionamido)-2,2-dimethyl-3-(1-[2]-pivaloyloxymethyltetrazol-5-yl)penam,
6-(2-phenoxyacetamido)-2,2-dimethyl-3-(1[2]-pivaloyloxymethyltetrazol-5-yl)penam,
6-acetamido-2,2-dimethyl-3-(1[2]-[1-acetoxymethyl]tetrazol-5-yl)penam,
6-(2-cyclohexylacetamido)-2,2-dimethyl-3-(1[2]-[1-propionyloxyethyl]tetrazol-5-yl)penam,
6-(2-phenylacetamido)-2,2-dimethyl-3-(1[2]-[1-pivaloyloxyethyl]tetrazol-5-yl)penam,
6-(2-phenoxyacetamido)-2,2-dimethyl-3-(1[2]-[1-n-hexanoyloxyethyl]tetrazolyl)penam,
6-(2-[3-thienyl]acetamido)-2,2-dimethyl-3-(1-[2]-[1-acetoxyethyl]tetrazolyl)penam,
6-propionamido-2,2-dimethyl-3-(1[2]-phthalidyltetrazol-5-yl)penam
6-(2-phenylacetamido)-2,2-dimethyl-3-(1-[2]-phthalidyltetrazol-5-yl)penam,
6-(2-phenoxyacetamido)-2,2-dimethyl-3-(1[2]-phthalidyltetrazol-5-yl)penam,
6-(2-[4-hydroxyphenyl]acetamido)-2,2-dimethyl-3-(1[2]-phthalidyltetrazol-5-yl)penam,
6-(2-[2-furyl]acetamido)-2,2-dimethyl-3-(1[2]-phthalidyltetrazol-5-yl)penam and
6-(2-[5-methyl-2-thienyl]acetamido)-2,2-dimethyl-3-(1[2]-phthalidyltetrazol-5-yl)penam,
respectively.

EXAMPLE CLXXIV 6-(2-[2-Azidomethylphenyl]acetamido)-2,2-dimethyl-3-(1-[2]-pivaloyloxymethyltetrazol-5-yl)penam A solution of 5.0 g. of 6-(2-[2-azidomethylphenyl]acetamido)-2,2-dimethyl-3-(5-tetrazolyl)penam, 1.9 g. of chloromethylpivalate, 50 ml. of acetone and 1.25 ml. of a 25% solution of sodium iodide in water is heated under reflux for 4 hours. The mixture is cooled, 100 ml. of water is added and the mixture is extracted with ethyl acetate. The extract is dried and evaporated, yielding 4.9 g. (83% yield) of the title compound, as a mixture of isomers as indicated. IR($CHCl_3$): 2110, 1790, 1769, 1685 and 1510 $cm.^{-1}$ NMR ($CDCl_3$): 7.40 (2s, 4H), 6.45 and 6.35 (2s, 2H), 5.70 (m, 2H), 5.50 and 5.30 (2s, 1H), 4.50 (s, 2H), 3.72 (s, 2H), 1.63 and 1.55 (2s, 3H), 1.23 (s, 9H) and 1.06 ppm (s, 3H).

EXAMPLE CLXXV 6-(2-[2-Aminomethylphenyl]acetamido)-2,2-dimethyl-3-(1-[2]-pivaloyloxymethyltetrazol-5-yl)penam To a solution of 4.0 g. of 6-(2-[2-azidomethylphenyl]acetamido)-2,2-dimethyl-3-(1-[2]-pivaloyloxymethyltetrazol-5-yl)penam in 60 ml. of ethyl acetate is added 60 ml. of water, followed by 2 g. of 10% palladium-on-carbon. The two-phase system is stirred rapidly while hydrogen is bubbled through, and the pH is maintained at 3.0–3.5 by addition of dilute hydrochloric acid. Reaction is allowed to proceed in this manner for 4 hours, and then the catalyst is removed by filtration. The layers are separated, the ethyl acetate is washed with water, and the combined aqueous layers are lyophilized. This affords a mixture of the title compounds as their hydrochloride salts: yield 2.2 g (54%). IR (KBr disc): 1790, 1760, 1645 and 1550 $cm.^{-1}$ NMR (DMSO-$d_6$/$D_2O$): 7.46 (s, 4H), 6.65 (s, 2H), 5.7-5.5 (m, 2H), 5.38

(s, 1H), 4.20 (s, 2H), 3.83 (s, 2H), 1.77 and 1.73 (2s, 3H), 1.20 (s, 9H) and 1.06 (s, 3H).

EXAMPLE CLXXVI

6-Amino-2,2-dimethyl-3-(2-[pivaloyloxymethyl]tetrazol-5-yl)penam

To a stirred solution of 0.932 g. (7.21 m mole) of quinoline in 8.0 ml. of chloroform is added 0.840 g. (4.05 m mole) of phosphorus pentachloride. The suspension is cooled to −15° C., and then 1.81 g. (3.84 m mole) of 6-(2-phenylacetamido)-2,2-dimethyl-3-(2-[pivaloyloxymethyl]tetrazol-5-yl)penam is added. Stirring is continued for a further 30 minutes, at ca. −5° C., and then 2.15 g. (35.7 m mole) of n-propanol is added. Stirring is continued for a further 30 minutes, again at ca. −5° C., and then 25 ml. of 90:10 isopropyl ether-acetone is added, followed immediately by a solution of 1.35 g. of sodium chloride in 6.02 ml. of water. The temperature rises to 15° C. and then it is lowered again to −15° C. The precipitate which has formed is filtered off and dried, giving 1.33 g. (88% yield) of 6-amino-2,2-dimethyl-3-(2-[pivaloyloxymethyl]tetrazol-5-yl)penam hydrochloride. The infrared spectrum (KBr disc) shows absorptions at 1785 $cm^{-1}$ (β-lactam) and 1750 $cm^{-1}$ (ester). The NMR spectrum ($DMSO-d_6$) shows absorptions at 6.70 ppm (singlet, 2H, pivaloyloxy methylene hydrogens), 5.75 ppm (doublet, 1H, C-5 hydrogen), 5.50 ppm (singlet, 1H, C-3 hydrogen), 5.70 ppm (doublet, 1H, C-6 hydrogen), 1.75 ppm (singlet, 3H, C-2 methyl hydrogens), 1.20 ppm (singlet, 9H, t-butyl hydrogens) and 1.10 ppm (singlet, 3H, C-2 methyl hydrogens).

EXAMPLE CLXXVII

6-Amino-2,2-dimethyl-3-(1-[pivaloyloxymethyl]tetrazol-5-yl)penam

The title compound is prepared as its hydrochloride, in 90% yield, from 6-(2-phenylacetamido)-2,2-dimethyl-3-(1-[pivaloyloxymethyl]tetrazol-5-yl)penam, using the method of Example CLXXVI. The infrared spectrum (KBr disc) shows absorptions at 1780 $cm^{-1}$ (β-lactam) and 1740 $cm^{-1}$ (ester). The NMR spectrum ($DMSO-d_6$) shows absorptions at 6.71 ppm (singlet, 2H, pivaloyloxy methylene hydrogens), 5.88 ppm (singlet, 1H, C-3 hydrogen), 5.83 ppm (doublet, 1H, C-5 hydrogen), 5.20 ppm (doublet, 1H, C-6 hydrogen), 1.80 ppm (singlet, 3H, C-2 methyl hydrogens), 1.20 ppm (singlet, 9H, t-butyl hydrogens) and 1.16 ppm (singlet, 3H, C-2 methyl hydrogens).

EXAMPLE CLXXVIII

Using the procedure of Example CLXXVI, and utilizing as starting material an appropriate 6-acylamino-2,2-dimethyl-3-(1[2]-substituted tetrazol-5-yl)penam chosen from those in Example CLXXIII, the following compounds are prepared:

6-amino-2,2-dimethyl-3-(1[2]-acetoxymethyltetrazol-5-yl)penam,
6-amino-2,2-dimethyl-3-(1[2]-isobutyryloxymethyltetrazol-5-yl)penam,
6-amino-2,2-dimethyl-3-(1[2]-propionoxymethyltetrazol-5-yl)penam,
6-amino-2,2-dimethyl-3-(1[2]-n-hexanoyloxymethyltetrazol-5-yl)penam,
6-amino-2,2-dimethyl-3-(1-[2]-[1-acetoxyethyl]tetrazol-5-yl)penam,
6-amino-2,2-dimethyl-3-(1[2]-[1-propionyloxyethyl]tetrazol-5-yl)penam,
6-amino-2,2-dimethyl-3-(1[2]-[1-pivaloyloxyethyl]tetrazol-5-yl)penam,
6-amino-2,2-dimethyl-3-(1[2]-[1-n-hexanoyloxymethyl]-tetrazol-5-yl)penam and
6-amino-2,2-dimethyl-3-(1[2]-phthalidyltetrazol-5-yl)penam, respectively.

EXAMPLE CLXXIX

6-(D-2-Amino-2-[p-hydroxyphenyl]acetamido)-2,2-dimethyl-3-(2-[pivaloyloxymethyl]tetrazol-5-yl)penam To a stirred suspension of 287 mg. (1.0 m mole) of sodium N-(2-methoxycarbonyl-1-methylvinyl)-D-2-amino-2-(p-hydroxyphenyl)acetate (Long, et. al., Journal of the Chemical Society [London], Part C, 1920 [1971]) and 1 drop of N-methylmorpholine in 6 ml. of ethyl acetate, is added 0.97 ml. (1.03 mole) of ethylchloroformate, at −15° C. Stirring is continued for a further 30 minutes at −15° C. This mixture is then added to a pre-cooled (−15° C.) suspension of 390.5 mg. (1.0 m mole) of 6-amino-2,2-dimethyl-3-(2-[pivaloyloxymethyl]tetrazol-5-yl)penam hydrochloride in 2 ml. of ethyl acetate containing 101 mg. (1.0 m mole) of triethylamine. The reaction mixture is then stirred at −15° C. for 1 hour followed by 5° C. for 1 hour. The ethyl acetate is removed by evaporation in vacuo, and the white solid thus obtained is suspended in 10 ml. of 1:1 water-tetrahydrofuran. The suspension is cooled to 0° C., and then its pH is adjusted to 2.1. The suspension is stirred at 0° C. for 45 minutes, with further acid being added to maintain the pH at 2.1 as necessary. At this point, the tetrahydrofuran is removed by evaporation in vacuo, the residual aqueous phase is saturated with sodium chloride, and the product is extracted into ethyl acetate. The ethyl acetate is dried and evaporated in vacuo giving after trituration of the residue with ether, 425 mg. (81% yield) of 6-(D-2-amino-2-[p-hydroxyphenyl]acetamido)-2,2-dimethyl-3-(2-[pivaloyloxymethyl]tetrazol-5-yl)penam hydrochloride. The infrared spectrum (KBr disc) shows absorptions at 1780 $cm^{-1}$ (β-lactam) 1755 $cm^{-1}$ (ester), 1682 $cm^{-1}$ (amide I). The NMR spectrum ($DMSO-d_6$) shows absorptions at 7.09 ppm (quartet, 4H, aromatic hydrogens), 6.59 ppm (singlet, 2H, pivaloyloxy methylene), 5.52 ppm (multiplet 2H, C-5 and C-6 hydrogens), 5.22 ppm (singlet, 1H, side chain methine hydrogen) 5.00 ppm (singlet, 1H, C-3 hydrogen), 1.47 ppm (singlet, 3H, C-2 methyl hydrogen), 1.07 ppm (singlet, 9H, t-butyl hydrogens), and 0.96 ppm (singlet, 3H, C-2 methyl hydrogens).

The MIC of the title compound against *Strep. pyogenes* is 0.39 μg./ml.

EXAMPLE CLXXX

6-(D-2-Amino-2-[p-hydroxyphenyl]acetamido)-2,2-dimethyl-3-(1-[pivaloyloxymethyl]tetrazol-5-yl)penam The title compound is prepared as its hydrochloride, in 50% yield, from 6-amino-2,2-dimethyl-3-(1-[pivaloyloxymethyl]tetrazol-5-yl)penam, using the procedure of Example CLXXIX. The infrared spectrum of the product (KBr disc) shows absorptions at 1780 $cm^{-1}$ (β-lactam) and 1680 $cm^{-1}$ (amide I). The NMR spectrum ($DMSO-d_6$) shows absorptions at 7.09 ppm (quartet, 4H, aromatic hydrogens), 6.55 ppm (singlet, 2H, pivaloyloxy methylene hydrogens), 5.61 ppm (multiplet, 3H, C-3, C-5 and C-6 hydrogens), 5.06 ppm (singlet, 1H, side-chain methine hydrogen), 1.55 ppm (singlet, 3H, C-2 methyl hydrogen), 1.10 ppm (singlet, 3H, C-2 methyl hydrogen), 1.10 ppm (singlet, 9H, t-butyl hydrogens) and 1.03 ppm (singlet, 3H, C-2 methyl hydrogens).

EXAMPLE CLXXXI

Using the procedure of Example CLXXIX, reaction of the appropriate 6-amino-2,2-dimethyl-3-(pivaloyloxymethyltetrazol-5-yl)penam with the requisite sodium N-(2-methoxycarbonyl-1-methylvinyl)-2-amino-2-substituted acetate provides the following compounds:

6-(D-2-amino-2-phenylacetamido)-2,2-dimethyl-3-(1-pivaloyloxymethyltetrazol-5-yl)penam, 6-(D-2-amino-2-phenylacetamido)-2,2-dimethyl-3-(2-pivaloyloxymethyltetrazol-5-yl)penam, 6-(D-2-amino-2-[2-thienyl]acetamido)-2,2-dimethyl-3-(2-pivaloyloxymethyltetrazol-5-yl)penam 6-(D-2-amino-2-[3-chloro-4-hydroxyphenyl-]acetamido)-2,2-dimethyl-3-(2-pivaloyloxymethyltetrazol-5-yl)penam and 6-(D-2-amino-2-[3-thienyl]acetamido)-2,2-dimethyl-3-2-pivaloyloxymethyltetrazol-5-yl)penam, respectively.

EXAMPLE CLXXXII 6-(D-2-[3-(2-Furoyl)ureido]-2-phenylacetamido)-2,2-dimethyl-3-(1-pivaloyloxymethyltetrazol-5-yl)penam To a stirred solution of 455 mg. of 6-(D-2-amino-2-phenylacetamido)-2,2-dimethyl-3-(1-pivaloyloxymethyltetrazol-5-yl)penam in 20 ml. of methylene chloride, at 0° C., is added 137 mg. of 2-furoyl isocyanate dissolved in 5 ml. of methylene chloride. The cooling bath is then removed, and stirring is continued for 2 hours. The solvent is removed in vacuo to give the title compound.

EXAMPLE CLXXXIII

The procedure of Example CLXXXII, is repeated, except the 6-(D-2-amino-2-phenylacetamido)-2,2-dimethyl-3-(1-pivaloyloxymethyltetrazol-5-yl)penam used therein is replaced by the appropriate 6-(D-2-amino-2-substituted acetamido)-2,2-dimethyl-3-(1[2]-substituted tetrazol-5-yl)penam, and the 2-furoyl isocyanate is replaced by the requisite isocyanate. This affords:

6-(D-2-[3-(3-furoyl)ureido]-2-phenylacetamido)-2,2-dimethyl-3-(1-[1-acetoxy)ethyl]tetrazol-5-yl)penam, 6-(D-2-[3-benzoylureido]-2-[2-thienyl]acetamido)-2,2-dimethyl-3-(2-pivaloyloxymethyl]tetrazol-5-yl)penam and 6-(D-2-[3-(3-thienyl)ureido]-2-[3-chloro-4-hydroxyphenyl]acetamido)-2,2-dimethyl-3-(2-pivaloyloxymethyl]tetrazol-5-yl)penam, respectively.

EXAMPLE CLXXXIV

Reaction of the appropriate 6-(2-amino-2-substituted acetamido)-2,2-dimethyl-3-(substituted tetrazol-5-yl)penam compound with the requisite aldehyde or ketone, according to the procedure of Example CLXI, produces the following compounds:

6-(2,2-dimethyl-5-oxo-4-phenyl-1-imidazolidinyl)-2,2-dimethyl-3-(1-[pivaloyloxymethyl]tetrazol-5-yl)penam, 6-(2,2-dimethyl-5-oxo-4-[4-hydroxyphenyl]-1-imidazolindinyl)-2,2-dimethyl-3-(1-[acetoxymethyl]-tetrazol-5-yl)penam, 6-(2-methyl-5-oxo-4-[2-thienyl]-1-imidazolindinyl)-2,2-dimethyl-3-(1-[n-hexanoyloxymethyl]tetrazol-5-yl)penam, 6-(2,2-dimethyl-5-oxo-4-[3-chloro-4-hydroxyphenyl-]imidazolindinyl)-2,2-dimethyl-3-(1-[1-(acetoxy)ethyl]tetrazol-5-yl)penam, 6-(2,2-diethyl-5-oxo-4-[3-thienyl]-1-imidazolidinyl)-2,2-dimethyl-3-(1-[1-(n-hexanoyloxy)ethyl]tetrazol-5-yl)penam, 6-(2,2-dimethyl-5-oxo-4-phenyl-1-imidazolindinyl)-2,2-dimethyl-3-(1-phthalidyltetrazol-5-yl)penam and 6-(2,2-dimethyl-5-oxo-4-phenyl-1-imidazolindinyl)-2,2-dimethyl-3-(2-[pivaloyloxymethyl]tetrazol-5-yl)penam, respectively.

EXAMPLE CLXXXV 6-(Triphenylmethylamino)-2,2-dimethyl-3-(1[2]-pivaloyloxymethyltetrazol-5-yl)penam To a stirred solution of 932 mg. of 6-(triphenylmethylamino)-2,2-dimethyl-3-(5-tetrazolyl)penam and 0.28 ml. of triethylamine in 10 ml. of dimethylformamide, at 0° C. is added 301 mg. of chloromethyl pivalate. The cooling bath is removed after 15 minutes and the reaction mixture is stirred at ambient temperature for 2 hours. At this point the solvent is removed by evaporation under high vacuum and to the residue is added water and ethyl acetate. The pH is adjusted to 7.0, and the water is removed and discarded. The ethyl acetate is washed with water, dried using anhydrous sodium sulfate and evaporated to dryness in vacuo. This affords the title product as a mixture of isomers as indicated. The individual isomers can be obtained by chromatography.

EXAMPLE CLXXXVI

6-Amino-2,2-dimethyl-3-(1[2]-pivaloyloxymethyltetrazol-5-yl)penam

The title product is prepared as its p-toluenesulfonate salt, by treating 6-(triphenylmethylamino)-2,2-dimethyl-3-(1[2]-pivaloyloxytetrazol-5-yl)penam with p-toluenesulfonic acid in acetone, according to the procedure of Example XX.

EXAMPLE CLXXXVII

6-Amino-2,2-dimethyl-3-(1-pivaloyloxymethyltetrazol-5-yl)penam and

6-Amino-2,2-dimethyl-3-(2-pivaloyloxymethyltetrazol-5-yl)penam

To a stirred suspension of 2.40 g. of 6-amino-2,2-dimethyl-3-(5-tetrazolyl)penam in 15 ml. of N,N-dimethylformamide, is added 2.8 ml. of triethylamine. Stirring is continued for a further 15 minutes, and then 2.68 g. of chloromethyl pivalate is added. The mixture is stirred at ambient temperature for 5 hours, and then it is diluted with 100 ml. of water. It is then extracted with ethyl acetate. The extract is washed with water, dried using anhydrous sodium sulfate, and then it is evaporated in vacuo to give a mixture of the title compounds. The individual isomers are obtained by chromatographic separation of the crude product.

EXAMPLE CLXXXVIII

6-(2-Phenylacetamido)-2,2-dimethyl-3-(1-[4-benzyloxybenzyl]tetrazol-5-yl)penam To a stirred solution of 189 mg of 6-amino-2,2-dimethyl-3-(1-[4-benzyloxybenzyl]tetrazol-5-yl)penam in 4 ml of chloroform, is added, at ambient temperature, 0.038 ml of pyridine followed by 0.057 ml of phenylacetyl chloride. Stirring is continued for a further 45 minutes, and then the reaction mixture is diluted with 25 ml of chloroform and then washed with water. The organic phase is dried using anhydrous magnesium sulfate and then evaporated in vacuo. The residue is 209 mg (86% yield) of 6-(2-phenylacetamido)-2,2-dimethyl-3-(1-[4-benzyloxybenzyl]tetrazol-5-yl)penam. The NMR spectrum (in $CDCl_3$) shows absorptions at 7.50–6.70 ppm (multiplet, aromatic hydrogens), 6.4 ppm (doublet, amide hydrogen), 5.80–5.20 ppm (multiplet, benzyl hydrogens and C-5 and C-6 hydrogens), 5.10 ppm (singlet, C-3 hydrogen), 5.05 ppm (singlet, benzyl hydrogens), 3.60 ppm (singlet, phenylacetyl methylene hydrogens), 1.30 ppm (singlet, C-2 methyl hydrogens) and 0.85 ppm (singlet, C-2 methyl hydrogens).

EXAMPLE CLXXXIX

Reaction of the appropriate 6-amino-2,2-dimethyl-3-(1-substituted tetrazol-5-yl)penam with the requisite acid chloride, according to the procedure of Example CLXXXVIII provides the following compounds:

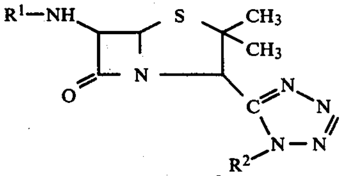

| $R^1$ | $R^2$ |
|---|---|
| acetyl | p-methoxy-benzyl |
| acetyl | m-ethoxybenzyl |
| acroloyl | p-benzyloxybenzyl |
| cyclohexanecarbonyl | benzyl |
| benzoyl | 2-furylmethyl |
| p-chlorobenzoyl | 3-furylmethyl |
| o-flourobenzoyl | p-isopropoxybenzyl |
| 2-phenylacetyl | p-hydroxybenzyl |
| 3-phenylpropionyl | p-methoxybenzyl |
| 2-(p-tolyl)acetyl | o-methoxybenzyl |
| 2-(p-(isopropylphenyl)acetyl | 2-furylmethylbenzyl |
| 2-(m-chlorophenyl)acetyl | p-n-butoxybenzyl |
| 2-(3,5-dibromophenyl)acetyl | pivaloyloxymethyl |
| 2-(p-chlorophenoxy)acetyl | p-methoxybenzyl |
| 2-thienylcarbonyl | o-methoxybenzyl |
| 2-(3-thienyl)acetyl | p-methoxybenzyl |
| 2-(2-furyl)acetyl | p-hydroxybenzyl |
| 2-(3-pyridyl)acetyl | p-n-hexyloxybenzyl |
| 2-(5-tetrazolyl)acetyl | 2-furylmethyl |
| 2-azido-2-phenylacetyl | p-methoxybenzyl |
| 2-(p-cyanophenyl)acetyl | p-benzyloxybenzyl |
| dodecanoyl | p-methoxybenzyl |
| acryloyl | p-ethoxybenzyl |
| $\Delta^2$-octenoyl | o-methoxybenzyl |
| $\Delta^{11}$-undecenoyl | m-methoxybenzyl |
| $\Delta^{12}$-dodecenoyl | 2-furylmethyl |
| 2-(phenylthio)acetyl | p-methoxybenzyl |
| 2-phenylacetyl | 4-phenylbenzyl |
| 2-phenoxyacetyl | 3-chlorobenzyl |
| 2-phenoxyacetyl | 3-chloro-4-methoxybenzyl |
| 2-(2-thienyl)acetyl | 2,4-dimethoxybenzyl |
| 2-(3-thienyl)acetyl | 4-n-hexylbenzyl |
| 2,6-diethoxybenzoyl | 4-flourobenzyl |
| 2-2(thienyl)acetyl | 3,4-dimethoxybenzyl |
| 2-n-butoxy-1-naphthoyl | 4-nitrobenzyl |

-continued

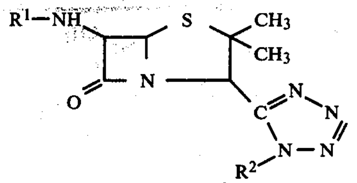

| $R^1$ | $R^2$ |
|---|---|
| 2-cycloheptylacetyl | 3,5-dichlorobenzyl |
| 2-(cyclohex-3-enyl)acetyl | 3-chloro-4-ethoxybenzyl |
| 3-phenylpropionyl | 4-isopropylbenzyl |
| 2-phenylthioacetyl | 4-iodobenzyl |
| 2-(1-pyrazolyl)acetyl | 4-n-hexylbenzyl |
| 2-(1-pyrrolyl)acetyl | 4-n-hexyloxybenzyl |
| 2-(1,2,4-triazol-1-yl)acetyl | 4-biphenylylmethyl |
| 2-(3-sydnonyl)acetyl | 4-bromophenyl |
| 2-bromoacetyl | 4-ethylbenzyl |
| 2-phenylacetyl | 4-(n-hexyloxymethoxy)-benzyl |
| 2-phenoxyacetyl | 4-(2-chlorophenyl)benzyl |
| 2-(3-thienyl)acetyl | 4-(4-tolyl)benzyl |
| 2-(3-chlorophenyl)acetyl | 2-(4-methoxyphenyl)-benzyl |
| 2-phenylacetyl | $COOC_2H_5$ |
| 2-phenylbutyryl | $COOCH_3$ |
| 2-phenoxyacetyl | $COOC_2H_5$ |
| 2-phenylthioacetyl | COO-n-$C_6H_3$ |
| 2-thienylacetyl | $COOCH_2C_6H_5$ |
| 3-thienylacetyl | $COOC_6H_5$ |
| 3-thienylacetyl | COO-[4-(n-$C_4H_9$)$C_6H_4$] |
| 2-bromoacetyl | COO-[4-$NO_2C_6H_4$] |
| 2-chloracetyl | COO-(3-$BrC_6H_4$) |
| 4-bromobutyryl | COO-[4-(i-$C_3H_7O$)$C_6H_4$] |
| 2-(4-fluorophenyl)acetyl | COO-(2,4-$Cl_2C_6H_3$) |
| phenoxycarbonyl | COO-(2-$CH_3OC_6H_4$) |
| benzyloxycarbonyl | COO[4-(n-$C_6H_{13}O$)$C_6H_3$] |
| 2-(4-fluorophenyl)acetyl | COO-(2-$FC_6H_4$) |
| 2,6-diethoxybenzoyl | COO-(2-$CH_3C_6H_4$) |
| 2-(4-pyridylthio)acetyl | COO-[4-(t-$C_4H_9$)$C_6H_4$] |
| 5-methyl-3-phenyl-4-isoxazolyl carbonyl | COO-[2,4-$(NO_2)_2C_6H_3$] |
| 2-cyanoacetyl | $COOCH_3$ |
| 2-(5-tetrazolyl)acetyl | $COOC_2H_5$ |
| 2-(1-tetrazolyl)acetyl | COO-n-$C_4H_9$ |
| 2-azido-2-phenylacetyl | $COOCH_2C_6H_5$ |
| 2-sulfo-2-phenylacetyl | COO-[2-$NO_2$-4-($C_3H_7O$)$C_6H_3$] |
| 4-methyl-1-(2,6-dichlorophenyl)-5-pyrazolylcarbonyl | $COOC_2H_5$ |
| $\Delta^{12}$dodecenoyl | $COOCH_2C_6H_5$ |
| acryloyl | $COOC_6H_5$ |
| cyclbutylcarbonyl | $COOC_2H_5$ |
| 2-phenylacetyl | $SO_2CH_3$ |
| 2-phenoxyacetyl | $SO_2CH_2(CH_2)_4CH_3$ |
| 2-(3-thienyl)acetyl | $SO_2CH_2C_6H_5$ |
| 2-cyanoacetyl | $SO_2C_6H_5$ |
| 2-(2-fluorophenyl)acetyl | $SO_2$-[4-$NO_2$)$C_6H_4$] |
| 2-(3,4-dichlorophenyl)acetyl | $SO_2$-(4-$BrC_6H_4$) |
| 2-(3-bromophenyl)acetyl | $SO_2$-(2-$ClC_6H_4$) |
| 2-(3-tolyl)acetyl | $SO_2$-[2-$C_2H_5$)$C_6H_4$) |
| 2-(4-isopropylphenyl)acetyl | $SO_2$-[3-(n-$C_4H_9$)$C_6H_4$] |
| 2-(4-amyloxyphenyl)acetyl | $SO_2$-[4-($CH_3O$)$C_6H_4$] |
| acryloyl | $SO_2$-(2,4-$Cl_2C_6H_3$) |
| 2-(4-cyanophenyl)acetyl | $SO_2$-[3-$CH_3$-4-($CH_3O$)$C_6H_3$] |
| 2-(2-furyl)acetyl | $SO_2$-[2,4-$(NO_2)_2C_6H_3$] |
| ethoxycarbonyl | $SO_2$-[2-$CH_3O$-5-($NO_2$)$C_6H_3$] |
| acetyl | $SO_2$-$CH_2$-(4-$ClC_6H_4$) |
| butyryl | $SO_2$-$CH_2$-(2-$BrC_6H_4$) |
| benzoyl | $SO_2CH_2$-(3-$CH_3C_6H_4$) |
| cyclopentanecarbonyl | $SO_2C_2H_5$ |
| 1,4-cyclohexadienylcarbonyl | $SO_2C_2H_5$ |
| 2-(2-tetrazolyl)acetyl | $SO_2$-[4-(n-$C_4H_9O$)$C_6H_4$] |
| 2-(4-chlorophenyl)thioacetyl | $SO_2C_6H_5$ |
| 2-phenylacetyl | phthalidyl |
| 2-(2-thienyl)acetyl | " |
| 2-(3-thienyl)acetyl | " |
| 2-phenoxyacetyl | " |

-continued

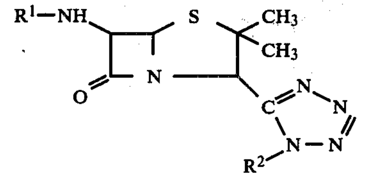

| $R^1$ | $R^2$ |
|---|---|
| 2-bromoacetyl | " |
| 1,4-cyclohexadienylcarbonyl | " |

EXAMPLE CXC

Reaction of the appropriate 6-amino-2,2-dimethyl-3-(1-substituted tetrazol-5-yl)penam with the requisite sodium N-(2-methoxycarbonyl-1-methylvinyl)-2-amino-2-substituted acetate, according to the procedure of Example CLXXIX, affords the following congeners:

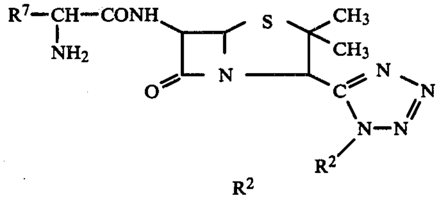

| $R^7$ | $R^2$ |
|---|---|
| methyl | p-methoxybenzyl |
| isopropyl | p-hydroxybenzyl |
| cyclopentyl | p-methoxybenzyl |
| phenyl | m-ethoxybenzyl |
| phenyl | p-methoxybenzyl |
| phenyl | phenyl |
| phenyl | 2-furylmethyl |
| phenyl | p-methoxybenzyl |
| p-hydroxyphenyl | p-methoxybenzyl |
| p-hydroxyphenyl | p-hydroxybenzyl |
| 3-chloro-4-hydroxyphenyl | 2-furylmethyl |
| 2-thienyl | p-methoxybenzyl |
| 3-thienyl | p-hydroxybenzyl |
| 2-furyl | 2-furylmethyl |
| 4-methoxyphenyl | 3-chloro-4-methoxybenzyl |
| 4-N,N-dimethylaminophenyl | 3-chloroenzyl |
| 3-pyridyl | 4-benzyloxybenzyl |
| phenyl | 4-phenylbenzyl |
| benzyl | 2,4-dimethoxybenzyl |
| 3-indolylmethyl | 4-iodobenzyl |
| 2,4-dichlorophenyl | 4-n-hexylbenzyl |
| 3-tolylphenyl | 4-bromophenyl |
| 2-methoxyphenyl | 4-ethylbenzyl |
| 3,5-dimethoxyphenyl | 4-biphenylmethyl |
| 4-methylthiophenyl | 1-(4-methoxyphenyl)ethyl |
| 3-furyl | 4-nitrobenzyl |
| 4-methylthiophenyl | 2-fluorobenzyl |
| cyclohexyl | 4-methoxybenzyl |
| phenyl | $COOC_2H_5$ |
| 3-thienyl | $COOC_2H_5$ |
| 1,4-cyclohexadienyl | $COOC_2H_5$ |
| p-hydroxyphenyl | $COOCH_3$ |
| 3-chloro-4-hydroxyphenyl | $COOC_2H_5$ |
| phenyl | $COOC_6H_{13}$ |
| phenyl | $COOC_6H_5$ |
| 4-chlorophenyl | $COOCH_2C_6H_5$ |
| cyclohexyl | COO-[4-$(CH_3)C_6H_4$] |
| 3-thienyl | COO-[2-$(CH_3O)C_6H_4$] |
| phenyl | COO-[2-$NO_2$-4-$(C_3H_7O)C_6H_3$] |
| methyl | COO-[2,4-$(NO_2)_2C_6H_3$] |
| n-octyl | COO-(2-$FC_6H_4$) |
| cyclopropyl | COO-(3-$BrC_6H_4$) |
| $\Delta^2$-prophenyl | COO-[4-(n-$C_4H_9)C_6H_4$] |
| $\Delta^2$-butenyl | COO-[4-Cl-3-$CH_3C_6H_3$] |
| 5-ethyl-2-thienyl | COO-COO-i-$C_3H_7$ |
| 4-dimethylaminophenyl | $COOCH_3$ |

-continued

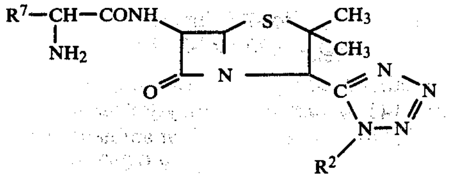

| $R^7$ | $R^2$ |
|---|---|
| phenyl | $SO_2CH_3$ |
| phenyl | $SO_2C_2H_5$ |
| 2-thienyl | $SO_2C_2H_5$ |
| methyl | $SO_2C_2H_5$ |
| n-butyl | $SO_2$-n-$C_6H_{13}$ |
| dodecyl | $SO_2C_6H_5$ |
| cyclobutyl | $SO_2CH_2C_6H_5$ |
| 4-hydroxyphenyl | $SO_2CH_2C_6H_5$ |
| 3-chloro-4-hydroxyphenyl | $SO_2C_6H_5$ |
| 2-butenyl | $SO_2(CH_2)_5CH_3$ |
| 2-chlorophenyl | $SO_2$-[4-$(NO_2)C_6H_4$] |
| 4-methoxyphenyl | $SO_2$-[4-$BrC_6H_4$) |
| 4-n-hexoxyphenyl | $SO_2$-(2-$C_2H_5C_6H_4$) |
| 4-isopropylthiophenyl | $SO_2$-[3-(n-$C_4H_9)C_6H_4$] |
| 3,4-dimethoxyphenyl | $SO_2$-[4-$(CH_3O)C_6H_4$] |
| 3-bromophenyl | $SO_2$-(3,4-$Cl_2C_6H_3$) |
| 4-fluorophenyl | $SO_2$-[3-$CH_3$-4-$(CH_3O)C_6H_3$] |
| 2,4-dichlorophenyl | $SO_2$-[2,4-$(NO_2)_2C_6H_3$] |
| 3-furyl | $SO_2$-[2-$CH_3O$-5-$(NO_2)C_6H_3$] |
| 5-ethyl-2-thienyl | $SO_2$-[3-$FC_6H_4$) |
| 1,4-cyclohexadienyl | $SO_2C_2H_5$ |
| phenyl | phthalidyl |
| 2-thienyl | phthalidyl |
| 1,4-cyclohexadienyl | phthalidyl |
| 4-hydroxyphenyl | phthalidyl |
| 3-chloro-4-hydroxyphenyl | phthalidyl |
| methyl | acetoxymethyl |
| propyl | propionoxymethyl |
| phenyl | isobutyryloxymethyl |
| 4-hydroxyphenyl | acetoxymethyl |
| 3-chloro-4-hydroxyphenyl | 1-(acetoxy)ethyl |
| 2-thienyl | n-hexanoyloxymethyl |
| 3-thienyl | 1-(n-hexanoyloxy)ethyl |
| 1,4-cyclohexadienyl | pivaloyloxymethyl |
| 3-pyridyl | 1-(acetoxy)ethyl |
| cyclohexyl | 1-(butyrloxy)ethyl |
| 2-cyclohexenyl | 1-(propionyloxy)ethyl |
| 2-furyl | n-pentyloxymethyl |
| 2-isothiazolyl | pivaloyloxymethyl |
| 4-methoxyphenyl | acetoxymethyl |
| 3-fluorophenyl | 1-(pivaloyloxy)ethyl |
| 4-tolyl | pivaloyloxymethyl |
| 5-ethyl-2-thienyl | pivaloyloxymethyl |

EXAMPLE CXCI

Reaction of the appropriate 6-acylamino-2,2-dimethyl-3-(1[2]-substituted tetrazol-5-yl)penam compound, chosen from those in Examples CLXXXI and CXC with sodium N-(2-ethoxycarbonyl-1-methylvinyl)-2-aminoacetate, according to the procedure of Example CLXXIX produces the following compounds:

6-(2-[2-aminoacetamido]-2-phenylacetamido)-2,2-dimethyl-3-(1[4-methoxybenzyl]tetrazol-5-yl)penam, 6-(2-[2-aminoacetamido]-2-[4-hydroxyphenyl-]acetamido)-2,2-dimethyl-3-(1-[methoxycarbonyl]tetrazol-5-yl)penam, 6-(2-[2-aminoacetamido]-2-[3-chloro-4-hydroxy]acetamido)-2,2-dimethyl-3-(1-[ethoxycarbonyl]tetrazol-5-yl)penam, 6-(2-[2-aminoacetamido]-2-[2-thienyl]acetamido)-2,2-dimethyl-3-(1-[ethylsulfonyl]tetrazol-5-yl)penam, 6-(2-[2-aminoacetamido]-n-valeramido)-2,2-dimethyl-3-(1-[n-hexylsulfonyl]tetrazol-5-yl)penam, 6-(2-[2-aminoacetamido]propionamido)-2,2-dimethyl-3-(1-[acetoxymethyl]tetrazol-5-yl)penam, 6-(2-[2-aminoacetamido]-2-phenylacetamido)-2,2-dimethyl-3-(1-[isobutyryloxymethyl]tetrazol-5-yl)penam,
6-(2-[2-aminoacetamido]-2-[3-chloro-4-hydroxyphenyl]-acetamido)-2,2-dimethyl-3-(1-[1-(acetoxy)ethyl]tetrazol-5-yl)penam,
6-(2-[2-aminoacetamido]-2-[2-furyl]acetamido)-2,2-dimethyl-3-(1-[n-pentyloxymethyl]tetrazol-5-yl)penam,
6-(2-[2-aminoacetamido]-2-[2-cyclohexyl]acetamido)-2,2-dimethyl-3-(1-[1-(propionyloxy)ethyl]tetrazol-5-yl)penam,
6-(2-[2-aminoacetamido]-2-phenylacetamido)-2,2-dimethyl-3-(2-[pivaloyloxymethyl]tetrazol-5-yl)penam,
6-(2-[2-aminoacetamido]-2-[2-thienyl]acetamido)-2,2-dimethyl-3-(2-[pivaloyloxymethyl]tetrazol-5-yl)penam and
6-(2-[2-aminoacetamido]-2-[3-chloro-4-hydroxyphenyl]-acetamido)-2,2-dimethyl-3-(2-[pivaloyloxymethyl]tetrazol-5-yl)penam, respectively.

EXAMPLE CXCII 6-(2-Phenoxyacetamido)-2,2-dimethyl-3-(5-tetrazolyl)penam

A mixture of 100 mg. (1 mmole) of potassium bicarbonate and 2.3 g. of 10% palladium-on-carbon, in a mixture of 12 ml. of methanol and 3 ml. of water, is stirred under an atmosphere of hydrogen until hydrogen uptake ceases. A solution of 464 mg. of 6-(2-phenoxyacetamido)-2,2-dimethyl-3-(1-benzyltetrazol-5-yl)penam in 10 ml. of ethyl acetate is then added, and stirring under an atmosphere of hydrogen is continued for an additional 5 hours. At this point the reaction mixture is filtered, and the residue is washed with aqueous methanol. The washings and the filtrate are combined and evaporated in vacuo. To this latter residue is added chloroform and water and the pH is adjusted to 8.0. The chloroform is removed and discarded, and fresh chloroform is added to the aqueous phase. The pH is lowered to 2.5 and the chloroform layer is separated. The dried chloroform is evaporated in vacuo, leaving 190 mg. (51% yield) of 6-(2-phenoxyacetamido)-2,2-dimethyl-3-(5-tetrazolyl)penam.

EXAMPLE CXCIII

The procedure of Example CXCII is repeated, except that the starting material is:

6-(2-phenoxyacetamido)-2,2-dimethyl-3-(1-[4-methoxybenzyl]tetrazol-5-yl)penam,
6-(2-phenoxyacetamido)-2,2-dimethyl-3-(1-[4-hydroxybenzyl]tetrazol-5-yl)penam,
6-(2-[4-methoxyphenoxy]acetamido)-2,2-dimethyl-3-(1-[4-fluorobenzyl]tetrazol-5-yl)penam,
6-benzamido-2,2-dimethyl-3-[1-(3-tolylmethyl)tetrazol-5-yl]penam,
6-isobutyramido-2,2-dimethyl-3-(1-[4-phenylbenzyl]tetrazol-5-yl)penam,
6-(2-amino-2-phenylacetamido)-2,2-dimethyl-3-(1-benzyltetrazol-5-yl)penam,
6-(2-naphthamido)-2,2-dimethyl-3-(1-[3-chloro-4-hydroxybenzyl]tetrazol-5-yl)penam and
6-(1-aminocyclohexanecarboxamido)-2,2-dimethyl-3-(1-benzyltetrazol-5-yl)penam respectively. This affords:

6-(2-phenoxyacetamido)-2,2-dimethyl-3-(5-tetrazolyl)penam,
6-(2-phenoxyacetamido)-2,2-dimethyl-3-(5-tetrazolyl)penam,
6-(2-[4-methoxyphenoxy]acetamido)-2,2-dimethyl-3-(5-tetrazolyl)penam,
6-benzamido-2,2-dimethyl-3-(5-tetrazolyl)penam,
6-(isobutyramido-2,2-dimethyl-3-(5-tetrazolyl)penam,
6-(2-amino-2-phenylacetamido)-2,2-dimethyl-3-(5-tetrazolyl)penam,,
6-(2-naphthamido)-2,2-dimethyl-3-(5-tetrazolyl)penam and
6-(1-aminocyclohexanecarboxamido)-2,2-dimethyl-3-(5-tetrazolyl)penam, respectively.

EXAMPLE CXCIV 6-(2-Phenylacetamido)-2,2-dimethyl-3-(5-tetrazolyl)penam

To a stirred suspension of 2.4 g of 6-amino-2,2-dimethyl-3-(5-tetrazolyl)penam in 50 ml of chloroform is added 2.8 ml of triethylamine. Stirring is continued for a further 15 minutes, and then the solution thus obtained, is cooled to 0° C. To this solution is then 1.08 g of trimethylsilyl chloride. The cooling bath is removed, and the reaction mixture is stirred for a further 1 hour at ambient temperature, to give a chloroform solution of the mono-trimethylsilyl derivative of 6-amino-2,2-dimethyl-3-(5-tetrazolyl)penam. This latter solution is then recooled to 0° C., and 1.56 g of phenylacetyl chloride is added dropwise, with stirring. The cooling bath is removed, and the mixture is stirred for 1 hour at ambient temperature. The chloroform is then washed with water, dried using anhydrous sodium sulfate, and concentrated to dryness in vacuo. This affords crude 6-(2-phenylacetamido)-2,2-dimethyl-3-(5-tetrazolyl)penam.

EXAMPLE CXCV

When the procedure of Example CXCIV is repeated, except that the trimethylsilyl chloride used therein is replaced by an equimolar amount of triethylsilyl chloride and tri-n-butylsilyl chloride, respectively, the product in each case is 6-(2-phenylacetamido)-2,2-dimethyl-3-(5-tetrazolyl)penam. The intermediate products in these experiments are the mono-triethylsilyl and the mono-tri-n-butylsilyl derivative of 6-amino-2,2-dimethyl-3-(5-tetrazolyl)penam, respectively.

EXAMPLE CXCVI 6-(2-Phenoxyacetamido)-2,2-dimethyl-3-(5-tetrazolyl)penam

To a stirred suspension of 2.4 g of 6-amino-2,2-dimethyl-3-(5-tetrazolyl)penam in 50 ml of chloroform is added 4.2 ml of triethylamine. Stirring is continued for a further 15 minutes, and then the solution thus obtained is cooled to 0° C. To this solution is then added 2.16 g of trimethylsilyl chloride. The cooling bath is removed, and then the reaction mixture is stirred at ambient temperature for 1 hour and then it is refluxed for 1 hour. It is then cooled to ambient temperature giving a chloroform solution of the bis-trimethylsilyl derivative of 6-amino-2,2-dimethyl-3-(5-tetrazolyl)penam. This latter solution is then cooled to 0° C., and 1.72 g of phenoxyacetyl chloride is added dropwise with stirring. The cooling bath is removed, and the mixture is stirred for 1 hour at ambient temperature. The chloroform is then washed with water, dried using anhydrous sodium sulfate, and then evaporated to dryness in vacuo. This affords crude 6-(phenoxyacetamido)-2,2-dimethyl-3-(5-tetrazolyl)penam.

EXAMPLE CXCVII

When the procedure of Example CXCVI is repeated, except that the trimethylsilyl chloride used therein is replaced by an equimolar amount of triethylsilyl chloride and triisopropylsilyl chloride, respectively, the product in each case is 6-(2-phenoxyacetamido)-2,2-dimethyl-3-(5-tetrazolyl)penam. The intermediate products in these experiments are the bis-triethylsilyl and the bis-triisopropyl derivative of 6-amino-2,2-dimethyl-3-(5-tetrazolyl)penam, respectively.

EXAMPLE CXCVIII

6-Amino-2,2-dimethyl-3-(1[2]-triphenylmethyltetrazol-5-yl)penam

To a stirred slurry of 240 mg. of 6-amino-2,2-dimethyl-3-(5-tetrazolyl)penam in 1.5 ml. of dry, ethanol-free chloroform, is added 0.36 ml. of triethylamine. The mixture is stirred until a cloudy isolution is obtained, and then ca. 200 mg. of anhydrous sodium sulfate is added. Stirring is continued for a further 15 minutes and then the mixture is filtered. To the filtrate is added 278.5 mg. of triphenylmethyl chloride, and the reaction mixture is stored at ambient temperature for 4.5 hours. At this point, the solvent is removed by evaporation in vacuo, leaving the crude title product as a mixture of isomers as indicated. The crude product is re-dissolved in a small volume of chloroform and then adsorbed on a small column of silica gel. The column is eluted with chloroform and the first 20 ml. of eluate and collected and evaporated to dryness in vacuo. A small volume of ether is added to the residue, and the mixture is again evaporated to dryness in vacuo. The latter residue is washed with ether, to give 357.4 mg. (77% yield) of a white solid. The NMR spectrum ($CDCl_3$) shows absorptions at 7.15 ppm (broad singlet), 5.70 ppm (doublet), 5.35 (singlet), 4.55 (doublet), 1.60 (singlet) and 1.10 (singlet).

EXAMPLE CIC

Reaction of 6-amino-2,2-dimethyl-3-(5-tetrazolyl)penam with a substituted triphenylmethyl chloride of formula $(R^5)''$-Cl, according to the procedure of Example CXCVIII affords in each ease a mixture of the corresponding 6-amino-2,2-dimethyl-3-(1-[substituted triphenylmethyl]tetrazol-5-yl)penam and 6-amino-2,2-dimethyl-3-(2-[substituted triphenylmethyl]tetrazol-5-yl)penam compounds. In this way, the following mixtures are produced:

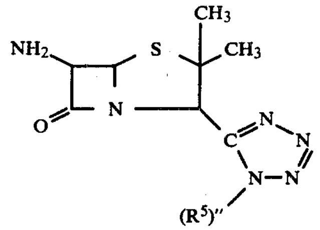

and

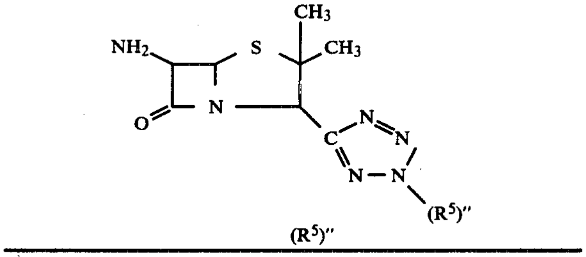

| $(R^5)''$ |
|---|
| diphenyl(2-fluorophenyl)methyl |
| diphenyl(3-chlorophenyl)methyl |
| diphenyl(4-bromophenyl)methyl |
| diphenyl(2-ethylphenyl)methyl |
| diphenyl(4-n-propylphenyl)methyl |
| diphenyl(3-sec-butylphenyl)methyl |
| diphenyl(4-ethoxyphenyl)methyl |
| diphenylbiphenylylmethyl |
| phenyldi(3-tolyl)methyl |
| phenyldi(3-chlorophenyl)methyl |
| phenyl(4-chlorophenyl((4-methoxyphenyl)methyl |
| phenyldi(biphenylyl)methyl |
| tri(4-tolyl)methyl |
| (4-isopropylphenyl)di(3-methoxyphenyl)methyl |

The mixtures are separated into the two isomers by chromatography.

EXAMPLE CC

6-(2-Phenoxyacetamido)-2,2-dimethyl-3-(1[2]-triphenylmethyltetrazol-5-yl)penam To a stirred solution of 932 mg. of 6-amino-2,2-dimethyl-3-(1[2]-triphenylmethyltetrazol-5-yl)penam, and 0.30 ml. of triethylamine, in 20 ml. of methylene chloride, at 0° C., is added dropwise, 341 mg. of phenoxyacetyl chloride dissolved in 5 ml. of methylene chloride. Stirring is continued at 0° C. for 15 minutes, and then at 25° C. for one hour. The solvent is removed by evaporation in vacuo, and the residue is partitioned between ethyl acetate and water at pH 7.0. The ethyl acetate layer is removed, washed with water, dried using anhydrous sodium sulfate, and then the solvent is removed by evaporation in vacuo. This affords the title compound as a mixture of isomers as indicated.

In like manner, acylation of 6-amino-2,2-dimethyl-3-(1-triphenylmethyltetrazol-5-yl)penam with phenoxyacetyl chloride provides 6-(2-phenoxyacetamido)-2,2-dimethyl-3-(1-triphenylmethyltetrazol-5-yl)penam; and acylation of 6-amino-2,2-dimethyl-3-(2-triphenylmethyltetrazol-5-yl)penam with phenoxyacetyl chloride provides 6-(2-phenoxyacetamido)-2,2-dimethyl-3-(2-triphenylmethyltetrazol-5-yl)penam.

EXAMPLE CCI

Acylation of the 6-amino-2,2-dimethyl-3(1-[substituted triphenylmethyl]tetrazol-5-yl)penam and 6-amino-2,2-dimethyl-3-(2-[substituted triphenylmethyl]- tetrazol-5-yl)penam mixtures of Example CIC with phenoxyacetyl chloride, according to the procedure of Example CC, provides, in each case, mixtures of the corresponding 6-(2-phenoxyacetamido)-2,2-dimethyl-3-(1-[substituted triphenylmethyl]tetrazol-5-yl)penam and 6-(2-phenoxyacetamido)-2,2-dimethyl-3-(2-[substituted triphenylmethyl]tetrazol-5-yl)penam compounds. In this way, the following mixtures are produced.

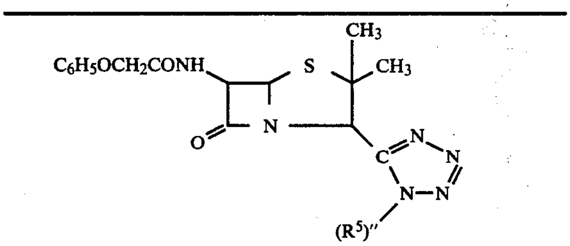

and

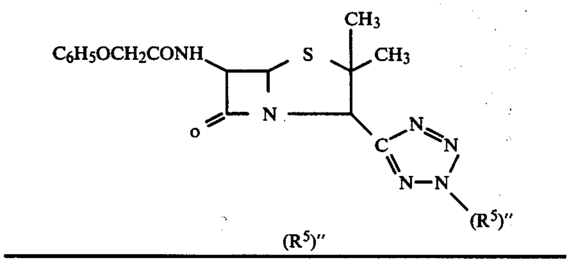

diphenyl(2-fluorophenyl)methyl
diphenyl(3-chlorophenyl)methyl
diphenyl(4-bromophenyl)methyl
diphenyl(2-ethylphenyl)methyl
diphenyl(4-n-prophenyl)methyl
diphenyl(3-sec-butylphenyl)methyl
diphenyl(4-ethoxyphenyl)menthyl
diphenylbiphenylylmethyl
phenyldi(3-tolyl)methyl
phenyldi(3-chlorphenyl)methyl
phenyl(4-chlorophenyl)(4-methoxyphenyl)methyl
phenyldi(biphenylyl)methyl
tri(4-tolyl)methyl
(4-isopropylphenyl)di(3-methoxyphenyl)methyl

EXAMPLE CCII 6-(2-Phenoxyacetamido)-2,2-dimethyl-3-(5-tetrazolyl)penam

To a stirred solution of 1.17 g. of 6-(2-phenoxyacetamido)-2,2-dimethyl-3-(1[2]-triphenylmethyltetrazol-5-yl)penam in 20 ml. of acetone is added 1.0 ml. of water followed by 50 mg. of p-toluenesulfonic acid monohydrate. The mixture is stirred at ambient temperature for one hour, and then the solvent is removed by evaporation in vacuo. To the residue is added 50 ml. of water and 50 ml. of ethyl acetate. The pH is adjusted to 7.0, the layers are separated, and the ethyl acetate is discarded. Fresh ethyl acetate is added to the remaining aqueous phase, and the pH is adjusted to 2.0. The ethyl acetate layer is removed, washed with water, and dried using anhydrous sodium sulfate. Evaporation of the solvent in vacuo leaves the crude title product.

EXAMPLE CCIII

When each of the 6-(2-phenoxyacetamido)-2,2-dimethyl-3-(1-[substituted triphenylmethyl]tetrazol-5-yl)penam and 6-(2-phenoxyacetamido)-2,2-dimethyl-3-(2-[substituted triphenylmethyl]tetrazol-5-yl)penam mixtures, selected from those in Example CCI, are subjected to the reaction conditions of Example CCII, the product in each case is 2-(phenoxyacetamido)-2,2-dimethyl-3-(5-tetrazolyl)penam.

EXAMPLE CCIV 6-(D-2-Amino-2-phenylacetamido)-2,2-dimethyl-3-(5-tetrazolyl)penam hydrochloride A slurry of 50 mg. of 6-(D-2-amino-2-phenylacetamido)-2,2-dimethyl-3-(5-tetrazolyl)penam in 2 ml. of de-ionized water is stirred for 5 minutes at ambient temperature. The pH is then adjusted to 2.45 using dilute hydrochloric acid, and the solution thus obtained is immediately lyophilized. This affords 52 mg. Of 6-(D-2-amino-2-phenylacetamido)-2,2-dimethyl-3-(5-tetrazolyl)penam hydrochloride as a fluffy white solid.

EXAMPLE CCV 6-(D-2-Amino-2-[4-hydroxyphenyl]acetamido)-2,2-dimethyl-3-(5-tetrazolyl)penam, Potassium Salt To a stirred solution of 1.94 g. (D-2-amino-2-[4-hydroxyphenylacetamido)-2,2-dimethyl-3-(5-tetrazolyl)penam in 100 ml. of methanol, cooled to −30° C., is added dropwise 5 ml. of a 1.0 N solution of potassium hydroxide in methanol. The mixture is allowed to warm to 0° C., and then it is added dropwise with stirring to 700 ml. of ether. The solid which precipitates is removed by filtration and dried under high vacuum. This affords 1.65 g. (76% yield) of the title potassium salt, m.p. 185° C. (dec.).

When the above procedure is repeated, except that the potassium hydroxide used therein is replaced by an equimolar amount of sodium hydroxide, the product is the sodium salt of 6-(D-2-amino-2-(4-hydroxyphenyl-]acetamido)-2,2-dimethyl-3-(5-tetrazolyl)penam.

EXAMPLE CCVI 6-(D-2-Amino-2-[4-hydroxyphenyl]acetamido)-2,2-dimethyl-3-(5-tetrazolyl)penam Calcium Salt To a stirred solution of 2.0 g. of 6-(D-2-amino-2-[4-hydroxyphenyl]acetamido)-2,2-dimethyl-3-(5-tetrazolyl)penam in 20 ml. of dimethylformamide is added a turbid solution of 0.19 g. of calcium hydroxide in 100 ml. of dimethylforamamide, over 5 minutes. The mixture is heated at 35°–40° C. for 1 hour, and then an additional 30 ml. of dimethylformamide is added. Heating at 35°–40° C. is continued for a further 30 minutes, and then the cooled solution is added dropwise to 700 ml. of ether. An oil precipitates. The solvent is decanted off and to the residue is added 100 ml. of ethanol, followed by 400 ml. of ether. The oil slowly solidifies and then it is recovered by filtration and dried under high vacuum. This affords 1.4 g. (67% yield) of the title calcium salt.

EXAMPLE CCX

In vitro antibacterial activities for a number of the compounds of this invention are presented below.

In Table II, the minimum inhibitory concentrations (MIC's) of compounds of formula I, wherein $R^2$ is hydrogen, against a strain of *Streptococcus pyogenes*, are reported; and in Table III, minimum inhibitory concentrations of compounds of formula I, wherein $R^2$ is hydrogen, against a strain of *Staphylococcus aureus*, are presented. Because of the tautomeric nature of such tetrazole derivatives, referred to hereinbefore, each of the preparations tested also contains some of the corresponding compound of formula II, wherein $R^3$ is hydrogen.

TABLE II

| $R^1$ | MIC (μg/ml) vs. *Strep. pyogenes* |
|---|---|
| 2-phenylacetyl | <0.1 |
| 3-(o-chlorophenyl)-5-methyl-4-isoxazolecarbonyl | <0.1 |
| 2-azido-2-phenylacetyl | <0.1 |
| 2-cyanoacetyl | 0.1 |
| 2-(1-tetrazolyl)acetyl | <0.39 |
| 2-phenoxyacetyl | <0.1 |
| phenoxycarbonyl | <0.1 |
| benzyloxycarbonyl | <0.1 |
| ethoxycarbonyl | <0.1 |
| acetyl | <0.1 |
| 2-bromoacetyl | <0.1 |
| 2-(4-pyridylthio)acetyl | <0.1 |
| 2-(N,N'-diethylamidinothio)acetyl | <0.1 |
| hydrogen | <0.1 |
| 3-(carbamoyl)acryloyl | <0.1 |
| 2,6-dimethoxybenzoyl | 0.2 |
| D-2-amino-2-phenylacetyl | <0.1 |
| D-2-amino-2-(m-hydroxyphenyl)acetyl | <0.1 |
| DL-2-amino-2-(3,4-dihydroxyphenyl)acetyl | <0.1 |
| L-2-amino-2-(p-hydroxyphenyl)acetyl | <0.1 |
| D-2-amino-2-(2-thienyl)acetyl | 0.1 |
| DL-2-amino-2-(p-[N,N-dimethylamino]phenyl)acetyl | 0.39 |
| D-2-amino-2-(3-chloro-4-hydroxyphenyl)acetyl | 0.1 |
| DL-2-amino-2-(p-chlorophenyl)acetyl | <0.1 |
| DL-2-amino-2-(m-chlorophenyl)acetyl | 0.78 |
| DL-2-amino-2-(2-bromo-5-hydroxyphenyl)acetyl | <0.1 |
| D-2-amino-2-(m-fluorophenyl)acetyl | <0.1 |
| D-2-amino-3-methylbutyryl | 0.2 |
| D-2-amino-3-phenylpropionyl | 0.39 |
| D-2-amino-2-(p-hydroxyphenyl)acetyl | <0.1 |
| 1-aminocyclohexylcarbonyl | 25 |
| D-2-amino-2-(1,4-cyclohexadienyl)acetyl | <0.1 |
| DL-3-amino-2-phenylpropionyl | 12.5 |
| 2-(o-[aminomethyl]phenyl)acetyl | <0.1 |
| 2-(o-[2-aminoethoxy]phenyl)acetyl | <0.1 |
| L-2-amino-3-(p-hydroxyphenyl)propionyl | 0.2 |
| 2-(benzamido)acetyl | 0.1 |
| 2-(2-bromoacetamido)-2-phenylacetyl | <0.1 |
| 2-(2-[$\Delta^1$-imidazolin-2-ylthio]acetamido)-2-phenylacetyl | <0.1 |
| D-2-(p-methoxybenzenesulfonamido)-2-phenylacetyl | 0.2 |
| D-2-(naphthalenesulfonamido)-2-phenylacetyl | 0.2 |
| D-2-(2-thiophenesulfonamido)-2-phenylacetyl | 0.39 |
| D-2-(ethanesulfonamido)-2-phenylacetyl | 0.39 |
| D-2-(2-[methanesulfonamido]acetamido)-2-phenylacetyl | <0.1 |
| D-2-(2-[benzenesulfonamido]acetamido)-2-phenylacetyl | <0.1 |
| D-2-(2-[α-toluenesulfonamido]acetamido)-2-phenylacetyl | <0.1 |
| D-2-(benzenesulfonamido)-2-(p-hydroxyphenyl)acetyl | <0.1 |
| D-2-(propanesulfonamido)-2-(p-hydroxyphenyl)acetyl | 0.1 |
| D-2-(2-[benzamido]acetamido)-2-phenylacetyl | <0.1 |
| D-2-(2-[acetamido]acetamido)-2-phenylacetyl | <0.1 |
| D-2-(2-[propionamido]acetamido)-2-phenylacetyl | <0.1 |
| D-2-(2-[p-chlorobenzamido]acetamido)-2-phenylacetyl | 0.1 |
| D-2-(2-[p-nitrobenzamido]acetamido)-2-phenylacetyl | <0.1 |
| D-2-(2-[p-methoxybenzamido]acetamido)-2-phenylacetyl | 0.1 |
| D-2-(2-[butyramido]acetamido)-2-phenylacetyl | <0.1 |
| D-2-(2-[ethoxycarbonylamino]acetamido)-2-phenylacetyl | <0.1 |
| D-2-(2-[benzyloxycarbonylamino]acetamido)-2-phenylacetyl | 0.39 |
| D-2-(3-phenylureido)-2-(p-hydroxyphenyl)acetyl | <0.1 |
| D-2-(3-[p-methoxyphenyl]ureido)-2-phenylacetyl | <0.1 |
| D-2-(3-[p-chlorophenyl]ureido)-2-phenylacetyl | <0.1 |
| D-2-(3-[p-tolyl]ureido)-2-phenylacetyl | <0.1 |
| D-2-(3-phenylureido)-2-phenylacetyl | <0.1 |
| D-2-(3-methylureido)-2-phenylacetyl | 50 |
| D-2-(3-[p-methoxyphenyl]ureido)-2-(p-hydroxyphenyl)acetyl | <0.1 |
| D-2-(3-[p-chlorophenyl]ureido)-2-(p-hydroxyphenyl)acetyl | <0.1 |
| D-2-(2-aminoacetamido)-2-phenylacetyl | <0.1 |
| D-2-(2-aminoacetamido)-2-(p-hydroxyphenyl)acetyl | <0.1 |
| D-2-(2-[benzamidino]acetamido)-2-phenylacetyl | <0.1 |
| D-2-(2-[4-pyridinecarboxamidino]acetamido)-2-phenylacetyl | <0.1 |
| D-2-(2-[4-pyridine-N-oxide-carboxamidino]acetamido)-2-phenylacetyl | <0.1 |
| D-2-(2-[2-(p-chlorophenyl)acetamidino]acetamido)-2-phenylacetyl | 0.2 |
| D-2-(2-[p-nitrobenzamidino]acetamido)-2-phenylacetyl | <0.1 |
| D-2-(2-[m-sulfamoylbenzamidino]acetamido)-2-phenylacetyl | <0.1 |
| D-2-(2-[m-cyanobenzamidino]acetamido)-2-phenylacetyl | 6.25 |

TABLE II-continued

| $R^1$ | MIC (μg/ml) vs. *Strep. pyogenes* |
|---|---|
| D-2-(2-[2-benzimidizolecarboxamidino]acetamido)-2-phenylacetyl | <0.1 |
| D-2-(2-[2-pyridmidinecarboxamidino]acetamido)-2-phenylacetyl | 0.78 |
| D-2-(2-[3-cyano-5-iodobenzamidino]acetamido)-2-phenylacetyl | <0.1 |
| 2-(3,5-dimethylbenzamidino)acetyl | 0.39 |
| 2-(4-pyridinecarboxamidino)acetyl | <0.1 |
| 2-(acetamidino)acetyl | <0.1 |
| 2-(2-thiophenecarboxamidino)acetyl | <0.1 |
| 2-(4-pyridinecarboxamidino)-3-phenylpropionyl | 0.2 |
| D-2-(2-[4-pyridinecarboxamidino]acetamido)-2-(p-hydroxyphenyl)acetyl | <0.1 |
| D-2-(2-[3-ethylureido]acetamido)-2-phenylacetyl | <0.1 |
| D-2-(2-[3-phenylureido]acetamido)-2-phenylacetyl | <0.1 |
| D-2-(2-[3-methylureido]acetamido)-2-phenylacetyl | <0.1 |
| D-2-(3-guanylureido)-2-phenylacetyl | <0.1 |
| D-2-ureido-2-phenylacetyl | 0.1 |
| 2-sulfamoyl-2-phenylacetyl | <0.1 |
| D-2-(p-guanidinobenzamido)-2-phenylacetyl | 1.56 |
| D-2-(2-[guanidino]acetamido)-2-phenylacetyl | <0.1 |
| D-2-(2-[p-guanidinophenyl]acetamido)-2-phenylacetyl | 1.56 |
| D-2-(3-[guanyl]propionamido)-2-phenylacetyl | <0.1 |
| D-2-(2-[N-methylguanidino]acetamido)-2-phenylacetyl | <0.1 |
| D-2-(2-[3-guanyl)ureido]acetamido)-2-phenylacetyl | 3.12 |
| D-2-(3-[2-furoyl]ureido)-2-phenylacetyl | <0.1 |
| 2-(3-acetylureido)-2-phenylacetyl | <0.1 |
| 2-(3-butyrylureido)-2-phenylacetyl | <0.1 |
| 2-(3-[chloroacetyl]ureido)-2-phenylacetyl | 0.2 |
| 2-(3-[3-pyridylcarbonyl]-ureido)-2-phenylacetyl | 0.1 |
| 2-(3-benzoylureido)-2-phenylacetyl | <0.1 |
| 2-(3-[3,5-dibromobenzoyl]-ureido)-2-phenylacetyl | <0.1 |
| 2-(3-[4-pyridylcarbonyl]-ureido)-2-phenylacetyl | 0.2 |
| 2-(3-propionylureido)-2-phenylacetyl | <0.1 |
| 2-(3-[cyclopropylcarbonyl]-ureido)-2-phenylacetyl | <0.1 |
| 2-(3-[1-adamantylcarbonyl]-ureido)-2-phenylacetyl | <0.1 |
| 2-(3-benzoylthioureido)-2-phenylacetyl | 1.56 |
| N-acetylcarbomoyl | 1.56 |
| N-(2-furoyl)carbamoyl | 1.56 |
| N-(p-toluenesulfonyl)carbonyl | 1.56 |
| 2-carboxy-2-phenylacetyl | 0.002 |
| 2-carboxy-2-(2-thienyl)acetyl | 0.1 |
| 2-carboxy-2-(3-thienyl)acetyl | 0.1 |
| 2-sulfo-2-phenylacetyl | 200 |
| 2-(5-indanyloxycarbonyl)-2-phenylacetyl | <0.1 |
| D-2-sulfoamino-2-phenylacetyl | 12.5 |
| phenylpyruvoyl | <0.1 |
| phenylglyoxyloyl | <0.1 |
| D-2-(benzoylformamido)-2-phenylacetyl | 25 |
| D-2-(acetylformamido)-2-phenylacetyl | 50 |
| D-2-(ethoxycarbonylformamido)-2-phenylacetyl | <0.1 |
| D-2-(phenoxycarbonylformamido)-2-phenylacetyl | 25 |
| D-2-(ethoxycarbonylamino)-2-phenylacetyl | 6.25 |
| D-2-(benzyloxycarbonylamino)-2-phenylacetyl | <0.1 |
| D-2-(2-carboxy-3-[2-thienyl]acrylamido)-2-phenylacetyl | <0.1 |
| D-2-(2-carboxy-3-[p-chlorophenyl]acrylamido)-2-phenylacetyl | <0.1 |
| D-2-allophanamido-2-phenylacetyl | <0.1 |
| 3-aminomethyl-2-phenylisocrotonoyl | 12.5 |
| D-2-(dimethylaminomethyleneamino)-2-phenylacetyl | <0.1 |
| D-2-(dimethylaminomethyleneamine)-2-(p-hydroxyphenyl)acetyl | <0.1 |
| 2-(3-[2-(p-chlorophenyl)acetimidoyl]ureido)acetyl | 100 |
| 2-(3-[benzimidoyl]ureido)-acetyl | <0.1 |
| 2-(3-[p-methoxybenzimidoyl]-uredio)acetyl | 0.1 |
| 2-(2-[3-(2-[p-chlorophenyl]-acetimidoyl)ureido]acetamido)-2-phenylacetyl | <0.1 |
| 2-(2-[3-(benzimidoyl)ureido]-acetamido)-2-phenylacetyl | 0.78 |
| 2-(2-[3-(p-methoxybenzimidoyl)ureido]acetamido-2-phenylacetyl | 1.56 |
| 3-phenylcarbamoyl | <0.1 |
| 3-ethylcarbamoyl | <0.1 |
| D-2-(2-phenylacetamido)-2-phenylacetyl | <0.1 |
| D-2-(benzamido)-2-phenylacetyl | <0.1 |
| D-2-(butyramido)-2-phenylacetyl | 0.39 |
| D-2-(2-furancarboxamido)-2-phenylacetyl | 0.1 |
| D-2-(2-thiophenecarboxamido)-2-phenylacetyl | <0.1 |
| D-2-(2-[2-thienyl]acetamido)-2-phenylacetyl | 0.1 |
| D-2-(3-pyridinecarboxamido)-2-phenylacetyl | <0.1 |
| D-2-(2-pyrrolecarboxamido)-2-phenylacetyl | <0.1 |
| D-2-(2-[2-quinoxalinecarboxamidino]acetamido)-2-phenylacetyl | 0.1 |
| D-2-(2-[m-carbamoylbenzamidino]acetamido)-2-phenylacetyl | <0.1 |

TABLE II-continued

| $R^1$ | MIC (μg/ml) vs. *Strep. pyogenes* |
|---|---|
| D-2-(carboxymethyl)acetamido-2-phenylacetyl | 0.2 |
| D-2-(4-carboxy-2,3-epoxypropionamido)-2-phenylacetyl | 0.2 |
| 2-(4-aminomethylphenyl)acetyl | <0.1 |
| 2-(2-[carboxymethyl]phenyl)acetyl | 0.2 |
| 2-amino-2-(4-aminophenyl)acetyl | 0.039 |
| D-2-amino-2-(3-aminophenyl)acetyl | |
| D-2-acetyl-2-phenylacetyl | 0.004 |
| 2-(4-[2-azidoethoxy]phenyl)acetyl | <0.1 |
| D-2-(3-[2-(guanylthio)acetyl]ureido)-2-phenylacetyl | 0.004 |
| D-2-(3-phenylthioureido)-2-phenylacetyl | <0.1 |
| D-2-phthalimido-2-phenylacetyl | 0.004 |
| D-2-(4-aminobenzamido)-2-phenylacetyl | <0.1 |
| D-2-(2-[4-aminophenyl]acetamido)-2-phenylacetyl | <0.1 |
| D-2-(2-phenoxyacetamido)-2-(4-hydroxyphenyl)acetyl | 0.2 |
| D-2-(3-[2-(N,N'-diethylguanylthio)acetyl]-ureido)-2-phenylacetyl | 0.004 |
| 2-ethoxy-1-naphthoyl | <0.1 |
| DL-2-amino-2-(m-nitrophenyl)acetyl | 0.004 |
| DL-2-amino-2-(p-sulfamoylphenyl)acetyl | <0.1 |
| D-2-amino-2-(p-fluorophenyl)acetyl | 3.12 |
| D-2-amino-2-(2-furyl)acetyl | 0.39 |
| D-2-amino-2-(2-tetrahydrofuryl)acetyl | <0.1 |
| DL-2-amino-2-(3-pyridyl)acetyl | <0.1 |
| D-2-amino-(4-aminophenyl)acetyl | 0.39 |
| D-2-amino-(3-aminophenyl)acetyl | <0.01 |
| 2-(2-[aminomethyl]phenylthio)acetyl | 1.56 |
| 2-(3-[2-aminoethoxy]phenyl)acetyl | <0.1 |
| 2-(4-[2-aminoethoxy]phenyl)acetyl | <0.1 |
| D-2-(2-chloroacetamido)-2-phenylacetyl | <0.1 |
| D-2-(2-chloroacetamido)-2-(2-furyl)acetyl | <0.1 |
| D-2-([N,N'-dimethylamidinothio]acetamido-2-phenylacetyl | 0.004 |
| D-2-(2-[pentamethyleneamidinothio]-acetamido)-2-phenylacetyl | <0.1 |
| D-2-(2-[2-benzimidazoylthio]acetamido)-2-phenylacetyl | <0.1 |
| D-2-(2-[N,N'-diethylamidinothio]acetamido)-2-phenylacetyl | 0.004 |
| D-2-(2-[N,N'-dibutylamidinothio]acetamido)-2-phenylacetyl | 0.004 |
| D-2-(2-[4-oxo-$\Delta^2$-imidazolin-2-ylthio]-acetamido)-2-phenylacetyl | 0.1 |
| D-2-(2-[amidinothio]acetamido)-2-phenylacetyl | 0.004 |
| D-2-(2-[2-imidazolythio]acetamido)-2-phenylacetyl | 0.2 |
| D-2-(3-aminopropionamido)-2-phenylacetyl | <0.1 |
| 2-(phenylthio)acetyl | 0.78 |
| D-2-(2-[phenylthio]acetamido)-2-phenylacetyl | <0.1 |
| 2-(ethylthio)acetyl | <0.1 |
| D-2-(2-[ethylthio]acetamido)-2-phenylacetyl | <0.1 |
| 3-(methoxycarbonyl)butyryl | 6.25 |
| D-2-(3-[methoxycarbonyl]butyramido)-2-phenylacetyl | 6.25 |
| 2-(ethoxycarbonyl)acetyl | 0.39 |
| D-2-(2-[ethoxycarbonyl]acetamido)-2-phenylacetyl | <0.1 |
| 2-(benzylthio)acetyl | 0.2 |
| D-2-(2-[benzylthio]acetamido)-2-phenylacetyl | 0.78 |
| D-2-(3-benzamidopropionamido)-2-phenylacetyl | <0.1 |
| D-2-(3-[4-chlorobenzamido]propionamido)-2-phenylacetyl | <0.1 |
| D-2-(3-[3-chlorobenzamido]propionamido)-2-phenylacetyl | <0.1 |
| D-2-(3-[2-furancarboxamido]propionamido)-2-phenylacetyl | <0.1 |
| D-2-(3-acetamidopropionamido)-2-phenylacetyl | <0.1 |
| D-2-(3-benzamidinopropionamido)-2-phenylacetyl | 3.12 |
| D-2-(3-[3,5-dibromobenzamidino]propion- | <0.1 |

TABLE II-continued

| $R^1$ | MIC (μg/ml) vs. *Strep. pyogenes* |
|---|---|
| amido)-2-phenylacetyl | |
| D-2-(3-acetamidinopropionamido)-2-phenyl-acetyl | <0.1 |
| D-2-(3-[3,4-dichlorobenzamidino]propion-amido)-2-phenylacetyl | 0.78 |
| D-2-(3-[4-chlorophenyl]acetamidinopropion-amido)-2-phenylacetyl | 1.56 |
| D-2-(2-[3-(N-methylguanyl)ureido]acetamido)-2-phenylacetyl | <0.1 |
| D-2-(2-[3-(N-ethylguanyl)ureido]-acetami-do)-2-phenylacetyl | <0.1 |
| D-2-(2-[3-(N-benzylguanyl)ureido]acet-amido)-2-phenylacetyl | 0.1 |
| D-2-(2-[2-benzthiazolecarboxamidino]-acetamido)-2-phenylacetyl | <0.1 |
| D-2-(2-[3,5-disulfamoylbenzamidino]-acetamido)-2-phenylacetyl | 0.004 |
| D-2-(2-[3-sulfamoyl-5-bromobenzamidino]-acetamido)-2-phenylacetyl | 0.0004 |
| D-2-(2-[3-chloro-5-cyanobenzamidino]acet-amido)-2-phenylacetyl | 0.004 |
| D-2-(2-[2-benzoxazolecarboxamidino]acet-amido)-2-phenylacetyl | 0.39 |
| D-2-(2-[3-sulfamoyl-5-chlorobenzamidino]-acetamido)-2-phenylacetyl | 0.004 |
| D-2-(3-[4-pyridinecarboxamidino)propion-amido)-2-phenylacetyl | <0.1 |
| D-2-(3-pyridine-1-oxide-4-carboxamidino]-propionamido)-2-phenylacetyl | 3.12 |
| D-2-(3-[2-thienylcarboxamidino]propion-amido)-2-phenylacetyl | <0.1 |
| D-2-(2-[3-(N-p-chlorobenzylgurnyl)ureido]-acetamido)-2-phenylacetyl | 0.39 |
| D-2-(2-[3-(N-[ cyclohexylmethyl]guanyl)-ureido]acetamido)-2-phenylacetyl | 0.2 |
| D-2-(2-[3-(N-[4-pyridylmethyl]guanyl)-ureido]acetamido)-2-phenylacetyl | 0.004 |
| D-2-(2-[3-(guanyl)ureido]acetamido)-2-(4-hydroxyphenyl(acetyl | 0.004 |
| D-2-(3-[2-phenylacetyl]ureido)-2-phenylacetyl | <0.1 |
| D-2-(3-[benzyloxycarbonyl]ureido)-2-phenylacetyl | 0.004 |
| D-2-(3-[acetyl]thioureido)-2-phenylacetyl | 3.2 |
| D-2-(3-[3-methyl-5-isoxazolycarbonyl]-ureido)-2-phenylacetyl | <0.1 |
| D-2-(2-[4-bromophenyl]acetamido)-2-phenyl-acetyl | 0.2 |
| D-2-(2-[4-methoxyphenyl]acetamido)-2-phenyl-acetyl | 0.1 |
| D-2-(4-pyridinecarboxamido)-2-phenylacetyl | 3.12 |
| D-2-(2-[4-nitrophenyl]acetamido)-2-phenyl-acetyl | <0.1 |
| D-2-(2-[2-furyl]acetamido)-2-phenylacetyl | <0.1 |
| D-2-(4-nitrobenzamido)-2-phenylacetyl | 0.004 |
| D-2-(2-phenoxyacetamido)-2-phenylacetyl | 0.004 |
| D-2-(2-cyanoacetamido)-2-phenylacetyl | 0.004 |
| D-2-(2-azicoacetamido)-2-phenylacetyl | 0.2 |
| D-2-(2-[3-(guanyl)ureido]acetamido)-2-(4-hydroxyphenyl)acetyl | 0.004 |
| D-2-(3-[guanyl]ureido)-2-(4-hydroxyphenyl)-acetyl | 0.004 |
| D-2-(2-[3-benzoylureido]acetamido)-2-phenyl-acetyl | <0.1 |
| D-2-(2-[3-methanesulfonylureido]acetamido)-2-phenylacetyl | 0.2 |
| D-2-(3-[3-ethylthioureido]propionamido)-2-phenylacetyl | 0.39 |
| D-2-(3-[3-phenylthioureido]propionamido)-2-phenylacetyl | 1.56 |
| D-2-(3-[3-methylureido]propionamido)-2-phenylacetyl | <0.1 |
| D-2-(3-[3-phenylureido]propionamido)-2-phenylacetyl | <0.1 |
| 2-(3-azidomethyl-2-thienyl-acetyl | ≦0.1 |
| 2-(3-aminomethyl-2-thienyl)-acetyl | ≦0.1 |
| 2-(5-azidomethyl-2-thienyl)-acetyl | ≦0.1 |

TABLE II-continued

| $R^1$ | MIC (μg/ml) vs. *Strep. pyogenes* |
|---|---|
| 2-(5-aminomethyl-2-thienyl)-acetyl | ≦0.1 |
| 2-(2-azidomethylphenyl)acetyl | ≦0.1 |

TABLE III

| $R^1$ | MIC (μg/ml) vs. *Staph. aureus* |
|---|---|
| D-2-amino-2-(p-methoxyphenyl)acetyl | <0.1 |
| 2-aminoacetyl | 200 |
| D-2-amino-3-(3-indolyl)propionyl | 6.25 |
| D-2-amino-2-(3-thienyl)acetyl | <0.1 |
| 2-(2-[4-pyridylthio]acetamido)-2-phenylacetyl | 100 |
| D-2-(methanesulfonamido)-2-phenylacetyl | 1.56 |
| D-2-(propanesulfonamido)-2-phenylacetyl | 0.78 |
| D-2-(p-chlorobenzenesulfonamido)-2-phenylacetyl | 1.56 |
| D-2-(p-nitrobenzenesulfonamido)-2-phenylacetyl | 1.56 |
| D-2-(α-toluenesulfonamido)-2-phenylacetyl | 0.39 |
| D-2-(2-[3,5-dibromobenzamidino]acetamido)-2-phenylacetyl | 1.56 |
| D-2-(2-[acetamidino]acetamido)-2-phenylacetyl | 1.56 |
| 2-(4-pyridinecarboxamidino)-3-methylbutyryl | 50 |
| D-2-(2-[guanyl]acetamido)-2-phenylacetyl | 12.5 |
| D-2-(2-[$\Delta^1$-imidazolin-2-yl]acetamido)-2-phenylacetyl | 3.12 |
| 2-(3-[2-furoyl]thioureido)-2-phenylacetyl | 0.78 |
| 2-(3-[p-toluenesulfonly]-ureido)-2-phenylacetyl | 6.25 |
| L-2-hydroxy-2-phenylacetyl | <0.1 |
| D-2-hydroxy-2-phenylacetyl | <0.1 |
| D-2-(2-[dimethylaminomethyleneamino]acetamido)-2-phenyl-acetyl | 6.25 |
| D-2-(acetamido)-2-phenylacetyl | 0.78 |
| D-2-(2-[2-pyrrolecarboxamidino]acetamido)-2-phenylacetyl | 50 |

Minimum inhibitory concentrations of other compounds of this invention are presented in Table IV.

TABLE IV

| Compound | MIC (μg/ml) vs. *Strep. pyrogenes* |
|---|---|
| 6-(5-oxo-4-phenyl-1-imidazolidinyl)-2,2-dimethyl-3-(5-tetrazolyl)penam | 6.25 |
| 6-(5-oxo-4-[p-hydroxyphenyl]imidazolidinyl)-2,-2-dimethyl-3-(5-tetrazolyl)penam | 6.25 |
| 6-(2,2-dimethyl-5-oxo-4-phenyl-1-imidazolidinyl)-2,2-dimethyl-3-(5-tetrazolyl)penam | 1.56* |
| 6-(2,2-dimethyl-5-oxo-4-[p-hydroxyphenyl]-1-imidazolidinyl)-2,2-dimethyl-3-(5-tetrazolyl)-penam | 0.78* |
| 6-([hexahydro-1-azepinyl]methayleneamino)-2,2-dimethyl-3-(5-tetrazolyl)penam | 50 |
| 6-([dimethylamino]methyleneamino-2,2-dimethyl-3-(5-tetrazolyl)penam | 12.5 |
| 6-(2-phenylacetamido)-2,2-dimethyl-3-(1-[2]-pivaloyloxymethyl-tetrazol-5-yl)penam | 0.2 |
| 6-(D-2-amino-2-[p-hydroxyphenyl]acetamido)-2,2-dimethyl-3-(2-pivaloyloxymethyltetrazol-5-yl)penam | 0.39 |
| 6-(2-[2-aminomethylphenyl]acetamido)-2,2-dimethyl-3-(1-[2]pivaloyloxymethyltetrazol-5-yl)penam | <0.1 |

*MIC against *Staph. aureus*

What is claimed is:

1. A method of treating bacterial infections in a mammal which comprises administering to said mammal an antibacterial effective amount of a compound having antibacterial activity and selected from the group consisting of

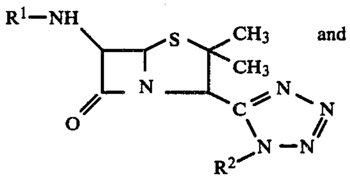

and

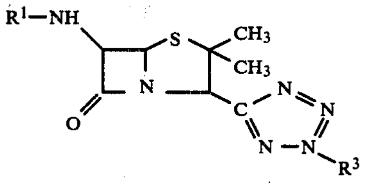

and the pharmaceutically acceptable salts thereof wherein $R^1$ is an acyl group of an organic carboxylic acid or the acyl group of an acyl derivative selected from the group consisting of esters, amides and chlorides of organic carboxylic acids and $R^2$ and $R^3$ are each selected from the group consisting of hydrogen, alkanoyloxymethyl having from 3 to 8 carbon atoms, 1-(alkanoyloxy)ethyl having from 4 to 9 carbon atoms and 3-phthalidyl.

2. The method according to claim 1, wherein $R^1$ is

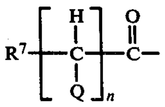

wherein n is 0 or 1;

$R^7$ is selected from the group consisting of hydrogen, alkyl having from one to twelve carbon atoms, alkenyl having from two to twelve carbon atoms, cycloalkyl having from three to seven carbon atoms, cycloalkenyl having from five to eight carbon atoms, cycloheptatrienyl, 1,4-cyclohexadienyl, 1-aminocycloalkyl having from four to seven carbon atoms, cyanomethyl, 5-methyl-3-phenyl-4-isoxazolyl, 5-methyl-3-(o-chlorophenyl)-4-isoxazolyl, 5-methyl-3-(2,6-dichlorophenyl)-4-isoxazolyl, 5-methyl-3-(2-chloro-6-fluorophenyl)-4-isoxazolyl, 2-alkoxy-1-naphthyl having from one to four carbon atoms in said alkoxy, phenyl, phenoxy, phenylthio, pyridylthio, benzyl, sydnonyl, thienyl, furyl, pyridyl, thiazolyl, isothiazolyl, pyrimidinyl, tetrazolyl, triazolyl, imidazolyl, pyrazolyl, substituted phenyl, substituted phenoxy, substituted phenylthio, substituted pyridylthio, substituted benzyl, substituted thienyl, substituted furyl, substituted pyridyl, substituted tetrazolyl, substitued thiazolyl, substituted isothiazolyl, substitued pyrimidinyl, subtriazolyl, substitued imidazolyl and substituted pyrazolyl, each substituted moiety being substituted by up to two members selected from the group consisting of fluoro, chloro, bromo, hydroxy, hydroxymethyl, amino, N,N-dialkylamino having from one to four carbon atoms in each of said alkyl groups, alkyl having from one to four carbon atoms, aminomethyl, aminoethyl, alkoxy having from one to four carbon atoms, alkylthio having from one to four carbon atoms, 2-aminoethoxy and N-alkylamino having from one to four carbon atoms;

and Q is selected from the group consisting of hydrogen, alkyl having from one to six carbon atoms, hydroxy, azido, carboxy, sulfo, carbamoyl, phenoxycarbonyl, indanyloxycarbonyl, sulfoamino, aminomethyl, amino and NH—(CO—$CH_2$—NH-$)_m$—CO—Z;

wherein Z is selected from the group consisting of alkyl having from one to six carbon atoms, phenyl, substituted phenyl, furyl, thienyl, pyridyl, pyrrolyl, amino, N-alkylamino having from one to six carbon atoms, anilino, substituted anilino, guanidino, alkanoylamino having from two to seven carbon atoms, benzamido, substituted benzamido, thiophenecarboxyamido, furancarboxamido, pyridinecarboxamido, aminomethyl, guanidinomethyl, alkanecarboxyamidinomethyl having from three to eight carbon atoms, benzamidinomethyl, (substituted benzamidino)methyl, thiophenecarboxamidinomethyl, furancarboxamidinomethyl, pyridinecarboxamidinomethyl, pyrrolecarboxamidinomethyl and 2-benzimidazolecarboxamidinomethyl, each substituted moiety being substituted by up to two members selected from the group consisting of fluoro, chloro, bromo, iodo, alkyl having from one to four carbon atoms alkoxy having from one to four carbon atoms, sulfamyl, carbamoyl and cyano;

and m is 0 or 1:

provided that when $R^7$ is 1-aminocycloalkyl, n is 0; and provided that when $R^7$ is selected from the group consisting of phenoxy, phenylthio, pyridylthio, substituted phenoxy, substituted phenylthio and substitued pyridylthio and n is 1, Q is selected from the group consisting of hydrogen, alkyl having from one to six carbon atoms, carboxy, sulfo, carbamoyl, phenoxycarbonyl, substituted phenoxycarbonyl, indanyloxycarbonyl and aminomethyl.

3. The method according to claim 2, wherein $R^2$ and $R^3$ are each hydrogen, n is 1, $R^7$ is phenyl and Q is hydrogen.

4. The method according to claim 2, wherein $R^2$ and $R^3$ are each hydrogen, n is 1, $R^7$ is phenoxy and Q is hydrogen.

5. The method according to claim 2, wherein $R^2$ and $R^3$ are each hydrogen, n is 1, and $R^7$ is selected from the group consisting of phenyl and said substituted phenyl.

6. The method according to claim 5, wherein Q is amino.

7. The method according to claim 6, wherein $R^7$ is phenyl.

8. The method according to claim 6, wherein $R^7$ is 4-hydroxyphenyl.

9. The method according to claim 6, wherein $R^7$ is 3-chloro-4-hydroxyphenyl.

* * * * *

UNITED STATES PATENT AND TRADEMARK OFFICE
CERTIFICATE OF CORRECTION

PATENT NO. : 4,179,511

DATED : December 18, 1979

INVENTOR(S) : Wayne E. Barth

It is certified that error appears in the above-identified patent and that said Letters Patent are hereby corrected as shown below:

Column 160, lines 41 - 48, that portion of the formula reading

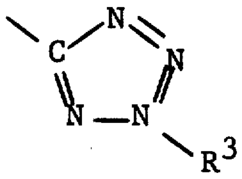

should read

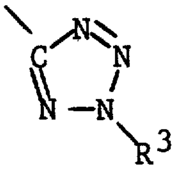

Column 162, line 1, "thiophenecarboxyamido" should read --thiophenecarboxamido--.

Signed and Sealed this

*Eighteenth* Day of *March 1980*

[SEAL]

*Attest:*

SIDNEY A. DIAMOND

*Attesting Officer* *Commissioner of Patents and Trademarks*